United States Patent
Wang et al.

(10) Patent No.: US 11,718,673 B2
(45) Date of Patent: Aug. 8, 2023

(54) BISPECIFIC BINDING MOLECULES THAT TARGET THE TUMOR MICROENVIRONMENT AND AN IMMUNE CHECKPOINT PROTEIN

(71) Applicant: Immetas Therapeutics, Inc., East Hanover, NJ (US)

(72) Inventors: Jin Wang, East Hanover, NJ (US); Godfrey Jonah Rainey, East Hanover, NJ (US)

(73) Assignee: Immetas Therapeutics, Inc., East Hanover, NJ (US)

( * ) Notice: Subject to any disclaimer, the term of this patent is extended or adjusted under 35 U.S.C. 154(b) by 297 days.

(21) Appl. No.: 16/836,197

(22) Filed: Mar. 31, 2020

(65) Prior Publication Data

US 2020/0308285 A1    Oct. 1, 2020

Related U.S. Application Data

(60) Provisional application No. 62/827,381, filed on Apr. 1, 2019.

(51) Int. Cl.
*C07K 16/28* (2006.01)
*C07K 16/24* (2006.01)
*A61K 39/00* (2006.01)
*C12N 15/63* (2006.01)

(52) U.S. Cl.
CPC ........ *C07K 16/2818* (2013.01); *C07K 16/244* (2013.01); *C07K 16/2827* (2013.01); *C07K 16/2866* (2013.01); *C12N 15/63* (2013.01); *A61K 2039/505* (2013.01); *C07K 2317/31* (2013.01); *C07K 2317/522* (2013.01); *C07K 2317/524* (2013.01); *C07K 2317/526* (2013.01); *C07K 2317/55* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 2016/0009824 A1 | 1/2016 | Lo et al. |
| 2017/0037131 A1 | 2/2017 | Bernett et al. |
| 2017/0298106 A1 | 10/2017 | Roschke et al. |
| 2018/0022807 A1 | 1/2018 | Kasturirangan et al. |
| 2018/0264130 A1 | 9/2018 | Pienta |
| 2019/0048072 A1* | 2/2019 | Ligueros-Saylan ........... A61K 39/00114 |

FOREIGN PATENT DOCUMENTS

| | | |
|---|---|---|
| WO | 2017/058859 A1 | 4/2017 |
| WO | 2018119001 A1 | 6/2018 |
| WO | 2018/235056 A1 | 12/2018 |

OTHER PUBLICATIONS

Dahlen et al. 'Bispecific antibodies in cancer immunotherpy.' Ther. Adv. Vacc. Immuno. 6(1):3-17, 2018.*
Serrano et al. 'Therapeutic cancer prevention: achievements and ongoing challenges—a focus on breast and colorectal cancer.' Molecular Oncology 13:579-590, 2019.*
Jin et al. 'Emerging new therapeutic antibody derivatives for cancer treatment.' Signal Transduction and Targeted Therapy (2022) 7:39 ; https://doi.org/10.1038/s41392-021-00868-x.*
Search report and Written Opinion in corresponding International Patent Application No. PCT/US2020/025979, dated Aug. 12, 2020.
Kaplanov, I., et al., "Blocking IL-1beta reverses the immunosuppression in mouse breast cancer and synergizes with anti-PD-1 for tumor abrogation", Proceedings of the National Academy of Sciences, vol. 116 No. 4, Jan. 22, 2019, pp. 1361-1369.
Guo, B., et al., "Inflammasones/IL-1 pathways in myeloid cells modulate PD-1/PD-L1 checkpoint molecules", The Journal of Immunology, May 1, 2017, 1 page.
Tulotta, C., et al., "The role of IL-1B in breast cancer bone metastasis", Endocrine Related Cancer, vol. 25 No.7, Jul. 1, 2018, pp. R421-R434.
European Search Report in corresponding EP Application No. 20784051.3, dated Aug. 8, 2022, 12 pages.

* cited by examiner

*Primary Examiner* — Nora M Rooney
(74) *Attorney, Agent, or Firm* — Edell, Shapiro & Finnan, LLC

(57) ABSTRACT

Bispecific binding proteins that bind IL-1β or IL-1R and a checkpoint protein are provided, together with methods of making the proteins. The checkpoint protein may be PD-1 or PD-L1. The binding proteins may have immunoglobulin-like structures that contain human Fab or scFv domains. A novel bispecific antibody format is provided. Methods of making the binding proteins are provided, together with pharmaceutical compositions containing the proteins. The binding proteins and pharmaceutical compositions may be used for treating or preventing diseases such as cancer.

8 Claims, 45 Drawing Sheets

Specification includes a Sequence Listing.

Figure 5: Amino acid sequences of binding proteins:

Figure 5A:

ITA101

Chain 1 (SEQ ID NO:73)

MGWSCIILFLVATATGVHSQVQLVQSGVEVKKPGASVKVSCKASGYTFTNYYMYWVR
QAPGQGLEWMGGINPSNGGTNFNEKFKNRVTLTTDSSTTTAYMELKSLQFDDTAVYYC
ARRDYRFDMGFDYWGQGTTVTVSSGGGGSGGGGSGGGGSGGGGSEIVLTQSPATLSLS
PGERATLSCRASKGVSTSGYSYLHWYQQKPGQAPRLLIYLASYLESGVPARFSGSGSGT
DFTLTISSLEPEDFAVYYCQHSRDLPLTFGGGTKVEIKGGGGSGGGGSQVQLVESGGGV
VQPGRSLRLSCAASGFTFSVYGMNWVRQAPGKGLEWVAIIWYDGDNQYYADSVKGRF
TISRDNSKNTLYLQMNGLRAEDTAVYYCARDLRTGPFDYWGQGTLVTVSSASTKGPSV
FPLAPCSRSTSESTAALGCLVKDYFPEPVTVSWNSGALTSGVHTFPAVLQSSGLYSLSSV
VTVPSSSLGTKTYTCNVDHKPSNTKVDKRVESKYGPPCPPCPAPEFLGGPSVFLFPPKPK
DTLMISRTPEVTCVVVDVSQEDPEVQFNWYVDGVEVHNAKTKPREEQFNSTYRVVSVL
TVLHQDWLNGKEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDKSRWQEGNVFS
CSVMHEALHNHYTQKSLSLSLGK

Chain 2 (SEQ ID NO:74)

MGWSCIILFLVATATGVHSEIVLTQSPDFQSVTPKEKVTITCRASQSIGSSLHWYQQKPD
QSPKLLIKYASQSFSGVPSRFSGSGSGTDFTLTINSLEAEDAAAYYCHQSSSLPFTFGPGT
KVDIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC

Figure 5B:

ITA102

Chain 1 (SEQ ID NO:75)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC
ATNDDYWGQGTLVTVSSGGGGSGGGGSGGGGSGGGGSEIVLTQSPATLSLSPGERATLS
CRASQSVSSYLAWYQQKPGQAPRLLIYDASNRATGIPARFSGSGSGTDFTLTISSLEPEDF
AVYYCQQSSNWPRTFGQGTKVEIKGGGGSGGGGSQVQLVESGGGVVQPGRSLRLSCA
ASGFTFSVYGMNWVRQAPGKGLEWVAIIWYDGDNQYYADSVKGRFTISRDNSKNTLY
LQMNGLRAEDTAVYYCARDLRTGPFDYWGQGTLVTVSSASTKGPSVFPLAPCSRSTSES
TAALGCLVKDYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDTLMISRTPEVT
CVVVDVSQEDPEVQFNWYVDGVEVHNAKTKPREEQFNSTYRVVSVLTVLHQDWLNG
KEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHN
HYTQKSLSLSLGK

Figure 5B (cont.)

Chain 2 same as chain 2 of ITA101

Figure 5C:

ITA103

Chain 1 (SEQ ID NO:76)

MGWSCIILFLVATATGVHSQVQLVESGGGVVQPGRSLRLSCAASGFTFSVYGMNWVRQ
APGKGLEWVAIIWYDGDNQYYADSVKGRFTISRDNSKNTLYLQMNGLRAEDTAVYYC
ARDLRTGPFDYWGQGTLVTVSSGGGGSGGGGSGGGGSGGGGSEIVLTQSPDFQSVTPK
EKVTITCRASQSIGSSLHWYQQKPDQSPKLLIKYASQSFSGVPSRFSGSGSGTDFTLTINSL
EAEDAAAYYCHQSSSLPFTFGPGTKVDIKGGGGSGGGGSQVQLVQSGVEVKKPGASVK
VSCKASGYTFTNYYMYWVRQAPGQGLEWMGGINPSNGGTNFNEKFKNRVTLTTDSST
TTAYMELKSLQFDDTAVYYCARRDYRFDMGFDYWGQGTTVTVSSASTKGPSVFPLAPC
SRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMIS
RTPEVTCVVVDVSQEDPEVQFNWYVDGVEVHNAKTKPREEQFNSTYRVVSVLTVLHQ
DWLNGKEYKCKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEGNVFSCSVMH
EALHNHYTQKSLSLSLGK

Chain 2 (SEQ ID NO:77)

MGWSCIILFLVATATGVHSEIVLTQSPATLSLSPGERATLSCRASKGVSTSGYSYLHWYQ
QKPGQAPRLLIYLASYLESGVPARFSGSGSGTDFTLTISSLEPEDFAVYYCQHSRDLPLTF
GGGTKVEIKRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFNRGEC

ITA104

Chain 1 (SEQ ID NO:78)

MGWSCIILFLVATATGVHSQVQLVESGGGVVQPGRSLRLSCAASGFTFSVYGMNWVRQ
APGKGLEWVAIIWYDGDNQYYADSVKGRFTISRDNSKNTLYLQMNGLRAEDTAVYYC
ARDLRTGPFDYWGQGTLVTVSSGGGGSGGGGSGGGGSGGGGSEIVLTQSPDFQSVTPK
EKVTITCRASQSIGSSLHWYQQKPDQSPKLLIKYASQSFSGVPSRFSGSGSGTDFTLTINSL
EAEDAAAYYCHQSSSLPFTFGPGTKVDIKGGGGSGGGGSQVQLVESGGGVVQPGRSLR
LDCKASGITFSNSGMHWVRQAPGKGLEWVAVIWYDGSKRYYADSVKGRFTISRDNSK
NTLFLQMNSLRAEDTAVYYCATNDDYWGQGTLVTVSSASTKGPSVFPLAPCSRSTSEST
AALGCLVKDYFPEPVTVSWNSGALTSGVHTFPAVLQSSGLYSLSSVVTVPSSSLGTKTY
TCNVDHKPSNTKVDKRVESKYGPPCPPCPAPEFLGGPSVFLFPPKPKDTLMISRTPEVTC
VVVDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYPSDIA

Figure 5C (cont.)

VEWESNGQPENNYKTTPPVLDSDGSFFLYSRLTVDKSRWQEGNVFSCSVMHEALHNHY
TQKSLSLSLGK

Chain 2 (SEQ ID NO:79)

MGWSCIILFLVATATGVHSEIVLTQSPATLSLSPGERATLSCRASQSVSSYLAWYQQKPG
QAPRLLIYDASNRATGIPARFSGSGSGTDFTLTISSLEPEDFAVYYCQQSSNWPRTFGQGT
KVEIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC

Figure 5D:

ITA201

Chain 1 (SEQ ID NO:80)

MGWSCIILFLVATATGVHSQVQLVESGGGVVQPGRSLRLSCAASGFTFSVYGMNWVRQ
APGKGLEWVAIIWYDGDNQYYADSVKGRFTISRDNSKNTLYLQMNGLRAEDTAVYYC
ARDLRTGPFDYWGQGTLVTVSSASTKGPSVFPLAPCSRSTSESTAALGCLVKDYFPEPVT
VSWNSGALTSGVHTFPAVLQSSGLYSLSSVVTVPSSSLGTKTYTCNVDHKPSNTKVDKR
VESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNGQPENNYKTT
PPVLDSDGSFFLYSRLTVDKSRWQEGNVFSCSVMHEALHNHYTQKSLSLSLGKGGGGS
GGGGSQVQLVQSGVEVKKPGASVKVSCKASGYTFTNYYMYWVRQAPGQGLEWMGGI
NPSNGGTNFNEKFKNRVTLTTDSSTTTAYMELKSLQFDDTAVYYCARRDYRFDMGFDY
WGQGTTVTVSSGGGGSGGGGSGGGGSGGGGSEIVLTQSPATLSLSPGERATLSCRASKG
VSTSGYSYLHWYQQKPGQAPRLLIYLASYLESGVPARFSGSGSGTDFTLTISSLEPEDFA
VYYCQHSRDLPLTFGGGTKVEIK

Chain 2 same as chain 2 of ITA101

Figure 5E:

ITA202

Chain 1 (SEQ ID NO:81)

MGWSCIILFLVATATGVHSQVQLVESGGGVVQPGRSLRLSCAASGFTFSVYGMNWVRQ
APGKGLEWVAIIWYDGDNQYYADSVKGRFTISRDNSKNTLYLQMNGLRAEDTAVYYC
ARDLRTGPFDYWGQGTLVTVSSASTKGPSVFPLAPCSRSTSESTAALGCLVKDYFPEPVT
VSWNSGALTSGVHTFPAVLQSSGLYSLSSVVTVPSSSLGTKTYTCNVDHKPSNTKVDKR
VESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNGQPENNYKTT
PPVLDSDGSFFLYSRLTVDKSRWQEGNVFSCSVMHEALHNHYTQKSLSLSLGKGGGGS

Figure 5E (cont.)

GGGGSQVQLVESGGGVVQPGRSLRLDCKASGITFSNSGMHWVRQAPGKGLEWVAVIW
YDGSKRYYADSVKGRFTISRDNSKNTLFLQMNSLRAEDTAVYYCATNDDYWGQGTLV
TVSSGGGGSGGGGSGGGGSGGGGSEIVLTQSPATLSLSPGERATLSCRASQSVSSYLAW
YQQKPGQAPRLLIYDASNRATGIPARFSGSGSGTDFTLTISSLEPEDFAVYYCQQSSNWP
RTFGQGTKVEIK

Chain 2 same as chain 2 of ITA101

Figure 5F:

ITA203

Chain 1  (SEQ ID NO:82)

MGWSCIILFLVATATGVHSQVQLVQSGVEVKKPGASVKVSCKASGYTFTNYYMYWVR
QAPGQGLEWMGGINPSNGGTNFNEKFKNRVTLTTDSSTTTAYMELKSLQFDDTAVYYC
ARRDYRFDMGFDYWGQGTTVTVSSASTKGPSVFPLAPCSRSTSESTAALGCLVKDYFPE
PVTVSWNSGALTSGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAVEWESNGQPENNY
KTTPPVLDSDGSFFLYSRLTVDKSRWQEGNVFSCSVMHEALHNHYTQKSLSLSLGKGG
GGSGGGGSQVQLVESGGGVVQPGRSLRLSCAASGFTFSVYGMNWVRQAPGKGLEWVA
IIWYDGDNQYYADSVKGRFTISRDNSKNTLYLQMNGLRAEDTAVYYCARDLRTGPFDY
WGQGTLVTVSSGGGGSGGGGSGGGGSGGGGSEIVLTQSPDFQSVTPKEKVTITCRASQS
IGSSLHWYQQKPDQSPKLLIKYASQSFSGVPSRFSGSGSGTDFTLTINSLEAEDAAAYYC
HQSSSLPFTFGPGTKVDIK

Chain 2 same as chain 2 of ITA103

Figure 5G:

ITA204

Chain 1  (SEQ ID NO:83)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC
ATNDDYWGQGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDKRVESK
YGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGKGGGGSGGGGS
QVQLVESGGGVVQPGRSLRLSCAASGFTFSVYGMNWVRQAPGKGLEWVAIIWYDGDN
QYYADSVKGRFTISRDNSKNTLYLQMNGLRAEDTAVYYCARDLRTGPFDYWGQGTLV

Figure 5G (cont.)
TVSSGGGGSGGGGSGGGGSGGGGSEIVLTQSPDFQSVTPKEKVTITCRASQSIGSSLHWY
QQKPDQSPKLLIKYASQSFSGVPSRFSGSGSGTDFTLTINSLEAEDAAAYYCHQSSSLPFT
FGPGTKVDIK

Chain 2 same as chain 2 of ITA 104

Figure 5H:

<u>ITA301</u>

Chain 1 (SEQ ID NO:84)

MGWSCIILFLVATATGVHSEIVLTQSPATLSLSPGERATLSCRASKGVSTSGYSYLHWYQ
QKPGQAPRLLIYLASYLESGVPARFSGSGSGTDFTLTISSLEPEDFAVYYCQHSRDLPLTF
GGGTKVEIKRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFNRGECQV
QLVESGGGVVQPGRSLRLSCAASGFTFSVYGMNWVRQAPGKGLEWVAIIWYDGDNQY
YADSVKGRFTISRDNSKNTLYLQMNGLRAEDTAVYYCARDLRTGPFDYWGQGTLVTV
SSASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPPCPAPEFLGGP
SVFLFPPKPKDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKS
RWQEGNVFSCSVMHEALHNHYTQKSLSLSLGK

Chain 2 same as Chain 2 of ITA101

Chain 3 (SEQ ID NO:85)

MGWSCIILFLVATATGVHSQVQLVQSGVEVKKPGASVKVSCKASGYTFTNYYMYWVR
QAPGQGLEWMGGINPSNGGTNFNEKFKNRVTLTTDSSTTTAYMELKSLQFDDTAVYYC
ARRDYRFDMGFDYWGQGTTVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKV
DKRVEPKSC

Figure 5I:

<u>ITA302</u>

Chain 1 (SEQ ID NO:86)

MGWSCIILFLVATATGVHSEIVLTQSPATLSLSPGERATLSCRASQSVSSYLAWYQQKPG
QAPRLLIYDASNRATGIPARFSGSGSGTDFTLTISSLEPEDFAVYYCQQSSNWPRTFGQGT
KVEIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGECQVQLVE
SGGGVVQPGRSLRLSCAASGFTFSVYGMNWVRQAPGKGLEWVAIIWYDGDNQYYADS
VKGRFTISRDNSKNTLYLQMNGLRAEDTAVYYCARDLRTGPFDYWGQGTLVTVSSAST
KGPSVFPLAPCSRSTSESTAALGCLVKDYFPEPVTVSWNSGALTSGVHTFPAVLQSSGLY

Figure 5I (cont.)

SLSSVVTVPSSSLGTKTYTCNVDHKPSNTKVDKRVESKYGPPCPPCPAPEFLGGPSVFLFP
PKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKN
QVSLTCLVKGFYPSDIAVEWESNGQPENNYKTTPPVLDSDGSFFLYSRLTVDKSRWQEG
NVFSCSVMHEALHNHYTQKSLSLSLGK

Chain 2 same as chain 2 of ITA101

Chain 3 (SEQ ID NO:87)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC
ATNDDYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKRVEPK
SC

Figure 5J:

ITA303

Chain 1 (SEQ ID NO:88)

MGWSCIILFLVATATGVHSEIVLTQSPDFQSVTPKEKVTITCRASQSIGSSLHWYQQKPD
QSPKLLIKYASQSFSGVPSRFSGSGSGTDFTLTINSLEAEDAAAYYCHQSSSLPFTFGPGT
KVDIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGECQVQLVQ
SGVEVKKPGASVKVSCKASGYTFTNYYMYWVRQAPGQGLEWMGGINPSNGGTNFNE
KFKNRVTLTTDSSTTTAYMELKSLQFDDTAVYYCARRDYRFDMGFDYWGQGTTVTVS
SASTKGPSVFPLAPCSRSTSESTAALGCLVKDYFPEPVTVSWNSGALTSGVHTFPAVLQS
SGLYSLSSVVTVPSSSLGTKTYTCNVDHKPSNTKVDKRVESKYGPPCPPCPAPEFLGGPS
VFLFPPKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLYSRLTVDKSR
WQEGNVFSCSVMHEALHNHYTQKSLSLSLGK

Chain 2 same as chain 2 of ITA103

Chain 3 (SEQ ID NO:89)

MGWSCIILFLVATATGVHSQVQLVESGGGVVQPGRSLRLSCAASGFTFSVYGMNWVRQ
APGKGLEWVAIIWYDGDNQYYADSVKGRFTISRDNSKNTLYLQMNGLRAEDTAVYYC
ARDLRTGPFDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDK
RVEPKSC

Figure 5K:

ITA304

Chain 1 (SEQ ID NO:90)

MGWSCIILFLVATATGVHSEIVLTQSPDFQSVTPKEKVTITCRASQSIGSSLHWYQQKPD
QSPKLLIKYASQSFSGVPSRFSGSGSGTDFTLTINSLEAEDAAAYYCHQSSSLPFTFGPGT
KVDIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGECQVQLVE
SGGGVVQPGRSLRLDCKASGITFSNSGMHWVRQAPGKGLEWVAVIWYDGSKRYYADS
VKGRFTISRDNSKNTLFLQMNSLRAEDTAVYYCATNDDYWGQGTLVTVSSASTKGPSV
FPLAPCSRSTSESTAALGCLVKDYFPEPVTVSWNSGALTSGVHTFPAVLQSSGLYSLSSV
VTVPSSSLGTKTYTCNVDHKPSNTKVDKRVESKYGPPCPPCPAPEFLGGPSVFLFPPKPK
DTLMISRTPEVTCVVVDVSQEDPEVQFNWYVDGVEVHNAKTKPREEQFNSTYRVVSVL
TVLHQDWLNGKEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDKSRWQEGNVFS
CSVMHEALHNHYTQKSLSLSLGK

Chain 2 same as chain 2 of ITA104

Chain 3 same as chain 3 of ITA303

ITA401: X=2, Y=4 (SEQ ID NO: 91); ITC401: X=1, Y=5 (SEQ ID NO: 125); ITC402: X=3, Y=3 (SEQ ID NO: 126); ITC403: X=4, Y=2 (SEQ ID NO: 127);

ITC404: X=5, Y=1 (SEQ ID NO: 128); ITC405: X=4, Y=4 (SEQ ID NO: 129); ITC406: X=2, Y=2 (SEQ ID NO: 130); ITD401: X=5, Y=5 (SEQ ID NO: 131);

ITD402: X=4, Y=5 (SEQ ID NO: 132); ITD403: X=5, Y=4 (SEQ ID NO: 133)

Chain 1

MGWSCIILFLVATATGVHSQVQLVESGGGVVQPGRSLRLSCAASGFTFSVYGMNWVRQ
APGKGLEWVAIIWYDGDNQYYADSVKGRFTISRDNSKNTLYLQMNGLRAEDTAVYYC
ARDLRTGPFDYWGQGTLVTVSSASTKGPSVFPLAPCSRSTSESTAALGCLVKDYFPEPVT
VSWNSGALTSGVHTFPAVLQSSGLYSLSSVVTVPSSSLGTKTYTCNVDHKPSNTKVDKR
VESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESN(GGGGS)xEIVL
TQSPATLSLSPGERATLSCRASKGVSTSGYSYLHWYQQKPGQAPRLLIYLASYLESGVPA
RFSGSGSGTDFTLTISSLEPEDFAVYYCQHSRDLPLTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC(GGGGS)yQPENNYKTTPPVLDSDGSF
FLYSRLTVDKSRWQEGNVFSCSVMHEALHNHYTQKSLSLSLGK

Figure 5K (cont.)

Chain 2 same as chain 2 of ITA101

Chain 3 (SEQ ID NO:92)

MGWSCIILFLVATATGVHSQVQLVQSGVEVKKPGASVKVSCKASGYTFTNYYMYWVR
QAPGQGLEWMGGINPSNGGTNFNEKFKNRVTLTTDSSTTTAYMELKSLQFDDTAVYYC
ARRDYRFDMGFDYWGQGTTVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKV
DKRVEPKSC

Figure 5L:

ITA402

Chain 1 (SEQ ID NO:93)

MGWSCIILFLVATATGVHSQVQLVESGGGVVQPGRSLRLSCAASGFTFSVYGMNWVRQ
APGKGLEWVAIIWYDGDNQYYADSVKGRFTISRDNSKNTLYLQMNGLRAEDTAVYYC
ARDLRTGPFDYWGQGTLVTVSSASTKGPSVFPLAPCSRSTSESTAALGCLVKDYFPEPVT
VSWNSGALTSGVHTFPAVLQSSGLYSLSSVVTVPSSSLGTKTYTCNVDHKPSNTKVDKR
VESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNGGGGSGGGGS
EIVLTQSPATLSLSPGERATLSCRASQSVSSYLAWYQQKPGQAPRLLIYDASNRATGIPA
RFSGSGSGTDFTLTISSLEPEDFAVYYCQQSSNWPRTFGQGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGECGGGGSGGGGSGGGGSGGGGSGQ
PENNYKTTPPVLDSDGSFFLYSRLTVDKSRWQEGNVFSCSVMHEALHNHYTQKSLSLSL
GK

Chain 2 same as chain 2 of ITA101

Chain 3 same as chain 3 of ITA302

Figure 5M:

ITA403

Chain 1 (SEQ ID NO:94)

MGWSCIILFLVATATGVHSQVQLVQSGVEVKKPGASVKVSCKASGYTFTNYYMYWVR
QAPGQGLEWMGGINPSNGGTNFNEKFKNRVTLTTDSSTTTAYMELKSLQFDDTAVYYC
ARRDYRFDMGFDYWGQGTTVTVSSASTKGPSVFPLAPCSRSTSESTAALGCLVKDYFPE
PVTVSWNSGALTSGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSS

Figure 5M (cont.)

IEKTISKAKGQPREPQVYTLPPSQEEMTKNQVSLTCLVKGFYPSDIAVEWESNGGGGSG
GGGSEIVLTQSPDFQSVTPKEKVTITCRASQSIGSSLHWYQQKPDQSPKLLIKYASQSFSG
VPSRFSGSGSGTDFTLTINSLEAEDAAAYYCHQSSSLPFTFGPGTKVDIKRTVAAPSVFIFP
PSDEQLKSGTASVVCLLNNFYPREAKVQWKVDNALQSGNSQESVTEQDSKDSTYSLSST
LTLSKADYEKHKVYACEVTHQGLSSPVTKSFNRGECGGGGSGGGGSGGGGSGGGGSG
QPENNYKTTPPVLDSDGSFFLYSRLTVDKSRWQEGNVFSCSVMHEALHNHYTQKSLSLS
LGK

Chain 2 same as chain 2 of ITA103

Chain 3 same as chain 3 of ITA303

Figure 5N:

ITA404

Chain 1  (SEQ ID NO:95)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC
ATNDDYWGQGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDKRVESK
YGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGGGGSGGGGSEIVLT
QSPDFQSVTPKEKVTITCRASQSIGSSLHWYQQKPDQSPKLLIKYASQSFSGVPSRFSGSG
SGTDFTLTINSLEAEDAAAYYCHQSSSLPFTFGPGTKVDIKRTVAAPSVFIFPPSDEQLKS
GTASVVCLLNNFYPREAKVQWKVDNALQSGNSQESVTEQDSKDSTYSLSSTLTLSKAD
YEKHKVYACEVTHQGLSSPVTKSFNRGECGGGGSGGGGSGGGGSGGGGSGQPENNYK
TTPPVLDSDGSFFLYSRLTVDKSRWQEGNVFSCSVMHEALHNHYTQKSLSLSLGK

Chain 2 same as chain 2 of ITA104

Chain 3 same as chain 3 of ITA303

Figure 5O:

ITB101

Chain 1  (SEQ ID NO:96)

MGWSCIILFLVATATGVHSSERCDDWGLDTMRQIQVFEDEPARIKCPLFEHFLKFNYSTA
HSAGLTLIWYWTRQDRDLEEPINFRLPENRISKEKDVLWFRPTLLNDTGNYTCMLRNTT
YCSKVAFPLEVVQKDSCFNSPMKLPVHKLYIEYGIQRITCPNVDGYFPSSVKPTITWYMG
CYKIQNFNNVIPEGMNLSFLIALISNNGNYTCVVTYPENGRTFHLTRTLTVKVVGSPKNA

Figure 5O (cont.)

VPPVIHSPNDHVVYEKEPGEELLIPCTVYFSFLMDSRNEVWWTIDGKKPDDITIDVTINES
ISHSRTEDETRTQILSIKKVTSEDLKRSYVCHARSAKGEVAKAAKVKQKVPAPRYTVEK
CKEREEKIILVSSANEIDVRPCPLNPNEHKGTITWYKDDSKTPVSTEQASRIHQHKEKLW
FVPAKVEDSGHYYCVVRNSSYCLRIKISAKFVENEPNLCYNAQAIFKQKLPVAGDGGLV
CPYMEFFKNENNELPKLQWYKDCKPLLLDNIHFSGVKDRLIVMNVAEKHRGNYTCHAS
YTYLGKQYPITRVIEFITLEENKPTRPVIVSPANETMEVDLGSQIQLICNVTGQLSDIAYW
KWNGSVIDEDDPVLGEDYYSVENPANKRRSTLITVLNISEIESRFYKHPFTCFAKNTHGID
AAYIQLIYPVTNGGGGSGGGGSQVQLVQSGVEVKKPGASVKVSCKASGYTFTNYYMY
WVRQAPGQGLEWMGGINPSNGGTNFNEKFKNRVTLTTDSSTTTAYMELKSLQFDDTAV
YYCARRDYRFDMGFDYWGQGTTVTVSSASTKGPSVFPLAPCSRSTSESTAALGCLVKD
YFPEPVTVSWNSGALTSGVHTFPAVLQSSGLYSLSSVVTVPSSSLGTKTYTCNVDHKPSN
TKVDKRVESKYGPPCPPCPAPEFLGGPSVFLFPPKPKDTLMISRTPEVTCVVVDVSQEDP
EVQFNWYVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSLSLSLG
K

Chain 2 same as chain 2 of ITA103

Figure 5P:

ITB102

Chain 1 (SEQ ID NO:97)

MGWSCIILFLVATATGVHSSERCDDWGLDTMRQIQVFEDEPARIKCPLFEHFLKFNYSTA
HSAGLTLIWYWTRQDRDLEEPINFRLPENRISKEKDVLWFRPTLLNDTGNYTCMLRNTT
YCSKVAFPLEVVQKDSCFNSPMKLPVHKLYIEYGIQRITCPNVDGYFPSSVKPTITWYMG
CYKIQNFNNVIPEGMNLSFLIALISNNGNYTCVVTYPENGRTFHLTRTLTVKVVGSPKNA
VPPVIHSPNDHVVYEKEPGEELLIPCTVYFSFLMDSRNEVWWTIDGKKPDDITIDVTINES
ISHSRTEDETRTQILSIKKVTSEDLKRSYVCHARSAKGEVAKAAKVKQKVPAPRYTVEK
CKEREEKIILVSSANEIDVRPCPLNPNEHKGTITWYKDDSKTPVSTEQASRIHQHKEKLW
FVPAKVEDSGHYYCVVRNSSYCLRIKISAKFVENEPNLCYNAQAIFKQKLPVAGDGGLV
CPYMEFFKNENNELPKLQWYKDCKPLLLDNIHFSGVKDRLIVMNVAEKHRGNYTCHAS
YTYLGKQYPITRVIEFITLEENKPTRPVIVSPANETMEVDLGSQIQLICNVTGQLSDIAYW
KWNGSVIDEDDPVLGEDYYSVENPANKRRSTLITVLNISEIESRFYKHPFTCFAKNTHGID
AAYIQLIYPVTNGGGGSGGGGSQVQLVESGGGVVQPGRSLRLDCKASGITFSNSGMHW
VRQAPGKGLEWVAVIWYDGSKRYYADSVKGRFTISRDNSKNTLFLQMNSLRAEDTAV
YYCATNDDYWGQGTLVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKVDKRV
ESKYGPPCPPCPAPEFLGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGLPSSIEKTIS
KAKGQPREPQVYTLPPSQEEMTKNQVSLTCLVKGFYPSDIAVEWESNGQPENNYKTTPP
VLDSDGSFFLYSRLTVDKSRWQEGNVFSCSVMHEALHNHYTQKSLSLSLGK

Figure 5P (cont.)

Chain 2 same as chain 2 of ITA104

Figure 5Q:

ITB103

Chain 1 (SEQ ID NO:98)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC
ATNDDYWGQGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDKRVESK
YGGGGSGGGGSERCDDWGLDTMRQIQVFEDEPARIKCPLFEHFLKFNYSTAHSAGLTLI
WYWTRQDRDLEEPINFRLPENRISKEKDVLWFRPTLLNDTGNYTCMLRNTTYCSKVAFP
LEVVQKDSCFNSPMKLPVHKLYIEYGIQRITCPNVDGYFPSSVKPTITWYMGCYKIQNFN
NVIPEGMNLSFLIALISNNGNYTCVVTYPENGRTFHLTRTLTVKVVGSPKNAVPPVIHSP
NDHVVYEKEPGEELLIPCTVYFSFLMDSRNEVWWTIDGKKPDDITIDVTINESISHSRTED
ETRTQILSIKKVTSEDLKRSYVCHARSAKGEVAKAAKVKQKVPAPRYTVEKCKEREEKII
LVSSANEIDVRPCPLNPNEHKGTITWYKDDSKTPVSTEQASRIHQHKEKLWFVPAKVED
SGHYYCVVRNSSYCLRIKISAKFVENEPNLCYNAQAIFKQKLPVAGDGGLVCPYMEFFK
NENNELPKLQWYKDCKPLLLDNIHFSGVKDRLIVMNVAEKHRGNYTCHASYTYLGKQ
YPITRVIEFITLEENKPTRPVIVSPANETMEVDLGSQIQLICNVTGQLSDIAYWKWNGSVI
DEDDPVLGEDYYSVENPANKRRSTLITVLNISEIESRFYKHPFTCFAKNTHGIDAAYIQLI
YPVTNSGDKTHTCPPCPAPEFLGGPSVFLFPPKPKDTLMISRTPEVTCVVVDVSQEDPEV
QFNWYVDGVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKSLSLSLGK

Chain 2 same as chain 2 of ITA104

Figure 5R:

ITB104

Chain 1 (SEQ ID NO:99)

MGWSCIILFLVATATGVHSQVQLVQSGVEVKKPGASVKVSCKASGYTFTNYYMYWVR
QAPGQGLEWMGGINPSNGGTNFNEKFKNRVTLTTDSSTTTAYMELKSLQFDDTAVYYC
ARRDYRFDMGFDYWGQGTTVTVSSASTKGPSVFPLAPCSRSTSESTAALGCLVKDYFPE
PVTVSWNSGALTSGVHTFPAVLQSSGLYSLSSVVTVPSSSLGTKTYTCNVDHKPSNTKV
DKRVESKYGGGGSGGGGSERCDDWGLDTMRQIQVFEDEPARIKCPLFEHFLKFNYSTA
HSAGLTLIWYWTRQDRDLEEPINFRLPENRISKEKDVLWFRPTLLNDTGNYTCMLRNTT
YCSKVAFPLEVVQKDSCFNSPMKLPVHKLYIEYGIQRITCPNVDGYFPSSVKPTITWYMG
CYKIQNFNNVIPEGMNLSFLIALISNNGNYTCVVTYPENGRTFHLTRTLTVKVVGSPKNA

Figure 5R (cont.)

VPPVIHSPNDHVVYEKEPGEELLIPCTVYFSFLMDSRNEVWWTIDGKKPDDITIDVTINES
ISHSRTEDETRTQILSIKKVTSEDLKRSYVCHARSAKGEVAKAAKVKQKVPAPRYTVEK
CKEREEKIILVSSANEIDVRPCPLNPNEHKGTITWYKDDSKTPVSTEQASRIHQHKEKLW
FVPAKVEDSGHYYCVVRNSSYCLRIKISAKFVENEPNLCYNAQAIFKQKLPVAGDGGLV
CPYMEFFKNENNELPKLQWYKDCKPLLLDNIHFSGVKDRLIVMNVAEKHRGNYTCHAS
YTYLGKQYPITRVIEFITLEENKPTRPVIVSPANETMEVDLGSQIQLICNVTGQLSDIAYW
KWNGSVIDEDDPVLGEDYYSVENPANKRRSTLITVLNISEIESRFYKHPFTCFAKNTHGID
AAYIQLIYPVTNSGDKTHTCPPCPAPEFLGGPSVFLFPPKPKDTLMISRTPEVTCVVVDVS
QEDPEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLS
LSLGK

Chain 2 same as chain 2 of ITA103

Figure 5S:

<u>ITB105</u> (SEQ ID NO:100)

MGWSCIILFLVATATGVHSSERCDDWGLDTMRQIQVFEDEPARIKCPLFEHFLKFNYSTA
HSAGLTLIWYWTRQDRDLEEPINFRLPENRISKEKDVLWFRPTLLNDTGNYTCMLRNTT
YCSKVAFPLEVVQKDSCFNSPMKLPVHKLYIEYGIQRITCPNVDGYFPSSVKPTITWYMG
CYKIQNFNNVIPEGMNLSFLIALISNNGNYTCVVTYPENGRTFHLTRTLTVKVVGSPKNA
VPPVIHSPNDHVVYEKEPGEELLIPCTVYFSFLMDSRNEVWWTIDGKKPDDITIDVTINES
ISHSRTEDETRTQILSIKKVTSEDLKRSYVCHARSAKGEVAKAAKVKQKVPAPRYTVEK
CKEREEKIILVSSANEIDVRPCPLNPNEHKGTITWYKDDSKTPVSTEQASRIHQHKEKLW
FVPAKVEDSGHYYCVVRNSSYCLRIKISAKFVENEPNLCYNAQAIFKQKLPVAGDGGLV
CPYMEFFKNENNELPKLQWYKDCKPLLLDNIHFSGVKDRLIVMNVAEKHRGNYTCHAS
YTYLGKQYPITRVIEFITLEENKPTRPVIVSPANETMEVDLGSQIQLICNVTGQLSDIAYW
KWNGSVIDEDDPVLGEDYYSVENPANKRRSTLITVLNISEIESRFYKHPFTCFAKNTHGID
AAYIQLIYPVTNSGDKTHTCPPCPAPEFLGGPSVFLFPPKPKDTLMISRTPEVTCVVVDVS
QEDPEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLS
LSLGKGGGGSGGGGSQVQLVESGGGVVQPGRSLRLDCKASGITFSNSGMHWVRQAPG
KGLEWVAVIWYDGSKRYYADSVKGRFTISRDNSKNTLFLQMNSLRAEDTAVYYCATN
DDYWGQGTLVTVSSGGGGSGGGGSGGGGSGGGGSEIVLTQSPATLSLSPGERATLSCRA
SQSVSSYLAWYQQKPGQAPRLLIYDASNRATGIPARFSGSGSGTDFTLTISSLEPEDFAVY
YCQQSSNWPRTFGQGTKVEIK

Figure 5T:

<u>ITB106</u>

Figure 5T (cont.)

Chain 1 (SEQ ID NO:101)

MGWSCIILFLVATATGVHSSERCDDWGLDTMRQIQVFEDEPARIKCPLFEHFLKFNYSTA
HSAGLTLIWYWTRQDRDLEEPINFRLPENRISKEKDVLWFRPTLLNDTGNYTCMLRNTT
YCSKVAFPLEVVQKDSCFNSPMKLPVHKLYIEYGIQRITCPNVDGYFPSSVKPTITWYMG
CYKIQNFNNVIPEGMNLSFLIALISNNGNYTCVVTYPENGRTFHLTRTLTVKVVGSPKNA
VPPVIHSPNDHVVYEKEPGEELLIPCTVYFSFLMDSRNEVWWTIDGKKPDDITIDVTINES
ISHSRTEDETRTQILSIKKVTSEDLKRSYVCHARSAKGEVAKAAKVKQKVPAPRYTVEK
CKEREEKIILVSSANEIDVRPCPLNPNEHKGTITWYKDDSKTPVSTEQASRIHQHKEKLW
FVPAKVEDSGHYYCVVRNSSYCLRIKISAKFVENEPNLCYNAQAIFKQKLPVAGDGGLV
CPYMEFFKNENNELPKLQWYKDCKPLLLDNIHFSGVKDRLIVMNVAEKHRGNYTCHAS
YTYLGKQYPITRVIEFITLEENKPTRPVIVSPANETMEVDLGSQIQLICNVTGQLSDIAYW
KWNGSVIDEDDPVLGEDYYSVENPANKRRSTLITVLNISEIESRFYKHPFTCFAKNTHGID
AAYIQLIYPVTNGGGSGGGGSEIVLTQSPATLSLSPGERATLSCRASKGVSTSGYSYLH
WYQQKPGQAPRLLIYLASYLESGVPARFSGSGSGTDFTLTISSLEPEDFAVYYCQHSRDL
PLTFGGGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRG
ECGPPCPPCPAPEFLGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGK

Chain 2 same as chain 2 of ITA301

Figure 5U:

ITB107

Chain 1 (SEQ ID NO:102)

MGWSCIILFLVATATGVHSSERCDDWGLDTMRQIQVFEDEPARIKCPLFEHFLKFNYSTA
HSAGLTLIWYWTRQDRDLEEPINFRLPENRISKEKDVLWFRPTLLNDTGNYTCMLRNTT
YCSKVAFPLEVVQKDSCFNSPMKLPVHKLYIEYGIQRITCPNVDGYFPSSVKPTITWYMG
CYKIQNFNNVIPEGMNLSFLIALISNNGNYTCVVTYPENGRTFHLTRTLTVKVVGSPKNA
VPPVIHSPNDHVVYEKEPGEELLIPCTVYFSFLMDSRNEVWWTIDGKKPDDITIDVTINES
ISHSRTEDETRTQILSIKKVTSEDLKRSYVCHARSAKGEVAKAAKVKQKVPAPRYTVEK
CKEREEKIILVSSANEIDVRPCPLNPNEHKGTITWYKDDSKTPVSTEQASRIHQHKEKLW
FVPAKVEDSGHYYCVVRNSSYCLRIKISAKFVENEPNLCYNAQAIFKQKLPVAGDGGLV
CPYMEFFKNENNELPKLQWYKDCKPLLLDNIHFSGVKDRLIVMNVAEKHRGNYTCHAS
YTYLGKQYPITRVIEFITLEENKPTRPVIVSPANETMEVDLGSQIQLICNVTGQLSDIAYW
KWNGSVIDEDDPVLGEDYYSVENPANKRRSTLITVLNISEIESRFYKHPFTCFAKNTHGID
AAYIQLIYPVTNGGGSGGGGSEIVLTQSPATLSLSPGERATLSCRASQSVSSYLAWYQQ
KPGQAPRLLIYDASNRATGIPARFSGSGSGTDFTLTISSLEPEDFAVYYCQQSSNWPRTFG
QGTKVEIKRTVAAPSVFIFPPSDEQLKSGTASVVCLLNNFYPREAKVQWKVDNALQSGN

Figure 5U (cont.)

SQESVTEQDSKDSTYSLSSTLTLSKADYEKHKVYACEVTHQGLSSPVTKSFNRGECGPPC
PPCPAPEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK

Chain 2 same as chain 2 of ITA302

Figure 5V:

ITB108

Chain 1 (SEQ ID NO:103)

MGWSCIILFLVATATGVHSEIVLTQSPATLSLSPGERATLSCRASQSVSSYLAWYQQKPG
QAPRLLIYDASNRATGIPARFSGSGSGTDFTLTISSLEPEDFAVYYCQQSSNWPRTFGQGT
KVEIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGECGGGGSG
GGGSERCDDWGLDTMRQIQVFEDEPARIKCPLFEHFLKFNYSTAHSAGLTLIWYWTRQD
RDLEEPINFRLPENRISKEKDVLWFRPTLLNDTGNYTCMLRNTTYCSKVAFPLEVVQKD
SCFNSPMKLPVHKLYIEYGIQRITCPNVDGYFPSSVKPTITWYMGCYKIQNFNNVIPEGM
NLSFLIALISNNGNYTCVVTYPENGRTFHLTRTLTVKVVGSPKNAVPPVIHSPNDHVVYE
KEPGEELLIPCTVYFSFLMDSRNEVWWTIDGKKPDDITIDVTINESISHSRTEDETRTQILSI
KKVTSEDLKRSYVCHARSAKGEVAKAAKVKQKVPAPRYTVEKCKEREEKIILVSSANEI
DVRPCPLNPNEHKGTITWYKDDSKTPVSTEQASRIHQHKEKLWFVPAKVEDSGHYYCV
VRNSSYCLRIKISAKFVENEPNLCYNAQAIFKQKLPVAGDGGLVCPYMEFFKNENNELP
KLQWYKDCKPLLLDNIHFSGVKDRLIVMNVAEKHRGNYTCHASYTYLGKQYPITRVIEF
ITLEENKPTRPVIVSPANETMEVDLGSQIQLICNVTGQLSDIAYWKWNGSVIDEDDPVLG
EDYYSVENPANKRRSTLITVLNISEIESRFYKHPFTCFAKNTHGIDAAYIQLIYPVTNSGD
KTHTCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK

Chain 2 same as chain 2 of ITA302

Figure 5W:

ITB109

Chain 1 (SEQ ID NO:104)

MGWSCIILFLVATATGVHSEIVLTQSPATLSLSPGERATLSCRASKGVSTSGYSYLHWYQ
QKPGQAPRLLIYLASYLESGVPARFSGSGSGTDFTLTISSLEPEDFAVYYCQHSRDLPLTF
GGGTKVEIKRTVAAPSVFIFPPSDEQLKSGTASVVCLLNNFYPREAKVQWKVDNALQSG

Figure 5W (cont.)

NSQESVTEQDSKDSTYSLSSTLTLSKADYEKHKVYACEVTHQGLSSPVTKSFNRGECGG
GGSGGGGSERCDDWGLDTMRQIQVFEDEPARIKCPLFEHFLKFNYSTAHSAGLTLIWY
WTRQDRDLEEPINFRLPENRISKEKDVLWFRPTLLNDTGNYTCMLRNTTYCSKVAFPLE
VVQKDSCFNSPMKLPVHKLYIEYGIQRITCPNVDGYFPSSVKPTITWYMGCYKIQNFNN
VIPEGMNLSFLIALISNNGNYTCVVTYPENGRTFHLTRTLTVKVVGSPKNAVPPVIHSPN
DHVVYEKEPGEELLIPCTVYFSFLMDSRNEVWWTIDGKKPDDITIDVTINESISHSRTEDE
TRTQILSIKKVTSEDLKRSYVCHARSAKGEVAKAAKVKQKVPAPRYTVEKCKEREEKIIL
VSSANEIDVRPCPLNPNEHKGTITWYKDDSKTPVSTEQASRIHQHKEKLWFVPAKVEDS
GHYYCVVRNSSYCLRIKISAKFVENEPNLCYNAQAIFKQKLPVAGDGGLVCPYMEFFKN
ENNELPKLQWYKDCKPLLLDNIHFSGVKDRLIVMNVAEKHRGNYTCHASYTYLGKQYP
ITRVIEFITLEENKPTRPVIVSPANETMEVDLGSQIQLICNVTGQLSDIAYWKWNGSVIDE
DDPVLGEDYYSVENPANKRRSTLITVLNISEIESRFYKHPFTCFAKNTHGIDAAYIQLIYP
VTNSGDKTHTCPPCPAPEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWESNGQPENNY
KTTPPVLDSDGSFFLYSRLTVDKSRWQEGNVFSCSVMHEALHNHYTQKSLSLSLGK

Chain 2 same as chain 2 of ITA301

Figure 5X:

<u>ITE101</u>

Chain 1 (SEQ ID NO:105)

MGWSCIILFLVATATGVHSQVQLVESGGGVVQPGRSLRLDCKASGITFSNSGMHWVRQ
APGKCLEWVAVIWYDGSKRYYADSVKGRFTISRDNSKNTLFLQMNSLRAEDTAVYYC
ATNDDYWGQGTLVTVSSGGGGSGGGGSGGGGSGGGGSEIVLTQSPATLSLSPGERATLS
CRASQSVSSYLAWYQQKPGQAPRLLIYDASNRATGIPARFSGSGSGTDFTLTISSLEPEDF
AVYYCQQSSNWPRTFGCGTKVEIKGGGGSGGGGSQVQLVESGGGVVQPGRSLRLSCAA
SGFTFSVYGMNWVRQAPGKGLEWVAIIWYDGDNQYYADSVKGRFTISRDNSKNTLYL
QMNGLRAEDTAVYYCARDLRTGPFDYWGQGTLVTVSSASTKGPSVFPLAPCSRSTSEST
AALGCLVKDYFPEPVTVSWNSGALTSGVHTFPAVLQSSGLYSLSSVVTVPSSSLGTKTY
TCNVDHKPSNTKVDKRVESKYGPPCPPCPAPEFLGGPSVFLFPPKPKDTLMISRTPEVTC
VVVDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEALHNHY
TQKSLSLSLGK

Chain 2 same as chain 2 of ITA101

Figure 5Y:

<u>ITE102</u> (SEQ ID NO:106)

Figure 5Y (cont.)

MGWSCIILFLVATATGVHSEIVLTQSPATLSLSPGERATLSCRASQSVSSYLAWYQQKPG
QAPRLLIYDASNRATGIPARFSGSGSGTDFTLTISSLEPEDFAVYYCQQSSNWPRTFGCGT
KVEIKGGGGSGGGGSGGGGSGGGGSQVQLVESGGGVVQPGRSLRLDCKASGITFSNSG
MHWVRQAPGKCLEWVAVIWYDGSKRYYADSVKGRFTISRDNSKNTLFLQMNSLRAED
TAVYYCATNDDYWGQGTLVTVSSGGGGSGGGGSQVQLVESGGGVVQPGRSLRLSCAA
SGFTFSVYGMNWVRQAPGKGLEWVAIIWYDGDNQYYADSVKGRFTISRDNSKNTLYL
QMNGLRAEDTAVYYCARDLRTGPFDYWGQGTLVTVSSASTKGPSVFPLAPCSRSTSEST
AALGCLVKDYFPEPVTVSWNSGALTSGVHTFPAVLQSSGLYSLSSVVTVPSSSLGTKTY
TCNVDHKPSNTKVDKRVESKYGPPCPPCPAPEFLGGPSVFLFPPKPKDTLMISRTPEVTC
VVVDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEALHNHY
TQKSLSLSLGK

Chain 2 same as chain 2 of ITA101

Figure 5Z:

ITE201

Chain 1 (SEQ ID NO:107)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC
ATNDDYWGQGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDKRVESK
YGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGKGGGGSGGGGS
QVQLVESGGGVVQPGRSLRLSCAASGFTFSVYGMNWVRQAPGKCLEWVAIIWYDGDN
QYYADSVKGRFTISRDNSKNTLYLQMNGLRAEDTAVYYCARDLRTGPFDYWGQGTLV
TVSSGGGGSGGGGSGGGGSGGGGSEIVLTQSPDFQSVTPKEKVTITCRASQSIGSSLHWY
QQKPDQSPKLLIKYASQSFSGVPSRFSGSGSGTDFTLTINSLEAEDAAAYYCHQSSSLPFT
FGCGTKVDIK

Chain 2 same as chain 2 of ITA104

Figure 5AA:

ITE202

Chain 1 (SEQ ID NO:108)

Figure 5AA (cont.)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC
ATNDDYWGQGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDKRVESK
YGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGKGGGGSGGGGS
EIVLTQSPDFQSVTPKEKVTITCRASQSIGSSLHWYQQKPDQSPKLLIKYASQSFSGVPSR
FSGSGSGTDFTLTINSLEAEDAAAYYCHQSSSLPFTFGCGTKVDIKGGGGSGGGGSGGG
GSGGGGSQVQLVESGGGVVQPGRSLRLSCAASGFTFSVYGMNWVRQAPGKCLEWVAII
WYDGDNQYYADSVKGRFTISRDNSKNTLYLQMNGLRAEDTAVYYCARDLRTGPFDY
WGQGTLVTVSS

Chain 2 same as chain 2 of ITA104

Figure 5BB:

ITE301

Chain 1 (SEQ ID NO:109)

MGWSCIILFLVATATGVHSEIVLTQSPDFQSVTPKEKVTITCRASQSIGSSLHWYQQKPD
QSPKLLIKYASQSFSGVPSRFSGSGSGTDFTLTINSLEAEDAAAYYCHQSSSLPFTFGPGT
KVDIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGECGSGQVQ
LVQSGVEVKKPGASVKVSCKASGYTFTNYYMYWVRQAPGQGLEWMGGINPSNGGTN
FNEKFKNRVTLTTDSSTTTAYMELKSLQFDDTAVYYCARRDYRFDMGFDYWGQGTTV
TVSSASTKGPSVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPCPPCPAPEFLG
GPSVFLFPPKPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYSRLTVD
KSRWQEGNVFSCSVMHEALHNHYTQKSLSLSLGK

Chain 2 and chain 3 same as chain 2 and chain 3 of ITA301

Figure 5CC:

ITE302

Chain 1 (SEQ ID NO:110)

MGWSCIILFLVATATGVHSEIVLTQSPDFQSVTPKEKVTITCRASQSIGSSLHWYQQKPD
QSPKLLIKYASQSFSGVPSRFSGSGSGTDFTLTINSLEAEDAAAYYCHQSSSLPFTFGPGT
KVDIKRTVAAPSVFIFPPSDEQLKSGTASVVCLLNNFYPREAKVQWKVDNALQSGNSQE

Figure 5CC (cont.)
SVTEQDSKDSTYSLSSTLTLSKADYEKHKVYACEVTHQGLSSPVTKSFNRGECGGGGSG
SQVQLVQSGVEVKKPGASVKVSCKASGYTFTNYYMYWVRQAPGQGLEWMGGINPSN
GGTNFNEKFKNRVTLTTDSSTTTAYMELKSLQFDDTAVYYCARRDYRFDMGFDYWGQ
GTTVTVSSASTKGPSVFPLAPCSRSTSESTAALGCLVKDYFPEPVTVSWNSGALTSGVHT
FPAVLQSSGLYSLSSVVTVPSSSLGTKTYTCNVDHKPSNTKVDKRVESKYGPPCPPCPAP
EFLGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRL
TVDKSRWQEGNVFSCSVMHEALHNHYTQKSLSLSLGK Chain 2 and chain 3 same as chain 2 and chain 3 of ITA301

Figure 5DD:

ITF101

Chain 1 (SEQ ID NO:111)

MGWSCIILFLVATATGVHSEIVLTQSPATLSLSPGERATLSCRASQSVSSYLAWYQQKPG
QAPRLLIYDASNRATGIPARFSGSGSGTDFTLTISSLEPEDFAVYYCQQSSNWPRTFGCGT
KVEIKGGGGSGGGGSGGGGSGGGGSQVQLVESGGGVVQPGRSLRLDCKASGITFSNSG
MHWVRQAPGKCLEWVAVIWYDGSKRYYADSVKGRFTISRDNSKNTLFLQMNSLRAED
TAVYYCATNDDYWGQGTLVTVSSGGGGSGGGGSEVQLVESGGGVVQPGRSLRLSCSSS
GFIFSSYDMSWVRQAPGKGLEWVAYISSGGGGTYYPDTVKGRFTISRDNSKNTLFLQM
DSLRPEDTGVYFCARGGVTKGYFDVWGQGTPVTVSSASTKGPSVFPLAPCSRSTSESTA
ALGCLVKDYFPEPVTVSWNSGALTSGVHTFPAVLQSSGLYSLSSVVTVPSSSLGTKTYTC
NVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQ
KSLSLSLGK

Chain 2 (SEQ ID NO:112)

MGWSCIILFLVATATGVHSDIQMTQSPSSLSASVGDRVTITCRASGNIHNYLTWYQQTPG
KAPKLLIYNAKTLADGVPSRFSGSGSGTDYTFTISSLQPEDIATYYCQHFWSIPYTFGQGT
KLEIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC

Figure 5EE:

ITF102

Chain 1 (SEQ ID NO:113)

Figure 5EE (cont.)

MGWSCIILFLVATATGVHSDIQMTQSPSSLSASVGDRVTITCRASGNIHNYLTWYQQTPG
KAPKLLIYNAKTLADGVPSRFSGSGSGTDYTFTISSLQPEDIATYYCQHFWSIPYTFGCGT
KLEIKGGGGSGGGGSGGGGSGGGGSEVQLVESGGGVVQPGRSLRLSCSSSGFIFSSYDM
SWVRQAPGKCLEWVAYISSGGGGTYYPDTVKGRFTISRDNSKNTLFLQMDSLRPEDTG
VYFCARGGVTKGYFDVWGQGTPVTVSSGGGGSGGGGSQVQLVESGGGVVQPGRSLRL
DCKASGITFSNSGMHWVRQAPGKGLEWVAVIWYDGSKRYYADSVKGRFTISRDNSKN
TLFLQMNSLRAEDTAVYYCATNDDYWGQGTLVTVSSASTKGPSVFPLAPCSRSTSESTA
ALGCLVKDYFPEPVTVSWNSGALTSGVHTFPAVLQSSGLYSLSSVVTVPSSSLGTKTYTC
NVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQ
KSLSLSLGK

Chain 2 same as chain2 of ITA104

Figure 5FF:

ITF103

Chain 1 (SEQ ID NO:114)

MGWSCIILFLVATATGVHSEVQLVESGGGVVQPGRSLRLSCSSSGFIFSSYDMSWVRQA
PGKCLEWVAYISSGGGGTYYPDTVKGRFTISRDNSKNTLFLQMDSLRPEDTGVYFCARG
GVTKGYFDVWGQGTPVTVSSGGGGSGGGGSGGGGSGGGGSDIQMTQSPSSLSASVGDR
VTITCRASGNIHNYLTWYQQTPGKAPKLLIYNAKTLADGVPSRFSGSGSGTDYTFTISSL
QPEDIATYYCQHFWSIPYTFGCGTKLEIKGGGGSGGGGSQVQLVESGGGVVQPGRSLRL
DCKASGITFSNSGMHWVRQAPGKGLEWVAVIWYDGSKRYYADSVKGRFTISRDNSKN
TLFLQMNSLRAEDTAVYYCATNDDYWGQGTLVTVSSASTKGPSVFPLAPCSRSTSESTA
ALGCLVKDYFPEPVTVSWNSGALTSGVHTFPAVLQSSGLYSLSSVVTVPSSSLGTKTYTC
NVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQ
KSLSLSLGK

Chain 2 same as chain2 of ITA104

Figure 5GG:

ITF201

Chain 1 (SEQ ID NO:115)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC

Figure 5GG (cont.)

ATNDDYWGQGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDKRVESK
YGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGKGGGGSGGGGS
DIQMTQSPSSLSASVGDRVTITCRASGNIHNYLTWYQQTPGKAPKLLIYNAKTLADGVPS
RFSGSGSGTDYTFTISSLQPEDIATYYCQHFWSIPYTFGCGTKLEIKGGGGSGGGGSGGG
GSGGGGSEVQLVESGGGVVQPGRSLRLSCSSSGFIFSSYDMSWVRQAPGKCLEWVAYIS
SGGGGTYYPDTVKGRFTISRDNSKNTLFLQMDSLRPEDTGVYFCARGGVTKGYFDVWG
QGTPVTVSS

Chain 2 same as ITA104

Figure 5HH:

<u>ITF202</u>

Chain 1 (SEQ ID NO:116)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC
ATNDDYWGQGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDKRVESK
YGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGKGGGGSGGGGS
EVQLVESGGGVVQPGRSLRLSCSSSGFIFSSYDMSWVRQAPGKCLEWVAYISSGGGGTY
YPDTVKGRFTISRDNSKNTLFLQMDSLRPEDTGVYFCARGGVTKGYFDVWGQGTPVTV
SSGGGGSGGGGSGGGGSGGGGSDIQMTQSPSSLSASVGDRVTITCRASGNIHNYLTWYQ
QTPGKAPKLLIYNAKTLADGVPSRFSGSGSGTDYTFTISSLQPEDIATYYCQHFWSIPYTF
GCGTKLEIK

Chain 2 same as ITA104

Figure 5II:

<u>ITF301</u>

Chain 1 (SEQ ID NO:117)

MGWSCIILFLVATATGVHSDIQMTQSPSSLSASVGDRVTITCRASGNIHNYLTWYQQTPG
KAPKLLIYNAKTLADGVPSRFSGSGSGTDYTFTISSLQPEDIATYYCQHFWSIPYTFGQGT
KLEIKRTVAAPSVFIFPPSDEQLKSGTASVVCLLNNFYPREAKVQWKVDNALQSGNSQE

Figure 5II (cont.)

SVTEQDSKDSTYSLSSTLTLSKADYEKHKVYACEVTHQGLSSPVTKSFNRGECGSGQVQ
LVQSGVEVKKPGASVKVSCKASGYTFTNYYMYWVRQAPGQGLEWMGGINPSNGGTN
FNEKFKNRVTLTTDSSTTTAYMELKSLQFDDTAVYYCARRDYRFDMGFDYWGQGTTV
TVSSASTKGPSVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPCPPCPAPEFLG
GPSVFLFPPKPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYSRLTVD
KSRWQEGNVFSCSVMHEALHNHYTQKSLSLSLGK

Chain 2 same as chain 2 of ITA103

Chain 3 (SEQ ID NO:118)

MGWSCIILFLVATATGVHSEVQLVESGGGVVQPGRSLRLSCSSSGFIFSSYDMSWVRQA
PGKGLEWVAYISSGGGGTYYPDTVKGRFTISRDNSKNTLFLQMDSLRPEDTGVYFCARG
GVTKGYFDVWGQGTPVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKRV
EPKSC

Figure 5JJ:

ITF302

Chain 1 (SEQ ID NO:119)

MGWSCIILFLVATATGVHSDIQMTQSPSSLSASVGDRVTITCRASGNIHNYLTWYQQTPG
KAPKLLIYNAKTLADGVPSRFSGSGSGTDYTFTISSLQPEDIATYYCQHFWSIPYTFGQGT
KLEIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGECGGGGSG
SQVQLVQSGVEVKKPGASVKVSCKASGYTFTNYYMYWVRQAPGQGLEWMGGINPSN
GGTNFNEKFKNRVTLTTDSSTTTAYMELKSLQFDDTAVYYCARRDYRFDMGFDYWGQ
GTTVTVSSASTKGPSVFPLAPCSRSTSESTAALGCLVKDYFPEPVTVSWNSGALTSGVHT
FPAVLQSSGLYSLSSVVTVPSSSLGTKTYTCNVDHKPSNTKVDKRVESKYGPPCPPCPAP
EFLGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRL
TVDKSRWQEGNVFSCSVMHEALHNHYTQKSLSLSLGK

Chain 2 and Chain 3 same as chain 2 and chain 3 of ITF301

Figure 5KK:

ITF401

Chain 1 (SEQ ID NO:120)

MGWSCIILFLVATATGVHSEVQLVESGGGVVQPGRSLRLSCSSSGFIFSSYDMSWVRQA
PGKGLEWVAYISSGGGGTYYPDTVKGRFTISRDNSKNTLFLQMDSLRPEDTGVYFCARG
GVTKGYFDVWGQGTPVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKVDKRV
ESKYGPPCPPCPAPEFLGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGLPSSIEKTIS
KAKGQPREPQVYTLPPSQEEMTKNQVSLTCLVKGFYPSDIAVEWESNGGGGSGGGGSG
GGGSGGGGSGGGGSEIVLTQSPATLSLSPGERATLSCRASKGVSTSGYSYLHWYQQKPG
QAPRLLIYLASYLESGVPARFSGSGSGTDFTLTISSLEPEDFAVYYCQHSRDLPLTFGGGT
KVEIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGECGGGGSG
GGGSGGGGSGGGGSGGGGSGQPENNYKTTPPVLDSDGSFFLYSRLTVDKSRWQEGNVF
SCSVMHEALHNHYTQKSLSLSLGK

Chain 2 same as chain 2 of ITF101

Chain 3 same as chain 3 of ITA301

Figure 5LL:

ITF402

Chain 1 (SEQ ID NO:121)

MGWSCIILFLVATATGVHSQVQLVQSGVEVKKPGASVKVSCKASGYTFTNYYMYWVR
QAPGQGLEWMGGINPSNGGTNFNEKFKNRVTLTTDSSTTTAYMELKSLQFDDTAVYYC
ARRDYRFDMGFDYWGQGTTVTVSSASTKGPSVFPLAPCSRSTSESTAALGCLVKDYFPE
PVTVSWNSGALTSGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAVEWESNGGGGSG
GGGSGGGGSGGGGSGGGGSDIQMTQSPSSLSASVGDRVTITCRASGNIHNYLTWYQQTP
GKAPKLLIYNAKTLADGVPSRFSGSGSGTDYTFTISSLQPEDIATYYCQHFWSIPYTFGQG
TKLEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGECGGGGS
GGGGSGGGGSGGGGSGGGGSGQPENNYKTTPPVLDSDGSFFLYSRLTVDKSRWQEGNV
FSCSVMHEALHNHYTQKSLSLSLGK

Chain 2 and Chain 3 same as chain 2 and chain 3 of ITF302

Figure 5MM:

ITF403

Chain 1  (SEQ ID NO:122)

MGWSCIILFLVATATGVHSQVQLVESGGGVVQPGRSLRLDCKASGITFSNSGMHWVRQ
APGKGLEWVAVIWYDGSKRYYADSVKGRFTISRDNSKNTLFLQMNSLRAEDTAVYYC
ATNDDYWGQGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDKRVESK
YGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGGGGSGGGGSGGGG
SGGGGSGGGGSDIQMTQSPSSLSASVGDRVTITCRASGNIHNYLTWYQQTPGKAPKLLI
YNAKTLADGVPSRFSGSGSGTDYTFTISSLQPEDIATYYCQHFWSIPYTFGQGTKLEIKRT
VAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGECGGGGSGGGGSGG
GGSGGGGSGGGGSGQPENNYKTTPPVLDSDGSFFLYSRLTVDKSRWQEGNVFSCSVMH
EALHNHYTQKSLSLSLGK

Chain 2 same as chain 2 of ITA104

Chain 3 same as chain 3 of ITF402

| Binding protein | Summary |
|---|---|
| ABT-981 (Abbvie) | ABT-981 is an anti IL-1 alpha/ß dual variable domain immunoglobulin (DVD-Ig), under development for the treatment of osteoarthritis (OA) |
| Anakinra (Biovitrum) | Anakinra is a recombinant non-glycosylated, human interleukin-1 receptor antagonist |
| Avelumab (Merck KGaA) | Avelumab (MSB-0010718C) is an MAb against PD-L1 (programmed cell death ligand), developed for the treatment of solid tumours |
| BCD-100, (Biocad) | BCD-100 is an anti-PD1 monoclonal antibody, for the treatment of melanoma, non-small cell lung cancer and renal cell carcinoma |
| Bermekimab (XBiotech) | Bermekimab (MABp1) is a human IgG1 monoclonal antibody specific for human interleukin-1 alpha, for the treatment of peripheral vascular disease, type 2 diabetes, pyoderma gangrenosum, hiradentis suppurtiva, colorectal cancer, NSCLC, pancreatic cancer, psoriasis, acne, atopic dermatitis and cachexia. |
| BGB-A333 (BeiGene) | BGB-A333 is a humanized IgG1-variant monoclonal antibody against programmed cell death 1-ligand 1 (PD-L1), under development by for the treatment of cancer |
| Camrelizumab (Jiangsu Hengrui Medicine) | Camrelizumab (SHR-1210) is a humanized anti-PD1 IgG4 monoclonal antibody, under development by for the treatment of cancer |
| Canakinumab (Novartis) | Canakinumab (ACZ-885) is an anti-interleukin-1ß human MAb, developed for the treatment of cryopirin-associated periodic syndromes (CAPS) (familial cold urticaria syndrome (FCAS), Muckle-Wells syndrome (MWS) and neonatal-onset multisystem inflammatory disease (NOMID) (chronic infertile neurological cutaneous articular syndrome (CINCA)) |

FIG.6A

| | |
|---|---|
| Cemiplimab (Regeneron) | Cemiplimab (REGN-2810) is a fully-humanized monoclonal antibody targeting PD-1, developed for the treatment of cancer |
| CS-1001 (CStone Pharmaceuticals) | CS-1001 (WBP3155) is a fully humanized, recombinant anti PD-L1 IgG monoclonal antibody, under development for the treatment of cancer |
| Durvalumab (MedImmune) | Durvalumab (MEDI-4736) is an anti-PDL1 MAb, developed for the treatment of cancer. |
| envafolimab (Alphamab) | Envafolimab (KN-035) is a nanobody targeting PDL1, under development for the treatment of cancer |
| Gevokizumab (Xoma) | Gevokizumab (XOMA-052) is an anti-inflammatory humanized IgG2 MAb that binds to interleukin-1ß (IL-1ß), for the treatment of pyoderma gangrenosum. |
| JNJ-63723283 (Johnson & Johnson) | JNJ-3283 (JNJ-63723283) is an anti-PD-1 monoclonal antibody, under development for the treatment of cancer |
| M-7824 (Merck KGaA) | M-7824 (MSB0011359C) is a bi-functional fusion protein targeting PD-L1 monoclonal antibody and TGFß, for treatment of cancer |
| MEDI-0680 (MedImmune) | MEDI-0680 (AMP-514) is an anti-PD-1 monoclonal antibody, under development for the treatment of cancer and infectious disease |
| MGA-012 (MacroGenics) | MGA-012 is a humanized anti-PD-1 monoclonal antibody, under development for the treatment of solid tumours |
| Nivolumab (BMS) | Nivolumab (MDX-1106; ONO-4538) is a fully-human IgG4 MAb against PD-1, for the treatment of cancer and chronic viral infections |
| Rilonacept (Regeneron) | Rilonacept (RGN-303; Arcalyst) is a human Cytokine Trap protein which blocks the activity of interleukin-1a and interleukin-1b, for the treatment of cryopyrin-associated periodic syndrome (CAPS), a spectrum of rare inflammatory disorders including Muckle-Wells syndrome (MWS), familial cold |

FIG.6B

| | |
|---|---|
| | inflammatory syndrome (FCAS) and certain other conditions. |
| Sintilimab (Innovent Biologics) | Sintilimab is a fully human anti-PD-1 monoclonal antibody, developed for the treatment of cancer |
| SOBI-006 (Affibody) | SOBI-006 is an interleukin-1 (IL-1) inhibitor, under development for the treatment of inflammatory and autoimmune diseases |
| Spartalizumab (Novartis) | Spartalizumab (PDR-001) is a PD-1 humanized IgG4 antibody, under development for the treatment of cancer |

FIG.6C

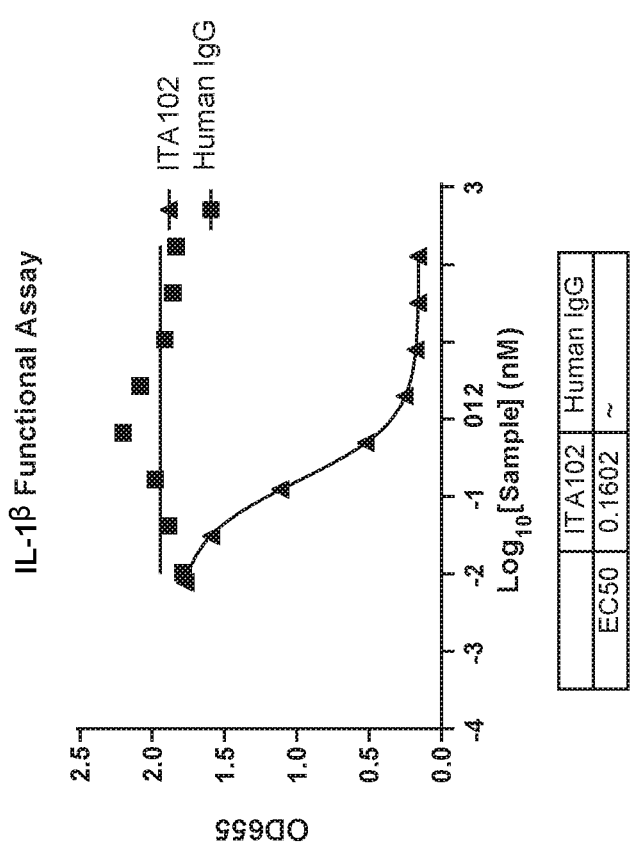

SEQUENCE LISTING

```
<160> NUMBER OF SEQ ID NOS: 133

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Tyr Tyr Met Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ile Asn Pro Ser Asn Gly Gly Thr Asn Phe Asn Glu Lys Phe Lys
1               5                   10                  15

Asn

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Arg Asp Tyr Arg Phe Asp Met Gly Phe Asp Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Lys Gly Val Ser Thr Ser Gly Tyr Ser Tyr Leu His
1               5                   10                  15

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Ala Ser Tyr Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln His Ser Arg Asp Leu Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Ser Gly Met His
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Ile Trp Tyr Asp Gly Ser Lys Arg Tyr Tyr Ala Asp Ser Val Lys
1               5                   10                  15

Gly

<210> SEQ ID NO 9
```

-continued

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Asp Asp Tyr
1

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Gln Ser Val Ser Ser Tyr Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ala Ser Asn Arg Ala Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Ser Ser Asn Trp Pro Arg Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Thr Phe Ser Asn Phe Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Ile Ser Gly Gly Gly Arg Asp Thr
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Lys Trp Gly Asn Ile Tyr Phe Asp Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Ser Ile Asn Thr Phe
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Ser
1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln Ser Ser Asn Thr Pro Phe Thr
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Ser Asp Ser Trp Ile His
1               5                   10

<210> SEQ ID NO 20
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Trp Ile Ser Pro Tyr Gly Gly Ser Thr
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg His Trp Pro Gly Gly Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Ser Gln Asp Val Ser Thr Ala Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ala Ser Phe Leu Tyr Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Tyr Leu Tyr His Pro Ala Thr
1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 25

Ser Tyr Ile Met
1

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ile Tyr Pro Ser Gly Gly Ile Thr Phe Tyr Ala Asp Thr Val Lys
1               5                   10                  15

Gly

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Lys Leu Gly Thr Val Thr Thr Val Asp Tyr
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Gly Thr Ser Ser Asp Val Gly Gly Tyr Asn Tyr Val Ser
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Val Ser Asn Arg Pro Ser
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ser Tyr Thr Ser Ser Ser Thr Arg Val
1               5                   10

```
<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Tyr Trp Met Ser
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Ile Lys Gln Asp Gly Ser Glu Lys Tyr Tyr Val Asp Ser Val Lys
1               5                   10                  15

Gly

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Gly Gly Trp Phe Gly Glu Leu Ala Phe Asp Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ala Ser Gln Arg Val Ser Ser Ser Tyr Leu Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Ala Ser Ser Arg Ala Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 36

Gln Gln Tyr Gly Ser Leu Pro Trp Thr
1               5

<210> SEQ ID NO 37
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 39
<211> LENGTH: 113
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 39

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 40
<211> LENGTH: 1
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 40

Ser
1

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 41

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser
        115

<210> SEQ ID NO 42

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
            100                 105

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys
             100                 105

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
             20                  25                  30

Ile Met Met Trp Val Arg Gln Ala Pro Gly Lys Gly Leu Glu Trp Val
         35                  40                  45

Ser Ser Ile Tyr Pro Ser Gly Gly Ile Thr Phe Tyr Ala Asp Thr Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Ile Lys Leu Gly Thr Val Thr Thr Val Asp Tyr Trp Gly Gln
             100                 105                 110

Gly Thr Leu Val Thr Val Ser Ser
         115                 120

<210> SEQ ID NO 46
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
                100                 105                 110

<210> SEQ ID NO 47
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
                100                 105                 110

Gln Gly Thr Leu Val Thr Val Ser Ser
            115                 120

<210> SEQ ID NO 48
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
                100                 105

<210> SEQ ID NO 49
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 49

Val Tyr Gly Met Asn
1               5

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Ile Trp Tyr Asp Gly Asp Asn Gln Tyr Tyr Ala Asp Ser Val Lys
1               5                   10                  15

Gly

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Leu Arg Thr Gly Pro
1               5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ala Ser Gln Ser Ile Gly Ser Ser Leu His
1               5                   10

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ser Gln Ser Phe Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Gln Ser Ser Ser Leu Pro
1               5

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Arg Asp Leu Arg Thr Gly Pro Phe Asp Tyr Trp Gly Gln Gly Thr
            100                 105                 110

Leu Val Thr Val Ser Ser
        115

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Phe
                85                  90                  95

Thr Phe Gly Pro Gly Thr Lys Val Asp Ile Lys
            100                 105

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Ser Arg Thr Pro
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Lys Gly Gln Pro
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Gly Gly Gly Ser Gly Gly Gly Gly Ser
1               5                   10

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Gly Gly Ser Gly Gly Gly Gly Ser Gly Gly Gly Gly Ser
1               5                   10                  15

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Gly Gly Ser Gly Gly Gly Gly Ser Gly Gly Gly Gly Ser Gly
1               5                   10                  15

Gly Gly Gly Ser
            20

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Tyr Asp Met Ser
1               5

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Ile Ser Ser Gly Gly Gly Gly Thr Tyr Tyr Pro Asp Thr Val Lys
1               5                   10                  15

Gly

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Val Arg Arg Gly Tyr Phe Asp Val
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Ala Ser Gly Asn Ile His Asn Tyr Leu Thr
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asn Ala Lys Thr Leu Ala Asp
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln His Phe Trp Ser Ile Pro Tyr Thr
1               5

<210> SEQ ID NO 68
<211> LENGTH: 119
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 68

Glu Val Gln Leu Val Glu Ser Gly Gly Gly Val Val Gln Pro Gly Arg
1               5                   10                  15

Ser Leu Arg Leu Ser Cys Ser Ser Gly Phe Ile Phe Ser Ser Tyr
            20                  25                  30

Asp Met Ser Trp Val Arg Gln Ala Pro Gly Lys Gly Leu Glu Trp Val
            35                  40                  45

Ala Tyr Ile Ser Ser Gly Gly Gly Thr Tyr Tyr Pro Asp Thr Val
50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Gly Gly Val Arg Arg Gly Tyr Phe Asp Val Trp Gly Gln Gly
            100                 105                 110

Thr Pro Val Thr Val Ser Ser
        115

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Thr Trp Tyr Gln Gln Thr Pro Gly Lys Ala Pro Lys Leu Leu Ile
            35                  40                  45

Tyr Asn Ala Lys Thr Leu Ala Asp Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Ile Pro Tyr
                85                  90                  95

Thr Phe Gly Gln Gly Thr Lys Leu Gln Ile Thr
            100                 105

<210> SEQ ID NO 70
<211> LENGTH: 312
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 70

Lys Cys Lys Glu Arg Glu Glu Lys Ile Ile Leu Val Ser Ser Ala Asn
1               5                   10                  15

Glu Ile Asp Val Arg Pro Cys Pro Leu Asn Pro Asn Glu His Lys Gly
            20                  25                  30

```
Thr Ile Thr Trp Tyr Lys Asp Asp Ser Lys Thr Pro Val Ser Thr Glu
            35                  40                  45

Gln Ala Ser Arg Ile His Gln His Lys Glu Lys Leu Trp Phe Val Pro
 50                  55                  60

Ala Lys Val Glu Asp Ser Gly His Tyr Tyr Cys Val Val Arg Asn Ser
 65                  70                  75                  80

Ser Tyr Cys Leu Arg Ile Lys Ile Ser Ala Lys Phe Val Glu Asn Glu
                85                  90                  95

Pro Asn Leu Cys Tyr Asn Ala Gln Ala Ile Phe Lys Gln Lys Leu Pro
            100                 105                 110

Val Ala Gly Asp Gly Leu Val Cys Pro Tyr Met Glu Phe Phe Lys
            115                 120                 125

Asn Glu Asn Asn Glu Leu Pro Lys Leu Gln Trp Tyr Lys Asp Cys Lys
            130                 135                 140

Pro Leu Leu Leu Asp Asn Ile His Phe Ser Gly Val Lys Asp Arg Leu
145                 150                 155                 160

Ile Val Met Asn Val Ala Glu Lys His Arg Gly Asn Tyr Thr Cys His
                165                 170                 175

Ala Ser Tyr Thr Tyr Leu Gly Lys Gln Tyr Pro Ile Thr Arg Val Ile
            180                 185                 190

Glu Phe Ile Thr Leu Glu Glu Asn Lys Pro Thr Arg Pro Val Ile Val
            195                 200                 205

Ser Pro Ala Asn Glu Thr Met Glu Val Asp Leu Gly Ser Gln Ile Gln
            210                 215                 220

Leu Ile Cys Asn Val Thr Gly Gln Leu Ser Asp Ile Ala Tyr Trp Lys
225                 230                 235                 240

Trp Asn Gly Ser Val Ile Asp Glu Asp Asp Pro Val Leu Gly Glu Asp
                245                 250                 255

Tyr Tyr Ser Val Glu Asn Pro Ala Asn Lys Arg Arg Ser Thr Leu Ile
            260                 265                 270

Thr Val Leu Asn Ile Ser Glu Ile Glu Ser Arg Phe Tyr Lys His Pro
            275                 280                 285

Phe Thr Cys Phe Ala Lys Asn Thr His Gly Ile Asp Ala Ala Tyr Ile
            290                 295                 300

Gln Leu Ile Tyr Pro Val Thr Asn
305                 310

<210> SEQ ID NO 71
<211> LENGTH: 651
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
                20                  25                  30

Phe Leu Lys Phe Asn Tyr Ser Thr Ala His Ser Ala Gly Leu Thr Leu
            35                  40                  45

Ile Trp Tyr Trp Thr Arg Gln Asp Arg Asp Leu Glu Glu Pro Ile Asn
 50                  55                  60
```

-continued

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu Lys Cys Lys Glu Arg Glu Glu Lys Ile Ile Leu Val Ser
            340                 345                 350

Ser Ala Asn Glu Ile Asp Val Arg Pro Cys Pro Leu Asn Pro Asn Glu
        355                 360                 365

His Lys Gly Thr Ile Thr Trp Tyr Lys Asp Asp Ser Lys Thr Pro Val
370                 375                 380

Ser Thr Glu Gln Ala Ser Arg Ile His Gln His Lys Glu Lys Leu Trp
385                 390                 395                 400

Phe Val Pro Ala Lys Val Glu Asp Ser Gly His Tyr Tyr Cys Val Val
                405                 410                 415

Arg Asn Ser Ser Tyr Cys Leu Arg Ile Lys Ile Ser Ala Lys Phe Val
            420                 425                 430

Glu Asn Glu Pro Asn Leu Cys Tyr Asn Ala Gln Ala Ile Phe Lys Gln
        435                 440                 445

Lys Leu Pro Val Ala Gly Asp Gly Gly Leu Val Cys Pro Tyr Met Glu
450                 455                 460

Phe Phe Lys Asn Glu Asn Asn Glu Leu Pro Lys Leu Gln Trp Tyr Lys
465                 470                 475                 480

```
Asp Cys Lys Pro Leu Leu Leu Asp Asn Ile His Phe Ser Gly Val Lys
            485                 490                 495

Asp Arg Leu Ile Val Met Asn Val Ala Glu Lys His Arg Gly Asn Tyr
            500                 505                 510

Thr Cys His Ala Ser Tyr Thr Tyr Leu Gly Lys Gln Tyr Pro Ile Thr
            515                 520                 525

Arg Val Ile Glu Phe Ile Thr Leu Glu Glu Asn Lys Pro Thr Arg Pro
            530                 535                 540

Val Ile Val Ser Pro Ala Asn Glu Thr Met Glu Val Asp Leu Gly Ser
545                 550                 555                 560

Gln Ile Gln Leu Ile Cys Asn Val Thr Gly Gln Leu Ser Asp Ile Ala
            565                 570                 575

Tyr Trp Lys Trp Asn Gly Ser Val Ile Asp Glu Asp Pro Val Leu
            580                 585                 590

Gly Glu Asp Tyr Tyr Ser Val Glu Asn Pro Ala Asn Lys Arg Arg Ser
            595                 600                 605

Thr Leu Ile Thr Val Leu Asn Ile Ser Glu Ile Glu Ser Arg Phe Tyr
            610                 615                 620

Lys His Pro Phe Thr Cys Phe Ala Lys Asn Thr His Gly Ile Asp Ala
625                 630                 635                 640

Ala Tyr Ile Gln Leu Ile Tyr Pro Val Thr Asn
            645                 650
```

<210> SEQ ID NO 72
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
            35                  40                  45

Val Val Pro Ile Glu Pro His Ala Leu Phe Leu Gly Ile His Gly Gly
            50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
            85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
            115                 120                 125

Asp Gln Pro Val Ser Leu Thr Asn Met Pro Asp Glu Gly Val Met Val
130                 135                 140

Thr Lys Phe Tyr Phe Gln Glu Asp Glu
145                 150
```

<210> SEQ ID NO 73
<211> LENGTH: 725
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Met Gly Trp Ser Cys Ile Ile Leu Phe Leu Val Ala Thr Ala Thr Gly
1               5                   10                  15

Val His Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Gly Gly Gly Gly Ser
130                 135                 140

Gly Gly Gly Gly Ser Gly Gly Gly Ser Gly Gly Gly Gly Ser Glu
145                 150                 155                 160

Ile Val Leu Thr Gln Ser Pro Ala Thr Leu Ser Leu Ser Pro Gly Glu
                165                 170                 175

Arg Ala Thr Leu Ser Cys Arg Ala Ser Lys Gly Val Ser Thr Ser Gly
            180                 185                 190

Tyr Ser Tyr Leu His Trp Tyr Gln Gln Lys Pro Gly Gln Ala Pro Arg
        195                 200                 205

Leu Leu Ile Tyr Leu Ala Ser Tyr Leu Glu Ser Gly Val Pro Ala Arg
210                 215                 220

Phe Ser Gly Ser Gly Ser Gly Thr Asp Phe Thr Leu Thr Ile Ser Ser
225                 230                 235                 240

Leu Glu Pro Glu Asp Phe Ala Val Tyr Tyr Cys Gln His Ser Arg Asp
                245                 250                 255

Leu Pro Leu Thr Phe Gly Gly Gly Thr Lys Val Glu Ile Lys Gly Gly
            260                 265                 270

Gly Gly Ser Gly Gly Gly Gly Ser Gln Val Gln Leu Val Glu Ser Gly
        275                 280                 285

Gly Gly Val Val Gln Pro Gly Arg Ser Leu Arg Leu Ser Cys Ala Ala
290                 295                 300

Ser Gly Phe Thr Phe Ser Val Tyr Gly Met Asn Trp Val Arg Gln Ala
305                 310                 315                 320

Pro Gly Lys Gly Leu Glu Trp Val Ala Ile Ile Trp Tyr Asp Gly Asp
                325                 330                 335

Asn Gln Tyr Tyr Ala Asp Ser Val Lys Gly Arg Phe Thr Ile Ser Arg
            340                 345                 350

Asp Asn Ser Lys Asn Thr Leu Tyr Leu Gln Met Asn Gly Leu Arg Ala
        355                 360                 365

Glu Asp Thr Ala Val Tyr Tyr Cys Ala Arg Asp Leu Arg Thr Gly Pro
370                 375                 380
```

Phe Asp Tyr Trp Gly Gln Gly Thr Leu Val Thr Val Ser Ser Ala Ser
385                 390                 395                 400

Thr Lys Gly Pro Ser Val Phe Pro Leu Ala Pro Cys Ser Arg Ser Thr
            405                 410                 415

Ser Glu Ser Thr Ala Ala Leu Gly Cys Leu Val Lys Asp Tyr Phe Pro
        420                 425                 430

Glu Pro Val Thr Val Ser Trp Asn Ser Gly Ala Leu Thr Ser Gly Val
    435                 440                 445

His Thr Phe Pro Ala Val Leu Gln Ser Ser Gly Leu Tyr Ser Leu Ser
450                 455                 460

Ser Val Val Thr Val Pro Ser Ser Ser Leu Gly Thr Lys Thr Tyr Thr
465                 470                 475                 480

Cys Asn Val Asp His Lys Pro Ser Asn Thr Lys Val Asp Lys Arg Val
                485                 490                 495

Glu Ser Lys Tyr Gly Pro Pro Cys Pro Pro Cys Pro Ala Pro Glu Phe
            500                 505                 510

Leu Gly Gly Pro Ser Val Phe Leu Phe Pro Pro Lys Pro Lys Asp Thr
        515                 520                 525

Leu Met Ile Ser Arg Thr Pro Glu Val Thr Cys Val Val Val Asp Val
530                 535                 540

Ser Gln Glu Asp Pro Glu Val Gln Phe Asn Trp Tyr Val Asp Gly Val
545                 550                 555                 560

Glu Val His Asn Ala Lys Thr Lys Pro Arg Glu Glu Gln Phe Asn Ser
                565                 570                 575

Thr Tyr Arg Val Val Ser Val Leu Thr Val Leu His Gln Asp Trp Leu
            580                 585                 590

Asn Gly Lys Glu Tyr Lys Cys Lys Val Ser Asn Lys Gly Leu Pro Ser
        595                 600                 605

Ser Ile Glu Lys Thr Ile Ser Lys Ala Lys Gly Gln Pro Arg Glu Pro
    610                 615                 620

Gln Val Tyr Thr Leu Pro Pro Ser Gln Glu Glu Met Thr Lys Asn Gln
625                 630                 635                 640

Val Ser Leu Thr Cys Leu Val Lys Gly Phe Tyr Pro Ser Asp Ile Ala
                645                 650                 655

Val Glu Trp Glu Ser Asn Gly Gln Pro Glu Asn Asn Tyr Lys Thr Thr
            660                 665                 670

Pro Pro Val Leu Asp Ser Asp Gly Ser Phe Phe Leu Tyr Ser Arg Leu
        675                 680                 685

Thr Val Asp Lys Ser Arg Trp Gln Glu Gly Asn Val Phe Ser Cys Ser
    690                 695                 700

Val Met His Glu Ala Leu His Asn His Tyr Thr Gln Lys Ser Leu Ser
705                 710                 715                 720

Leu Ser Leu Gly Lys
            725

<210> SEQ ID NO 74
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Phe Thr Phe Gly Pro Gly Thr Lys Val Asp Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 75
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
        35                  40                  45

Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110
```

```
Tyr Tyr Cys Ala Thr Asn Asp Asp Tyr Trp Gly Gln Gly Thr Leu Val
            115                 120                 125

Thr Val Ser Ser Gly Gly Gly Ser Gly Gly Gly Ser Gly Gly
    130             135                 140

Gly Gly Ser Gly Gly Gly Ser Glu Ile Val Leu Thr Gln Ser Pro
145             150                 155                 160

Ala Thr Leu Ser Leu Ser Pro Gly Glu Arg Ala Thr Leu Ser Cys Arg
            165                 170                 175

Ala Ser Gln Ser Val Ser Ser Tyr Leu Ala Trp Tyr Gln Gln Lys Pro
            180                 185                 190

Gly Gln Ala Pro Arg Leu Leu Ile Tyr Asp Ala Ser Asn Arg Ala Thr
            195                 200                 205

Gly Ile Pro Ala Arg Phe Ser Gly Ser Gly Ser Gly Thr Asp Phe Thr
            210                 215                 220

Leu Thr Ile Ser Ser Leu Glu Pro Glu Asp Phe Ala Val Tyr Tyr Cys
225                 230                 235                 240

Gln Gln Ser Ser Asn Trp Pro Arg Thr Phe Gly Gln Gly Thr Lys Val
            245                 250                 255

Glu Ile Lys Gly Gly Gly Gly Ser Gly Gly Gly Gly Ser Gln Val Gln
            260                 265                 270

Leu Val Glu Ser Gly Gly Gly Val Val Gln Pro Gly Arg Ser Leu Arg
            275                 280                 285

Leu Ser Cys Ala Ala Ser Gly Phe Thr Phe Ser Val Tyr Gly Met Asn
            290                 295                 300

Trp Val Arg Gln Ala Pro Gly Lys Gly Leu Glu Trp Val Ala Ile Ile
305                 310                 315                 320

Trp Tyr Asp Gly Asp Asn Gln Tyr Tyr Ala Asp Ser Val Lys Gly Arg
            325                 330                 335

Phe Thr Ile Ser Arg Asp Asn Ser Lys Asn Thr Leu Tyr Leu Gln Met
            340                 345                 350

Asn Gly Leu Arg Ala Glu Asp Thr Ala Val Tyr Tyr Cys Ala Arg Asp
            355                 360                 365

Leu Arg Thr Gly Pro Phe Asp Tyr Trp Gly Gln Gly Thr Leu Val Thr
            370                 375                 380

Val Ser Ser Ala Ser Thr Lys Gly Pro Ser Val Phe Pro Leu Ala Pro
385                 390                 395                 400

Cys Ser Arg Ser Thr Ser Glu Ser Thr Ala Ala Leu Gly Cys Leu Val
            405                 410                 415

Lys Asp Tyr Phe Pro Glu Pro Val Thr Val Ser Trp Asn Ser Gly Ala
            420                 425                 430

Leu Thr Ser Gly Val His Thr Phe Pro Ala Val Leu Gln Ser Ser Gly
            435                 440                 445

Leu Tyr Ser Leu Ser Ser Val Val Thr Val Pro Ser Ser Ser Leu Gly
            450                 455                 460

Thr Lys Thr Tyr Thr Cys Asn Val Asp His Lys Pro Ser Asn Thr Lys
465                 470                 475                 480

Val Asp Lys Arg Val Glu Ser Lys Tyr Gly Pro Pro Cys Pro Pro Cys
            485                 490                 495

Pro Ala Pro Glu Phe Leu Gly Gly Pro Ser Val Phe Leu Phe Pro Pro
            500                 505                 510

Lys Pro Lys Asp Thr Leu Met Ile Ser Arg Thr Pro Glu Val Thr Cys
            515                 520                 525
```

-continued

```
Val Val Val Asp Val Ser Gln Glu Asp Pro Glu Val Gln Phe Asn Trp
            530             535             540
Tyr Val Asp Gly Val Glu Val His Asn Ala Lys Thr Lys Pro Arg Glu
545             550             555             560
Glu Gln Phe Asn Ser Thr Tyr Arg Val Val Ser Val Leu Thr Val Leu
                565             570             575
His Gln Asp Trp Leu Asn Gly Lys Glu Tyr Lys Cys Lys Val Ser Asn
            580             585             590
Lys Gly Leu Pro Ser Ser Ile Glu Lys Thr Ile Ser Lys Ala Lys Gly
        595             600             605
Gln Pro Arg Glu Pro Gln Val Tyr Thr Leu Pro Pro Ser Gln Glu Glu
610             615             620
Met Thr Lys Asn Gln Val Ser Leu Thr Cys Leu Val Lys Gly Phe Tyr
625             630             635             640
Pro Ser Asp Ile Ala Val Glu Trp Glu Ser Asn Gly Gln Pro Glu Asn
                645             650             655
Asn Tyr Lys Thr Thr Pro Pro Val Leu Asp Ser Asp Gly Ser Phe Phe
            660             665             670
Leu Tyr Ser Arg Leu Thr Val Asp Lys Ser Arg Trp Gln Glu Gly Asn
        675             680             685
Val Phe Ser Cys Ser Val Met His Glu Ala Leu His Asn His Tyr Thr
690             695             700
Gln Lys Ser Leu Ser Leu Ser Leu Gly Lys
705                 710

<210> SEQ ID NO 76
<211> LENGTH: 721
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Gly Trp Ser Cys Ile Ile Leu Phe Leu Val Ala Thr Ala Thr Gly
1               5                   10                  15
Val His Ser Gln Val Gln Leu Val Glu Ser Gly Gly Val Val Gln
            20              25              30
Pro Gly Arg Ser Leu Arg Leu Ser Cys Ala Ala Ser Gly Phe Thr Phe
        35              40                  45
Ser Val Tyr Gly Met Asn Trp Val Arg Gln Ala Pro Gly Lys Gly Leu
    50              55              60
Glu Trp Val Ala Ile Ile Trp Tyr Asp Gly Asp Asn Gln Tyr Tyr Ala
65              70              75              80
Asp Ser Val Lys Gly Arg Phe Thr Ile Ser Arg Asp Asn Ser Lys Asn
            85              90              95
Thr Leu Tyr Leu Gln Met Asn Gly Leu Arg Ala Glu Asp Thr Ala Val
                100             105             110
Tyr Tyr Cys Ala Arg Asp Leu Arg Thr Gly Pro Phe Asp Tyr Trp Gly
            115             120             125
Gln Gly Thr Leu Val Thr Val Ser Ser Gly Gly Gly Gly Ser Gly Gly
        130             135             140
Gly Gly Ser Gly Gly Gly Gly Ser Gly Gly Gly Gly Ser Glu Ile Val
145             150             155             160
Leu Thr Gln Ser Pro Asp Phe Gln Ser Val Thr Pro Lys Glu Lys Val
                165             170             175
```

```
Thr Ile Thr Cys Arg Ala Ser Gln Ser Ile Gly Ser Ser Leu His Trp
            180                 185                 190

Tyr Gln Gln Lys Pro Asp Gln Ser Pro Lys Leu Leu Ile Lys Tyr Ala
        195                 200                 205

Ser Gln Ser Phe Ser Gly Val Pro Ser Arg Phe Ser Gly Ser Gly Ser
    210                 215                 220

Gly Thr Asp Phe Thr Leu Thr Ile Asn Ser Leu Glu Ala Glu Asp Ala
225                 230                 235                 240

Ala Ala Tyr Tyr Cys His Gln Ser Ser Ser Leu Pro Phe Thr Phe Gly
                245                 250                 255

Pro Gly Thr Lys Val Asp Ile Lys Gly Gly Gly Gly Ser Gly Gly Gly
            260                 265                 270

Gly Ser Gln Val Gln Leu Val Gln Ser Gly Val Glu Val Lys Lys Pro
        275                 280                 285

Gly Ala Ser Val Lys Val Ser Cys Lys Ala Ser Gly Tyr Thr Phe Thr
    290                 295                 300

Asn Tyr Tyr Met Tyr Trp Val Arg Gln Ala Pro Gly Gln Gly Leu Glu
305                 310                 315                 320

Trp Met Gly Gly Ile Asn Pro Ser Asn Gly Gly Thr Asn Phe Asn Glu
                325                 330                 335

Lys Phe Lys Asn Arg Val Thr Leu Thr Thr Asp Ser Ser Thr Thr Thr
            340                 345                 350

Ala Tyr Met Glu Leu Lys Ser Leu Gln Phe Asp Asp Thr Ala Val Tyr
        355                 360                 365

Tyr Cys Ala Arg Arg Asp Tyr Arg Phe Asp Met Gly Phe Asp Tyr Trp
    370                 375                 380

Gly Gln Gly Thr Thr Val Thr Val Ser Ser Ala Ser Thr Lys Gly Pro
385                 390                 395                 400

Ser Val Phe Pro Leu Ala Pro Cys Ser Arg Ser Thr Ser Glu Ser Thr
                405                 410                 415

Ala Ala Leu Gly Cys Leu Val Lys Asp Tyr Phe Pro Glu Pro Val Thr
            420                 425                 430

Val Ser Trp Asn Ser Gly Ala Leu Thr Ser Gly Val His Thr Phe Pro
        435                 440                 445

Ala Val Leu Gln Ser Ser Gly Leu Tyr Ser Leu Ser Ser Val Val Thr
    450                 455                 460

Val Pro Ser Ser Ser Leu Gly Thr Lys Thr Tyr Thr Cys Asn Val Asp
465                 470                 475                 480

His Lys Pro Ser Asn Thr Lys Val Asp Lys Arg Val Glu Ser Lys Tyr
                485                 490                 495

Gly Pro Pro Cys Pro Pro Cys Pro Ala Pro Glu Phe Leu Gly Gly Pro
            500                 505                 510

Ser Val Phe Leu Phe Pro Pro Lys Pro Lys Asp Thr Leu Met Ile Ser
        515                 520                 525

Arg Thr Pro Glu Val Thr Cys Val Val Val Asp Val Ser Gln Glu Asp
    530                 535                 540

Pro Glu Val Gln Phe Asn Trp Tyr Val Asp Gly Val Glu Val His Asn
545                 550                 555                 560

Ala Lys Thr Lys Pro Arg Glu Glu Gln Phe Asn Ser Thr Tyr Arg Val
                565                 570                 575

Val Ser Val Leu Thr Val Leu His Gln Asp Trp Leu Asn Gly Lys Glu
            580                 585                 590
```

Tyr Lys Cys Lys Val Ser Asn Lys Gly Leu Pro Ser Ser Ile Glu Lys
            595                 600                 605

Thr Ile Ser Lys Ala Lys Gly Gln Pro Arg Glu Pro Gln Val Tyr Thr
    610                 615                 620

Leu Pro Pro Ser Gln Glu Glu Met Thr Lys Asn Gln Val Ser Leu Thr
625                 630                 635                 640

Cys Leu Val Lys Gly Phe Tyr Pro Ser Asp Ile Ala Val Glu Trp Glu
                645                 650                 655

Ser Asn Gly Gln Pro Glu Asn Asn Tyr Lys Thr Thr Pro Pro Val Leu
            660                 665                 670

Asp Ser Asp Gly Ser Phe Phe Leu Tyr Ser Arg Leu Thr Val Asp Lys
    675                 680                 685

Ser Arg Trp Gln Glu Gly Asn Val Phe Ser Cys Ser Val Met His Glu
690                 695                 700

Ala Leu His Asn His Tyr Thr Gln Lys Ser Leu Ser Leu Ser Leu Gly
705                 710                 715                 720

Lys

<210> SEQ ID NO 77
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Lys Gly Val
        35                  40                  45

Ser Thr Ser Gly Tyr Ser Tyr Leu His Trp Tyr Gln Gln Lys Pro Gly
    50                  55                  60

Gln Ala Pro Arg Leu Leu Ile Tyr Leu Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
            100                 105                 110

His Ser Arg Asp Leu Pro Leu Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

-continued

Ser Ser Pro Val Thr Lys Ser Phe Asn Arg Gly Glu Cys
225                 230                 235

<210> SEQ ID NO 78
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Val Tyr Gly Met Asn Trp Val Arg Gln Ala Pro Gly Lys Gly Leu
        50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Gly Gly Gly Gly Ser Gly Gly
130                 135                 140

Gly Gly Ser Gly Gly Gly Gly Ser Gly Gly Gly Gly Ser Glu Ile Val
145                 150                 155                 160

Leu Thr Gln Ser Pro Asp Phe Gln Ser Val Thr Pro Lys Glu Lys Val
                165                 170                 175

Thr Ile Thr Cys Arg Ala Ser Gln Ser Ile Gly Ser Ser Leu His Trp
            180                 185                 190

Tyr Gln Gln Lys Pro Asp Gln Ser Pro Lys Leu Leu Ile Lys Tyr Ala
        195                 200                 205

Ser Gln Ser Phe Ser Gly Val Pro Ser Arg Phe Ser Gly Ser Gly Ser
    210                 215                 220

Gly Thr Asp Phe Thr Leu Thr Ile Asn Ser Leu Glu Ala Glu Asp Ala
225                 230                 235                 240

Ala Ala Tyr Tyr Cys His Gln Ser Ser Ser Leu Pro Phe Thr Phe Gly
                245                 250                 255

Pro Gly Thr Lys Val Asp Ile Lys Gly Gly Gly Gly Ser Gly Gly Gly
            260                 265                 270

Gly Ser Gln Val Gln Leu Val Glu Ser Gly Gly Val Val Gln Pro
        275                 280                 285

Gly Arg Ser Leu Arg Leu Asp Cys Lys Ala Ser Gly Ile Thr Phe Ser
    290                 295                 300

Asn Ser Gly Met His Trp Val Arg Gln Ala Pro Gly Lys Gly Leu Glu
305                 310                 315                 320

Trp Val Ala Val Ile Trp Tyr Asp Gly Ser Lys Arg Tyr Tyr Ala Asp
                325                 330                 335

Ser Val Lys Gly Arg Phe Thr Ile Ser Arg Asp Asn Ser Lys Asn Thr
            340                 345                 350

Leu Phe Leu Gln Met Asn Ser Leu Arg Ala Glu Asp Thr Ala Val Tyr
            355                 360                 365

Tyr Cys Ala Thr Asn Asp Asp Tyr Trp Gly Gln Gly Thr Leu Val Thr
    370                 375                 380

Val Ser Ser Ala Ser Thr Lys Gly Pro Ser Val Phe Pro Leu Ala Pro
385                 390                 395                 400

Cys Ser Arg Ser Thr Ser Glu Ser Thr Ala Ala Leu Gly Cys Leu Val
                405                 410                 415

Lys Asp Tyr Phe Pro Glu Pro Val Thr Val Ser Trp Asn Ser Gly Ala
            420                 425                 430

Leu Thr Ser Gly Val His Thr Phe Pro Ala Val Leu Gln Ser Ser Gly
        435                 440                 445

Leu Tyr Ser Leu Ser Ser Val Val Thr Val Pro Ser Ser Ser Leu Gly
    450                 455                 460

Thr Lys Thr Tyr Thr Cys Asn Val Asp His Lys Pro Ser Asn Thr Lys
465                 470                 475                 480

Val Asp Lys Arg Val Glu Ser Lys Tyr Gly Pro Pro Cys Pro Pro Cys
                485                 490                 495

Pro Ala Pro Glu Phe Leu Gly Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser Gln Glu Asp Pro Glu Val Gln Phe Asn Trp
    530                 535                 540

Tyr Val Asp Gly Val Glu Val His Asn Ala Lys Thr Lys Pro Arg Glu
545                 550                 555                 560

Glu Gln Phe Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Gly Leu Pro Ser Ser Ile Glu Lys Thr Ile Ser Lys Ala Lys Gly
        595                 600                 605

Gln Pro Arg Glu Pro Gln Val Tyr Thr Leu Pro Pro Ser Gln Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Arg Leu Thr Val Asp Lys Ser Arg Trp Gln Glu Gly Asn
        675                 680                 685

Val Phe Ser Cys Ser Val Met His Glu Ala Leu His Asn His Tyr Thr
    690                 695                 700

Gln Lys Ser Leu Ser Leu Ser Leu Gly Lys
705                 710

<210> SEQ ID NO 79
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Ser Ser Asn
            100                 105                 110

Trp Pro Arg Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 80
<211> LENGTH: 725
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

```
Tyr Tyr Cys Ala Arg Asp Leu Arg Thr Gly Pro Phe Asp Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
450                 455                 460

Gly Gly Gly Gly Ser Gly Gly Gly Ser Gln Val Gln Leu Val Gln
465                 470                 475                 480

Ser Gly Val Glu Val Lys Lys Pro Gly Ala Ser Val Lys Val Ser Cys
                485                 490                 495

Lys Ala Ser Gly Tyr Thr Phe Thr Asn Tyr Tyr Met Tyr Trp Val Arg
            500                 505                 510

Gln Ala Pro Gly Gln Gly Leu Glu Trp Met Gly Gly Ile Asn Pro Ser
        515                 520                 525
```

```
Asn Gly Gly Thr Asn Phe Asn Glu Lys Phe Lys Asn Arg Val Thr Leu
            530                 535                 540

Thr Thr Asp Ser Ser Thr Thr Ala Tyr Met Glu Leu Lys Ser Leu
545                 550                 555                 560

Gln Phe Asp Asp Thr Ala Val Tyr Tyr Cys Ala Arg Arg Asp Tyr Arg
                565                 570                 575

Phe Asp Met Gly Phe Asp Tyr Trp Gly Gln Gly Thr Thr Val Thr Val
                580                 585                 590

Ser Ser Gly Gly Gly Gly Ser Gly Gly Gly Gly Ser Gly Gly Gly Gly
                595                 600                 605

Ser Gly Gly Gly Gly Ser Glu Ile Val Leu Thr Gln Ser Pro Ala Thr
            610                 615                 620

Leu Ser Leu Ser Pro Gly Glu Arg Ala Thr Leu Ser Cys Arg Ala Ser
625                 630                 635                 640

Lys Gly Val Ser Thr Ser Gly Tyr Ser Tyr Leu His Trp Tyr Gln Gln
                645                 650                 655

Lys Pro Gly Gln Ala Pro Arg Leu Leu Ile Tyr Leu Ala Ser Tyr Leu
                660                 665                 670

Glu Ser Gly Val Pro Ala Arg Phe Ser Gly Ser Gly Ser Gly Thr Asp
            675                 680                 685

Phe Thr Leu Thr Ile Ser Ser Leu Glu Pro Glu Asp Phe Ala Val Tyr
690                 695                 700

Tyr Cys Gln His Ser Arg Asp Leu Pro Leu Thr Phe Gly Gly Gly Thr
705                 710                 715                 720

Lys Val Glu Ile Lys
            725

<210> SEQ ID NO 81
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Val Tyr Gly Met Asn Trp Val Arg Gln Ala Pro Gly Lys Gly Leu
        50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
                100                 105                 110

Tyr Tyr Cys Ala Arg Asp Leu Arg Thr Gly Pro Phe Asp Tyr Trp Gly
            115                 120                 125

Gln Gly Thr Leu Val Thr Val Ser Ser Ala Ser Thr Lys Gly Pro Ser
        130                 135                 140
```

```
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Lys Thr Tyr Thr Cys Asn Val Asp His
210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
            275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
            435                 440                 445

Leu His Asn His Tyr Thr Gln Lys Ser Leu Ser Leu Ser Leu Gly Lys
450                 455                 460

Gly Gly Gly Gly Ser Gly Gly Gly Ser Gln Val Gln Leu Val Glu
465                 470                 475                 480

Ser Gly Gly Gly Val Val Gln Pro Gly Arg Ser Leu Arg Leu Asp Cys
            485                 490                 495

Lys Ala Ser Gly Ile Thr Phe Ser Asn Ser Gly Met His Trp Val Arg
            500                 505                 510

Gln Ala Pro Gly Lys Gly Leu Glu Trp Val Ala Val Ile Trp Tyr Asp
            515                 520                 525

Gly Ser Lys Arg Tyr Tyr Ala Asp Ser Val Lys Gly Arg Phe Thr Ile
            530                 535                 540

Ser Arg Asp Asn Ser Lys Asn Thr Leu Phe Leu Gln Met Asn Ser Leu
545                 550                 555                 560
```

Arg Ala Glu Asp Thr Ala Val Tyr Tyr Cys Ala Thr Asn Asp Asp Tyr
            565                 570                 575

Trp Gly Gln Gly Thr Leu Val Thr Val Ser Ser Gly Gly Gly Gly Ser
        580                 585                 590

Gly Gly Gly Gly Ser Gly Gly Gly Ser Gly Gly Gly Gly Ser Glu
        595                 600                 605

Ile Val Leu Thr Gln Ser Pro Ala Thr Leu Ser Leu Ser Pro Gly Glu
        610                 615                 620

Arg Ala Thr Leu Ser Cys Arg Ala Ser Gln Ser Val Ser Ser Tyr Leu
625                 630                 635                 640

Ala Trp Tyr Gln Gln Lys Pro Gly Gln Ala Pro Arg Leu Leu Ile Tyr
                645                 650                 655

Asp Ala Ser Asn Arg Ala Thr Gly Ile Pro Ala Arg Phe Ser Gly Ser
                660                 665                 670

Gly Ser Gly Thr Asp Phe Thr Leu Thr Ile Ser Ser Leu Glu Pro Glu
        675                 680                 685

Asp Phe Ala Val Tyr Tyr Cys Gln Gln Ser Ser Asn Trp Pro Arg Thr
        690                 695                 700

Phe Gly Gln Gly Thr Lys Val Glu Ile Lys
705                 710

<210> SEQ ID NO 82
<211> LENGTH: 721
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Gly Trp Ser Cys Ile Ile Leu Phe Leu Val Ala Thr Ala Thr Gly
1               5                   10                  15

Val His Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

-continued

```
Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
450                 455                 460

Gly Lys Gly Gly Gly Gly Ser Gly Gly Gly Gly Ser Gln Val Gln Leu
465                 470                 475                 480

Val Glu Ser Gly Gly Gly Val Val Gln Pro Gly Arg Ser Leu Arg Leu
                485                 490                 495

Ser Cys Ala Ala Ser Gly Phe Thr Phe Ser Val Tyr Gly Met Asn Trp
            500                 505                 510

Val Arg Gln Ala Pro Gly Lys Gly Leu Glu Trp Val Ala Ile Ile Trp
        515                 520                 525

Tyr Asp Gly Asp Asn Gln Tyr Tyr Ala Asp Ser Val Lys Gly Arg Phe
530                 535                 540

Thr Ile Ser Arg Asp Asn Ser Lys Asn Thr Leu Tyr Leu Gln Met Asn
545                 550                 555                 560

Gly Leu Arg Ala Glu Asp Thr Ala Val Tyr Tyr Cys Ala Arg Asp Leu
                565                 570                 575

Arg Thr Gly Pro Phe Asp Tyr Trp Gly Gln Gly Thr Leu Val Thr Val
            580                 585                 590

Ser Ser Gly Gly Gly Gly Ser Gly Gly Gly Gly Ser Gly Gly Gly Gly
        595                 600                 605

Ser Gly Gly Gly Gly Ser Glu Ile Val Leu Thr Gln Ser Pro Asp Phe
610                 615                 620
```

```
Gln Ser Val Thr Pro Lys Glu Lys Val Thr Ile Thr Cys Arg Ala Ser
625                 630                 635                 640

Gln Ser Ile Gly Ser Ser Leu His Trp Tyr Gln Gln Lys Pro Asp Gln
            645                 650                 655

Ser Pro Lys Leu Leu Ile Lys Tyr Ala Ser Gln Ser Phe Ser Gly Val
            660                 665                 670

Pro Ser Arg Phe Ser Gly Ser Gly Ser Gly Thr Asp Phe Thr Leu Thr
            675                 680                 685

Ile Asn Ser Leu Glu Ala Glu Asp Ala Ala Tyr Tyr Cys His Gln
            690                 695                 700

Ser Ser Ser Leu Pro Phe Thr Phe Gly Pro Gly Thr Lys Val Asp Ile
705                 710                 715                 720

Lys
```

<210> SEQ ID NO 83
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
        35                  40                  45

Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255
```

```
Pro Lys Pro Lys Asp Thr Leu Met Ile Ser Arg Thr Pro Glu Val Thr
            260                 265                 270

Cys Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
        290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
        370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly Lys Gly Gly Gly Gly Ser
    450                 455                 460

Gly Gly Gly Gly Ser Gln Val Gln Leu Val Glu Ser Gly Gly Gly Val
465                 470                 475                 480

Val Gln Pro Gly Arg Ser Leu Arg Leu Ser Cys Ala Ala Ser Gly Phe
            485                 490                 495

Thr Phe Ser Val Tyr Gly Met Asn Trp Val Arg Gln Ala Pro Gly Lys
        500                 505                 510

Gly Leu Glu Trp Val Ala Ile Ile Trp Tyr Asp Gly Asp Asn Gln Tyr
        515                 520                 525

Tyr Ala Asp Ser Val Lys Gly Arg Phe Thr Ile Ser Arg Asp Asn Ser
    530                 535                 540

Lys Asn Thr Leu Tyr Leu Gln Met Asn Gly Leu Arg Ala Glu Asp Thr
545                 550                 555                 560

Ala Val Tyr Tyr Cys Ala Arg Asp Leu Arg Thr Gly Pro Phe Asp Tyr
                565                 570                 575

Trp Gly Gln Gly Thr Leu Val Thr Val Ser Ser Gly Gly Gly Gly Ser
            580                 585                 590

Gly Gly Gly Gly Ser Gly Gly Gly Gly Ser Gly Gly Gly Gly Ser Glu
        595                 600                 605

Ile Val Leu Thr Gln Ser Pro Asp Phe Gln Ser Val Thr Pro Lys Glu
        610                 615                 620

Lys Val Thr Ile Thr Cys Arg Ala Ser Gln Ser Ile Gly Ser Ser Leu
625                 630                 635                 640

His Trp Tyr Gln Gln Lys Pro Asp Gln Ser Pro Lys Leu Leu Ile Lys
                645                 650                 655

Tyr Ala Ser Gln Ser Phe Ser Gly Val Pro Ser Arg Phe Ser Gly Ser
            660                 665                 670
```

```
Gly Ser Gly Thr Asp Phe Thr Leu Thr Ile Asn Ser Leu Glu Ala Glu
            675                 680                 685

Asp Ala Ala Tyr Tyr Cys His Gln Ser Ser Leu Pro Phe Thr
        690                 695                 700

Phe Gly Pro Gly Thr Lys Val Asp Ile Lys
705                 710
```

<210> SEQ ID NO 84
<211> LENGTH: 682
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Lys Gly Val
        35                  40                  45

Ser Thr Ser Gly Tyr Ser Tyr Leu His Trp Tyr Gln Gln Lys Pro Gly
    50                  55                  60

Gln Ala Pro Arg Leu Leu Ile Tyr Leu Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
            100                 105                 110

His Ser Arg Asp Leu Pro Leu Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Gln Val Gln
225                 230                 235                 240

Leu Val Glu Ser Gly Gly Gly Val Val Gln Pro Gly Arg Ser Leu Arg
                245                 250                 255

Leu Ser Cys Ala Ala Ser Gly Phe Thr Phe Ser Val Tyr Gly Met Asn
            260                 265                 270

Trp Val Arg Gln Ala Pro Gly Lys Gly Leu Glu Trp Val Ala Ile Ile
        275                 280                 285

Trp Tyr Asp Gly Asp Asn Gln Tyr Tyr Ala Asp Ser Val Lys Gly Arg
    290                 295                 300
```

```
Phe Thr Ile Ser Arg Asp Asn Ser Lys Asn Thr Leu Tyr Leu Gln Met
305                 310                 315                 320

Asn Gly Leu Arg Ala Glu Asp Thr Ala Val Tyr Tyr Cys Ala Arg Asp
            325                 330                 335

Leu Arg Thr Gly Pro Phe Asp Tyr Trp Gly Gln Gly Thr Leu Val Thr
        340                 345                 350

Val Ser Ser Ala Ser Thr Lys Gly Pro Ser Val Phe Pro Leu Ala Pro
    355                 360                 365

Cys Ser Arg Ser Thr Ser Glu Ser Thr Ala Ala Leu Gly Cys Leu Val
370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
            405                 410                 415

Leu Tyr Ser Leu Ser Ser Val Val Thr Val Pro Ser Ser Ser Leu Gly
        420                 425                 430

Thr Lys Thr Tyr Thr Cys Asn Val Asp His Lys Pro Ser Asn Thr Lys
    435                 440                 445

Val Asp Lys Arg Val Glu Ser Lys Tyr Gly Pro Pro Cys Pro Pro Cys
450                 455                 460

Pro Ala Pro Glu Phe Leu Gly Gly Pro Ser Val Phe Leu Phe Pro Pro
465                 470                 475                 480

Lys Pro Lys Asp Thr Leu Met Ile Ser Arg Thr Pro Glu Val Thr Cys
            485                 490                 495

Val Val Val Asp Val Ser Gln Glu Asp Pro Glu Val Gln Phe Asn Trp
        500                 505                 510

Tyr Val Asp Gly Val Glu Val His Asn Ala Lys Thr Lys Pro Arg Glu
    515                 520                 525

Glu Gln Phe Asn Ser Thr Tyr Arg Val Val Ser Val Leu Thr Val Leu
530                 535                 540

His Gln Asp Trp Leu Asn Gly Lys Glu Tyr Lys Cys Lys Val Ser Asn
545                 550                 555                 560

Lys Gly Leu Pro Ser Ser Ile Glu Lys Thr Ile Ser Lys Ala Lys Gly
            565                 570                 575

Gln Pro Arg Glu Pro Gln Val Tyr Thr Leu Pro Pro Ser Gln Glu Glu
        580                 585                 590

Met Thr Lys Asn Gln Val Ser Leu Thr Cys Leu Val Lys Gly Phe Tyr
    595                 600                 605

Pro Ser Asp Ile Ala Val Glu Trp Glu Ser Asn Gly Gln Pro Glu Asn
610                 615                 620

Asn Tyr Lys Thr Thr Pro Pro Val Leu Asp Ser Asp Gly Ser Phe Phe
625                 630                 635                 640

Leu Tyr Ser Arg Leu Thr Val Asp Lys Ser Arg Trp Gln Glu Gly Asn
            645                 650                 655

Val Phe Ser Cys Ser Val Met His Glu Ala Leu His Asn His Tyr Thr
        660                 665                 670

Gln Lys Ser Leu Ser Leu Ser Leu Gly Lys
    675                 680

<210> SEQ ID NO 85
<211> LENGTH: 242
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 85

Met Gly Trp Ser Cys Ile Ile Leu Phe Leu Val Ala Thr Ala Thr Gly
1               5                   10                  15

Val His Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys

<210> SEQ ID NO 86
<211> LENGTH: 678
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 86

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

```
Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Ser Ser Asn
            100                 105                 110

Trp Pro Arg Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys Gln Val Gln Leu Val Glu Ser
225                 230                 235                 240

Gly Gly Gly Val Val Gln Pro Gly Arg Ser Leu Arg Leu Ser Cys Ala
                245                 250                 255

Ala Ser Gly Phe Thr Phe Ser Val Tyr Gly Met Asn Trp Val Arg Gln
            260                 265                 270

Ala Pro Gly Lys Gly Leu Glu Trp Val Ala Ile Ile Trp Tyr Asp Gly
        275                 280                 285

Asp Asn Gln Tyr Tyr Ala Asp Ser Val Lys Gly Arg Phe Thr Ile Ser
    290                 295                 300

Arg Asp Asn Ser Lys Asn Thr Leu Tyr Leu Gln Met Asn Gly Leu Arg
305                 310                 315                 320

Ala Glu Asp Thr Ala Val Tyr Tyr Cys Ala Arg Asp Leu Arg Thr Gly
                325                 330                 335

Pro Phe Asp Tyr Trp Gly Gln Gly Thr Leu Val Thr Val Ser Ser Ala
            340                 345                 350

Ser Thr Lys Gly Pro Ser Val Phe Pro Leu Ala Pro Cys Ser Arg Ser
        355                 360                 365

Thr Ser Glu Ser Thr Ala Ala Leu Gly Cys Leu Val Lys Asp Tyr Phe
    370                 375                 380

Pro Glu Pro Val Thr Val Ser Trp Asn Ser Gly Ala Leu Thr Ser Gly
385                 390                 395                 400

Val His Thr Phe Pro Ala Val Leu Gln Ser Ser Gly Leu Tyr Ser Leu
                405                 410                 415

Ser Ser Val Val Thr Val Pro Ser Ser Ser Leu Gly Thr Lys Thr Tyr
            420                 425                 430

Thr Cys Asn Val Asp His Lys Pro Ser Asn Thr Lys Val Asp Lys Arg
        435                 440                 445

Val Glu Ser Lys Tyr Gly Pro Pro Cys Pro Pro Cys Pro Ala Pro Glu
    450                 455                 460

Phe Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495
```

```
Val Ser Gln Glu Asp Pro Glu Val Gln Phe Asn Trp Tyr Val Asp Gly
            500                 505                 510

Val Glu Val His Asn Ala Lys Thr Lys Pro Arg Glu Glu Gln Phe Asn
            515                 520                 525

Ser Thr Tyr Arg Val Val Ser Val Leu Thr Val Leu His Gln Asp Trp
        530                 535                 540

Leu Asn Gly Lys Glu Tyr Lys Cys Lys Val Ser Asn Lys Gly Leu Pro
545                 550                 555                 560

Ser Ser Ile Glu Lys Thr Ile Ser Lys Ala Lys Gly Gln Pro Arg Glu
                565                 570                 575

Pro Gln Val Tyr Thr Leu Pro Pro Ser Gln Glu Glu Met Thr Lys Asn
            580                 585                 590

Gln Val Ser Leu Thr Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
        610                 615                 620

Thr Pro Pro Val Leu Asp Ser Asp Gly Ser Phe Phe Leu Tyr Ser Arg
625                 630                 635                 640

Leu Thr Val Asp Lys Ser Arg Trp Gln Glu Gly Asn Val Phe Ser Cys
                645                 650                 655

Ser Val Met His Glu Ala Leu His Asn His Tyr Thr Gln Lys Ser Leu
            660                 665                 670

Ser Leu Ser Leu Gly Lys
        675

<210> SEQ ID NO 87
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Val Val Gln
            20                  25                  30

Pro Gly Arg Ser Leu Arg Leu Asp Cys Lys Ala Ser Gly Ile Thr Phe
        35                  40                  45

Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175
```

```
Ala Leu Thr Ser Gly Val His Thr Phe Pro Ala Val Leu Gln Ser Ser
            180                 185                 190

Gly Leu Tyr Ser Leu Ser Ser Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys
225                 230                 235

<210> SEQ ID NO 88
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Gly Trp Ser Cys Ile Ile Leu Phe Leu Val Ala Thr Ala Thr Gly
1               5                   10                  15

Val His Ser Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Phe Thr Phe Gly Pro Gly Thr Lys Val Asp Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gln Val Gln Leu Val Gln Ser
225                 230                 235                 240

Gly Val Glu Val Lys Lys Pro Gly Ala Ser Val Lys Val Ser Cys Lys
                245                 250                 255

Ala Ser Gly Tyr Thr Phe Thr Asn Tyr Tyr Met Tyr Trp Val Arg Gln
            260                 265                 270

Ala Pro Gly Gln Gly Leu Glu Trp Met Gly Gly Ile Asn Pro Ser Asn
        275                 280                 285
```

Gly Gly Thr Asn Phe Asn Glu Lys Phe Lys Asn Arg Val Thr Leu Thr
290                 295                 300

Thr Asp Ser Ser Thr Thr Ala Tyr Met Glu Leu Lys Ser Leu Gln
305                 310                 315                 320

Phe Asp Asp Thr Ala Val Tyr Tyr Cys Ala Arg Arg Asp Tyr Arg Phe
            325                 330                 335

Asp Met Gly Phe Asp Tyr Trp Gly Gln Gly Thr Thr Val Thr Val Ser
            340                 345                 350

Ser Ala Ser Thr Lys Gly Pro Ser Val Phe Pro Leu Ala Pro Cys Ser
            355                 360                 365

Arg Ser Thr Ser Glu Ser Thr Ala Ala Leu Gly Cys Leu Val Lys Asp
370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
            405                 410                 415

Ser Leu Ser Ser Val Val Thr Val Pro Ser Ser Ser Leu Gly Thr Lys
            420                 425                 430

Thr Tyr Thr Cys Asn Val Asp His Lys Pro Ser Asn Thr Lys Val Asp
            435                 440                 445

Lys Arg Val Glu Ser Lys Tyr Gly Pro Pro Cys Pro Pro Cys Pro Ala
450                 455                 460

Pro Glu Phe Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
            485                 490                 495

Val Asp Val Ser Gln Glu Asp Pro Glu Val Gln Phe Asn Trp Tyr Val
            500                 505                 510

Asp Gly Val Glu Val His Asn Ala Lys Thr Lys Pro Arg Glu Glu Gln
            515                 520                 525

Phe Asn Ser Thr Tyr Arg Val Val Ser Val Leu Thr Val Leu His Gln
530                 535                 540

Asp Trp Leu Asn Gly Lys Glu Tyr Lys Cys Lys Val Ser Asn Lys Gly
545                 550                 555                 560

Leu Pro Ser Ser Ile Glu Lys Thr Ile Ser Lys Ala Lys Gly Gln Pro
            565                 570                 575

Arg Glu Pro Gln Val Tyr Thr Leu Pro Pro Ser Gln Glu Glu Met Thr
            580                 585                 590

Lys Asn Gln Val Ser Leu Thr Cys Leu Val Lys Gly Phe Tyr Pro Ser
            595                 600                 605

Asp Ile Ala Val Glu Trp Glu Ser Asn Gly Gln Pro Glu Asn Asn Tyr
610                 615                 620

Lys Thr Thr Pro Pro Val Leu Asp Ser Asp Gly Ser Phe Phe Leu Tyr
625                 630                 635                 640

Ser Arg Leu Thr Val Asp Lys Ser Arg Trp Gln Glu Gly Asn Val Phe
            645                 650                 655

Ser Cys Ser Val Met His Glu Ala Leu His Asn His Tyr Thr Gln Lys
            660                 665                 670

Ser Leu Ser Leu Ser Leu Gly Lys
            675                 680

<210> SEQ ID NO 89
<211> LENGTH: 240

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

<210> SEQ ID NO 90
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Gly Trp Ser Cys Ile Ile Leu Phe Leu Val Ala Thr Ala Thr Gly
1               5                   10                  15

Val His Ser Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

-continued

```
Phe Ser Gly Ser Gly Ser Gly Thr Asp Phe Thr Leu Thr Ile Asn Ser
                85                  90                  95
Leu Glu Ala Glu Asp Ala Ala Ala Tyr Tyr Cys His Gln Ser Ser Ser
            100                 105                 110
Leu Pro Phe Thr Phe Gly Pro Gly Thr Lys Val Asp Ile Lys Arg Thr
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys Gln Val Gln Leu Val Glu Ser
225                 230                 235                 240
Gly Gly Gly Val Val Gln Pro Gly Arg Ser Leu Arg Leu Asp Cys Lys
                245                 250                 255
Ala Ser Gly Ile Thr Phe Ser Asn Ser Gly Met His Trp Val Arg Gln
            260                 265                 270
Ala Pro Gly Lys Gly Leu Glu Trp Val Ala Val Ile Trp Tyr Asp Gly
        275                 280                 285
Ser Lys Arg Tyr Tyr Ala Asp Ser Val Lys Gly Arg Phe Thr Ile Ser
    290                 295                 300
Arg Asp Asn Ser Lys Asn Thr Leu Phe Leu Gln Met Asn Ser Leu Arg
305                 310                 315                 320
Ala Glu Asp Thr Ala Val Tyr Tyr Cys Ala Thr Asn Asp Asp Tyr Trp
                325                 330                 335
Gly Gln Gly Thr Leu Val Thr Val Ser Ser Ala Ser Thr Lys Gly Pro
            340                 345                 350
Ser Val Phe Pro Leu Ala Pro Cys Ser Arg Ser Thr Ser Glu Ser Thr
        355                 360                 365
Ala Ala Leu Gly Cys Leu Val Lys Asp Tyr Phe Pro Glu Pro Val Thr
    370                 375                 380
Val Ser Trp Asn Ser Gly Ala Leu Thr Ser Gly Val His Thr Phe Pro
385                 390                 395                 400
Ala Val Leu Gln Ser Ser Gly Leu Tyr Ser Leu Ser Ser Val Val Thr
                405                 410                 415
Val Pro Ser Ser Ser Leu Gly Thr Lys Thr Tyr Thr Cys Asn Val Asp
            420                 425                 430
His Lys Pro Ser Asn Thr Lys Val Asp Lys Arg Val Glu Ser Lys Tyr
        435                 440                 445
Gly Pro Pro Cys Pro Pro Cys Pro Ala Pro Glu Phe Leu Gly Gly Pro
    450                 455                 460
Ser Val Phe Leu Phe Pro Pro Lys Pro Lys Asp Thr Leu Met Ile Ser
465                 470                 475                 480
Arg Thr Pro Glu Val Thr Cys Val Val Val Asp Val Ser Gln Glu Asp
                485                 490                 495
```

Pro Glu Val Gln Phe Asn Trp Tyr Val Asp Gly Val Glu Val His Asn
                500                 505                 510

Ala Lys Thr Lys Pro Arg Glu Glu Gln Phe Asn Ser Thr Tyr Arg Val
            515                 520                 525

Val Ser Val Leu Thr Val Leu His Gln Asp Trp Leu Asn Gly Lys Glu
        530                 535                 540

Tyr Lys Cys Lys Val Ser Asn Lys Gly Leu Pro Ser Ser Ile Glu Lys
545                 550                 555                 560

Thr Ile Ser Lys Ala Lys Gly Gln Pro Arg Glu Pro Gln Val Tyr Thr
                565                 570                 575

Leu Pro Pro Ser Gln Glu Glu Met Thr Lys Asn Gln Val Ser Leu Thr
            580                 585                 590

Cys Leu Val Lys Gly Phe Tyr Pro Ser Asp Ile Ala Val Glu Trp Glu
        595                 600                 605

Ser Asn Gly Gln Pro Glu Asn Asn Tyr Lys Thr Thr Pro Pro Val Leu
610                 615                 620

Asp Ser Asp Gly Ser Phe Phe Leu Tyr Ser Arg Leu Thr Val Asp Lys
625                 630                 635                 640

Ser Arg Trp Gln Glu Gly Asn Val Phe Ser Cys Ser Val Met His Glu
                645                 650                 655

Ala Leu His Asn His Tyr Thr Gln Lys Ser Leu Ser Leu Ser Leu Gly
            660                 665                 670

Lys

<210> SEQ ID NO 91
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
            275                 280                 285

Glu Val Gln Phe Asn Trp Tyr Val Asp Gly Val Glu Val His Asn Ala
        290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
                340                 345                 350

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
            370                 375                 380

Leu Val Lys Gly Phe Tyr Pro Ser Asp Ile Ala Val Glu Trp Glu Ser
385                 390                 395                 400

Asn Gly Gly Gly Gly Ser Gly Gly Gly Ser Glu Ile Val Leu Thr
                    405                 410                 415

Gln Ser Pro Ala Thr Leu Ser Leu Ser Pro Gly Glu Arg Ala Thr Leu
            420                 425                 430

Ser Cys Arg Ala Ser Lys Gly Val Ser Thr Ser Gly Tyr Ser Tyr Leu
        435                 440                 445

His Trp Tyr Gln Gln Lys Pro Gly Gln Ala Pro Arg Leu Leu Ile Tyr
    450                 455                 460

Leu Ala Ser Tyr Leu Glu Ser Gly Val Pro Ala Arg Phe Ser Gly Ser
465                 470                 475                 480

Gly Ser Gly Thr Asp Phe Thr Leu Thr Ile Ser Ser Leu Glu Pro Glu
                485                 490                 495

Asp Phe Ala Val Tyr Tyr Cys Gln His Ser Arg Asp Leu Pro Leu Thr
            500                 505                 510

Phe Gly Gly Gly Thr Lys Val Glu Ile Lys Arg Thr Val Ala Ala Pro
            515                 520                 525

Ser Val Phe Ile Phe Pro Pro Ser Asp Glu Gln Leu Lys Ser Gly Thr
            530                 535                 540

Ala Ser Val Val Cys Leu Leu Asn Asn Phe Tyr Pro Arg Glu Ala Lys
545                 550                 555                 560

Val Gln Trp Lys Val Asp Asn Ala Leu Gln Ser Gly Asn Ser Gln Glu
                565                 570                 575

Ser Val Thr Glu Gln Asp Ser Lys Asp Ser Thr Tyr Ser Leu Ser Ser
            580                 585                 590
```

```
Thr Leu Thr Leu Ser Lys Ala Asp Tyr Glu Lys His Lys Val Tyr Ala
            595                 600                 605

Cys Glu Val Thr His Gln Gly Leu Ser Ser Pro Val Thr Lys Ser Phe
    610                 615                 620

Asn Arg Gly Glu Cys Gly Gly Gly Ser Gly Gly Gly Ser Gly
625                 630                 635                 640

Gly Gly Gly Ser Gly Gly Gly Ser Gln Pro Glu Asn Asn Tyr Lys
            645                 650                 655

Thr Thr Pro Pro Val Leu Asp Ser Asp Gly Ser Phe Phe Leu Tyr Ser
            660                 665                 670

Arg Leu Thr Val Asp Lys Ser Arg Trp Gln Glu Gly Asn Val Phe Ser
            675                 680                 685

Cys Ser Val Met His Glu Ala Leu His Asn His Tyr Thr Gln Lys Ser
            690                 695                 700

Leu Ser Leu Ser Leu Gly Lys
705                 710

<210> SEQ ID NO 92
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Gly Trp Ser Cys Ile Ile Leu Phe Leu Val Ala Thr Ala Thr Gly
1               5                   10                  15

Val His Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240
```

Ser Cys

<210> SEQ ID NO 93
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350
```

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gly Gly Ser Gly Gly Gly Ser Glu Ile Val Leu Thr
                405                 410                 415

Gln Ser Pro Ala Thr Leu Ser Leu Ser Pro Gly Glu Arg Ala Thr Leu
                420                 425                 430

Ser Cys Arg Ala Ser Gln Ser Val Ser Ser Tyr Leu Ala Trp Tyr Gln
            435                 440                 445

Gln Lys Pro Gly Gln Ala Pro Arg Leu Leu Ile Tyr Asp Ala Ser Asn
        450                 455                 460

Arg Ala Thr Gly Ile Pro Ala Arg Phe Ser Gly Ser Gly Ser Gly Thr
465                 470                 475                 480

Asp Phe Thr Leu Thr Ile Ser Ser Leu Glu Pro Glu Asp Phe Ala Val
                485                 490                 495

Tyr Tyr Cys Gln Gln Ser Ser Asn Trp Pro Arg Thr Phe Gly Gln Gly
            500                 505                 510

Thr Lys Val Glu Ile Lys Arg Thr Val Ala Ala Pro Ser Val Phe Ile
        515                 520                 525

Phe Pro Pro Ser Asp Glu Gln Leu Lys Ser Gly Thr Ala Ser Val Val
    530                 535                 540

Cys Leu Leu Asn Asn Phe Tyr Pro Arg Glu Ala Lys Val Gln Trp Lys
545                 550                 555                 560

Val Asp Asn Ala Leu Gln Ser Gly Asn Ser Gln Glu Ser Val Thr Glu
                565                 570                 575

Gln Asp Ser Lys Asp Ser Thr Tyr Ser Leu Ser Ser Thr Leu Thr Leu
            580                 585                 590

Ser Lys Ala Asp Tyr Glu Lys His Lys Val Tyr Ala Cys Glu Val Thr
        595                 600                 605

His Gln Gly Leu Ser Ser Pro Val Thr Lys Ser Phe Asn Arg Gly Glu
    610                 615                 620

Cys Gly Gly Gly Gly Ser Gly Gly Gly Gly Ser Gly Gly Gly Gly Ser
625                 630                 635                 640

Gly Gly Gly Gly Ser Gly Gln Pro Glu Asn Asn Tyr Lys Thr Thr Pro
                645                 650                 655

Pro Val Leu Asp Ser Asp Gly Ser Phe Phe Leu Tyr Ser Arg Leu Thr
            660                 665                 670

Val Asp Lys Ser Arg Trp Gln Glu Gly Asn Val Phe Ser Cys Ser Val
        675                 680                 685

Met His Glu Ala Leu His Asn His Tyr Thr Gln Lys Ser Leu Ser Leu
    690                 695                 700

Ser Leu Gly Lys
705

<210> SEQ ID NO 94
<211> LENGTH: 710
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 94

Met Gly Trp Ser Cys Ile Ile Leu Phe Leu Val Ala Thr Ala Thr Gly
1               5                   10                  15

Val His Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gly Gly Ser Gly Gly Gly Ser Glu Ile Val
                405                 410                 415
```

Leu Thr Gln Ser Pro Asp Phe Gln Ser Val Thr Pro Lys Glu Lys Val
            420                 425                 430

Thr Ile Thr Cys Arg Ala Ser Gln Ser Ile Gly Ser Ser Leu His Trp
        435                 440                 445

Tyr Gln Gln Lys Pro Asp Gln Ser Pro Lys Leu Leu Ile Lys Tyr Ala
    450                 455                 460

Ser Gln Ser Phe Ser Gly Val Pro Ser Arg Phe Ser Gly Ser Gly Ser
465                 470                 475                 480

Gly Thr Asp Phe Thr Leu Thr Ile Asn Ser Leu Glu Ala Glu Asp Ala
                485                 490                 495

Ala Ala Tyr Tyr Cys His Gln Ser Ser Ser Leu Pro Phe Thr Phe Gly
            500                 505                 510

Pro Gly Thr Lys Val Asp Ile Lys Arg Thr Val Ala Ala Pro Ser Val
        515                 520                 525

Phe Ile Phe Pro Pro Ser Asp Glu Gln Leu Lys Ser Gly Thr Ala Ser
    530                 535                 540

Val Val Cys Leu Leu Asn Asn Phe Tyr Pro Arg Glu Ala Lys Val Gln
545                 550                 555                 560

Trp Lys Val Asp Asn Ala Leu Gln Ser Gly Asn Ser Gln Glu Ser Val
                565                 570                 575

Thr Glu Gln Asp Ser Lys Asp Ser Thr Tyr Ser Leu Ser Ser Thr Leu
            580                 585                 590

Thr Leu Ser Lys Ala Asp Tyr Glu Lys His Lys Val Tyr Ala Cys Glu
        595                 600                 605

Val Thr His Gln Gly Leu Ser Ser Pro Val Thr Lys Ser Phe Asn Arg
    610                 615                 620

Gly Glu Cys Gly Gly Gly Gly Ser Gly Gly Gly Gly Ser Gly Gly Gly
625                 630                 635                 640

Gly Ser Gly Gly Gly Gly Ser Gly Gln Pro Glu Asn Asn Tyr Lys Thr
                645                 650                 655

Thr Pro Pro Val Leu Asp Ser Asp Gly Ser Phe Phe Leu Tyr Ser Arg
            660                 665                 670

Leu Thr Val Asp Lys Ser Arg Trp Gln Glu Gly Asn Val Phe Ser Cys
        675                 680                 685

Ser Val Met His Glu Ala Leu His Asn His Tyr Thr Gln Lys Ser Leu
    690                 695                 700

Ser Leu Ser Leu Gly Lys
705                 710

<210> SEQ ID NO 95
<211> LENGTH: 703
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
        35                  40                  45

```
Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gly Gly Gly
385                 390                 395                 400

Ser Gly Gly Gly Gly Ser Glu Ile Val Leu Thr Gln Ser Pro Asp Phe
                405                 410                 415

Gln Ser Val Thr Pro Lys Glu Lys Val Thr Ile Thr Cys Arg Ala Ser
            420                 425                 430

Gln Ser Ile Gly Ser Ser Leu His Trp Tyr Gln Gln Lys Pro Asp Gln
        435                 440                 445

Ser Pro Lys Leu Leu Ile Lys Tyr Ala Ser Gln Ser Phe Ser Gly Val
450                 455                 460
```

```
Pro Ser Arg Phe Ser Gly Ser Gly Thr Asp Phe Thr Leu Thr
465                 470                 475                 480

Ile Asn Ser Leu Glu Ala Glu Asp Ala Ala Tyr Tyr Cys His Gln
            485                 490                 495

Ser Ser Ser Leu Pro Phe Thr Phe Gly Pro Gly Thr Lys Val Asp Ile
        500                 505                 510

Lys Arg Thr Val Ala Ala Pro Ser Val Phe Ile Phe Pro Pro Ser Asp
        515                 520                 525

Glu Gln Leu Lys Ser Gly Thr Ala Ser Val Val Cys Leu Leu Asn Asn
        530                 535                 540

Phe Tyr Pro Arg Glu Ala Lys Val Gln Trp Lys Val Asp Asn Ala Leu
545                 550                 555                 560

Gln Ser Gly Asn Ser Gln Glu Ser Val Thr Glu Gln Asp Ser Lys Asp
            565                 570                 575

Ser Thr Tyr Ser Leu Ser Ser Thr Leu Thr Leu Ser Lys Ala Asp Tyr
            580                 585                 590

Glu Lys His Lys Val Tyr Ala Cys Glu Val Thr His Gln Gly Leu Ser
        595                 600                 605

Ser Pro Val Thr Lys Ser Phe Asn Arg Gly Glu Cys Gly Gly Gly Gly
        610                 615                 620

Ser Gly Gly Gly Gly Ser Gly Gly Gly Gly Ser Gly Gly Gly Gly Ser
625                 630                 635                 640

Gly Gln Pro Glu Asn Asn Tyr Lys Thr Thr Pro Pro Val Leu Asp Ser
            645                 650                 655

Asp Gly Ser Phe Phe Leu Tyr Ser Arg Leu Thr Val Asp Lys Ser Arg
        660                 665                 670

Trp Gln Glu Gly Asn Val Phe Ser Cys Ser Val Met His Glu Ala Leu
        675                 680                 685

His Asn His Tyr Thr Gln Lys Ser Leu Ser Leu Ser Leu Gly Lys
        690                 695                 700

<210> SEQ ID NO 96
<211> LENGTH: 1127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Gly Trp Ser Cys Ile Ile Leu Phe Leu Val Ala Thr Ala Thr Gly
1               5                   10                  15

Val His Ser Ser Glu Arg Cys Asp Asp Trp Gly Leu Asp Thr Met Arg
            20                  25                  30

Gln Ile Gln Val Phe Glu Asp Glu Pro Ala Arg Ile Lys Cys Pro Leu
        35                  40                  45

Phe Glu His Phe Leu Lys Phe Asn Tyr Ser Thr Ala His Ser Ala Gly
    50                  55                  60

Leu Thr Leu Ile Trp Tyr Trp Thr Arg Gln Asp Arg Asp Leu Glu Glu
65                  70                  75                  80

Pro Ile Asn Phe Arg Leu Pro Glu Asn Arg Ile Ser Lys Glu Lys Asp
                85                  90                  95

Val Leu Trp Phe Arg Pro Thr Leu Leu Asn Asp Thr Gly Asn Tyr Thr
            100                 105                 110

Cys Met Leu Arg Asn Thr Thr Tyr Cys Ser Lys Val Ala Phe Pro Leu
        115                 120                 125
```

```
Glu Val Val Gln Lys Asp Ser Cys Phe Asn Ser Pro Met Lys Leu Pro
    130                 135                 140
Val His Lys Leu Tyr Ile Glu Tyr Gly Ile Gln Arg Ile Thr Cys Pro
145                 150                 155                 160
Asn Val Asp Gly Tyr Phe Pro Ser Ser Val Lys Pro Thr Ile Thr Trp
                165                 170                 175
Tyr Met Gly Cys Tyr Lys Ile Gln Asn Phe Asn Asn Val Ile Pro Glu
            180                 185                 190
Gly Met Asn Leu Ser Phe Leu Ile Ala Leu Ile Ser Asn Asn Gly Asn
        195                 200                 205
Tyr Thr Cys Val Val Thr Tyr Pro Glu Asn Gly Arg Thr Phe His Leu
    210                 215                 220
Thr Arg Thr Leu Thr Val Lys Val Val Gly Ser Pro Lys Asn Ala Val
225                 230                 235                 240
Pro Pro Val Ile His Ser Pro Asn Asp His Val Val Tyr Glu Lys Glu
                245                 250                 255
Pro Gly Glu Glu Leu Leu Ile Pro Cys Thr Val Tyr Phe Ser Phe Leu
            260                 265                 270
Met Asp Ser Arg Asn Glu Val Trp Trp Thr Ile Asp Gly Lys Lys Pro
        275                 280                 285
Asp Asp Ile Thr Ile Asp Val Thr Ile Asn Glu Ser Ile Ser His Ser
    290                 295                 300
Arg Thr Glu Asp Glu Thr Arg Thr Gln Ile Leu Ser Ile Lys Lys Val
305                 310                 315                 320
Thr Ser Glu Asp Leu Lys Arg Ser Tyr Val Cys His Ala Arg Ser Ala
                325                 330                 335
Lys Gly Glu Val Ala Lys Ala Ala Lys Val Lys Gln Lys Val Pro Ala
            340                 345                 350
Pro Arg Tyr Thr Val Glu Lys Cys Lys Glu Arg Glu Lys Ile Ile
        355                 360                 365
Leu Val Ser Ser Ala Asn Glu Ile Asp Val Arg Pro Cys Pro Leu Asn
    370                 375                 380
Pro Asn Glu His Lys Gly Thr Ile Thr Trp Tyr Lys Asp Asp Ser Lys
385                 390                 395                 400
Thr Pro Val Ser Thr Glu Gln Ala Ser Arg Ile His Gln His Lys Glu
                405                 410                 415
Lys Leu Trp Phe Val Pro Ala Lys Val Glu Asp Ser Gly His Tyr Tyr
            420                 425                 430
Cys Val Val Arg Asn Ser Ser Tyr Cys Leu Arg Ile Lys Ile Ser Ala
        435                 440                 445
Lys Phe Val Glu Asn Glu Pro Asn Leu Cys Tyr Asn Ala Gln Ala Ile
    450                 455                 460
Phe Lys Gln Lys Leu Pro Val Ala Gly Asp Gly Gly Leu Val Cys Pro
465                 470                 475                 480
Tyr Met Glu Phe Phe Lys Asn Glu Asn Asn Glu Leu Pro Lys Leu Gln
                485                 490                 495
Trp Tyr Lys Asp Cys Lys Pro Leu Leu Leu Asp Asn Ile His Phe Ser
            500                 505                 510
Gly Val Lys Asp Arg Leu Ile Val Met Asn Val Ala Glu Lys His Arg
        515                 520                 525
Gly Asn Tyr Thr Cys His Ala Ser Tyr Thr Tyr Leu Gly Lys Gln Tyr
    530                 535                 540
```

-continued

```
Pro Ile Thr Arg Val Ile Glu Phe Ile Thr Leu Glu Glu Asn Lys Pro
545                 550                 555                 560

Thr Arg Pro Val Ile Val Ser Pro Ala Asn Glu Thr Met Glu Val Asp
            565                 570                 575

Leu Gly Ser Gln Ile Gln Leu Ile Cys Asn Val Thr Gly Gln Leu Ser
        580                 585                 590

Asp Ile Ala Tyr Trp Lys Trp Asn Gly Ser Val Ile Asp Glu Asp Asp
    595                 600                 605

Pro Val Leu Gly Glu Asp Tyr Tyr Ser Val Glu Pro Ala Asn Lys
610                 615                 620

Arg Arg Ser Thr Leu Ile Thr Val Leu Asn Ile Ser Glu Ile Glu Ser
625                 630                 635                 640

Arg Phe Tyr Lys His Pro Phe Thr Cys Phe Ala Lys Asn Thr His Gly
                645                 650                 655

Ile Asp Ala Ala Tyr Ile Gln Leu Ile Tyr Pro Val Thr Asn Gly Gly
            660                 665                 670

Gly Gly Ser Gly Gly Gly Ser Gln Val Gln Leu Val Gln Ser Gly
        675                 680                 685

Val Glu Val Lys Lys Pro Gly Ala Ser Val Lys Val Ser Cys Lys Ala
690                 695                 700

Ser Gly Tyr Thr Phe Thr Asn Tyr Tyr Met Tyr Trp Val Arg Gln Ala
705                 710                 715                 720

Pro Gly Gln Gly Leu Glu Trp Met Gly Gly Ile Asn Pro Ser Asn Gly
                725                 730                 735

Gly Thr Asn Phe Asn Glu Lys Phe Lys Asn Arg Val Thr Leu Thr Thr
            740                 745                 750

Asp Ser Ser Thr Thr Thr Ala Tyr Met Glu Leu Lys Ser Leu Gln Phe
        755                 760                 765

Asp Asp Thr Ala Val Tyr Tyr Cys Ala Arg Arg Asp Tyr Arg Phe Asp
    770                 775                 780

Met Gly Phe Asp Tyr Trp Gly Gln Gly Thr Thr Val Thr Val Ser Ser
785                 790                 795                 800

Ala Ser Thr Lys Gly Pro Ser Val Phe Pro Leu Ala Pro Cys Ser Arg
                805                 810                 815

Ser Thr Ser Glu Ser Thr Ala Ala Leu Gly Cys Leu Val Lys Asp Tyr
            820                 825                 830

Phe Pro Glu Pro Val Thr Val Ser Trp Asn Ser Gly Ala Leu Thr Ser
        835                 840                 845

Gly Val His Thr Phe Pro Ala Val Leu Gln Ser Ser Gly Leu Tyr Ser
850                 855                 860

Leu Ser Ser Val Val Thr Val Pro Ser Ser Ser Leu Gly Thr Lys Thr
865                 870                 875                 880

Tyr Thr Cys Asn Val Asp His Lys Pro Ser Asn Thr Lys Val Asp Lys
                885                 890                 895

Arg Val Glu Ser Lys Tyr Gly Pro Pro Cys Pro Pro Cys Pro Ala Pro
            900                 905                 910

Glu Phe Leu Gly Gly Pro Ser Val Phe Leu Phe Pro Pro Lys Pro Lys
        915                 920                 925

Asp Thr Leu Met Ile Ser Arg Thr Pro Glu Val Thr Cys Val Val Val
    930                 935                 940

Asp Val Ser Gln Glu Asp Pro Glu Val Gln Phe Asn Trp Tyr Val Asp
945                 950                 955                 960
```

Gly Val Glu Val His Asn Ala Lys Thr Lys Pro Arg Glu Glu Gln Phe
                965                 970                 975

Asn Ser Thr Tyr Arg Val Val Ser Val Leu Thr Val Leu His Gln Asp
            980                 985                 990

Trp Leu Asn Gly Lys Glu Tyr Lys Cys Lys Val Ser Asn Lys Gly Leu
        995                 1000                1005

Pro Ser Ser Ile Glu Lys Thr Ile Ser Lys Ala Lys Gly Gln Pro
    1010                1015                1020

Arg Glu Pro Gln Val Tyr Thr Leu Pro Pro Ser Gln Glu Glu Met
    1025                1030                1035

Thr Lys Asn Gln Val Ser Leu Thr Cys Leu Val Lys Gly Phe Tyr
    1040                1045                1050

Pro Ser Asp Ile Ala Val Glu Trp Glu Ser Asn Gly Gln Pro Glu
    1055                1060                1065

Asn Asn Tyr Lys Thr Thr Pro Pro Val Leu Asp Ser Asp Gly Ser
    1070                1075                1080

Phe Phe Leu Tyr Ser Arg Leu Thr Val Asp Lys Ser Arg Trp Gln
    1085                1090                1095

Glu Gly Asn Val Phe Ser Cys Ser Val Met His Glu Ala Leu His
    1100                1105                1110

Asn His Tyr Thr Gln Lys Ser Leu Ser Leu Ser Leu Gly Lys
    1115                1120                1125

<210> SEQ ID NO 97
<211> LENGTH: 1120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Gly Trp Ser Cys Ile Ile Leu Phe Leu Val Ala Thr Ala Thr Gly
1               5                   10                  15

Val His Ser Ser Glu Arg Cys Asp Asp Trp Gly Leu Asp Thr Met Arg
            20                  25                  30

Gln Ile Gln Val Phe Glu Asp Glu Pro Ala Arg Ile Lys Cys Pro Leu
        35                  40                  45

Phe Glu His Phe Leu Lys Phe Asn Tyr Ser Thr Ala His Ser Ala Gly
    50                  55                  60

Leu Thr Leu Ile Trp Tyr Trp Thr Arg Gln Asp Arg Asp Leu Glu Glu
65                  70                  75                  80

Pro Ile Asn Phe Arg Leu Pro Glu Asn Arg Ile Ser Lys Glu Lys Asp
                85                  90                  95

Val Leu Trp Phe Arg Pro Thr Leu Leu Asn Asp Thr Gly Asn Tyr Thr
            100                 105                 110

Cys Met Leu Arg Asn Thr Thr Tyr Cys Ser Lys Val Ala Phe Pro Leu
        115                 120                 125

Glu Val Val Gln Lys Asp Ser Cys Phe Asn Ser Pro Met Lys Leu Pro
    130                 135                 140

Val His Lys Leu Tyr Ile Glu Tyr Gly Ile Gln Arg Ile Thr Cys Pro
145                 150                 155                 160

Asn Val Asp Gly Tyr Phe Pro Ser Ser Val Lys Pro Thr Ile Thr Trp
                165                 170                 175

-continued

```
Tyr Met Gly Cys Tyr Lys Ile Gln Asn Phe Asn Asn Val Ile Pro Glu
            180                 185                 190
Gly Met Asn Leu Ser Phe Leu Ile Ala Leu Ile Ser Asn Asn Gly Asn
            195                 200                 205
Tyr Thr Cys Val Val Thr Tyr Pro Glu Asn Gly Arg Thr Phe His Leu
    210                 215                 220
Thr Arg Thr Leu Thr Val Lys Val Val Gly Ser Pro Lys Asn Ala Val
225                 230                 235                 240
Pro Pro Val Ile His Ser Pro Asn Asp His Val Val Tyr Glu Lys Glu
                245                 250                 255
Pro Gly Glu Glu Leu Leu Ile Pro Cys Thr Val Tyr Phe Ser Phe Leu
            260                 265                 270
Met Asp Ser Arg Asn Glu Val Trp Trp Thr Ile Asp Gly Lys Lys Pro
            275                 280                 285
Asp Asp Ile Thr Ile Asp Val Thr Ile Asn Glu Ser Ile Ser His Ser
    290                 295                 300
Arg Thr Glu Asp Glu Thr Arg Thr Gln Ile Leu Ser Ile Lys Lys Val
305                 310                 315                 320
Thr Ser Glu Asp Leu Lys Arg Ser Tyr Val Cys His Ala Arg Ser Ala
                325                 330                 335
Lys Gly Glu Val Ala Lys Ala Ala Lys Val Lys Gln Lys Val Pro Ala
            340                 345                 350
Pro Arg Tyr Thr Val Glu Lys Cys Lys Glu Arg Glu Glu Lys Ile Ile
            355                 360                 365
Leu Val Ser Ser Ala Asn Glu Ile Asp Val Arg Pro Cys Pro Leu Asn
    370                 375                 380
Pro Asn Glu His Lys Gly Thr Ile Thr Trp Tyr Lys Asp Asp Ser Lys
385                 390                 395                 400
Thr Pro Val Ser Thr Glu Gln Ala Ser Arg Ile His Gln His Lys Glu
                405                 410                 415
Lys Leu Trp Phe Val Pro Ala Lys Val Glu Asp Ser Gly His Tyr Tyr
            420                 425                 430
Cys Val Val Arg Asn Ser Ser Tyr Cys Leu Arg Ile Lys Ile Ser Ala
            435                 440                 445
Lys Phe Val Glu Asn Glu Pro Asn Leu Cys Tyr Asn Ala Gln Ala Ile
    450                 455                 460
Phe Lys Gln Lys Leu Pro Val Ala Gly Asp Gly Gly Leu Val Cys Pro
465                 470                 475                 480
Tyr Met Glu Phe Phe Lys Asn Glu Asn Asn Glu Leu Pro Lys Leu Gln
                485                 490                 495
Trp Tyr Lys Asp Cys Lys Pro Leu Leu Leu Asp Asn Ile His Phe Ser
            500                 505                 510
Gly Val Lys Asp Arg Leu Ile Val Met Asn Val Ala Glu Lys His Arg
            515                 520                 525
Gly Asn Tyr Thr Cys His Ala Ser Tyr Thr Tyr Leu Gly Lys Gln Tyr
    530                 535                 540
Pro Ile Thr Arg Val Ile Glu Phe Ile Thr Leu Glu Glu Asn Lys Pro
545                 550                 555                 560
Thr Arg Pro Val Ile Val Ser Pro Ala Asn Glu Thr Met Glu Val Asp
                565                 570                 575
Leu Gly Ser Gln Ile Gln Leu Ile Cys Asn Val Thr Gly Gln Leu Ser
            580                 585                 590
```

```
Asp Ile Ala Tyr Trp Lys Trp Asn Gly Ser Val Ile Asp Glu Asp
            595                 600                 605

Pro Val Leu Gly Glu Asp Tyr Tyr Ser Val Glu Asn Pro Ala Asn Lys
610                 615                 620

Arg Arg Ser Thr Leu Ile Thr Val Leu Asn Ile Ser Glu Ile Glu Ser
625                 630                 635                 640

Arg Phe Tyr Lys His Pro Phe Thr Cys Phe Ala Lys Asn Thr His Gly
                645                 650                 655

Ile Asp Ala Ala Tyr Ile Gln Leu Ile Tyr Pro Val Thr Asn Gly Gly
            660                 665                 670

Gly Gly Ser Gly Gly Gly Ser Gln Val Gln Leu Val Glu Ser Gly
            675                 680                 685

Gly Gly Val Val Gln Pro Gly Arg Ser Leu Arg Leu Asp Cys Lys Ala
690                 695                 700

Ser Gly Ile Thr Phe Ser Asn Ser Gly Met His Trp Val Arg Gln Ala
705                 710                 715                 720

Pro Gly Lys Gly Leu Glu Trp Val Ala Val Ile Trp Tyr Asp Gly Ser
                725                 730                 735

Lys Arg Tyr Tyr Ala Asp Ser Val Lys Gly Arg Phe Thr Ile Ser Arg
            740                 745                 750

Asp Asn Ser Lys Asn Thr Leu Phe Leu Gln Met Asn Ser Leu Arg Ala
            755                 760                 765

Glu Asp Thr Ala Val Tyr Tyr Cys Ala Thr Asn Asp Asp Tyr Trp Gly
770                 775                 780

Gln Gly Thr Leu Val Thr Val Ser Ser Ala Ser Thr Lys Gly Pro Ser
785                 790                 795                 800

Val Phe Pro Leu Ala Pro Cys Ser Arg Ser Thr Ser Glu Ser Thr Ala
                805                 810                 815

Ala Leu Gly Cys Leu Val Lys Asp Tyr Phe Pro Glu Pro Val Thr Val
            820                 825                 830

Ser Trp Asn Ser Gly Ala Leu Thr Ser Gly Val His Thr Phe Pro Ala
            835                 840                 845

Val Leu Gln Ser Ser Gly Leu Tyr Ser Leu Ser Ser Val Val Thr Val
850                 855                 860

Pro Ser Ser Ser Leu Gly Thr Lys Thr Tyr Thr Cys Asn Val Asp His
865                 870                 875                 880

Lys Pro Ser Asn Thr Lys Val Asp Lys Arg Val Glu Ser Lys Tyr Gly
                885                 890                 895

Pro Pro Cys Pro Pro Cys Pro Ala Pro Glu Phe Leu Gly Gly Pro Ser
            900                 905                 910

Val Phe Leu Phe Pro Pro Lys Pro Lys Asp Thr Leu Met Ile Ser Arg
            915                 920                 925

Thr Pro Glu Val Thr Cys Val Val Val Asp Val Ser Gln Glu Asp Pro
930                 935                 940

Glu Val Gln Phe Asn Trp Tyr Val Asp Gly Val Glu Val His Asn Ala
945                 950                 955                 960

Lys Thr Lys Pro Arg Glu Glu Gln Phe Asn Ser Thr Tyr Arg Val Val
                965                 970                 975

Ser Val Leu Thr Val Leu His Gln Asp Trp Leu Asn Gly Lys Glu Tyr
            980                 985                 990

Lys Cys Lys Val Ser Asn Lys Gly Leu Pro Ser Ser Ile Glu Lys Thr
            995                 1000                1005
```

```
Ile Ser Lys Ala Lys Gly Gln Pro Arg Glu Pro Gln Val Tyr Thr
    1010                1015                1020

Leu Pro Pro Ser Gln Glu Glu Met Thr Lys Asn Gln Val Ser Leu
    1025                1030                1035

Thr Cys Leu Val Lys Gly Phe Tyr Pro Ser Asp Ile Ala Val Glu
    1040                1045                1050

Trp Glu Ser Asn Gly Gln Pro Glu Asn Asn Tyr Lys Thr Thr Pro
    1055                1060                1065

Pro Val Leu Asp Ser Asp Gly Ser Phe Phe Leu Tyr Ser Arg Leu
    1070                1075                1080

Thr Val Asp Lys Ser Arg Trp Gln Glu Gly Asn Val Phe Ser Cys
    1085                1090                1095

Ser Val Met His Glu Ala Leu His Asn His Tyr Thr Gln Lys Ser
    1100                1105                1110

Leu Ser Leu Ser Leu Gly Lys
    1115                1120

<210> SEQ ID NO 98
<211> LENGTH: 1123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
        35                  40                  45

Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220
```

```
Lys Val Asp Lys Arg Val Glu Ser Lys Tyr Gly Gly Gly Ser Gly
225                 230                 235                 240

Gly Gly Gly Ser Glu Arg Cys Asp Asp Trp Gly Leu Asp Thr Met Arg
            245                 250                 255

Gln Ile Gln Val Phe Glu Asp Glu Pro Ala Arg Ile Lys Cys Pro Leu
        260                 265                 270

Phe Glu His Phe Leu Lys Phe Asn Tyr Ser Thr Ala His Ser Ala Gly
            275                 280                 285

Leu Thr Leu Ile Trp Tyr Trp Thr Arg Gln Asp Arg Asp Leu Glu Glu
290                 295                 300

Pro Ile Asn Phe Arg Leu Pro Glu Asn Arg Ile Ser Lys Glu Lys Asp
305                 310                 315                 320

Val Leu Trp Phe Arg Pro Thr Leu Leu Asn Asp Thr Gly Asn Tyr Thr
            325                 330                 335

Cys Met Leu Arg Asn Thr Thr Tyr Cys Ser Lys Val Ala Phe Pro Leu
            340                 345                 350

Glu Val Val Gln Lys Asp Ser Cys Phe Asn Ser Pro Met Lys Leu Pro
            355                 360                 365

Val His Lys Leu Tyr Ile Glu Tyr Gly Ile Gln Arg Ile Thr Cys Pro
370                 375                 380

Asn Val Asp Gly Tyr Phe Pro Ser Ser Val Lys Pro Thr Ile Thr Trp
385                 390                 395                 400

Tyr Met Gly Cys Tyr Lys Ile Gln Asn Phe Asn Asn Val Ile Pro Glu
            405                 410                 415

Gly Met Asn Leu Ser Phe Leu Ile Ala Leu Ile Ser Asn Asn Gly Asn
            420                 425                 430

Tyr Thr Cys Val Val Thr Tyr Pro Glu Asn Gly Arg Thr Phe His Leu
            435                 440                 445

Thr Arg Thr Leu Thr Val Lys Val Val Gly Ser Pro Lys Asn Ala Val
450                 455                 460

Pro Pro Val Ile His Ser Pro Asn Asp His Val Val Tyr Glu Lys Glu
465                 470                 475                 480

Pro Gly Glu Glu Leu Leu Ile Pro Cys Thr Val Tyr Phe Ser Phe Leu
            485                 490                 495

Met Asp Ser Arg Asn Glu Val Trp Trp Thr Ile Asp Gly Lys Lys Pro
            500                 505                 510

Asp Asp Ile Thr Ile Asp Val Thr Ile Asn Glu Ser Ile Ser His Ser
            515                 520                 525

Arg Thr Glu Asp Glu Thr Arg Thr Gln Ile Leu Ser Ile Lys Lys Val
            530                 535                 540

Thr Ser Glu Asp Leu Lys Arg Ser Tyr Val Cys His Ala Arg Ser Ala
545                 550                 555                 560

Lys Gly Glu Val Ala Lys Ala Ala Lys Val Lys Gln Lys Val Pro Ala
            565                 570                 575

Pro Arg Tyr Thr Val Glu Lys Cys Lys Glu Arg Glu Glu Lys Ile Ile
            580                 585                 590

Leu Val Ser Ser Ala Asn Glu Ile Asp Val Arg Pro Cys Pro Leu Asn
            595                 600                 605

Pro Asn Glu His Lys Gly Thr Ile Thr Trp Tyr Lys Asp Asp Ser Lys
            610                 615                 620

Thr Pro Val Ser Thr Glu Gln Ala Ser Arg Ile His Gln His Lys Glu
625                 630                 635                 640
```

```
Lys Leu Trp Phe Val Pro Ala Lys Val Glu Asp Ser Gly His Tyr Tyr
                645                 650                 655

Cys Val Val Arg Asn Ser Ser Tyr Cys Leu Arg Ile Lys Ile Ser Ala
            660                 665                 670

Lys Phe Val Glu Asn Glu Pro Asn Leu Cys Tyr Asn Ala Gln Ala Ile
        675                 680                 685

Phe Lys Gln Lys Leu Pro Val Ala Gly Asp Gly Gly Leu Val Cys Pro
    690                 695                 700

Tyr Met Glu Phe Phe Lys Asn Glu Asn Asn Glu Leu Pro Lys Leu Gln
705                 710                 715                 720

Trp Tyr Lys Asp Cys Lys Pro Leu Leu Leu Asp Asn Ile His Phe Ser
                725                 730                 735

Gly Val Lys Asp Arg Leu Ile Val Met Asn Val Ala Glu Lys His Arg
            740                 745                 750

Gly Asn Tyr Thr Cys His Ala Ser Tyr Thr Tyr Leu Gly Lys Gln Tyr
        755                 760                 765

Pro Ile Thr Arg Val Ile Glu Phe Ile Thr Leu Glu Glu Asn Lys Pro
    770                 775                 780

Thr Arg Pro Val Ile Val Ser Pro Ala Asn Glu Thr Met Glu Val Asp
785                 790                 795                 800

Leu Gly Ser Gln Ile Gln Leu Ile Cys Asn Val Thr Gly Gln Leu Ser
                805                 810                 815

Asp Ile Ala Tyr Trp Lys Trp Asn Gly Ser Val Ile Asp Glu Asp Asp
            820                 825                 830

Pro Val Leu Gly Glu Asp Tyr Tyr Ser Val Glu Asn Pro Ala Asn Lys
        835                 840                 845

Arg Arg Ser Thr Leu Ile Thr Val Leu Asn Ile Ser Glu Ile Glu Ser
    850                 855                 860

Arg Phe Tyr Lys His Pro Phe Thr Cys Phe Ala Lys Asn Thr His Gly
865                 870                 875                 880

Ile Asp Ala Ala Tyr Ile Gln Leu Ile Tyr Pro Val Thr Asn Ser Gly
                885                 890                 895

Asp Lys Thr His Thr Cys Pro Pro Cys Pro Ala Pro Glu Phe Leu Gly
            900                 905                 910

Gly Pro Ser Val Phe Leu Phe Pro Pro Lys Pro Lys Asp Thr Leu Met
        915                 920                 925

Ile Ser Arg Thr Pro Glu Val Thr Cys Val Val Val Asp Val Ser Gln
    930                 935                 940

Glu Asp Pro Glu Val Gln Phe Asn Trp Tyr Val Asp Gly Val Glu Val
945                 950                 955                 960

His Asn Ala Lys Thr Lys Pro Arg Glu Glu Gln Phe Asn Ser Thr Tyr
                965                 970                 975

Arg Val Val Ser Val Leu Thr Val Leu His Gln Asp Trp Leu Asn Gly
            980                 985                 990

Lys Glu Tyr Lys Cys Lys Val Ser Asn Lys Gly Leu Pro Ser Ser Ile
        995                 1000                1005

Glu Lys Thr Ile Ser Lys Ala Lys Gly Gln Pro Arg Glu Pro Gln
    1010                1015                1020

Val Tyr Thr Leu Pro Pro Ser Gln Glu Glu Met Thr Lys Asn Gln
    1025                1030                1035

Val Ser Leu Thr Cys Leu Val Lys Gly Phe Tyr Pro Ser Asp Ile
    1040                1045                1050
```

```
Ala Val Glu Trp Glu Ser Asn Gly Gln Pro Glu Asn Asn Tyr Lys
    1055                1060                1065

Thr Thr Pro Pro Val Leu Asp Ser Asp Gly Ser Phe Phe Leu Tyr
    1070                1075                1080

Ser Arg Leu Thr Val Asp Lys Ser Arg Trp Gln Glu Gly Asn Val
    1085                1090                1095

Phe Ser Cys Ser Val Met His Glu Ala Leu His Asn His Tyr Thr
    1100                1105                1110

Gln Lys Ser Leu Ser Leu Ser Leu Gly Lys
    1115                1120

<210> SEQ ID NO 99
<211> LENGTH: 1130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Gly Trp Ser Cys Ile Ile Leu Phe Leu Val Ala Thr Ala Thr Gly
1               5                   10                  15

Val His Ser Gln Val Gln Leu Val Gln Ser Gly Val Glu Val Lys Lys
                20                  25                  30

Pro Gly Ala Ser Val Lys Val Ser Cys Lys Ala Ser Gly Tyr Thr Phe
            35                  40                  45

Thr Asn Tyr Tyr Met Tyr Trp Val Arg Gln Ala Pro Gly Gln Gly Leu
        50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Gly Gly Gly Ser Gly Gly Gly Ser Glu Arg Cys Asp Asp
                245                 250                 255

Trp Gly Leu Asp Thr Met Arg Gln Ile Gln Val Phe Glu Asp Glu Pro
            260                 265                 270
```

```
Ala Arg Ile Lys Cys Pro Leu Phe Glu His Phe Leu Lys Phe Asn Tyr
        275                 280                 285

Ser Thr Ala His Ser Ala Gly Leu Thr Leu Ile Trp Tyr Trp Thr Arg
    290                 295                 300

Gln Asp Arg Asp Leu Glu Glu Pro Ile Asn Phe Arg Leu Pro Glu Asn
305                 310                 315                 320

Arg Ile Ser Lys Glu Lys Asp Val Leu Trp Phe Arg Pro Thr Leu Leu
                325                 330                 335

Asn Asp Thr Gly Asn Tyr Thr Cys Met Leu Arg Asn Thr Thr Tyr Cys
            340                 345                 350

Ser Lys Val Ala Phe Pro Leu Glu Val Val Gln Lys Asp Ser Cys Phe
        355                 360                 365

Asn Ser Pro Met Lys Leu Pro Val His Lys Leu Tyr Ile Glu Tyr Gly
370                 375                 380

Ile Gln Arg Ile Thr Cys Pro Asn Val Asp Gly Tyr Phe Pro Ser Ser
385                 390                 395                 400

Val Lys Pro Thr Ile Thr Trp Tyr Met Gly Cys Tyr Lys Ile Gln Asn
                405                 410                 415

Phe Asn Asn Val Ile Pro Glu Gly Met Asn Leu Ser Phe Leu Ile Ala
            420                 425                 430

Leu Ile Ser Asn Asn Gly Asn Tyr Thr Cys Val Val Thr Tyr Pro Glu
        435                 440                 445

Asn Gly Arg Thr Phe His Leu Thr Arg Thr Leu Thr Val Lys Val Val
450                 455                 460

Gly Ser Pro Lys Asn Ala Val Pro Pro Val Ile His Ser Pro Asn Asp
465                 470                 475                 480

His Val Val Tyr Glu Lys Glu Pro Gly Glu Glu Leu Leu Ile Pro Cys
                485                 490                 495

Thr Val Tyr Phe Ser Phe Leu Met Asp Ser Arg Asn Glu Val Trp Trp
            500                 505                 510

Thr Ile Asp Gly Lys Lys Pro Asp Asp Ile Thr Ile Asp Val Thr Ile
        515                 520                 525

Asn Glu Ser Ile Ser His Ser Arg Thr Glu Asp Glu Thr Arg Thr Gln
530                 535                 540

Ile Leu Ser Ile Lys Lys Val Thr Ser Glu Asp Leu Lys Arg Ser Tyr
545                 550                 555                 560

Val Cys His Ala Arg Ser Ala Lys Gly Glu Val Ala Lys Ala Ala Lys
                565                 570                 575

Val Lys Gln Lys Val Pro Ala Pro Arg Tyr Thr Val Glu Lys Cys Lys
            580                 585                 590

Glu Arg Glu Glu Lys Ile Ile Leu Val Ser Ser Ala Asn Glu Ile Asp
        595                 600                 605

Val Arg Pro Cys Pro Leu Asn Pro Asn Glu His Lys Gly Thr Ile Thr
610                 615                 620

Trp Tyr Lys Asp Asp Ser Lys Thr Pro Val Ser Thr Glu Gln Ala Ser
625                 630                 635                 640

Arg Ile His Gln His Lys Glu Lys Leu Trp Phe Val Pro Ala Lys Val
                645                 650                 655

Glu Asp Ser Gly His Tyr Tyr Cys Val Val Arg Asn Ser Ser Tyr Cys
            660                 665                 670

Leu Arg Ile Lys Ile Ser Ala Lys Phe Val Glu Asn Glu Pro Asn Leu
        675                 680                 685
```

-continued

```
Cys Tyr Asn Ala Gln Ala Ile Phe Lys Gln Lys Leu Pro Val Ala Gly
    690                 695                 700

Asp Gly Gly Leu Val Cys Pro Tyr Met Glu Phe Phe Lys Asn Glu Asn
705                 710                 715                 720

Asn Glu Leu Pro Lys Leu Gln Trp Tyr Lys Asp Cys Lys Pro Leu Leu
                725                 730                 735

Leu Asp Asn Ile His Phe Ser Gly Val Lys Asp Arg Leu Ile Val Met
                740                 745                 750

Asn Val Ala Glu Lys His Arg Gly Asn Tyr Thr Cys His Ala Ser Tyr
                755                 760                 765

Thr Tyr Leu Gly Lys Gln Tyr Pro Ile Thr Arg Val Ile Glu Phe Ile
770                 775                 780

Thr Leu Glu Glu Asn Lys Pro Thr Arg Pro Val Ile Val Ser Pro Ala
785                 790                 795                 800

Asn Glu Thr Met Glu Val Asp Leu Gly Ser Gln Ile Gln Leu Ile Cys
                805                 810                 815

Asn Val Thr Gly Gln Leu Ser Asp Ile Ala Tyr Trp Lys Trp Asn Gly
                820                 825                 830

Ser Val Ile Asp Glu Asp Asp Pro Val Leu Gly Glu Asp Tyr Tyr Ser
                835                 840                 845

Val Glu Asn Pro Ala Asn Lys Arg Arg Ser Thr Leu Ile Thr Val Leu
850                 855                 860

Asn Ile Ser Glu Ile Glu Ser Arg Phe Tyr Lys His Pro Phe Thr Cys
865                 870                 875                 880

Phe Ala Lys Asn Thr His Gly Ile Asp Ala Ala Tyr Ile Gln Leu Ile
                885                 890                 895

Tyr Pro Val Thr Asn Ser Gly Asp Lys Thr His Thr Cys Pro Pro Cys
                900                 905                 910

Pro Ala Pro Glu Phe Leu Gly Gly Pro Ser Val Phe Leu Phe Pro Pro
            915                 920                 925

Lys Pro Lys Asp Thr Leu Met Ile Ser Arg Thr Pro Glu Val Thr Cys
            930                 935                 940

Val Val Val Asp Val Ser Gln Glu Asp Pro Glu Val Gln Phe Asn Trp
945                 950                 955                 960

Tyr Val Asp Gly Val Glu Val His Asn Ala Lys Thr Lys Pro Arg Glu
                965                 970                 975

Glu Gln Phe Asn Ser Thr Tyr Arg Val Val Ser Val Leu Thr Val Leu
                980                 985                 990

His Gln Asp Trp Leu Asn Gly Lys Glu Tyr Lys Cys Lys Val Ser Asn
            995                 1000                1005

Lys Gly Leu Pro Ser Ser Ile Glu Lys Thr Ile Ser Lys Ala Lys
    1010                1015                1020

Gly Gln Pro Arg Glu Pro Gln Val Tyr Thr Leu Pro Pro Ser Gln
    1025                1030                1035

Glu Glu Met Thr Lys Asn Gln Val Ser Leu Thr Cys Leu Val Lys
    1040                1045                1050

Gly Phe Tyr Pro Ser Asp Ile Ala Val Glu Trp Glu Ser Asn Gly
    1055                1060                1065

Gln Pro Glu Asn Asn Tyr Lys Thr Thr Pro Pro Val Leu Asp Ser
    1070                1075                1080

Asp Gly Ser Phe Phe Leu Tyr Ser Arg Leu Thr Val Asp Lys Ser
    1085                1090                1095
```

```
Arg Trp Gln Glu Gly Asn Val Phe Ser Cys Ser Val Met His Glu
    1100                1105                1110

Ala Leu His Asn His Tyr Thr Gln Lys Ser Leu Ser Leu Ser Leu
    1115                1120                1125

Gly Lys
    1130

<210> SEQ ID NO 100
<211> LENGTH: 1149
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Gly Trp Ser Cys Ile Ile Leu Phe Leu Val Ala Thr Ala Thr Gly
1               5                   10                  15

Val His Ser Ser Glu Arg Cys Asp Asp Trp Gly Leu Asp Thr Met Arg
                20                  25                  30

Gln Ile Gln Val Phe Glu Asp Glu Pro Ala Arg Ile Lys Cys Pro Leu
            35                  40                  45

Phe Glu His Phe Leu Lys Phe Asn Tyr Ser Thr Ala His Ser Ala Gly
50                  55                  60

Leu Thr Leu Ile Trp Tyr Trp Thr Arg Gln Asp Arg Asp Leu Glu Glu
65                  70                  75                  80

Pro Ile Asn Phe Arg Leu Pro Glu Asn Arg Ile Ser Lys Glu Lys Asp
                85                  90                  95

Val Leu Trp Phe Arg Pro Thr Leu Leu Asn Asp Thr Gly Asn Tyr Thr
            100                 105                 110

Cys Met Leu Arg Asn Thr Thr Tyr Cys Ser Lys Val Ala Phe Pro Leu
        115                 120                 125

Glu Val Val Gln Lys Asp Ser Cys Phe Asn Ser Pro Met Lys Leu Pro
130                 135                 140

Val His Lys Leu Tyr Ile Glu Tyr Gly Ile Gln Arg Ile Thr Cys Pro
145                 150                 155                 160

Asn Val Asp Gly Tyr Phe Pro Ser Ser Val Lys Pro Thr Ile Thr Trp
                165                 170                 175

Tyr Met Gly Cys Tyr Lys Ile Gln Asn Phe Asn Asn Val Ile Pro Glu
            180                 185                 190

Gly Met Asn Leu Ser Phe Leu Ile Ala Leu Ile Ser Asn Asn Gly Asn
        195                 200                 205

Tyr Thr Cys Val Val Thr Tyr Pro Glu Asn Gly Arg Thr Phe His Leu
210                 215                 220

Thr Arg Thr Leu Thr Val Lys Val Val Gly Ser Pro Lys Asn Ala Val
225                 230                 235                 240

Pro Pro Val Ile His Ser Pro Asn Asp His Val Val Tyr Glu Lys Glu
                245                 250                 255

Pro Gly Glu Glu Leu Leu Ile Pro Cys Thr Val Tyr Phe Ser Phe Leu
            260                 265                 270

Met Asp Ser Arg Asn Glu Val Trp Trp Thr Ile Asp Gly Lys Lys Pro
        275                 280                 285

Asp Asp Ile Thr Ile Asp Val Thr Ile Asn Glu Ser Ile Ser His Ser
290                 295                 300
```

```
Arg Thr Glu Asp Glu Thr Arg Thr Gln Ile Leu Ser Ile Lys Lys Val
305                 310                 315                 320

Thr Ser Glu Asp Leu Lys Arg Ser Tyr Val Cys His Ala Arg Ser Ala
            325                 330                 335

Lys Gly Glu Val Ala Lys Ala Ala Lys Val Lys Gln Lys Val Pro Ala
        340                 345                 350

Pro Arg Tyr Thr Val Glu Lys Cys Lys Glu Arg Glu Lys Ile Ile
            355                 360                 365

Leu Val Ser Ser Ala Asn Glu Ile Asp Val Arg Pro Cys Pro Leu Asn
    370                 375                 380

Pro Asn Glu His Lys Gly Thr Ile Thr Trp Tyr Lys Asp Asp Ser Lys
385                 390                 395                 400

Thr Pro Val Ser Thr Glu Gln Ala Ser Arg Ile His Gln His Lys Glu
            405                 410                 415

Lys Leu Trp Phe Val Pro Ala Lys Val Glu Asp Ser Gly His Tyr Tyr
                420                 425                 430

Cys Val Val Arg Asn Ser Ser Tyr Cys Leu Arg Ile Lys Ile Ser Ala
        435                 440                 445

Lys Phe Val Glu Asn Glu Pro Asn Leu Cys Tyr Asn Ala Gln Ala Ile
    450                 455                 460

Phe Lys Gln Lys Leu Pro Val Ala Gly Asp Gly Gly Leu Val Cys Pro
465                 470                 475                 480

Tyr Met Glu Phe Phe Lys Asn Glu Asn Asn Glu Leu Pro Lys Leu Gln
                485                 490                 495

Trp Tyr Lys Asp Cys Lys Pro Leu Leu Asp Asn Ile His Phe Ser
        500                 505                 510

Gly Val Lys Asp Arg Leu Ile Val Met Asn Val Ala Glu Lys His Arg
    515                 520                 525

Gly Asn Tyr Thr Cys His Ala Ser Tyr Thr Tyr Leu Gly Lys Gln Tyr
530                 535                 540

Pro Ile Thr Arg Val Ile Glu Phe Ile Thr Leu Glu Glu Asn Lys Pro
545                 550                 555                 560

Thr Arg Pro Val Ile Val Ser Pro Ala Asn Glu Thr Met Glu Val Asp
                565                 570                 575

Leu Gly Ser Gln Ile Gln Leu Ile Cys Asn Val Thr Gly Gln Leu Ser
            580                 585                 590

Asp Ile Ala Tyr Trp Lys Trp Asn Gly Ser Val Ile Asp Glu Asp Asp
        595                 600                 605

Pro Val Leu Gly Glu Asp Tyr Tyr Ser Val Glu Asn Pro Ala Asn Lys
    610                 615                 620

Arg Arg Ser Thr Leu Ile Thr Val Leu Asn Ile Ser Glu Ile Glu Ser
625                 630                 635                 640

Arg Phe Tyr Lys His Pro Phe Thr Cys Phe Ala Lys Asn Thr His Gly
                645                 650                 655

Ile Asp Ala Ala Tyr Ile Gln Leu Ile Tyr Pro Val Thr Asn Ser Gly
            660                 665                 670

Asp Lys Thr His Thr Cys Pro Pro Cys Pro Ala Pro Glu Phe Leu Gly
        675                 680                 685

Gly Pro Ser Val Phe Leu Phe Pro Pro Lys Pro Lys Asp Thr Leu Met
    690                 695                 700

Ile Ser Arg Thr Pro Glu Val Thr Cys Val Val Val Asp Val Ser Gln
705                 710                 715                 720
```

```
Glu Asp Pro Glu Val Gln Phe Asn Trp Tyr Val Asp Gly Val Glu Val
                725                 730                 735

His Asn Ala Lys Thr Lys Pro Arg Glu Glu Gln Phe Asn Ser Thr Tyr
            740                 745                 750

Arg Val Val Ser Val Leu Thr Val Leu His Gln Asp Trp Leu Asn Gly
        755                 760                 765

Lys Glu Tyr Lys Cys Lys Val Ser Asn Lys Gly Leu Pro Ser Ser Ile
770                 775                 780

Glu Lys Thr Ile Ser Lys Ala Lys Gly Gln Pro Arg Glu Pro Gln Val
785                 790                 795                 800

Tyr Thr Leu Pro Pro Ser Gln Glu Glu Met Thr Lys Asn Gln Val Ser
                805                 810                 815

Leu Thr Cys Leu Val Lys Gly Phe Tyr Pro Ser Asp Ile Ala Val Glu
            820                 825                 830

Trp Glu Ser Asn Gly Gln Pro Glu Asn Asn Tyr Lys Thr Thr Pro Pro
        835                 840                 845

Val Leu Asp Ser Asp Gly Ser Phe Phe Leu Tyr Ser Arg Leu Thr Val
    850                 855                 860

Asp Lys Ser Arg Trp Gln Glu Gly Asn Val Phe Ser Cys Ser Val Met
865                 870                 875                 880

His Glu Ala Leu His Asn His Tyr Thr Gln Lys Ser Leu Ser Leu Ser
                885                 890                 895

Leu Gly Lys Gly Gly Gly Gly Ser Gly Gly Gly Gly Ser Gln Val Gln
            900                 905                 910

Leu Val Glu Ser Gly Gly Gly Val Val Gln Pro Gly Arg Ser Leu Arg
        915                 920                 925

Leu Asp Cys Lys Ala Ser Gly Ile Thr Phe Ser Asn Ser Gly Met His
    930                 935                 940

Trp Val Arg Gln Ala Pro Gly Lys Gly Leu Glu Trp Val Ala Val Ile
945                 950                 955                 960

Trp Tyr Asp Gly Ser Lys Arg Tyr Tyr Ala Asp Ser Val Lys Gly Arg
                965                 970                 975

Phe Thr Ile Ser Arg Asp Asn Ser Lys Asn Thr Leu Phe Leu Gln Met
            980                 985                 990

Asn Ser Leu Arg Ala Glu Asp Thr Ala Val Tyr Tyr Cys Ala Thr Asn
        995                 1000                1005

Asp Asp Tyr Trp Gly Gln Gly Thr Leu Val Thr Val Ser Ser Gly
    1010                1015                1020

Gly Gly Gly Ser Gly Gly Gly Gly Ser Gly Gly Gly Gly Ser Gly
    1025                1030                1035

Gly Gly Gly Ser Glu Ile Val Leu Thr Gln Ser Pro Ala Thr Leu
    1040                1045                1050

Ser Leu Ser Pro Gly Glu Arg Ala Thr Leu Ser Cys Arg Ala Ser
    1055                1060                1065

Gln Ser Val Ser Ser Tyr Leu Ala Trp Tyr Gln Gln Lys Pro Gly
    1070                1075                1080

Gln Ala Pro Arg Leu Leu Ile Tyr Asp Ala Ser Asn Arg Ala Thr
    1085                1090                1095

Gly Ile Pro Ala Arg Phe Ser Gly Ser Gly Ser Gly Thr Asp Phe
    1100                1105                1110

Thr Leu Thr Ile Ser Ser Leu Glu Pro Glu Asp Phe Ala Val Tyr
    1115                1120                1125
```

Tyr Cys Gln Gln Ser Ser Asn Trp Pro Arg Thr Phe Gly Gln Gly
1130                1135                1140

Thr Lys Val Glu Ile Lys
    1145

<210> SEQ ID NO 101
<211> LENGTH: 1123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Gly Trp Ser Cys Ile Ile Leu Phe Leu Val Ala Thr Ala Thr Gly
1               5                   10                  15

Val His Ser Ser Glu Arg Cys Asp Asp Trp Gly Leu Asp Thr Met Arg
            20                  25                  30

Gln Ile Gln Val Phe Glu Asp Glu Pro Ala Arg Ile Lys Cys Pro Leu
        35                  40                  45

Phe Glu His Phe Leu Lys Phe Asn Tyr Ser Thr Ala His Ser Ala Gly
50                  55                  60

Leu Thr Leu Ile Trp Tyr Trp Thr Arg Gln Asp Arg Asp Leu Glu Glu
65                  70                  75                  80

Pro Ile Asn Phe Arg Leu Pro Glu Asn Arg Ile Ser Lys Glu Lys Asp
                85                  90                  95

Val Leu Trp Phe Arg Pro Thr Leu Leu Asn Asp Thr Gly Asn Tyr Thr
            100                 105                 110

Cys Met Leu Arg Asn Thr Thr Tyr Cys Ser Lys Val Ala Phe Pro Leu
        115                 120                 125

Glu Val Val Gln Lys Asp Ser Cys Phe Asn Ser Pro Met Lys Leu Pro
130                 135                 140

Val His Lys Leu Tyr Ile Glu Tyr Gly Ile Gln Arg Ile Thr Cys Pro
145                 150                 155                 160

Asn Val Asp Gly Tyr Phe Pro Ser Ser Val Lys Pro Thr Ile Thr Trp
                165                 170                 175

Tyr Met Gly Cys Tyr Lys Ile Gln Asn Phe Asn Asn Val Ile Pro Glu
            180                 185                 190

Gly Met Asn Leu Ser Phe Leu Ile Ala Leu Ile Ser Asn Asn Gly Asn
        195                 200                 205

Tyr Thr Cys Val Val Thr Tyr Pro Glu Asn Gly Arg Thr Phe His Leu
210                 215                 220

Thr Arg Thr Leu Thr Val Lys Val Val Gly Ser Pro Lys Asn Ala Val
225                 230                 235                 240

Pro Pro Val Ile His Ser Pro Asn Asp His Val Val Tyr Glu Lys Glu
                245                 250                 255

Pro Gly Glu Glu Leu Leu Ile Pro Cys Thr Val Tyr Phe Ser Phe Leu
            260                 265                 270

Met Asp Ser Arg Asn Glu Val Trp Trp Thr Ile Asp Gly Lys Lys Pro
        275                 280                 285

Asp Asp Ile Thr Ile Asp Val Thr Ile Asn Glu Ser Ile Ser His Ser
290                 295                 300

Arg Thr Glu Asp Glu Thr Arg Thr Gln Ile Leu Ser Ile Lys Lys Val
305                 310                 315                 320

```
Thr Ser Glu Asp Leu Lys Arg Ser Tyr Val Cys His Ala Arg Ser Ala
            325                 330                 335

Lys Gly Glu Val Ala Lys Ala Ala Lys Val Lys Gln Lys Val Pro Ala
        340                 345                 350

Pro Arg Tyr Thr Val Glu Lys Cys Lys Glu Arg Glu Glu Lys Ile Ile
        355                 360                 365

Leu Val Ser Ser Ala Asn Glu Ile Asp Val Arg Pro Cys Pro Leu Asn
        370                 375                 380

Pro Asn Glu His Lys Gly Thr Ile Thr Trp Tyr Lys Asp Asp Ser Lys
385                 390                 395                 400

Thr Pro Val Ser Thr Glu Gln Ala Ser Arg Ile His Gln His Lys Glu
            405                 410                 415

Lys Leu Trp Phe Val Pro Ala Lys Val Glu Asp Ser Gly His Tyr Tyr
            420                 425                 430

Cys Val Val Arg Asn Ser Ser Tyr Cys Leu Arg Ile Lys Ile Ser Ala
            435                 440                 445

Lys Phe Val Glu Asn Glu Pro Asn Leu Cys Tyr Asn Ala Gln Ala Ile
            450                 455                 460

Phe Lys Gln Lys Leu Pro Val Ala Gly Asp Gly Gly Leu Val Cys Pro
465                 470                 475                 480

Tyr Met Glu Phe Phe Lys Asn Glu Asn Asn Glu Leu Pro Lys Leu Gln
            485                 490                 495

Trp Tyr Lys Asp Cys Lys Pro Leu Leu Leu Asp Asn Ile His Phe Ser
            500                 505                 510

Gly Val Lys Asp Arg Leu Ile Val Met Asn Val Ala Glu Lys His Arg
            515                 520                 525

Gly Asn Tyr Thr Cys His Ala Ser Tyr Thr Tyr Leu Gly Lys Gln Tyr
            530                 535                 540

Pro Ile Thr Arg Val Ile Glu Phe Ile Thr Leu Glu Glu Asn Lys Pro
545                 550                 555                 560

Thr Arg Pro Val Ile Val Ser Pro Ala Asn Glu Thr Met Glu Val Asp
            565                 570                 575

Leu Gly Ser Gln Ile Gln Leu Ile Cys Asn Val Thr Gly Gln Leu Ser
            580                 585                 590

Asp Ile Ala Tyr Trp Lys Trp Asn Gly Ser Val Ile Asp Glu Asp Asp
            595                 600                 605

Pro Val Leu Gly Glu Asp Tyr Tyr Ser Val Glu Asn Pro Ala Asn Lys
            610                 615                 620

Arg Arg Ser Thr Leu Ile Thr Val Leu Asn Ile Ser Glu Ile Glu Ser
625                 630                 635                 640

Arg Phe Tyr Lys His Pro Phe Thr Cys Phe Ala Lys Asn Thr His Gly
            645                 650                 655

Ile Asp Ala Ala Tyr Ile Gln Leu Ile Tyr Pro Val Thr Asn Gly Gly
            660                 665                 670

Gly Gly Ser Gly Gly Gly Ser Glu Ile Val Leu Thr Gln Ser Pro
            675                 680                 685

Ala Thr Leu Ser Leu Ser Pro Gly Glu Arg Ala Thr Leu Ser Cys Arg
            690                 695                 700

Ala Ser Lys Gly Val Ser Thr Ser Gly Tyr Ser Tyr Leu His Trp Tyr
705                 710                 715                 720

Gln Gln Lys Pro Gly Gln Ala Pro Arg Leu Leu Ile Tyr Leu Ala Ser
            725                 730                 735
```

-continued

```
Tyr Leu Glu Ser Gly Val Pro Ala Arg Phe Ser Gly Ser Gly
            740                 745                 750

Thr Asp Phe Thr Leu Thr Ile Ser Ser Leu Glu Pro Glu Asp Phe Ala
        755                 760                 765

Val Tyr Tyr Cys Gln His Ser Arg Asp Leu Pro Leu Thr Phe Gly Gly
770                 775                 780

Gly Thr Lys Val Glu Ile Lys Arg Thr Val Ala Ala Pro Ser Val Phe
785                 790                 795                 800

Ile Phe Pro Pro Ser Asp Glu Gln Leu Lys Ser Gly Thr Ala Ser Val
                805                 810                 815

Val Cys Leu Leu Asn Asn Phe Tyr Pro Arg Glu Ala Lys Val Gln Trp
            820                 825                 830

Lys Val Asp Asn Ala Leu Gln Ser Gly Asn Ser Gln Glu Ser Val Thr
        835                 840                 845

Glu Gln Asp Ser Lys Asp Ser Thr Tyr Ser Leu Ser Ser Thr Leu Thr
    850                 855                 860

Leu Ser Lys Ala Asp Tyr Glu Lys His Lys Val Tyr Ala Cys Glu Val
865                 870                 875                 880

Thr His Gln Gly Leu Ser Ser Pro Val Thr Lys Ser Phe Asn Arg Gly
                885                 890                 895

Glu Cys Gly Pro Pro Cys Pro Pro Cys Pro Ala Pro Glu Phe Leu Gly
            900                 905                 910

Gly Pro Ser Val Phe Leu Phe Pro Pro Lys Pro Lys Asp Thr Leu Met
        915                 920                 925

Ile Ser Arg Thr Pro Glu Val Thr Cys Val Val Val Asp Val Ser Gln
    930                 935                 940

Glu Asp Pro Glu Val Gln Phe Asn Trp Tyr Val Asp Gly Val Glu Val
945                 950                 955                 960

His Asn Ala Lys Thr Lys Pro Arg Glu Glu Gln Phe Asn Ser Thr Tyr
                965                 970                 975

Arg Val Val Ser Val Leu Thr Val Leu His Gln Asp Trp Leu Asn Gly
            980                 985                 990

Lys Glu Tyr Lys Cys Lys Val Ser  Asn Lys Gly Leu Pro  Ser Ser Ile
        995                 1000                1005

Glu Lys  Thr Ile Ser Lys Ala  Lys Gly Gln Pro Arg  Glu Pro Gln
    1010                1015                1020

Val Tyr  Thr Leu Pro Pro Ser  Gln Glu Glu Met Thr  Lys Asn Gln
    1025                1030                1035

Val Ser  Leu Thr Cys Leu Val  Lys Gly Phe Tyr Pro  Ser Asp Ile
    1040                1045                1050

Ala Val  Glu Trp Glu Ser Asn  Gly Gln Pro Glu Asn  Asn Tyr Lys
    1055                1060                1065

Thr Thr  Pro Pro Val Leu Asp  Ser Asp Gly Ser Phe  Phe Leu Tyr
    1070                1075                1080

Ser Arg  Leu Thr Val Asp Lys  Ser Arg Trp Gln Glu  Gly Asn Val
    1085                1090                1095

Phe Ser  Cys Ser Val Met His  Glu Ala Leu His Asn  His Tyr Thr
    1100                1105                1110

Gln Lys  Ser Leu Ser Leu Ser  Leu Gly Lys
    1115                1120

<210> SEQ ID NO 102
<211> LENGTH: 1119
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 102

```
Met Gly Trp Ser Cys Ile Ile Leu Phe Leu Val Ala Thr Ala Thr Gly
1               5                   10                  15

Val His Ser Ser Glu Arg Cys Asp Asp Trp Gly Leu Asp Thr Met Arg
            20                  25                  30

Gln Ile Gln Val Phe Glu Asp Glu Pro Ala Arg Ile Lys Cys Pro Leu
        35                  40                  45

Phe Glu His Phe Leu Lys Phe Asn Tyr Ser Thr Ala His Ser Ala Gly
    50                  55                  60

Leu Thr Leu Ile Trp Tyr Trp Thr Arg Gln Asp Arg Asp Leu Glu Glu
65                  70                  75                  80

Pro Ile Asn Phe Arg Leu Pro Glu Asn Arg Ile Ser Lys Glu Lys Asp
                85                  90                  95

Val Leu Trp Phe Arg Pro Thr Leu Leu Asn Asp Thr Gly Asn Tyr Thr
            100                 105                 110

Cys Met Leu Arg Asn Thr Thr Tyr Cys Ser Lys Val Ala Phe Pro Leu
        115                 120                 125

Glu Val Val Gln Lys Asp Ser Cys Phe Asn Ser Pro Met Lys Leu Pro
    130                 135                 140

Val His Lys Leu Tyr Ile Glu Tyr Gly Ile Gln Arg Ile Thr Cys Pro
145                 150                 155                 160

Asn Val Asp Gly Tyr Phe Pro Ser Ser Val Lys Pro Thr Ile Thr Trp
                165                 170                 175

Tyr Met Gly Cys Tyr Lys Ile Gln Asn Phe Asn Asn Val Ile Pro Glu
            180                 185                 190

Gly Met Asn Leu Ser Phe Leu Ile Ala Leu Ile Ser Asn Asn Gly Asn
        195                 200                 205

Tyr Thr Cys Val Val Thr Tyr Pro Glu Asn Gly Arg Thr Phe His Leu
    210                 215                 220

Thr Arg Thr Leu Thr Val Lys Val Val Gly Ser Pro Lys Asn Ala Val
225                 230                 235                 240

Pro Pro Val Ile His Ser Pro Asn Asp His Val Val Tyr Glu Lys Glu
                245                 250                 255

Pro Gly Glu Glu Leu Leu Ile Pro Cys Thr Val Tyr Phe Ser Phe Leu
            260                 265                 270

Met Asp Ser Arg Asn Glu Val Trp Trp Thr Ile Asp Gly Lys Lys Pro
        275                 280                 285

Asp Asp Ile Thr Ile Asp Val Thr Ile Asn Glu Ser Ile Ser His Ser
    290                 295                 300

Arg Thr Glu Asp Glu Thr Arg Thr Gln Ile Leu Ser Ile Lys Lys Val
305                 310                 315                 320

Thr Ser Glu Asp Leu Lys Arg Ser Tyr Val Cys His Ala Arg Ser Ala
                325                 330                 335

Lys Gly Glu Val Ala Lys Ala Ala Lys Val Lys Gln Lys Val Pro Ala
            340                 345                 350

Pro Arg Tyr Thr Val Glu Lys Cys Lys Glu Arg Glu Glu Lys Ile Ile
        355                 360                 365

Leu Val Ser Ser Ala Asn Glu Ile Asp Val Arg Pro Cys Pro Leu Asn
    370                 375                 380
```

-continued

```
Pro Asn Glu His Lys Gly Thr Ile Thr Trp Tyr Lys Asp Asp Ser Lys
385                 390                 395                 400

Thr Pro Val Ser Thr Glu Gln Ala Ser Arg Ile His Gln His Lys Glu
                405                 410                 415

Lys Leu Trp Phe Val Pro Ala Lys Val Glu Asp Ser Gly His Tyr Tyr
                420                 425                 430

Cys Val Val Arg Asn Ser Ser Tyr Cys Leu Arg Ile Lys Ile Ser Ala
                435                 440                 445

Lys Phe Val Glu Asn Glu Pro Asn Leu Cys Tyr Asn Ala Gln Ala Ile
    450                 455                 460

Phe Lys Gln Lys Leu Pro Val Ala Gly Asp Gly Gly Leu Val Cys Pro
465                 470                 475                 480

Tyr Met Glu Phe Phe Lys Asn Glu Asn Asn Glu Leu Pro Lys Leu Gln
                485                 490                 495

Trp Tyr Lys Asp Cys Lys Pro Leu Leu Leu Asp Asn Ile His Phe Ser
                500                 505                 510

Gly Val Lys Asp Arg Leu Ile Val Met Asn Val Ala Glu Lys His Arg
                515                 520                 525

Gly Asn Tyr Thr Cys His Ala Ser Tyr Thr Tyr Leu Gly Lys Gln Tyr
530                 535                 540

Pro Ile Thr Arg Val Ile Glu Phe Ile Thr Leu Glu Glu Asn Lys Pro
545                 550                 555                 560

Thr Arg Pro Val Ile Val Ser Pro Ala Asn Glu Thr Met Glu Val Asp
                565                 570                 575

Leu Gly Ser Gln Ile Gln Leu Ile Cys Asn Val Thr Gly Gln Leu Ser
                580                 585                 590

Asp Ile Ala Tyr Trp Lys Trp Asn Gly Ser Val Ile Asp Glu Asp Asp
                595                 600                 605

Pro Val Leu Gly Glu Asp Tyr Tyr Ser Val Glu Asn Pro Ala Asn Lys
                610                 615                 620

Arg Arg Ser Thr Leu Ile Thr Val Leu Asn Ile Ser Glu Ile Glu Ser
625                 630                 635                 640

Arg Phe Tyr Lys His Pro Phe Thr Cys Phe Ala Lys Asn Thr His Gly
                645                 650                 655

Ile Asp Ala Ala Tyr Ile Gln Leu Ile Tyr Pro Val Thr Asn Gly Gly
                660                 665                 670

Gly Gly Ser Gly Gly Gly Ser Glu Ile Val Leu Thr Gln Ser Pro
                675                 680                 685

Ala Thr Leu Ser Leu Ser Pro Gly Glu Arg Ala Thr Leu Ser Cys Arg
690                 695                 700

Ala Ser Gln Ser Val Ser Ser Tyr Leu Ala Trp Tyr Gln Gln Lys Pro
705                 710                 715                 720

Gly Gln Ala Pro Arg Leu Leu Ile Tyr Asp Ala Ser Asn Arg Ala Thr
                725                 730                 735

Gly Ile Pro Ala Arg Phe Ser Gly Ser Gly Ser Gly Thr Asp Phe Thr
                740                 745                 750

Leu Thr Ile Ser Ser Leu Glu Pro Glu Asp Phe Ala Val Tyr Tyr Cys
                755                 760                 765

Gln Gln Ser Ser Asn Trp Pro Arg Thr Phe Gly Gln Gly Thr Lys Val
    770                 775                 780

Glu Ile Lys Arg Thr Val Ala Ala Pro Ser Val Phe Ile Phe Pro Pro
785                 790                 795                 800
```

Ser Asp Glu Gln Leu Lys Ser Gly Thr Ala Ser Val Cys Leu Leu
            805                 810                 815

Asn Asn Phe Tyr Pro Arg Glu Ala Lys Val Gln Trp Lys Val Asp Asn
        820                 825                 830

Ala Leu Gln Ser Gly Asn Ser Gln Glu Ser Val Thr Glu Gln Asp Ser
            835                 840                 845

Lys Asp Ser Thr Tyr Ser Leu Ser Ser Thr Leu Thr Leu Ser Lys Ala
    850                 855                 860

Asp Tyr Glu Lys His Lys Val Tyr Ala Cys Glu Val Thr His Gln Gly
865                 870                 875                 880

Leu Ser Ser Pro Val Thr Lys Ser Phe Asn Arg Gly Glu Cys Gly Pro
                885                 890                 895

Pro Cys Pro Pro Cys Pro Ala Pro Glu Phe Leu Gly Gly Pro Ser Val
            900                 905                 910

Phe Leu Phe Pro Pro Lys Pro Lys Asp Thr Leu Met Ile Ser Arg Thr
        915                 920                 925

Pro Glu Val Thr Cys Val Val Val Asp Val Ser Gln Glu Asp Pro Glu
    930                 935                 940

Val Gln Phe Asn Trp Tyr Val Asp Gly Val Glu Val His Asn Ala Lys
945                 950                 955                 960

Thr Lys Pro Arg Glu Glu Gln Phe Asn Ser Thr Tyr Arg Val Val Ser
                965                 970                 975

Val Leu Thr Val Leu His Gln Asp Trp Leu Asn Gly Lys Glu Tyr Lys
            980                 985                 990

Cys Lys Val Ser Asn Lys Gly Leu Pro Ser Ser Ile Glu Lys Thr Ile
        995                 1000                1005

Ser Lys Ala Lys Gly Gln Pro Arg Glu Pro Gln Val Tyr Thr Leu
    1010                1015                1020

Pro Pro Ser Gln Glu Glu Met Thr Lys Asn Gln Val Ser Leu Thr
    1025                1030                1035

Cys Leu Val Lys Gly Phe Tyr Pro Ser Asp Ile Ala Val Glu Trp
    1040                1045                1050

Glu Ser Asn Gly Gln Pro Glu Asn Asn Tyr Lys Thr Thr Pro Pro
    1055                1060                1065

Val Leu Asp Ser Asp Gly Ser Phe Phe Leu Tyr Ser Arg Leu Thr
    1070                1075                1080

Val Asp Lys Ser Arg Trp Gln Glu Gly Asn Val Phe Ser Cys Ser
    1085                1090                1095

Val Met His Glu Ala Leu His Asn His Tyr Thr Gln Lys Ser Leu
    1100                1105                1110

Ser Leu Ser Leu Gly Lys
    1115

<210> SEQ ID NO 103
<211> LENGTH: 1122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Gly Trp Ser Cys Ile Ile Leu Phe Leu Val Ala Thr Ala Thr Gly
1               5                   10                  15

```
Val His Ser Glu Ile Val Leu Thr Gln Ser Pro Ala Thr Leu Ser Leu
             20                  25                  30

Ser Pro Gly Glu Arg Ala Thr Leu Ser Cys Arg Ala Ser Gln Ser Val
         35                  40                  45

Ser Ser Tyr Leu Ala Trp Tyr Gln Gln Lys Pro Gly Gln Ala Pro Arg
 50                  55                  60

Leu Leu Ile Tyr Asp Ala Ser Asn Arg Ala Thr Gly Ile Pro Ala Arg
 65                  70                  75                  80

Phe Ser Gly Ser Gly Ser Gly Thr Asp Phe Thr Leu Thr Ile Ser Ser
                 85                  90                  95

Leu Glu Pro Glu Asp Phe Ala Val Tyr Tyr Cys Gln Gln Ser Ser Asn
             100                 105                 110

Trp Pro Arg Thr Phe Gly Gln Gly Thr Lys Val Glu Ile Lys Arg Thr
         115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                 165                 170                 175

Asn Ser Gln Glu Ser Val Thr Glu Gln Asp Ser Lys Asp Ser Thr Tyr
             180                 185                 190

Ser Leu Ser Ser Thr Leu Thr Leu Ser Lys Ala Asp Tyr Glu Lys His
         195                 200                 205

Lys Val Tyr Ala Cys Glu Val Thr His Gln Gly Leu Ser Ser Pro Val
210                 215                 220

Thr Lys Ser Phe Asn Arg Gly Glu Cys Gly Gly Gly Ser Gly Gly
225                 230                 235                 240

Gly Gly Ser Glu Arg Cys Asp Asp Trp Gly Leu Asp Thr Met Arg Gln
                 245                 250                 255

Ile Gln Val Phe Glu Asp Glu Pro Ala Arg Ile Lys Cys Pro Leu Phe
             260                 265                 270

Glu His Phe Leu Lys Phe Asn Tyr Ser Thr Ala His Ser Ala Gly Leu
         275                 280                 285

Thr Leu Ile Trp Tyr Trp Thr Arg Gln Asp Arg Asp Leu Glu Glu Pro
290                 295                 300

Ile Asn Phe Arg Leu Pro Glu Asn Arg Ile Ser Lys Glu Lys Asp Val
305                 310                 315                 320

Leu Trp Phe Arg Pro Thr Leu Leu Asn Asp Thr Gly Asn Tyr Thr Cys
                 325                 330                 335

Met Leu Arg Asn Thr Thr Tyr Cys Ser Lys Val Ala Phe Pro Leu Glu
             340                 345                 350

Val Val Gln Lys Asp Ser Cys Phe Asn Ser Pro Met Lys Leu Pro Val
         355                 360                 365

His Lys Leu Tyr Ile Glu Tyr Gly Ile Gln Arg Ile Thr Cys Pro Asn
370                 375                 380

Val Asp Gly Tyr Phe Pro Ser Ser Val Lys Pro Thr Ile Thr Trp Tyr
385                 390                 395                 400

Met Gly Cys Tyr Lys Ile Gln Asn Phe Asn Asn Val Ile Pro Glu Gly
                 405                 410                 415

Met Asn Leu Ser Phe Leu Ile Ala Leu Ile Ser Asn Asn Gly Asn Tyr
             420                 425                 430
```

```
Thr Cys Val Val Thr Tyr Pro Glu Asn Gly Arg Thr Phe His Leu Thr
            435                 440                 445

Arg Thr Leu Thr Val Lys Val Val Gly Ser Pro Lys Asn Ala Val Pro
450                 455                 460

Pro Val Ile His Ser Pro Asn Asp His Val Val Tyr Glu Lys Glu Pro
465                 470                 475                 480

Gly Glu Glu Leu Leu Ile Pro Cys Thr Val Tyr Phe Ser Phe Leu Met
                485                 490                 495

Asp Ser Arg Asn Glu Val Trp Trp Thr Ile Asp Gly Lys Lys Pro Asp
            500                 505                 510

Asp Ile Thr Ile Asp Val Thr Ile Asn Glu Ser Ile Ser His Ser Arg
        515                 520                 525

Thr Glu Asp Glu Thr Arg Thr Gln Ile Leu Ser Ile Lys Lys Val Thr
    530                 535                 540

Ser Glu Asp Leu Lys Arg Ser Tyr Val Cys His Ala Arg Ser Ala Lys
545                 550                 555                 560

Gly Glu Val Ala Lys Ala Ala Lys Val Lys Gln Lys Val Pro Ala Pro
                565                 570                 575

Arg Tyr Thr Val Glu Lys Cys Lys Glu Arg Glu Lys Ile Ile Leu
            580                 585                 590

Val Ser Ser Ala Asn Glu Ile Asp Val Arg Pro Cys Pro Leu Asn Pro
        595                 600                 605

Asn Glu His Lys Gly Thr Ile Thr Trp Tyr Lys Asp Asp Ser Lys Thr
    610                 615                 620

Pro Val Ser Thr Glu Gln Ala Ser Arg Ile His Gln His Lys Glu Lys
625                 630                 635                 640

Leu Trp Phe Val Pro Ala Lys Val Glu Asp Ser Gly His Tyr Tyr Cys
                645                 650                 655

Val Val Arg Asn Ser Ser Tyr Cys Leu Arg Ile Lys Ile Ser Ala Lys
            660                 665                 670

Phe Val Glu Asn Glu Pro Asn Leu Cys Tyr Asn Ala Gln Ala Ile Phe
        675                 680                 685

Lys Gln Lys Leu Pro Val Ala Gly Asp Gly Gly Leu Val Cys Pro Tyr
    690                 695                 700

Met Glu Phe Phe Lys Asn Glu Asn Asn Glu Leu Pro Lys Leu Gln Trp
705                 710                 715                 720

Tyr Lys Asp Cys Lys Pro Leu Leu Leu Asp Asn Ile His Phe Ser Gly
                725                 730                 735

Val Lys Asp Arg Leu Ile Val Met Asn Val Ala Glu Lys His Arg Gly
            740                 745                 750

Asn Tyr Thr Cys His Ala Ser Tyr Thr Tyr Leu Gly Lys Gln Tyr Pro
        755                 760                 765

Ile Thr Arg Val Ile Glu Phe Ile Thr Leu Glu Glu Asn Lys Pro Thr
    770                 775                 780

Arg Pro Val Ile Val Ser Pro Ala Asn Glu Thr Met Glu Val Asp Leu
785                 790                 795                 800

Gly Ser Gln Ile Gln Leu Ile Cys Asn Val Thr Gly Gln Leu Ser Asp
                805                 810                 815

Ile Ala Tyr Trp Lys Trp Asn Gly Ser Val Ile Asp Glu Asp Asp Pro
            820                 825                 830

Val Leu Gly Glu Asp Tyr Tyr Ser Val Glu Asn Pro Ala Asn Lys Arg
        835                 840                 845
```

```
Arg Ser Thr Leu Ile Thr Val Leu Asn Ile Ser Glu Ile Glu Ser Arg
            850                 855                 860

Phe Tyr Lys His Pro Phe Thr Cys Phe Ala Lys Asn Thr His Gly Ile
865                 870                 875                 880

Asp Ala Ala Tyr Ile Gln Leu Ile Tyr Pro Val Thr Asn Ser Gly Asp
                885                 890                 895

Lys Thr His Thr Cys Pro Pro Cys Pro Ala Pro Glu Phe Leu Gly Gly
                900                 905                 910

Pro Ser Val Phe Leu Phe Pro Pro Lys Pro Lys Asp Thr Leu Met Ile
                915                 920                 925

Ser Arg Thr Pro Glu Val Thr Cys Val Val Val Asp Val Ser Gln Glu
            930                 935                 940

Asp Pro Glu Val Gln Phe Asn Trp Tyr Val Asp Gly Val Glu Val His
945                 950                 955                 960

Asn Ala Lys Thr Lys Pro Arg Glu Glu Gln Phe Asn Ser Thr Tyr Arg
                965                 970                 975

Val Val Ser Val Leu Thr Val Leu His Gln Asp Trp Leu Asn Gly Lys
                980                 985                 990

Glu Tyr Lys Cys Lys Val Ser Asn Lys Gly Leu Pro Ser Ser Ile Glu
            995                 1000                1005

Lys Thr Ile Ser Lys Ala Lys Gly Gln Pro Arg Glu Pro Gln Val
            1010                1015                1020

Tyr Thr Leu Pro Pro Ser Gln Glu Glu Met Thr Lys Asn Gln Val
            1025                1030                1035

Ser Leu Thr Cys Leu Val Lys Gly Phe Tyr Pro Ser Asp Ile Ala
            1040                1045                1050

Val Glu Trp Glu Ser Asn Gly Gln Pro Glu Asn Asn Tyr Lys Thr
            1055                1060                1065

Thr Pro Pro Val Leu Asp Ser Asp Gly Ser Phe Phe Leu Tyr Ser
            1070                1075                1080

Arg Leu Thr Val Asp Lys Ser Arg Trp Gln Glu Gly Asn Val Phe
            1085                1090                1095

Ser Cys Ser Val Met His Glu Ala Leu His Asn His Tyr Thr Gln
            1100                1105                1110

Lys Ser Leu Ser Leu Ser Leu Gly Lys
            1115                1120

<210> SEQ ID NO 104
<211> LENGTH: 1126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
                20                  25                  30

Ser Pro Gly Glu Arg Ala Thr Leu Ser Cys Arg Ala Ser Lys Gly Val
            35                  40                  45

Ser Thr Ser Gly Tyr Ser Tyr Leu His Trp Tyr Gln Gln Lys Pro Gly
        50                  55                  60
```

```
Gln Ala Pro Arg Leu Leu Ile Tyr Leu Ala Ser Tyr Leu Glu Ser Gly
 65                  70                  75                  80

Val Pro Ala Arg Phe Ser Gly Ser Gly Ser Gly Thr Asp Phe Thr Leu
                 85                  90                  95

Thr Ile Ser Ser Leu Glu Pro Glu Asp Phe Ala Val Tyr Tyr Cys Gln
            100                 105                 110

His Ser Arg Asp Leu Pro Leu Thr Phe Gly Gly Gly Thr Lys Val Glu
            115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
210                 215                 220

Ser Ser Pro Val Thr Lys Ser Phe Asn Arg Gly Glu Cys Gly Gly Gly
225                 230                 235                 240

Gly Ser Gly Gly Gly Gly Ser Glu Arg Cys Asp Asp Trp Gly Leu Asp
                245                 250                 255

Thr Met Arg Gln Ile Gln Val Phe Glu Asp Glu Pro Ala Arg Ile Lys
            260                 265                 270

Cys Pro Leu Phe Glu His Phe Leu Lys Phe Asn Tyr Ser Thr Ala His
            275                 280                 285

Ser Ala Gly Leu Thr Leu Ile Trp Tyr Trp Thr Arg Gln Asp Arg Asp
290                 295                 300

Leu Glu Glu Pro Ile Asn Phe Arg Leu Pro Glu Asn Arg Ile Ser Lys
305                 310                 315                 320

Glu Lys Asp Val Leu Trp Phe Arg Pro Thr Leu Leu Asn Asp Thr Gly
                325                 330                 335

Asn Tyr Thr Cys Met Leu Arg Asn Thr Thr Tyr Cys Ser Lys Val Ala
            340                 345                 350

Phe Pro Leu Glu Val Val Gln Lys Asp Ser Cys Phe Asn Ser Pro Met
            355                 360                 365

Lys Leu Pro Val His Lys Leu Tyr Ile Glu Tyr Gly Ile Gln Arg Ile
370                 375                 380

Thr Cys Pro Asn Val Asp Gly Tyr Phe Pro Ser Ser Val Lys Pro Thr
385                 390                 395                 400

Ile Thr Trp Tyr Met Gly Cys Tyr Lys Ile Gln Asn Phe Asn Asn Val
                405                 410                 415

Ile Pro Glu Gly Met Asn Leu Ser Phe Leu Ile Ala Leu Ile Ser Asn
            420                 425                 430

Asn Gly Asn Tyr Thr Cys Val Val Thr Tyr Pro Glu Asn Gly Arg Thr
            435                 440                 445

Phe His Leu Thr Arg Thr Leu Thr Val Lys Val Val Gly Ser Pro Lys
450                 455                 460

Asn Ala Val Pro Pro Val Ile Ser Pro Asn Asp His Val Val Tyr
465                 470                 475                 480
```

-continued

```
Glu Lys Glu Pro Gly Glu Leu Leu Ile Pro Cys Thr Val Tyr Phe
                485                 490                 495
Ser Phe Leu Met Asp Ser Arg Asn Glu Val Trp Trp Thr Ile Asp Gly
            500                 505                 510
Lys Lys Pro Asp Asp Ile Thr Ile Asp Val Thr Ile Asn Glu Ser Ile
            515                 520                 525
Ser His Ser Arg Thr Glu Asp Glu Thr Arg Thr Gln Ile Leu Ser Ile
            530                 535                 540
Lys Lys Val Thr Ser Glu Asp Leu Lys Arg Ser Tyr Val Cys His Ala
545                 550                 555                 560
Arg Ser Ala Lys Gly Glu Val Ala Lys Ala Lys Val Lys Gln Lys
                565                 570                 575
Val Pro Ala Pro Arg Tyr Thr Val Glu Lys Cys Lys Glu Arg Glu Glu
                580                 585                 590
Lys Ile Ile Leu Val Ser Ser Ala Asn Glu Ile Asp Val Arg Pro Cys
                595                 600                 605
Pro Leu Asn Pro Asn Glu His Lys Gly Thr Ile Thr Trp Tyr Lys Asp
            610                 615                 620
Asp Ser Lys Thr Pro Val Ser Thr Glu Gln Ala Ser Arg Ile His Gln
625                 630                 635                 640
His Lys Glu Lys Leu Trp Phe Val Pro Ala Lys Val Glu Asp Ser Gly
                645                 650                 655
His Tyr Tyr Cys Val Val Arg Asn Ser Ser Tyr Cys Leu Arg Ile Lys
                660                 665                 670
Ile Ser Ala Lys Phe Val Glu Asn Glu Pro Asn Leu Cys Tyr Asn Ala
                675                 680                 685
Gln Ala Ile Phe Lys Gln Lys Leu Pro Val Ala Gly Asp Gly Gly Leu
            690                 695                 700
Val Cys Pro Tyr Met Glu Phe Phe Lys Asn Glu Asn Asn Glu Leu Pro
705                 710                 715                 720
Lys Leu Gln Trp Tyr Lys Asp Cys Lys Pro Leu Leu Leu Asp Asn Ile
                725                 730                 735
His Phe Ser Gly Val Lys Asp Arg Leu Ile Val Met Asn Val Ala Glu
            740                 745                 750
Lys His Arg Gly Asn Tyr Thr Cys His Ala Ser Tyr Thr Tyr Leu Gly
            755                 760                 765
Lys Gln Tyr Pro Ile Thr Arg Val Ile Glu Phe Ile Thr Leu Glu Glu
            770                 775                 780
Asn Lys Pro Thr Arg Pro Val Ile Val Ser Pro Ala Asn Glu Thr Met
785                 790                 795                 800
Glu Val Asp Leu Gly Ser Gln Ile Gln Leu Ile Cys Asn Val Thr Gly
                805                 810                 815
Gln Leu Ser Asp Ile Ala Tyr Trp Lys Trp Asn Gly Ser Val Ile Asp
            820                 825                 830
Glu Asp Asp Pro Val Leu Gly Glu Asp Tyr Tyr Ser Val Glu Asn Pro
            835                 840                 845
Ala Asn Lys Arg Arg Ser Thr Leu Ile Thr Val Leu Asn Ile Ser Glu
            850                 855                 860
Ile Glu Ser Arg Phe Tyr Lys His Pro Phe Thr Cys Phe Ala Lys Asn
865                 870                 875                 880
Thr His Gly Ile Asp Ala Ala Tyr Ile Gln Leu Ile Tyr Pro Val Thr
                885                 890                 895
```

Asn Ser Gly Asp Lys Thr His Thr Cys Pro Pro Cys Pro Ala Pro Glu
            900                 905                 910

Phe Leu Gly Gly Pro Ser Val Phe Leu Phe Pro Pro Lys Pro Lys Asp
            915                 920                 925

Thr Leu Met Ile Ser Arg Thr Pro Glu Val Thr Cys Val Val Val Asp
        930                 935                 940

Val Ser Gln Glu Asp Pro Glu Val Gln Phe Asn Trp Tyr Val Asp Gly
945                 950                 955                 960

Val Glu Val His Asn Ala Lys Thr Lys Pro Arg Glu Gln Phe Asn
                965                 970                 975

Ser Thr Tyr Arg Val Val Ser Val Leu Thr Val Leu His Gln Asp Trp
        980                 985                 990

Leu Asn Gly Lys Glu Tyr Lys Cys Lys Val Ser Asn Lys Gly Leu Pro
            995                 1000                1005

Ser Ser Ile Glu Lys Thr Ile Ser Lys Ala Lys Gly Gln Pro Arg
    1010                1015                1020

Glu Pro Gln Val Tyr Thr Leu Pro Pro Ser Gln Glu Glu Met Thr
    1025                1030                1035

Lys Asn Gln Val Ser Leu Thr Cys Leu Val Lys Gly Phe Tyr Pro
    1040                1045                1050

Ser Asp Ile Ala Val Glu Trp Glu Ser Asn Gly Gln Pro Glu Asn
    1055                1060                1065

Asn Tyr Lys Thr Thr Pro Pro Val Leu Asp Ser Asp Gly Ser Phe
    1070                1075                1080

Phe Leu Tyr Ser Arg Leu Thr Val Asp Lys Ser Arg Trp Gln Glu
    1085                1090                1095

Gly Asn Val Phe Ser Cys Ser Val Met His Glu Ala Leu His Asn
    1100                1105                1110

His Tyr Thr Gln Lys Ser Leu Ser Leu Ser Leu Gly Lys
    1115                1120                1125

<210> SEQ ID NO 105
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Val Val Gln
                20                  25                  30

Pro Gly Arg Ser Leu Arg Leu Asp Cys Lys Ala Ser Gly Ile Thr Phe
            35                  40                  45

Ser Asn Ser Gly Met His Trp Val Arg Gln Ala Pro Gly Lys Cys Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
                100                 105                 110

```
Tyr Tyr Cys Ala Thr Asn Asp Asp Tyr Trp Gly Gln Gly Thr Leu Val
        115                 120                 125

Thr Val Ser Ser Gly Gly Gly Gly Ser Gly Gly Gly Gly Ser Gly Gly
    130                 135                 140

Gly Gly Ser Gly Gly Gly Gly Ser Glu Ile Val Leu Thr Gln Ser Pro
145                 150                 155                 160

Ala Thr Leu Ser Leu Ser Pro Gly Glu Arg Ala Thr Leu Ser Cys Arg
            165                 170                 175

Ala Ser Gln Ser Val Ser Ser Tyr Leu Ala Trp Tyr Gln Gln Lys Pro
            180                 185                 190

Gly Gln Ala Pro Arg Leu Leu Ile Tyr Asp Ala Ser Asn Arg Ala Thr
            195                 200                 205

Gly Ile Pro Ala Arg Phe Ser Gly Ser Gly Ser Gly Thr Asp Phe Thr
            210                 215                 220

Leu Thr Ile Ser Ser Leu Glu Pro Glu Asp Phe Ala Val Tyr Tyr Cys
225                 230                 235                 240

Gln Gln Ser Ser Asn Trp Pro Arg Thr Phe Gly Cys Gly Thr Lys Val
                245                 250                 255

Glu Ile Lys Gly Gly Gly Gly Ser Gly Gly Gly Gly Ser Gln Val Gln
            260                 265                 270

Leu Val Glu Ser Gly Gly Gly Val Val Gln Pro Gly Arg Ser Leu Arg
            275                 280                 285

Leu Ser Cys Ala Ala Ser Gly Phe Thr Phe Ser Val Tyr Gly Met Asn
            290                 295                 300

Trp Val Arg Gln Ala Pro Gly Lys Gly Leu Glu Trp Val Ala Ile Ile
305                 310                 315                 320

Trp Tyr Asp Gly Asp Asn Gln Tyr Tyr Ala Asp Ser Val Lys Gly Arg
                325                 330                 335

Phe Thr Ile Ser Arg Asp Asn Ser Lys Asn Thr Leu Tyr Leu Gln Met
                340                 345                 350

Asn Gly Leu Arg Ala Glu Asp Thr Ala Val Tyr Tyr Cys Ala Arg Asp
            355                 360                 365

Leu Arg Thr Gly Pro Phe Asp Tyr Trp Gly Gln Gly Thr Leu Val Thr
            370                 375                 380

Val Ser Ser Ala Ser Thr Lys Gly Pro Ser Val Phe Pro Leu Ala Pro
385                 390                 395                 400

Cys Ser Arg Ser Thr Ser Glu Ser Thr Ala Ala Leu Gly Cys Leu Val
                405                 410                 415

Lys Asp Tyr Phe Pro Glu Pro Val Thr Val Ser Trp Asn Ser Gly Ala
                420                 425                 430

Leu Thr Ser Gly Val His Thr Phe Pro Ala Val Leu Gln Ser Ser Gly
            435                 440                 445

Leu Tyr Ser Leu Ser Ser Val Val Thr Val Pro Ser Ser Ser Leu Gly
            450                 455                 460

Thr Lys Thr Tyr Thr Cys Asn Val Asp His Lys Pro Ser Asn Thr Lys
465                 470                 475                 480

Val Asp Lys Arg Val Glu Ser Lys Tyr Gly Pro Pro Cys Pro Pro Cys
                485                 490                 495

Pro Ala Pro Glu Phe Leu Gly Gly Pro Ser Val Phe Leu Phe Pro Pro
            500                 505                 510

Lys Pro Lys Asp Thr Leu Met Ile Ser Arg Thr Pro Glu Val Thr Cys
515                 520                 525
```

```
Val Val Val Asp Val Ser Gln Glu Asp Pro Glu Val Gln Phe Asn Trp
        530             535             540

Tyr Val Asp Gly Val Glu Val His Asn Ala Lys Thr Lys Pro Arg Glu
545             550             555             560

Glu Gln Phe Asn Ser Thr Tyr Arg Val Val Ser Val Leu Thr Val Leu
                565             570             575

His Gln Asp Trp Leu Asn Gly Lys Glu Tyr Lys Cys Lys Val Ser Asn
            580             585             590

Lys Gly Leu Pro Ser Ser Ile Glu Lys Thr Ile Ser Lys Ala Lys Gly
        595             600             605

Gln Pro Arg Glu Pro Gln Val Tyr Thr Leu Pro Pro Ser Gln Glu Glu
    610             615             620

Met Thr Lys Asn Gln Val Ser Leu Thr Cys Leu Val Lys Gly Phe Tyr
625             630             635             640

Pro Ser Asp Ile Ala Val Glu Trp Glu Ser Asn Gly Gln Pro Glu Asn
                645             650             655

Asn Tyr Lys Thr Thr Pro Pro Val Leu Asp Ser Asp Gly Ser Phe Phe
            660             665             670

Leu Tyr Ser Arg Leu Thr Val Asp Lys Ser Arg Trp Gln Glu Gly Asn
        675             680             685

Val Phe Ser Cys Ser Val Met His Glu Ala Leu His Asn His Tyr Thr
    690             695             700

Gln Lys Ser Leu Ser Leu Ser Leu Gly Lys
705             710

<210> SEQ ID NO 106
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Ser Ser Asn
            100                 105                 110

Trp Pro Arg Thr Phe Gly Cys Gly Thr Lys Val Glu Ile Lys Gly Gly
        115                 120                 125

Gly Gly Ser Gly Gly Gly Gly Ser Gly Gly Gly Ser Gly Gly Gly
    130                 135                 140

Gly Ser Gln Val Gln Leu Val Glu Ser Gly Gly Val Val Gln Pro
145                 150                 155                 160

Gly Arg Ser Leu Arg Leu Asp Cys Lys Ala Ser Gly Ile Thr Phe Ser
                165                 170                 175
```

```
Asn Ser Gly Met His Trp Val Arg Gln Ala Pro Gly Lys Cys Leu Glu
            180                 185                 190

Trp Val Ala Val Ile Trp Tyr Asp Gly Ser Lys Arg Tyr Tyr Ala Asp
            195                 200                 205

Ser Val Lys Gly Arg Phe Thr Ile Ser Arg Asp Asn Ser Lys Asn Thr
210                 215                 220

Leu Phe Leu Gln Met Asn Ser Leu Arg Ala Glu Asp Thr Ala Val Tyr
225                 230                 235                 240

Tyr Cys Ala Thr Asn Asp Asp Tyr Trp Gly Gln Gly Thr Leu Val Thr
                245                 250                 255

Val Ser Ser Gly Gly Gly Gly Ser Gly Gly Gly Gly Ser Gln Val Gln
            260                 265                 270

Leu Val Glu Ser Gly Gly Gly Val Val Gln Pro Gly Arg Ser Leu Arg
            275                 280                 285

Leu Ser Cys Ala Ala Ser Gly Phe Thr Phe Ser Val Tyr Gly Met Asn
            290                 295                 300

Trp Val Arg Gln Ala Pro Gly Lys Gly Leu Glu Trp Val Ala Ile Ile
305                 310                 315                 320

Trp Tyr Asp Gly Asp Asn Gln Tyr Tyr Ala Asp Ser Val Lys Gly Arg
                325                 330                 335

Phe Thr Ile Ser Arg Asp Asn Ser Lys Asn Thr Leu Tyr Leu Gln Met
                340                 345                 350

Asn Gly Leu Arg Ala Glu Asp Thr Ala Val Tyr Tyr Cys Ala Arg Asp
                355                 360                 365

Leu Arg Thr Gly Pro Phe Asp Tyr Trp Gly Gln Gly Thr Leu Val Thr
            370                 375                 380

Val Ser Ser Ala Ser Thr Lys Gly Pro Ser Val Phe Pro Leu Ala Pro
385                 390                 395                 400

Cys Ser Arg Ser Thr Ser Glu Ser Thr Ala Ala Leu Gly Cys Leu Val
                405                 410                 415

Lys Asp Tyr Phe Pro Glu Pro Val Thr Val Ser Trp Asn Ser Gly Ala
                420                 425                 430

Leu Thr Ser Gly Val His Thr Phe Pro Ala Val Leu Gln Ser Ser Gly
            435                 440                 445

Leu Tyr Ser Leu Ser Ser Val Val Thr Val Pro Ser Ser Ser Leu Gly
            450                 455                 460

Thr Lys Thr Tyr Thr Cys Asn Val Asp His Lys Pro Ser Asn Thr Lys
465                 470                 475                 480

Val Asp Lys Arg Val Glu Ser Lys Tyr Gly Pro Pro Cys Pro Pro Cys
                485                 490                 495

Pro Ala Pro Glu Phe Leu Gly Gly Pro Ser Val Phe Leu Phe Pro Pro
            500                 505                 510

Lys Pro Lys Asp Thr Leu Met Ile Ser Arg Thr Pro Glu Val Thr Cys
            515                 520                 525

Val Val Val Asp Val Ser Gln Glu Asp Pro Glu Val Gln Phe Asn Trp
            530                 535                 540

Tyr Val Asp Gly Val Glu Val His Asn Ala Lys Thr Lys Pro Arg Glu
545                 550                 555                 560

Glu Gln Phe Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590
```

```
Lys Gly Leu Pro Ser Ser Ile Glu Lys Thr Ile Ser Lys Ala Lys Gly
            595                 600                 605

Gln Pro Arg Glu Pro Gln Val Tyr Thr Leu Pro Pro Ser Gln Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
                660                 665                 670

Leu Tyr Ser Arg Leu Thr Val Asp Lys Ser Arg Trp Gln Glu Gly Asn
            675                 680                 685

Val Phe Ser Cys Ser Val Met His Glu Ala Leu His Asn His Tyr Thr
    690                 695                 700

Gln Lys Ser Leu Ser Leu Ser Leu Gly Lys
705                 710

<210> SEQ ID NO 107
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
        35                  40                  45

Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240
```

```
Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly Lys Gly Gly Gly Gly Ser
    450                 455                 460

Gly Gly Gly Gly Ser Gln Val Gln Leu Val Glu Ser Gly Gly Gly Val
465                 470                 475                 480

Val Gln Pro Gly Arg Ser Leu Arg Leu Ser Cys Ala Ala Ser Gly Phe
                485                 490                 495

Thr Phe Ser Val Tyr Gly Met Asn Trp Val Arg Gln Ala Pro Gly Lys
            500                 505                 510

Cys Leu Glu Trp Val Ala Ile Ile Trp Tyr Asp Gly Asp Asn Gln Tyr
        515                 520                 525

Tyr Ala Asp Ser Val Lys Gly Arg Phe Thr Ile Ser Arg Asp Asn Ser
    530                 535                 540

Lys Asn Thr Leu Tyr Leu Gln Met Asn Gly Leu Arg Ala Glu Asp Thr
545                 550                 555                 560

Ala Val Tyr Tyr Cys Ala Arg Asp Leu Arg Thr Gly Pro Phe Asp Tyr
                565                 570                 575

Trp Gly Gln Gly Thr Leu Val Thr Val Ser Ser Gly Gly Gly Gly Ser
            580                 585                 590

Gly Gly Gly Gly Ser Gly Gly Gly Ser Gly Gly Gly Gly Ser Glu
        595                 600                 605

Ile Val Leu Thr Gln Ser Pro Asp Phe Gln Ser Val Thr Pro Lys Glu
    610                 615                 620

Lys Val Thr Ile Thr Cys Arg Ala Ser Gln Ser Ile Gly Ser Ser Leu
625                 630                 635                 640

His Trp Tyr Gln Gln Lys Pro Asp Gln Ser Pro Lys Leu Leu Ile Lys
                645                 650                 655
```

```
Tyr Ala Ser Gln Ser Phe Ser Gly Val Pro Ser Arg Phe Ser Gly Ser
            660                 665                 670

Gly Ser Gly Thr Asp Phe Thr Leu Thr Ile Asn Ser Leu Glu Ala Glu
        675                 680                 685

Asp Ala Ala Tyr Tyr Cys His Gln Ser Ser Ser Leu Pro Phe Thr
690                 695                 700

Phe Gly Cys Gly Thr Lys Val Asp Ile Lys
705                 710

<210> SEQ ID NO 108
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
        35                  40                  45

Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300
```

```
Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly Lys Gly Gly Gly Gly Ser
    450                 455                 460

Gly Gly Gly Gly Ser Glu Ile Val Leu Thr Gln Ser Pro Asp Phe Gln
465                 470                 475                 480

Ser Val Thr Pro Lys Glu Lys Val Thr Ile Thr Cys Arg Ala Ser Gln
                485                 490                 495

Ser Ile Gly Ser Ser Leu His Trp Tyr Gln Gln Lys Pro Asp Gln Ser
            500                 505                 510

Pro Lys Leu Leu Ile Lys Tyr Ala Ser Gln Ser Phe Ser Gly Val Pro
        515                 520                 525

Ser Arg Phe Ser Gly Ser Gly Ser Gly Thr Asp Phe Thr Leu Thr Ile
    530                 535                 540

Asn Ser Leu Glu Ala Glu Asp Ala Ala Ala Tyr Tyr Cys His Gln Ser
545                 550                 555                 560

Ser Ser Leu Pro Phe Thr Phe Gly Cys Gly Thr Lys Val Asp Ile Lys
                565                 570                 575

Gly Gly Gly Gly Ser Gly Gly Gly Ser Gly Gly Gly Gly Ser Gly
            580                 585                 590

Gly Gly Gly Ser Gln Val Gln Leu Val Glu Ser Gly Gly Gly Val Val
        595                 600                 605

Gln Pro Gly Arg Ser Leu Arg Leu Ser Cys Ala Ala Ser Gly Phe Thr
    610                 615                 620

Phe Ser Val Tyr Gly Met Asn Trp Val Arg Gln Ala Pro Gly Lys Cys
625                 630                 635                 640

Leu Glu Trp Val Ala Ile Ile Trp Tyr Asp Gly Asp Asn Gln Tyr Tyr
                645                 650                 655

Ala Asp Ser Val Lys Gly Arg Phe Thr Ile Ser Arg Asp Asn Ser Lys
            660                 665                 670

Asn Thr Leu Tyr Leu Gln Met Asn Gly Leu Arg Ala Glu Asp Thr Ala
        675                 680                 685

Val Tyr Tyr Cys Ala Arg Asp Leu Arg Thr Gly Pro Phe Asp Tyr Trp
    690                 695                 700

Gly Gln Gly Thr Leu Val Thr Val Ser Ser
705                 710
```

<210> SEQ ID NO 109
<211> LENGTH: 683
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Phe Thr Phe Gly Pro Gly Thr Lys Val Asp Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Ser Gly Gln Val Gln Leu
225                 230                 235                 240

Val Gln Ser Gly Val Glu Val Lys Lys Pro Gly Ala Ser Val Lys Val
                245                 250                 255

Ser Cys Lys Ala Ser Gly Tyr Thr Phe Thr Asn Tyr Tyr Met Tyr Trp
            260                 265                 270

Val Arg Gln Ala Pro Gly Gln Gly Leu Glu Trp Met Gly Gly Ile Asn
        275                 280                 285

Pro Ser Asn Gly Gly Thr Asn Phe Asn Glu Lys Phe Lys Asn Arg Val
    290                 295                 300

Thr Leu Thr Thr Asp Ser Ser Thr Thr Thr Ala Tyr Met Glu Leu Lys
305                 310                 315                 320

Ser Leu Gln Phe Asp Asp Thr Ala Val Tyr Tyr Cys Ala Arg Arg Asp
                325                 330                 335

Tyr Arg Phe Asp Met Gly Phe Asp Tyr Trp Gly Gln Gly Thr Thr Val
            340                 345                 350

Thr Val Ser Ser Ala Ser Thr Lys Gly Pro Ser Val Phe Pro Leu Ala
        355                 360                 365
```

```
Pro Cys Ser Arg Ser Thr Ser Glu Ser Thr Ala Ala Leu Gly Cys Leu
    370                 375                 380

Val Lys Asp Tyr Phe Pro Glu Pro Val Thr Val Ser Trp Asn Ser Gly
385                 390                 395                 400

Ala Leu Thr Ser Gly Val His Thr Phe Pro Ala Val Leu Gln Ser Ser
                405                 410                 415

Gly Leu Tyr Ser Leu Ser Ser Val Val Thr Val Pro Ser Ser Ser Leu
            420                 425                 430

Gly Thr Lys Thr Tyr Thr Cys Asn Val Asp His Lys Pro Ser Asn Thr
        435                 440                 445

Lys Val Asp Lys Arg Val Glu Ser Lys Tyr Gly Pro Pro Cys Pro Pro
450                 455                 460

Cys Pro Ala Pro Glu Phe Leu Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser Gln Glu Asp Pro Glu Val Gln Phe Asn
            500                 505                 510

Trp Tyr Val Asp Gly Val Glu Val His Asn Ala Lys Thr Lys Pro Arg
        515                 520                 525

Glu Glu Gln Phe Asn Ser Thr Tyr Arg Val Val Ser Val Leu Thr Val
530                 535                 540

Leu His Gln Asp Trp Leu Asn Gly Lys Glu Tyr Lys Cys Lys Val Ser
545                 550                 555                 560

Asn Lys Gly Leu Pro Ser Ser Ile Glu Lys Thr Ile Ser Lys Ala Lys
                565                 570                 575

Gly Gln Pro Arg Glu Pro Gln Val Tyr Thr Leu Pro Pro Ser Gln Glu
            580                 585                 590

Glu Met Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
610                 615                 620

Asn Asn Tyr Lys Thr Thr Pro Pro Val Leu Asp Ser Asp Gly Ser Phe
625                 630                 635                 640

Phe Leu Tyr Ser Arg Leu Thr Val Asp Lys Ser Arg Trp Gln Glu Gly
                645                 650                 655

Asn Val Phe Ser Cys Ser Val Met His Glu Ala Leu His Asn His Tyr
            660                 665                 670

Thr Gln Lys Ser Leu Ser Leu Ser Leu Gly Lys
        675                 680
```

<210> SEQ ID NO 110
<211> LENGTH: 687
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Asp Phe Gln Ser Val
                20                  25                  30
```

```
Thr Pro Lys Glu Lys Val Thr Ile Thr Cys Arg Ala Ser Gln Ser Ile
         35                  40                  45

Gly Ser Ser Leu His Trp Tyr Gln Gln Lys Pro Asp Gln Ser Pro Lys
 50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
             85                  90                  95

Leu Glu Ala Glu Asp Ala Ala Ala Tyr Tyr Cys His Gln Ser Ser Ser
            100                 105                 110

Leu Pro Phe Thr Phe Gly Pro Gly Thr Lys Val Asp Ile Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
            210                 215                 220

Thr Lys Ser Phe Asn Arg Gly Glu Cys Gly Gly Gly Ser Gly Ser
225                 230                 235                 240

Gln Val Gln Leu Val Gln Ser Gly Val Glu Val Lys Lys Pro Gly Ala
                245                 250                 255

Ser Val Lys Val Ser Cys Lys Ala Ser Gly Tyr Thr Phe Thr Asn Tyr
            260                 265                 270

Tyr Met Tyr Trp Val Arg Gln Ala Pro Gly Gln Gly Leu Glu Trp Met
            275                 280                 285

Gly Gly Ile Asn Pro Ser Asn Gly Gly Thr Asn Phe Asn Glu Lys Phe
            290                 295                 300

Lys Asn Arg Val Thr Leu Thr Thr Asp Ser Ser Thr Thr Thr Ala Tyr
305                 310                 315                 320

Met Glu Leu Lys Ser Leu Gln Phe Asp Thr Ala Val Tyr Tyr Cys
                325                 330                 335

Ala Arg Arg Asp Tyr Arg Phe Asp Met Gly Phe Asp Tyr Trp Gly Gln
            340                 345                 350

Gly Thr Thr Val Thr Val Ser Ser Ala Ser Thr Lys Gly Pro Ser Val
            355                 360                 365

Phe Pro Leu Ala Pro Cys Ser Arg Ser Thr Ser Glu Ser Thr Ala Ala
            370                 375                 380

Leu Gly Cys Leu Val Lys Asp Tyr Phe Pro Glu Pro Val Thr Val Ser
385                 390                 395                 400

Trp Asn Ser Gly Ala Leu Thr Ser Gly Val His Thr Phe Pro Ala Val
                405                 410                 415

Leu Gln Ser Ser Gly Leu Tyr Ser Leu Ser Ser Val Val Thr Val Pro
            420                 425                 430

Ser Ser Ser Leu Gly Thr Lys Thr Tyr Thr Cys Asn Val Asp His Lys
            435                 440                 445
```

```
Pro Ser Asn Thr Lys Val Asp Lys Arg Val Glu Ser Lys Tyr Gly Pro
450                 455                 460

Pro Cys Pro Pro Cys Pro Ala Pro Glu Phe Leu Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser Gln Glu Asp Pro Glu
            500                 505                 510

Val Gln Phe Asn Trp Tyr Val Asp Gly Val Glu Val His Asn Ala Lys
        515                 520                 525

Thr Lys Pro Arg Glu Glu Gln Phe Asn Ser Thr Tyr Arg Val Val Ser
530                 535                 540

Val Leu Thr Val Leu His Gln Asp Trp Leu Asn Gly Lys Glu Tyr Lys
545                 550                 555                 560

Cys Lys Val Ser Asn Lys Gly Leu Pro Ser Ser Ile Glu Lys Thr Ile
                565                 570                 575

Ser Lys Ala Lys Gly Gln Pro Arg Glu Pro Gln Val Tyr Thr Leu Pro
            580                 585                 590

Pro Ser Gln Glu Glu Met Thr Lys Asn Gln Val Ser Leu Thr Cys Leu
        595                 600                 605

Val Lys Gly Phe Tyr Pro Ser Asp Ile Ala Val Glu Trp Glu Ser Asn
610                 615                 620

Gly Gln Pro Glu Asn Asn Tyr Lys Thr Thr Pro Pro Val Leu Asp Ser
625                 630                 635                 640

Asp Gly Ser Phe Phe Leu Tyr Ser Arg Leu Thr Val Asp Lys Ser Arg
                645                 650                 655

Trp Gln Glu Gly Asn Val Phe Ser Cys Ser Val Met His Glu Ala Leu
            660                 665                 670

His Asn His Tyr Thr Gln Lys Ser Leu Ser Leu Ser Leu Gly Lys
        675                 680                 685

<210> SEQ ID NO 111
<211> LENGTH: 715
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Ser Ser Asn
            100                 105                 110

Trp Pro Arg Thr Phe Gly Cys Gly Thr Lys Val Glu Ile Lys Gly Gly
        115                 120                 125
```

Gly Gly Ser Gly Gly Gly Ser Gly Gly Gly Ser Gly Gly Gly
    130                 135                 140
Gly Ser Gln Val Gln Leu Val Glu Ser Gly Gly Val Val Gln Pro
145                 150                 155                 160
Gly Arg Ser Leu Arg Leu Asp Cys Lys Ala Ser Gly Ile Thr Phe Ser
                165                 170                 175
Asn Ser Gly Met His Trp Val Arg Gln Ala Pro Gly Lys Cys Leu Glu
            180                 185                 190
Trp Val Ala Val Ile Trp Tyr Asp Gly Ser Lys Arg Tyr Tyr Ala Asp
        195                 200                 205
Ser Val Lys Gly Arg Phe Thr Ile Ser Arg Asp Asn Ser Lys Asn Thr
    210                 215                 220
Leu Phe Leu Gln Met Asn Ser Leu Arg Ala Glu Asp Thr Ala Val Tyr
225                 230                 235                 240
Tyr Cys Ala Thr Asn Asp Asp Tyr Trp Gly Gln Gly Thr Leu Val Thr
                245                 250                 255
Val Ser Ser Gly Gly Gly Gly Ser Gly Gly Gly Gly Ser Glu Val Gln
            260                 265                 270
Leu Val Glu Ser Gly Gly Val Val Gln Pro Gly Arg Ser Leu Arg
        275                 280                 285
Leu Ser Cys Ser Ser Ser Gly Phe Ile Phe Ser Ser Tyr Asp Met Ser
    290                 295                 300
Trp Val Arg Gln Ala Pro Gly Lys Gly Leu Glu Trp Val Ala Tyr Ile
305                 310                 315                 320
Ser Ser Gly Gly Gly Thr Tyr Tyr Pro Asp Thr Val Lys Gly Arg
                325                 330                 335
Phe Thr Ile Ser Arg Asp Asn Ser Lys Asn Thr Leu Phe Leu Gln Met
            340                 345                 350
Asp Ser Leu Arg Pro Glu Asp Thr Gly Val Tyr Phe Cys Ala Arg Gly
        355                 360                 365
Gly Val Thr Lys Gly Tyr Phe Asp Val Trp Gly Gln Gly Thr Pro Val
    370                 375                 380
Thr Val Ser Ser Ala Ser Thr Lys Gly Pro Ser Val Phe Pro Leu Ala
385                 390                 395                 400
Pro Cys Ser Arg Ser Thr Ser Glu Ser Thr Ala Ala Leu Gly Cys Leu
                405                 410                 415
Val Lys Asp Tyr Phe Pro Glu Pro Val Thr Val Ser Trp Asn Ser Gly
            420                 425                 430
Ala Leu Thr Ser Gly Val His Thr Phe Pro Ala Val Leu Gln Ser Ser
        435                 440                 445
Gly Leu Tyr Ser Leu Ser Ser Val Val Thr Val Pro Ser Ser Ser Leu
    450                 455                 460
Gly Thr Lys Thr Tyr Thr Cys Asn Val Asp His Lys Pro Ser Asn Thr
465                 470                 475                 480
Lys Val Asp Lys Arg Val Glu Ser Lys Tyr Gly Pro Pro Cys Pro Pro
                485                 490                 495
Cys Pro Ala Pro Glu Phe Leu Gly Gly Pro Ser Val Phe Leu Phe Pro
            500                 505                 510
Pro Lys Pro Lys Asp Thr Leu Met Ile Ser Arg Thr Pro Glu Val Thr
        515                 520                 525
Cys Val Val Val Asp Val Ser Gln Glu Asp Pro Glu Val Gln Phe Asn
    530                 535                 540

Trp Tyr Val Asp Gly Val Glu Val His Asn Ala Lys Thr Lys Pro Arg
545                 550                 555                 560

Glu Glu Gln Phe Asn Ser Thr Tyr Arg Val Val Ser Val Leu Thr Val
            565                 570                 575

Leu His Gln Asp Trp Leu Asn Gly Lys Glu Tyr Lys Cys Lys Val Ser
        580                 585                 590

Asn Lys Gly Leu Pro Ser Ser Ile Glu Lys Thr Ile Ser Lys Ala Lys
    595                 600                 605

Gly Gln Pro Arg Glu Pro Gln Val Tyr Thr Leu Pro Pro Ser Gln Glu
610                 615                 620

Glu Met Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
            645                 650                 655

Asn Asn Tyr Lys Thr Thr Pro Pro Val Leu Asp Ser Asp Gly Ser Phe
        660                 665                 670

Phe Leu Tyr Ser Arg Leu Thr Val Asp Lys Ser Arg Trp Gln Glu Gly
    675                 680                 685

Asn Val Phe Ser Cys Ser Val Met His Glu Ala Leu His Asn His Tyr
690                 695                 700

Thr Gln Lys Ser Leu Ser Leu Ser Leu Gly Lys
705                 710                 715

<210> SEQ ID NO 112
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gly Asn Ile
        35                  40                  45

His Asn Tyr Leu Thr Trp Tyr Gln Gln Thr Pro Gly Lys Ala Pro Lys
    50                  55                  60

Leu Leu Ile Tyr Asn Ala Lys Thr Leu Ala Asp Gly Val Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln His Phe Trp Ser
            100                 105                 110

Ile Pro Tyr Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 113
<211> LENGTH: 715
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gly Asn Ile
        35                  40                  45

His Asn Tyr Leu Thr Trp Tyr Gln Gln Thr Pro Gly Lys Ala Pro Lys
    50                  55                  60

Leu Leu Ile Tyr Asn Ala Lys Thr Leu Ala Asp Gly Val Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln His Phe Trp Ser
            100                 105                 110

Ile Pro Tyr Thr Phe Gly Cys Gly Thr Lys Leu Glu Ile Lys Gly Gly
        115                 120                 125

Gly Gly Ser Gly Gly Gly Ser Gly Gly Gly Ser Gly Gly Gly
    130                 135                 140

Gly Ser Glu Val Gln Leu Val Glu Ser Gly Gly Gly Val Val Gln Pro
145                 150                 155                 160

Gly Arg Ser Leu Arg Leu Ser Cys Ser Ser Gly Phe Ile Phe Ser
                165                 170                 175

Ser Tyr Asp Met Ser Trp Val Arg Gln Ala Pro Gly Lys Cys Leu Glu
            180                 185                 190

Trp Val Ala Tyr Ile Ser Ser Gly Gly Gly Thr Tyr Tyr Pro Asp
        195                 200                 205

Thr Val Lys Gly Arg Phe Thr Ile Ser Arg Asp Asn Ser Lys Asn Thr
    210                 215                 220

Leu Phe Leu Gln Met Asp Ser Leu Arg Pro Glu Asp Thr Gly Val Tyr
225                 230                 235                 240

Phe Cys Ala Arg Gly Gly Val Thr Lys Gly Tyr Phe Asp Val Trp Gly
                245                 250                 255

Gln Gly Thr Pro Val Thr Val Ser Ser Gly Gly Gly Ser Gly Gly
            260                 265                 270

Gly Gly Ser Gln Val Gln Leu Val Glu Ser Gly Gly Gly Val Val Gln
        275                 280                 285

Pro Gly Arg Ser Leu Arg Leu Asp Cys Lys Ala Ser Gly Ile Thr Phe
    290                 295                 300

```
Ser Asn Ser Gly Met His Trp Val Arg Gln Ala Pro Gly Lys Gly Leu
305                 310                 315                 320

Glu Trp Val Ala Val Ile Trp Tyr Asp Gly Ser Lys Arg Tyr Tyr Ala
            325                 330                 335

Asp Ser Val Lys Gly Arg Phe Thr Ile Ser Arg Asp Asn Ser Lys Asn
            340                 345                 350

Thr Leu Phe Leu Gln Met Asn Ser Leu Arg Ala Glu Asp Thr Ala Val
            355                 360                 365

Tyr Tyr Cys Ala Thr Asn Asp Asp Tyr Trp Gly Gln Gly Thr Leu Val
    370                 375                 380

Thr Val Ser Ser Ala Ser Thr Lys Gly Pro Ser Val Phe Pro Leu Ala
385                 390                 395                 400

Pro Cys Ser Arg Ser Thr Ser Glu Ser Thr Ala Ala Leu Gly Cys Leu
                405                 410                 415

Val Lys Asp Tyr Phe Pro Glu Pro Val Thr Val Ser Trp Asn Ser Gly
            420                 425                 430

Ala Leu Thr Ser Gly Val His Thr Phe Pro Ala Val Leu Gln Ser Ser
            435                 440                 445

Gly Leu Tyr Ser Leu Ser Ser Val Val Thr Val Pro Ser Ser Ser Leu
    450                 455                 460

Gly Thr Lys Thr Tyr Thr Cys Asn Val Asp His Lys Pro Ser Asn Thr
465                 470                 475                 480

Lys Val Asp Lys Arg Val Glu Ser Lys Tyr Gly Pro Pro Cys Pro Pro
                485                 490                 495

Cys Pro Ala Pro Glu Phe Leu Gly Gly Pro Ser Val Phe Leu Phe Pro
            500                 505                 510

Pro Lys Pro Lys Asp Thr Leu Met Ile Ser Arg Thr Pro Glu Val Thr
            515                 520                 525

Cys Val Val Val Asp Val Ser Gln Glu Asp Pro Glu Val Gln Phe Asn
    530                 535                 540

Trp Tyr Val Asp Gly Val Glu Val His Asn Ala Lys Thr Lys Pro Arg
545                 550                 555                 560

Glu Glu Gln Phe Asn Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Gly Leu Pro Ser Ser Ile Glu Lys Thr Ile Ser Lys Ala Lys
            595                 600                 605

Gly Gln Pro Arg Glu Pro Gln Val Tyr Thr Leu Pro Pro Ser Gln Glu
    610                 615                 620

Glu Met Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Arg Leu Thr Val Asp Lys Ser Arg Trp Gln Glu Gly
            675                 680                 685

Asn Val Phe Ser Cys Ser Val Met His Glu Ala Leu His Asn His Tyr
    690                 695                 700

Thr Gln Lys Ser Leu Ser Leu Ser Leu Gly Lys
705                 710                 715
```

<210> SEQ ID NO 114
<211> LENGTH: 715
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Val Val Gln
            20                  25                  30

Pro Gly Arg Ser Leu Arg Leu Ser Cys Ser Ser Gly Phe Ile Phe
        35                  40                  45

Ser Ser Tyr Asp Met Ser Trp Val Arg Gln Ala Pro Gly Lys Cys Leu
    50                  55                  60

Glu Trp Val Ala Tyr Ile Ser Ser Gly Gly Gly Thr Tyr Tyr Pro
65                  70                  75                  80

Asp Thr Val Lys Gly Arg Phe Thr Ile Ser Arg Asp Asn Ser Lys Asn
                85                  90                  95

Thr Leu Phe Leu Gln Met Asp Ser Leu Arg Pro Glu Asp Thr Gly Val
            100                 105                 110

Tyr Phe Cys Ala Arg Gly Gly Val Thr Lys Gly Tyr Phe Asp Val Trp
        115                 120                 125

Gly Gln Gly Thr Pro Val Thr Val Ser Ser Gly Gly Gly Gly Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Arg Ala Ser Gly Asn Ile His Asn Tyr Leu Thr
            180                 185                 190

Trp Tyr Gln Gln Thr Pro Gly Lys Ala Pro Lys Leu Leu Ile Tyr Asn
        195                 200                 205

Ala Lys Thr Leu Ala Asp Gly Val Pro Ser Arg Phe Ser Gly Ser Gly
    210                 215                 220

Ser Gly Thr Asp Tyr Thr Phe Thr Ile Ser Ser Leu Gln Pro Glu Asp
225                 230                 235                 240

Ile Ala Thr Tyr Tyr Cys Gln His Phe Trp Ser Ile Pro Tyr Thr Phe
                245                 250                 255

Gly Cys Gly Thr Lys Leu Glu Ile Lys Gly Gly Gly Ser Gly Gly
            260                 265                 270

Gly Gly Ser Gln Val Gln Leu Val Glu Ser Gly Gly Gly Val Val Gln
        275                 280                 285

Pro Gly Arg Ser Leu Arg Leu Asp Cys Lys Ala Ser Gly Ile Thr Phe
    290                 295                 300

Ser Asn Ser Gly Met His Trp Val Arg Gln Ala Pro Gly Lys Gly Leu
305                 310                 315                 320

Glu Trp Val Ala Val Ile Trp Tyr Asp Gly Ser Lys Arg Tyr Tyr Ala
                325                 330                 335

Asp Ser Val Lys Gly Arg Phe Thr Ile Ser Arg Asp Asn Ser Lys Asn
            340                 345                 350

Thr Leu Phe Leu Gln Met Asn Ser Leu Arg Ala Glu Asp Thr Ala Val
        355                 360                 365
```

Tyr Tyr Cys Ala Thr Asn Asp Asp Tyr Trp Gly Gln Gly Thr Leu Val
370                 375                 380

Thr Val Ser Ser Ala Ser Thr Lys Gly Pro Ser Val Phe Pro Leu Ala
385                 390                 395                 400

Pro Cys Ser Arg Ser Thr Ser Glu Ser Thr Ala Ala Leu Gly Cys Leu
        405                 410                 415

Val Lys Asp Tyr Phe Pro Glu Pro Val Thr Val Ser Trp Asn Ser Gly
        420                 425                 430

Ala Leu Thr Ser Gly Val His Thr Phe Pro Ala Val Leu Gln Ser Ser
        435                 440                 445

Gly Leu Tyr Ser Leu Ser Ser Val Val Thr Val Pro Ser Ser Ser Leu
        450                 455                 460

Gly Thr Lys Thr Tyr Thr Cys Asn Val Asp His Lys Pro Ser Asn Thr
465                 470                 475                 480

Lys Val Asp Lys Arg Val Glu Ser Lys Tyr Gly Pro Pro Cys Pro Pro
        485                 490                 495

Cys Pro Ala Pro Glu Phe Leu Gly Gly Pro Ser Val Phe Leu Phe Pro
        500                 505                 510

Pro Lys Pro Lys Asp Thr Leu Met Ile Ser Arg Thr Pro Glu Val Thr
        515                 520                 525

Cys Val Val Val Asp Val Ser Gln Glu Asp Pro Glu Val Gln Phe Asn
530                 535                 540

Trp Tyr Val Asp Gly Val Glu Val His Asn Ala Lys Thr Lys Pro Arg
545                 550                 555                 560

Glu Glu Gln Phe Asn Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Gly Leu Pro Ser Ser Ile Glu Lys Thr Ile Ser Lys Ala Lys
        595                 600                 605

Gly Gln Pro Arg Glu Pro Gln Val Tyr Thr Leu Pro Pro Ser Gln Glu
610                 615                 620

Glu Met Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Arg Leu Thr Val Asp Lys Ser Arg Trp Gln Glu Gly
        675                 680                 685

Asn Val Phe Ser Cys Ser Val Met His Glu Ala Leu His Asn His Tyr
        690                 695                 700

Thr Gln Lys Ser Leu Ser Leu Ser Leu Gly Lys
705                 710                 715

<210> SEQ ID NO 115
<211> LENGTH: 715
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 115

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
        35                  40                  45

Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
            405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
            435                 440                 445

Thr Gln Lys Ser Leu Ser Leu Ser Leu Gly Lys Gly Gly Gly Gly Ser
            450                 455                 460

Gly Gly Gly Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Gly
                485                 490                 495

Asn Ile His Asn Tyr Leu Thr Trp Tyr Gln Gln Thr Pro Gly Lys Ala
            500                 505                 510

Pro Lys Leu Leu Ile Tyr Asn Ala Lys Thr Leu Ala Asp Gly Val Pro
            515                 520                 525

Ser Arg Phe Ser Gly Ser Gly Ser Gly Thr Asp Tyr Thr Phe Thr Ile
            530                 535                 540

Ser Ser Leu Gln Pro Glu Asp Ile Ala Thr Tyr Tyr Cys Gln His Phe
545                 550                 555                 560

Trp Ser Ile Pro Tyr Thr Phe Gly Cys Gly Thr Lys Leu Glu Ile Lys
                565                 570                 575

Gly Gly Gly Gly Ser Gly Gly Gly Ser Gly Gly Gly Gly Ser Gly
            580                 585                 590

Gly Gly Gly Ser Glu Val Gln Leu Val Glu Ser Gly Gly Val Val
            595                 600                 605

Gln Pro Gly Arg Ser Leu Arg Leu Ser Cys Ser Ser Ser Gly Phe Ile
610                 615                 620

Phe Ser Ser Tyr Asp Met Ser Trp Val Arg Gln Ala Pro Gly Lys Cys
625                 630                 635                 640

Leu Glu Trp Val Ala Tyr Ile Ser Ser Gly Gly Gly Thr Tyr Tyr
                645                 650                 655

Pro Asp Thr Val Lys Gly Arg Phe Thr Ile Ser Arg Asp Asn Ser Lys
            660                 665                 670

Asn Thr Leu Phe Leu Gln Met Asp Ser Leu Arg Pro Glu Asp Thr Gly
            675                 680                 685

Val Tyr Phe Cys Ala Arg Gly Gly Val Thr Lys Gly Tyr Phe Asp Val
            690                 695                 700

Trp Gly Gln Gly Thr Pro Val Thr Val Ser Ser
705                 710                 715

<210> SEQ ID NO 116
<211> LENGTH: 715
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
         35                  40                  45

Ser Asn Ser Gly Met His Trp Val Arg Gln Ala Pro Gly Lys Gly Leu
 50                  55                  60

Glu Trp Val Ala Val Ile Trp Tyr Asp Gly Ser Lys Arg Tyr Tyr Ala
 65                  70                  75                  80

Asp Ser Val Lys Gly Arg Phe Thr Ile Ser Arg Asp Asn Ser Lys Asn
                 85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
            115                 120                 125

Thr Val Ser Ser Ala Ser Thr Lys Gly Pro Ser Val Phe Pro Leu Ala
            130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Lys Thr Tyr Thr Cys Asn Val Asp His Lys Pro Ser Asn Thr
            210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser Gln Glu Asp Pro Glu Val Gln Phe Asn
            275                 280                 285

Trp Tyr Val Asp Gly Val Glu Val His Asn Ala Lys Thr Lys Pro Arg
            290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
                340                 345                 350

Gly Gln Pro Arg Glu Pro Gln Val Tyr Thr Leu Pro Pro Ser Gln Glu
            355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
            435                 440                 445

Thr Gln Lys Ser Leu Ser Leu Ser Leu Gly Lys Gly Gly Gly Ser
    450                 455                 460

Gly Gly Gly Gly Ser Glu Val Gln Leu Val Glu Ser Gly Gly Gly Val
465                 470                 475                 480

Val Gln Pro Gly Arg Ser Leu Arg Leu Ser Cys Ser Ser Gly Phe
            485                 490                 495

Ile Phe Ser Ser Tyr Asp Met Ser Trp Val Arg Gln Ala Pro Gly Lys
                500                 505                 510

Cys Leu Glu Trp Val Ala Tyr Ile Ser Ser Gly Gly Gly Thr Tyr
            515                 520                 525

Tyr Pro Asp Thr Val Lys Gly Arg Phe Thr Ile Ser Arg Asp Asn Ser
530                 535                 540

Lys Asn Thr Leu Phe Leu Gln Met Asp Ser Leu Arg Pro Glu Asp Thr
545                 550                 555                 560

Gly Val Tyr Phe Cys Ala Arg Gly Gly Val Thr Lys Gly Tyr Phe Asp
                565                 570                 575

Val Trp Gly Gln Gly Thr Pro Val Thr Val Ser Ser Gly Gly Gly Gly
            580                 585                 590

Ser Gly Gly Gly Gly Ser Gly Gly Gly Ser Gly Gly Gly Gly Ser
            595                 600                 605

Asp Ile Gln Met Thr Gln Ser Pro Ser Ser Leu Ser Ala Ser Val Gly
            610                 615                 620

Asp Arg Val Thr Ile Thr Cys Arg Ala Ser Gly Asn Ile His Asn Tyr
625                 630                 635                 640

Leu Thr Trp Tyr Gln Gln Thr Pro Gly Lys Ala Pro Lys Leu Leu Ile
                645                 650                 655

Tyr Asn Ala Lys Thr Leu Ala Asp Gly Val Pro Ser Arg Phe Ser Gly
            660                 665                 670

Ser Gly Ser Gly Thr Asp Tyr Thr Phe Thr Ile Ser Ser Leu Gln Pro
            675                 680                 685

Glu Asp Ile Ala Thr Tyr Tyr Cys Gln His Phe Trp Ser Ile Pro Tyr
            690                 695                 700

Thr Phe Gly Cys Gly Thr Lys Leu Glu Ile Lys
705                 710                 715

<210> SEQ ID NO 117
<211> LENGTH: 683
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gly Asn Ile
        35                  40                  45

His Asn Tyr Leu Thr Trp Tyr Gln Gln Thr Pro Gly Lys Ala Pro Lys
    50                  55                  60

Leu Leu Ile Tyr Asn Ala Lys Thr Leu Ala Asp Gly Val Pro Ser Arg
65                  70                  75                  80

Phe Ser Gly Ser Gly Ser Gly Thr Asp Tyr Thr Phe Thr Ile Ser Ser
                85                  90                  95

```
Leu Gln Pro Glu Asp Ile Ala Thr Tyr Tyr Cys Gln His Phe Trp Ser
            100                 105                 110

Ile Pro Tyr Thr Phe Gly Gln Gly Thr Lys Leu Glu Ile Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
210                 215                 220

Thr Lys Ser Phe Asn Arg Gly Glu Cys Gly Ser Gly Gln Val Gln Leu
225                 230                 235                 240

Val Gln Ser Gly Val Glu Val Lys Lys Pro Gly Ala Ser Val Lys Val
            245                 250                 255

Ser Cys Lys Ala Ser Gly Tyr Thr Phe Thr Asn Tyr Tyr Met Tyr Trp
            260                 265                 270

Val Arg Gln Ala Pro Gly Gln Gly Leu Glu Trp Met Gly Gly Ile Asn
            275                 280                 285

Pro Ser Asn Gly Gly Thr Asn Phe Asn Glu Lys Phe Lys Asn Arg Val
            290                 295                 300

Thr Leu Thr Thr Asp Ser Ser Thr Thr Thr Ala Tyr Met Glu Leu Lys
305                 310                 315                 320

Ser Leu Gln Phe Asp Asp Thr Ala Val Tyr Tyr Cys Ala Arg Arg Asp
                325                 330                 335

Tyr Arg Phe Asp Met Gly Phe Asp Tyr Trp Gly Gln Gly Thr Thr Val
            340                 345                 350

Thr Val Ser Ser Ala Ser Thr Lys Gly Pro Ser Val Phe Pro Leu Ala
            355                 360                 365

Pro Cys Ser Arg Ser Thr Ser Glu Ser Thr Ala Ala Leu Gly Cys Leu
370                 375                 380

Val Lys Asp Tyr Phe Pro Glu Pro Val Thr Val Ser Trp Asn Ser Gly
385                 390                 395                 400

Ala Leu Thr Ser Gly Val His Thr Phe Pro Ala Val Leu Gln Ser Ser
                405                 410                 415

Gly Leu Tyr Ser Leu Ser Ser Val Val Thr Val Pro Ser Ser Ser Leu
            420                 425                 430

Gly Thr Lys Thr Tyr Thr Cys Asn Val Asp His Lys Pro Ser Asn Thr
            435                 440                 445

Lys Val Asp Lys Arg Val Glu Ser Lys Tyr Gly Pro Pro Cys Pro Pro
450                 455                 460

Cys Pro Ala Pro Glu Phe Leu Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser Gln Glu Asp Pro Glu Val Gln Phe Asn
            500                 505                 510
```

Trp Tyr Val Asp Gly Val Glu Val His Asn Ala Lys Thr Lys Pro Arg
            515                 520                 525

Glu Glu Gln Phe Asn Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Gly Leu Pro Ser Ser Ile Glu Lys Thr Ile Ser Lys Ala Lys
                565                 570                 575

Gly Gln Pro Arg Glu Pro Gln Val Tyr Thr Leu Pro Pro Ser Gln Glu
            580                 585                 590

Glu Met Thr Lys Asn Gln Val Ser Leu Thr Cys Leu Val Lys Gly Phe
    595                 600                 605

Tyr Pro Ser Asp Ile Ala Val Glu Trp Glu Ser Asn Gly Gln Pro Glu
            610                 615                 620

Asn Asn Tyr Lys Thr Thr Pro Pro Val Leu Asp Ser Asp Gly Ser Phe
625                 630                 635                 640

Phe Leu Tyr Ser Arg Leu Thr Val Asp Lys Ser Arg Trp Gln Glu Gly
                645                 650                 655

Asn Val Phe Ser Cys Ser Val Met His Glu Ala Leu His Asn His Tyr
            660                 665                 670

Thr Gln Lys Ser Leu Ser Leu Ser Leu Gly Lys
            675                 680

<210> SEQ ID NO 118
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Val Val Gln
            20                  25                  30

Pro Gly Arg Ser Leu Arg Leu Ser Cys Ser Ser Ser Gly Phe Ile Phe
        35                  40                  45

Ser Ser Tyr Asp Met Ser Trp Val Arg Gln Ala Pro Gly Lys Gly Leu
    50                  55                  60

Glu Trp Val Ala Tyr Ile Ser Ser Gly Gly Gly Thr Tyr Tyr Pro
65                  70                  75                  80

Asp Thr Val Lys Gly Arg Phe Thr Ile Ser Arg Asp Asn Ser Lys Asn
                85                  90                  95

Thr Leu Phe Leu Gln Met Asp Ser Leu Arg Pro Glu Asp Thr Gly Val
            100                 105                 110

Tyr Phe Cys Ala Arg Gly Gly Val Thr Lys Gly Tyr Phe Asp Val Trp
        115                 120                 125

Gly Gln Gly Thr Pro Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

```
Ala Val Leu Gln Ser Ser Gly Leu Tyr Ser Leu Ser Val Val Thr
            195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys

<210> SEQ ID NO 119
<211> LENGTH: 687
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gly Asn Ile
        35                  40                  45

His Asn Tyr Leu Thr Trp Tyr Gln Gln Thr Pro Gly Lys Ala Pro Lys
    50                  55                  60

Leu Leu Ile Tyr Asn Ala Lys Thr Leu Ala Asp Gly Val Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln His Phe Trp Ser
            100                 105                 110

Ile Pro Tyr Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Gly Gly Ser Gly Ser
225                 230                 235                 240

Gln Val Gln Leu Val Gln Ser Gly Val Glu Val Lys Lys Pro Gly Ala
                245                 250                 255

Ser Val Lys Val Ser Cys Lys Ala Ser Gly Tyr Thr Phe Thr Asn Tyr
            260                 265                 270

Tyr Met Tyr Trp Val Arg Gln Ala Pro Gly Gln Gly Leu Glu Trp Met
        275                 280                 285

Gly Gly Ile Asn Pro Ser Asn Gly Gly Thr Asn Phe Asn Glu Lys Phe
    290                 295                 300
```

-continued

Lys Asn Arg Val Thr Leu Thr Thr Asp Ser Ser Thr Thr Thr Ala Tyr
305                 310                 315                 320

Met Glu Leu Lys Ser Leu Gln Phe Asp Asp Thr Ala Val Tyr Tyr Cys
            325                 330                 335

Ala Arg Arg Asp Tyr Arg Phe Asp Met Gly Phe Asp Tyr Trp Gly Gln
        340                 345                 350

Gly Thr Thr Val Thr Val Ser Ser Ala Ser Thr Lys Gly Pro Ser Val
    355                 360                 365

Phe Pro Leu Ala Pro Cys Ser Arg Ser Thr Ser Glu Ser Thr Ala Ala
370                 375                 380

Leu Gly Cys Leu Val Lys Asp Tyr Phe Pro Glu Pro Val Thr Val Ser
385                 390                 395                 400

Trp Asn Ser Gly Ala Leu Thr Ser Gly Val His Thr Phe Pro Ala Val
                405                 410                 415

Leu Gln Ser Ser Gly Leu Tyr Ser Leu Ser Ser Val Val Thr Val Pro
            420                 425                 430

Ser Ser Ser Leu Gly Thr Lys Thr Tyr Thr Cys Asn Val Asp His Lys
        435                 440                 445

Pro Ser Asn Thr Lys Val Asp Lys Arg Val Glu Ser Lys Tyr Gly Pro
    450                 455                 460

Pro Cys Pro Pro Cys Pro Ala Pro Glu Phe Leu Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser Gln Glu Asp Pro Glu
            500                 505                 510

Val Gln Phe Asn Trp Tyr Val Asp Gly Val Glu Val His Asn Ala Lys
        515                 520                 525

Thr Lys Pro Arg Glu Glu Gln Phe Asn Ser Thr Tyr Arg Val Val Ser
    530                 535                 540

Val Leu Thr Val Leu His Gln Asp Trp Leu Asn Gly Lys Glu Tyr Lys
545                 550                 555                 560

Cys Lys Val Ser Asn Lys Gly Leu Pro Ser Ser Ile Glu Lys Thr Ile
                565                 570                 575

Ser Lys Ala Lys Gly Gln Pro Arg Glu Pro Gln Val Tyr Thr Leu Pro
            580                 585                 590

Pro Ser Gln Glu Glu Met Thr Lys Asn Gln Val Ser Leu Thr Cys Leu
        595                 600                 605

Val Lys Gly Phe Tyr Pro Ser Asp Ile Ala Val Glu Trp Glu Ser Asn
    610                 615                 620

Gly Gln Pro Glu Asn Asn Tyr Lys Thr Thr Pro Pro Val Leu Asp Ser
625                 630                 635                 640

Asp Gly Ser Phe Phe Leu Tyr Ser Arg Leu Thr Val Asp Lys Ser Arg
                645                 650                 655

Trp Gln Glu Gly Asn Val Phe Ser Cys Ser Val Met His Glu Ala Leu
            660                 665                 670

His Asn His Tyr Thr Gln Lys Ser Leu Ser Leu Ser Leu Gly Lys
        675                 680                 685

<210> SEQ ID NO 120
<211> LENGTH: 733
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 120

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Val Val Gln
            20                  25                  30

Pro Gly Arg Ser Leu Arg Leu Ser Cys Ser Ser Ser Gly Phe Ile Phe
        35                  40                  45

Ser Ser Tyr Asp Met Ser Trp Val Arg Gln Ala Pro Gly Lys Gly Leu
    50                  55                  60

Glu Trp Val Ala Tyr Ile Ser Ser Gly Gly Gly Thr Tyr Tyr Pro
65                  70                  75                  80

Asp Thr Val Lys Gly Arg Phe Thr Ile Ser Arg Asp Asn Ser Lys Asn
                85                  90                  95

Thr Leu Phe Leu Gln Met Asp Ser Leu Arg Pro Glu Asp Thr Gly Val
            100                 105                 110

Tyr Phe Cys Ala Arg Gly Gly Val Thr Lys Gly Tyr Phe Asp Val Trp
        115                 120                 125

Gly Gln Gly Thr Pro Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400
```

Ser Asn Gly Gly Gly Ser Gly Gly Gly Ser Gly Gly Gly
              405                 410                 415

Ser Gly Gly Gly Ser Gly Gly Gly Ser Glu Ile Val Leu Thr
        420                 425                 430

Gln Ser Pro Ala Thr Leu Ser Leu Ser Pro Gly Glu Arg Ala Thr Leu
        435                 440                 445

Ser Cys Arg Ala Ser Lys Gly Val Ser Thr Ser Gly Tyr Ser Tyr Leu
450                     455                 460

His Trp Tyr Gln Gln Lys Pro Gly Gln Ala Pro Arg Leu Leu Ile Tyr
465                     470                 475                 480

Leu Ala Ser Tyr Leu Glu Ser Gly Val Pro Ala Arg Phe Ser Gly Ser
                485                 490                 495

Gly Ser Gly Thr Asp Phe Thr Leu Thr Ile Ser Ser Leu Glu Pro Glu
            500                 505                 510

Asp Phe Ala Val Tyr Tyr Cys Gln His Ser Arg Asp Leu Pro Leu Thr
        515                 520                 525

Phe Gly Gly Gly Thr Lys Val Glu Ile Lys Arg Thr Val Ala Ala Pro
    530                 535                 540

Ser Val Phe Ile Phe Pro Pro Ser Asp Glu Gln Leu Lys Ser Gly Thr
545                 550                 555                 560

Ala Ser Val Val Cys Leu Leu Asn Asn Phe Tyr Pro Arg Glu Ala Lys
                565                 570                 575

Val Gln Trp Lys Val Asp Asn Ala Leu Gln Ser Gly Asn Ser Gln Glu
                580                 585                 590

Ser Val Thr Glu Gln Asp Ser Lys Asp Ser Thr Tyr Ser Leu Ser Ser
            595                 600                 605

Thr Leu Thr Leu Ser Lys Ala Asp Tyr Glu Lys His Lys Val Tyr Ala
        610                 615                 620

Cys Glu Val Thr His Gln Gly Leu Ser Ser Pro Val Thr Lys Ser Phe
625                 630                 635                 640

Asn Arg Gly Glu Cys Gly Gly Gly Ser Gly Gly Gly Ser Gly
                645                 650                 655

Gly Gly Gly Ser Gly Gly Gly Ser Gly Gly Gly Ser Gly Gln
            660                 665                 670

Pro Glu Asn Asn Tyr Lys Thr Thr Pro Pro Val Leu Asp Ser Asp Gly
        675                 680                 685

Ser Phe Phe Leu Tyr Ser Arg Leu Thr Val Asp Lys Ser Arg Trp Gln
690                 695                 700

Glu Gly Asn Val Phe Ser Cys Ser Val Met His Glu Ala Leu His Asn
705                 710                 715                 720

His Tyr Thr Gln Lys Ser Leu Ser Leu Ser Leu Gly Lys
                725                 730

<210> SEQ ID NO 121
<211> LENGTH: 730
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Gly Trp Ser Cys Ile Ile Leu Phe Leu Val Ala Thr Ala Thr Gly
1               5                   10                  15

```
Val His Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gly Gly Gly Ser Gly Gly Gly Gly Ser Gly Gly Gly
                405                 410                 415

Gly Ser Gly Gly Gly Gly Ser Gly Gly Gly Gly Ser Asp Ile Gln Met
            420                 425                 430
```

```
Thr Gln Ser Pro Ser Ser Leu Ser Ala Ser Val Gly Asp Arg Val Thr
            435                 440                 445

Ile Thr Cys Arg Ala Ser Gly Asn Ile His Asn Tyr Leu Thr Trp Tyr
450                 455                 460

Gln Gln Thr Pro Gly Lys Ala Pro Lys Leu Leu Ile Tyr Asn Ala Lys
465                 470                 475                 480

Thr Leu Ala Asp Gly Val Pro Ser Arg Phe Ser Gly Ser Gly Ser Gly
            485                 490                 495

Thr Asp Tyr Thr Phe Thr Ile Ser Ser Leu Gln Pro Glu Asp Ile Ala
            500                 505                 510

Thr Tyr Tyr Cys Gln His Phe Trp Ser Ile Pro Tyr Thr Phe Gly Gln
            515                 520                 525

Gly Thr Lys Leu Glu Ile Lys Arg Thr Val Ala Ala Pro Ser Val Phe
            530                 535                 540

Ile Phe Pro Pro Ser Asp Glu Gln Leu Lys Ser Gly Thr Ala Ser Val
545                 550                 555                 560

Val Cys Leu Leu Asn Asn Phe Tyr Pro Arg Glu Ala Lys Val Gln Trp
                565                 570                 575

Lys Val Asp Asn Ala Leu Gln Ser Gly Asn Ser Gln Glu Ser Val Thr
            580                 585                 590

Glu Gln Asp Ser Lys Asp Ser Thr Tyr Ser Leu Ser Ser Thr Leu Thr
            595                 600                 605

Leu Ser Lys Ala Asp Tyr Glu Lys His Lys Val Tyr Ala Cys Glu Val
            610                 615                 620

Thr His Gln Gly Leu Ser Ser Pro Val Thr Lys Ser Phe Asn Arg Gly
625                 630                 635                 640

Glu Cys Gly Gly Gly Gly Ser Gly Gly Gly Gly Ser Gly Gly Gly Gly
                645                 650                 655

Ser Gly Gly Gly Gly Ser Gly Gly Gly Gly Ser Gly Gln Pro Glu Asn
            660                 665                 670

Asn Tyr Lys Thr Thr Pro Pro Val Leu Asp Ser Asp Gly Ser Phe Phe
            675                 680                 685

Leu Tyr Ser Arg Leu Thr Val Asp Lys Ser Arg Trp Gln Glu Gly Asn
            690                 695                 700

Val Phe Ser Cys Ser Val Met His Glu Ala Leu His Asn His Tyr Thr
705                 710                 715                 720

Gln Lys Ser Leu Ser Leu Ser Leu Gly Lys
            725                 730

<210> SEQ ID NO 122
<211> LENGTH: 723
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
            35                  40                  45

Ser Asn Ser Gly Met His Trp Val Arg Gln Ala Pro Gly Lys Gly Leu
50                  55                  60
```

```
Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
            85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
            115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Lys Thr Tyr Thr Cys Asn Val Asp His Lys Pro Ser Asn Thr
210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
            275                 280                 285

Trp Tyr Val Asp Gly Val Glu Val His Asn Ala Lys Thr Lys Pro Arg
290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
            355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gly Gly Gly
385                 390                 395                 400

Ser Gly Gly Gly Gly Ser Gly Gly Gly Gly Ser Gly Gly Gly Gly Ser
                405                 410                 415

Gly Gly Gly Gly Ser Asp Ile Gln Met Thr Gln Ser Pro Ser Ser Leu
            420                 425                 430

Ser Ala Ser Val Gly Asp Arg Val Thr Ile Thr Cys Arg Ala Ser Gly
            435                 440                 445

Asn Ile His Asn Tyr Leu Thr Trp Tyr Gln Gln Thr Pro Gly Lys Ala
            450                 455                 460

Pro Lys Leu Leu Ile Tyr Asn Ala Lys Thr Leu Ala Asp Gly Val Pro
465                 470                 475                 480
```

```
Ser Arg Phe Ser Gly Ser Gly Ser Gly Thr Asp Tyr Thr Phe Thr Ile
                485                 490                 495

Ser Ser Leu Gln Pro Glu Asp Ile Ala Thr Tyr Tyr Cys Gln His Phe
            500                 505                 510

Trp Ser Ile Pro Tyr Thr Phe Gly Gln Gly Thr Lys Leu Glu Ile Lys
        515                 520                 525

Arg Thr Val Ala Ala Pro Ser Val Phe Ile Phe Pro Pro Ser Asp Glu
    530                 535                 540

Gln Leu Lys Ser Gly Thr Ala Ser Val Val Cys Leu Leu Asn Asn Phe
545                 550                 555                 560

Tyr Pro Arg Glu Ala Lys Val Gln Trp Lys Val Asp Asn Ala Leu Gln
            565                 570                 575

Ser Gly Asn Ser Gln Glu Ser Val Thr Glu Gln Asp Ser Lys Asp Ser
        580                 585                 590

Thr Tyr Ser Leu Ser Ser Thr Leu Thr Leu Ser Lys Ala Asp Tyr Glu
    595                 600                 605

Lys His Lys Val Tyr Ala Cys Glu Val Thr His Gln Gly Leu Ser Ser
610                 615                 620

Pro Val Thr Lys Ser Phe Asn Arg Gly Glu Cys Gly Gly Gly Gly Ser
625                 630                 635                 640

Gly Gly Gly Gly Ser Gly Gly Gly Ser Gly Gly Gly Gly Ser Gly
            645                 650                 655

Gly Gly Gly Ser Gly Gln Pro Glu Asn Asn Tyr Lys Thr Thr Pro Pro
        660                 665                 670

Val Leu Asp Ser Asp Gly Ser Phe Phe Leu Tyr Ser Arg Leu Thr Val
    675                 680                 685

Asp Lys Ser Arg Trp Gln Glu Gly Asn Val Phe Ser Cys Ser Val Met
690                 695                 700

His Glu Ala Leu His Asn His Tyr Thr Gln Lys Ser Leu Ser Leu Ser
705                 710                 715                 720

Leu Gly Lys

<210> SEQ ID NO 123
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 "Gly Gly Gly
      Gly Ser" repeating units

<400> SEQUENCE: 123

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
```

```
<222> LOCATION: (1)..(10)
<223> OTHER INFORMATION: This sequence may encompass 1-5 "Gly Ser"
      repeating units

<400> SEQUENCE: 124

Gly Ser Gly Ser Gly Ser Gly Ser Gly Ser
1               5                   10

<210> SEQ ID NO 125
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Val Tyr Gly Met Asn Trp Val Arg Gln Ala Pro Gly Lys Gly Leu
        50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320
```

-continued

Ser Val Leu Thr Val Leu His Gln Asp Trp Leu Asn Gly Lys Glu Tyr
            325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
            370                 375                 380

Leu Val Lys Gly Phe Tyr Pro Ser Asp Ile Ala Val Glu Trp Glu Ser
385                 390                 395                 400

Asn Gly Gly Gly Ser Glu Ile Val Leu Thr Gln Ser Pro Ala Thr
            405                 410                 415

Leu Ser Leu Ser Pro Gly Glu Arg Ala Thr Leu Ser Cys Arg Ala Ser
            420                 425                 430

Lys Gly Val Ser Thr Ser Gly Tyr Ser Tyr Leu His Trp Tyr Gln Gln
            435                 440                 445

Lys Pro Gly Gln Ala Pro Arg Leu Leu Ile Tyr Leu Ala Ser Tyr Leu
            450                 455                 460

Glu Ser Gly Val Pro Ala Arg Phe Ser Gly Ser Gly Ser Gly Thr Asp
465                 470                 475                 480

Phe Thr Leu Thr Ile Ser Ser Leu Glu Pro Glu Asp Phe Ala Val Tyr
            485                 490                 495

Tyr Cys Gln His Ser Arg Asp Leu Pro Leu Thr Phe Gly Gly Gly Thr
            500                 505                 510

Lys Val Glu Ile Lys Arg Thr Val Ala Ala Pro Ser Val Phe Ile Phe
            515                 520                 525

Pro Pro Ser Asp Glu Gln Leu Lys Ser Gly Thr Ala Ser Val Val Cys
            530                 535                 540

Leu Leu Asn Asn Phe Tyr Pro Arg Glu Ala Lys Val Gln Trp Lys Val
545                 550                 555                 560

Asp Asn Ala Leu Gln Ser Gly Asn Ser Gln Glu Ser Val Thr Glu Gln
            565                 570                 575

Asp Ser Lys Asp Ser Thr Tyr Ser Leu Ser Ser Thr Leu Thr Leu Ser
            580                 585                 590

Lys Ala Asp Tyr Glu Lys His Lys Val Tyr Ala Cys Glu Val Thr His
            595                 600                 605

Gln Gly Leu Ser Ser Pro Val Thr Lys Ser Phe Asn Arg Gly Glu Cys
            610                 615                 620

Gly Gly Gly Gly Ser Gly Gly Gly Gly Ser Gly Gly Gly Gly Ser Gly
625                 630                 635                 640

Gly Gly Gly Ser Gly Gly Gly Ser Gln Pro Glu Asn Asn Tyr Lys
            645                 650                 655

Thr Thr Pro Pro Val Leu Asp Ser Asp Gly Ser Phe Phe Leu Tyr Ser
            660                 665                 670

Arg Leu Thr Val Asp Lys Ser Arg Trp Gln Glu Gly Asn Val Phe Ser
            675                 680                 685

Cys Ser Val Met His Glu Ala Leu His Asn His Tyr Thr Gln Lys Ser
            690                 695                 700

Leu Ser Leu Ser Leu Gly Lys
705                 710

<210> SEQ ID NO 126
<211> LENGTH: 711

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

```
Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380
```

```
Leu Val Lys Gly Phe Tyr Pro Ser Asp Ile Ala Val Glu Trp Glu Ser
385                 390                 395                 400

Asn Gly Gly Gly Ser Gly Gly Gly Ser Gly Gly Gly Ser
            405                 410                 415

Glu Ile Val Leu Thr Gln Ser Pro Ala Thr Leu Ser Leu Ser Pro Gly
            420                 425                 430

Glu Arg Ala Thr Leu Ser Cys Arg Ala Ser Lys Gly Val Ser Thr Ser
            435                 440                 445

Gly Tyr Ser Tyr Leu His Trp Tyr Gln Gln Lys Pro Gly Gln Ala Pro
            450                 455                 460

Arg Leu Leu Ile Tyr Leu Ala Ser Tyr Leu Glu Ser Gly Val Pro Ala
465                 470                 475                 480

Arg Phe Ser Gly Ser Gly Ser Gly Thr Asp Phe Thr Leu Thr Ile Ser
            485                 490                 495

Ser Leu Glu Pro Glu Asp Phe Ala Val Tyr Tyr Cys Gln His Ser Arg
            500                 505                 510

Asp Leu Pro Leu Thr Phe Gly Gly Gly Thr Lys Val Glu Ile Lys Arg
            515                 520                 525

Thr Val Ala Ala Pro Ser Val Phe Ile Phe Pro Pro Ser Asp Glu Gln
            530                 535                 540

Leu Lys Ser Gly Thr Ala Ser Val Val Cys Leu Leu Asn Asn Phe Tyr
545                 550                 555                 560

Pro Arg Glu Ala Lys Val Gln Trp Lys Val Asp Asn Ala Leu Gln Ser
            565                 570                 575

Gly Asn Ser Gln Glu Ser Val Thr Glu Gln Asp Ser Lys Asp Ser Thr
            580                 585                 590

Tyr Ser Leu Ser Ser Thr Leu Thr Leu Ser Lys Ala Asp Tyr Glu Lys
            595                 600                 605

His Lys Val Tyr Ala Cys Glu Val Thr His Gln Gly Leu Ser Ser Pro
            610                 615                 620

Val Thr Lys Ser Phe Asn Arg Gly Glu Cys Gly Gly Gly Gly Ser Gly
625                 630                 635                 640

Gly Gly Gly Ser Gly Gly Gly Gly Ser Gln Pro Glu Asn Asn Tyr Lys
            645                 650                 655

Thr Thr Pro Pro Val Leu Asp Ser Asp Gly Ser Phe Phe Leu Tyr Ser
            660                 665                 670

Arg Leu Thr Val Asp Lys Ser Arg Trp Gln Glu Gly Asn Val Phe Ser
            675                 680                 685

Cys Ser Val Met His Glu Ala Leu His Asn His Tyr Thr Gln Lys Ser
            690                 695                 700

Leu Ser Leu Ser Leu Gly Lys
705                 710

<210> SEQ ID NO 127
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Gly Trp Ser Cys Ile Ile Leu Phe Leu Val Ala Thr Ala Thr Gly
1               5                   10                  15
```

```
Val His Ser Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
            35                  40                  45

Ser Val Tyr Gly Met Asn Trp Val Arg Gln Ala Pro Gly Lys Gly Leu
 50                  55                  60

Glu Trp Val Ala Ile Ile Trp Tyr Asp Gly Asp Asn Gln Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Leu Gly Thr Lys Thr Tyr Thr Cys Asn Val Asp His
210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
            275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gly Gly Gly Ser Gly Gly Gly Gly Ser Gly Gly Gly Gly Ser
                405                 410                 415

Gly Gly Gly Gly Ser Glu Ile Val Leu Thr Gln Ser Pro Ala Thr Leu
            420                 425                 430
```

Ser Leu Ser Pro Gly Glu Arg Ala Thr Leu Ser Cys Arg Ala Ser Lys
            435                 440                 445

Gly Val Ser Thr Ser Gly Tyr Ser Tyr Leu His Trp Tyr Gln Gln Lys
        450                 455                 460

Pro Gly Gln Ala Pro Arg Leu Leu Ile Tyr Leu Ala Ser Tyr Leu Glu
465                 470                 475                 480

Ser Gly Val Pro Ala Arg Phe Ser Gly Ser Gly Ser Gly Thr Asp Phe
                485                 490                 495

Thr Leu Thr Ile Ser Ser Leu Glu Pro Glu Asp Phe Ala Val Tyr Tyr
            500                 505                 510

Cys Gln His Ser Arg Asp Leu Pro Leu Thr Phe Gly Gly Gly Thr Lys
        515                 520                 525

Val Glu Ile Lys Arg Thr Val Ala Ala Pro Ser Val Phe Ile Phe Pro
530                 535                 540

Pro Ser Asp Glu Gln Leu Lys Ser Gly Thr Ala Ser Val Val Cys Leu
545                 550                 555                 560

Leu Asn Asn Phe Tyr Pro Arg Glu Ala Lys Val Gln Trp Lys Val Asp
                565                 570                 575

Asn Ala Leu Gln Ser Gly Asn Ser Gln Glu Ser Val Thr Glu Gln Asp
            580                 585                 590

Ser Lys Asp Ser Thr Tyr Ser Leu Ser Ser Thr Leu Thr Leu Ser Lys
        595                 600                 605

Ala Asp Tyr Glu Lys His Lys Val Tyr Ala Cys Glu Val Thr His Gln
610                 615                 620

Gly Leu Ser Ser Pro Val Thr Lys Ser Phe Asn Arg Gly Glu Cys Gly
625                 630                 635                 640

Gly Gly Gly Ser Gly Gly Gly Gly Ser Gln Pro Glu Asn Asn Tyr Lys
                645                 650                 655

Thr Thr Pro Pro Val Leu Asp Ser Asp Gly Ser Phe Phe Leu Tyr Ser
            660                 665                 670

Arg Leu Thr Val Asp Lys Ser Arg Trp Gln Gly Asn Val Phe Ser
        675                 680                 685

Cys Ser Val Met His Glu Ala Leu His Asn His Tyr Thr Gln Lys Ser
690                 695                 700

Leu Ser Leu Ser Leu Gly Lys
705                 710

<210> SEQ ID NO 128
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

```
Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gly Gly Ser Gly Gly Gly Ser Gly Gly Gly Gly Ser
                405                 410                 415

Gly Gly Gly Gly Ser Gly Gly Gly Ser Glu Ile Val Leu Thr Gln
            420                 425                 430

Ser Pro Ala Thr Leu Ser Leu Ser Pro Gly Glu Arg Ala Thr Leu Ser
        435                 440                 445

Cys Arg Ala Ser Lys Gly Val Ser Thr Ser Gly Tyr Ser Tyr Leu His
    450                 455                 460

Trp Tyr Gln Gln Lys Pro Gly Gln Ala Pro Arg Leu Leu Ile Tyr Leu
465                 470                 475                 480

Ala Ser Tyr Leu Glu Ser Gly Val Pro Ala Arg Phe Ser Gly Ser Gly
                485                 490                 495
```

Ser Gly Thr Asp Phe Thr Leu Thr Ile Ser Ser Leu Glu Pro Glu Asp
              500                 505                 510

Phe Ala Val Tyr Tyr Cys Gln His Ser Arg Asp Leu Pro Leu Thr Phe
          515                 520                 525

Gly Gly Gly Thr Lys Val Glu Ile Lys Arg Thr Val Ala Ala Pro Ser
      530                 535                 540

Val Phe Ile Phe Pro Pro Ser Asp Glu Gln Leu Lys Ser Gly Thr Ala
545                 550                 555                 560

Ser Val Val Cys Leu Leu Asn Asn Phe Tyr Pro Arg Glu Ala Lys Val
              565                 570                 575

Gln Trp Lys Val Asp Asn Ala Leu Gln Ser Gly Asn Ser Gln Glu Ser
          580                 585                 590

Val Thr Glu Gln Asp Ser Lys Asp Ser Thr Tyr Ser Leu Ser Ser Thr
      595                 600                 605

Leu Thr Leu Ser Lys Ala Asp Tyr Glu Lys His Lys Val Tyr Ala Cys
610                 615                 620

Glu Val Thr His Gln Gly Leu Ser Ser Pro Val Thr Lys Ser Phe Asn
625                 630                 635                 640

Arg Gly Glu Cys Gly Gly Gly Ser Gln Pro Glu Asn Asn Tyr Lys
              645                 650                 655

Thr Thr Pro Pro Val Leu Asp Ser Asp Gly Ser Phe Phe Leu Tyr Ser
          660                 665                 670

Arg Leu Thr Val Asp Lys Ser Arg Trp Gln Gly Asn Val Phe Ser
              675                 680                 685

Cys Ser Val Met His Glu Ala Leu His Asn His Tyr Thr Gln Lys Ser
690                 695                 700

Leu Ser Leu Ser Leu Gly Lys
705                 710

<210> SEQ ID NO 129
<211> LENGTH: 721
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

```
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
                195                 200                 205

Pro Ser Ser Ser Leu Gly Thr Lys Thr Tyr Thr Cys Asn Val Asp His
210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
            245                 250                 255

Val Phe Leu Phe Pro Pro Lys Pro Lys Asp Thr Leu Met Ile Ser Arg
        260                 265                 270

Thr Pro Glu Val Thr Cys Val Val Val Asp Val Ser Gln Glu Asp Pro
            275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gly Gly Gly Ser Gly Gly Gly Gly Ser Gly Gly Gly Gly Ser
                405                 410                 415

Gly Gly Gly Gly Ser Glu Ile Val Leu Thr Gln Ser Pro Ala Thr Leu
            420                 425                 430

Ser Leu Ser Pro Gly Glu Arg Ala Thr Leu Ser Cys Arg Ala Ser Lys
        435                 440                 445

Gly Val Ser Thr Ser Gly Tyr Ser Tyr Leu His Trp Tyr Gln Gln Lys
450                 455                 460

Pro Gly Gln Ala Pro Arg Leu Leu Ile Tyr Leu Ala Ser Tyr Leu Glu
465                 470                 475                 480

Ser Gly Val Pro Ala Arg Phe Ser Gly Ser Gly Ser Gly Thr Asp Phe
                485                 490                 495

Thr Leu Thr Ile Ser Ser Leu Glu Pro Glu Asp Phe Ala Val Tyr Tyr
            500                 505                 510

Cys Gln His Ser Arg Asp Leu Pro Leu Thr Phe Gly Gly Gly Thr Lys
        515                 520                 525

Val Glu Ile Lys Arg Thr Val Ala Ala Pro Ser Val Phe Ile Phe Pro
530                 535                 540

Pro Ser Asp Glu Gln Leu Lys Ser Gly Thr Ala Ser Val Val Cys Leu
545                 550                 555                 560
```

```
Leu Asn Asn Phe Tyr Pro Arg Glu Ala Lys Val Gln Trp Lys Val Asp
                565                 570                 575

Asn Ala Leu Gln Ser Gly Asn Ser Gln Glu Ser Val Thr Glu Gln Asp
            580                 585                 590

Ser Lys Asp Ser Thr Tyr Ser Leu Ser Ser Thr Leu Thr Leu Ser Lys
        595                 600                 605

Ala Asp Tyr Glu Lys His Lys Val Tyr Ala Cys Glu Val Thr His Gln
    610                 615                 620

Gly Leu Ser Ser Pro Val Thr Lys Ser Phe Asn Arg Gly Glu Cys Gly
625                 630                 635                 640

Gly Gly Gly Ser Gly Gly Gly Ser Gly Gly Gly Ser Gly Gly
                645                 650                 655

Gly Gly Ser Gln Pro Glu Asn Asn Tyr Lys Thr Thr Pro Pro Val Leu
            660                 665                 670

Asp Ser Asp Gly Ser Phe Phe Leu Tyr Ser Arg Leu Thr Val Asp Lys
        675                 680                 685

Ser Arg Trp Gln Glu Gly Asn Val Phe Ser Cys Ser Val Met His Glu
    690                 695                 700

Ala Leu His Asn His Tyr Thr Gln Lys Ser Leu Ser Leu Ser Leu Gly
705                 710                 715                 720

Lys

<210> SEQ ID NO 130
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190
```

```
Val Leu Gln Ser Ser Gly Leu Tyr Ser Leu Ser Ser Val Val Thr Val
            195                 200                 205

Pro Ser Ser Leu Gly Thr Lys Thr Tyr Thr Cys Asn Val Asp His
210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gly Gly Gly Ser Gly Gly Gly Gly Ser Glu Ile Val Leu Thr
                405                 410                 415

Gln Ser Pro Ala Thr Leu Ser Leu Ser Pro Gly Glu Arg Ala Thr Leu
            420                 425                 430

Ser Cys Arg Ala Ser Lys Gly Val Ser Thr Ser Gly Tyr Ser Tyr Leu
        435                 440                 445

His Trp Tyr Gln Gln Lys Pro Gly Gln Ala Pro Arg Leu Leu Ile Tyr
450                 455                 460

Leu Ala Ser Tyr Leu Glu Ser Gly Val Pro Ala Arg Phe Ser Gly Ser
465                 470                 475                 480

Gly Ser Gly Thr Asp Phe Thr Leu Thr Ile Ser Ser Leu Glu Pro Glu
                485                 490                 495

Asp Phe Ala Val Tyr Tyr Cys Gln His Ser Arg Asp Leu Pro Leu Thr
            500                 505                 510

Phe Gly Gly Gly Thr Lys Val Glu Ile Lys Arg Thr Val Ala Ala Pro
        515                 520                 525

Ser Val Phe Ile Phe Pro Pro Ser Asp Glu Gln Leu Lys Ser Gly Thr
530                 535                 540

Ala Ser Val Val Cys Leu Leu Asn Asn Phe Tyr Pro Arg Glu Ala Lys
545                 550                 555                 560

Val Gln Trp Lys Val Asp Asn Ala Leu Gln Ser Gly Asn Ser Gln Glu
                565                 570                 575

Ser Val Thr Glu Gln Asp Ser Lys Asp Ser Thr Tyr Ser Leu Ser Ser
            580                 585                 590

Thr Leu Thr Leu Ser Lys Ala Asp Tyr Glu Lys His Lys Val Tyr Ala
        595                 600                 605
```

```
Cys Glu Val Thr His Gln Gly Leu Ser Ser Pro Val Thr Lys Ser Phe
            610                 615                 620

Asn Arg Gly Glu Cys Gly Gly Gly Ser Gly Gly Gly Ser Gln
625                 630                 635                 640

Pro Glu Asn Asn Tyr Lys Thr Thr Pro Pro Val Leu Asp Ser Asp Gly
                    645                 650                 655

Ser Phe Phe Leu Tyr Ser Arg Leu Thr Val Asp Lys Ser Arg Trp Gln
                660                 665                 670

Glu Gly Asn Val Phe Ser Cys Ser Val Met His Glu Ala Leu His Asn
675                 680                 685

His Tyr Thr Gln Lys Ser Leu Ser Leu Ser Leu Gly Lys
            690                 695                 700
```

<210> SEQ ID NO 131
<211> LENGTH: 731
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255
```

```
Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gly Gly Gly Ser Gly Gly Gly Ser Gly Gly Gly Gly Ser
                405                 410                 415

Gly Gly Gly Gly Ser Gly Gly Gly Gly Ser Glu Ile Val Leu Thr Gln
            420                 425                 430

Ser Pro Ala Thr Leu Ser Leu Ser Pro Gly Glu Arg Ala Thr Leu Ser
        435                 440                 445

Cys Arg Ala Ser Lys Gly Val Ser Thr Ser Gly Tyr Ser Tyr Leu His
    450                 455                 460

Trp Tyr Gln Gln Lys Pro Gly Gln Ala Pro Arg Leu Leu Ile Tyr Leu
465                 470                 475                 480

Ala Ser Tyr Leu Glu Ser Gly Val Pro Ala Arg Phe Ser Gly Ser Gly
                485                 490                 495

Ser Gly Thr Asp Phe Thr Leu Thr Ile Ser Ser Leu Glu Pro Glu Asp
            500                 505                 510

Phe Ala Val Tyr Tyr Cys Gln His Ser Arg Asp Leu Pro Leu Thr Phe
        515                 520                 525

Gly Gly Gly Thr Lys Val Glu Ile Lys Arg Thr Val Ala Ala Pro Ser
    530                 535                 540

Val Phe Ile Phe Pro Pro Ser Asp Glu Gln Leu Lys Ser Gly Thr Ala
545                 550                 555                 560

Ser Val Val Cys Leu Leu Asn Asn Phe Tyr Pro Arg Glu Ala Lys Val
                565                 570                 575

Gln Trp Lys Val Asp Asn Ala Leu Gln Ser Gly Asn Ser Gln Glu Ser
            580                 585                 590

Val Thr Glu Gln Asp Ser Lys Asp Ser Thr Tyr Ser Leu Ser Ser Thr
        595                 600                 605

Leu Thr Leu Ser Lys Ala Asp Tyr Glu Lys His Lys Val Tyr Ala Cys
    610                 615                 620

Glu Val Thr His Gln Gly Leu Ser Ser Pro Val Thr Lys Ser Phe Asn
625                 630                 635                 640

Arg Gly Glu Cys Gly Gly Gly Gly Ser Gly Gly Gly Gly Ser Gly Gly
                645                 650                 655

Gly Gly Ser Gly Gly Gly Gly Ser Gly Gly Gly Gly Ser Gln Pro Glu
            660                 665                 670
```

```
Asn Asn Tyr Lys Thr Thr Pro Pro Val Leu Asp Ser Asp Gly Ser Phe
            675                 680                 685

Phe Leu Tyr Ser Arg Leu Thr Val Asp Lys Ser Arg Trp Gln Glu Gly
        690                 695                 700

Asn Val Phe Ser Cys Ser Val Met His Glu Ala Leu His Asn His Tyr
705                 710                 715                 720

Thr Gln Lys Ser Leu Ser Leu Ser Leu Gly Lys
                725                 730

<210> SEQ ID NO 132
<211> LENGTH: 726
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300
```

```
Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gly Gly Ser Gly Gly Gly Ser Gly Gly Gly Ser
                405                 410                 415

Gly Gly Gly Ser Glu Ile Val Leu Thr Gln Ser Pro Ala Thr Leu
            420                 425                 430

Ser Leu Ser Pro Gly Glu Arg Ala Thr Leu Ser Cys Arg Ala Ser Lys
        435                 440                 445

Gly Val Ser Thr Ser Gly Tyr Ser Tyr Leu His Trp Tyr Gln Gln Lys
450                 455                 460

Pro Gly Gln Ala Pro Arg Leu Leu Ile Tyr Leu Ala Ser Tyr Leu Glu
465                 470                 475                 480

Ser Gly Val Pro Ala Arg Phe Ser Gly Ser Gly Ser Gly Thr Asp Phe
                485                 490                 495

Thr Leu Thr Ile Ser Ser Leu Glu Pro Glu Asp Phe Ala Val Tyr Tyr
            500                 505                 510

Cys Gln His Ser Arg Asp Leu Pro Leu Thr Phe Gly Gly Gly Thr Lys
        515                 520                 525

Val Glu Ile Lys Arg Thr Val Ala Ala Pro Ser Val Phe Ile Phe Pro
530                 535                 540

Pro Ser Asp Glu Gln Leu Lys Ser Gly Thr Ala Ser Val Val Cys Leu
545                 550                 555                 560

Leu Asn Asn Phe Tyr Pro Arg Glu Ala Lys Val Gln Trp Lys Val Asp
                565                 570                 575

Asn Ala Leu Gln Ser Gly Asn Ser Gln Glu Ser Val Thr Glu Gln Asp
            580                 585                 590

Ser Lys Asp Ser Thr Tyr Ser Leu Ser Ser Thr Leu Thr Leu Ser Lys
        595                 600                 605

Ala Asp Tyr Glu Lys His Lys Val Tyr Ala Cys Glu Val Thr His Gln
610                 615                 620

Gly Leu Ser Ser Pro Val Thr Lys Ser Phe Asn Arg Gly Glu Cys Gly
625                 630                 635                 640

Gly Gly Gly Ser Gly Gly Gly Gly Ser Gly Gly Gly Gly Ser Gly Gly
                645                 650                 655

Gly Gly Ser Gly Gly Gly Ser Gln Pro Glu Asn Asn Tyr Lys Thr
            660                 665                 670

Thr Pro Pro Val Leu Asp Ser Asp Gly Ser Phe Phe Leu Tyr Ser Arg
        675                 680                 685

Leu Thr Val Asp Lys Ser Arg Trp Gln Glu Gly Asn Val Phe Ser Cys
690                 695                 700

Ser Val Met His Glu Ala Leu His Asn His Tyr Thr Gln Lys Ser Leu
705                 710                 715                 720
```

```
Ser Leu Ser Leu Gly Lys
                725

<210> SEQ ID NO 133
<211> LENGTH: 726
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
            35                  40                  45

Ser Val Tyr Gly Met Asn Trp Val Arg Gln Ala Pro Gly Lys Gly Leu
        50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350
```

```
Ile Ser Lys Ala Lys Gly Gln Pro Arg Glu Pro Gln Val Tyr Thr Leu
            355                 360                 365
Pro Pro Ser Gln Glu Glu Met Thr Lys Asn Gln Val Ser Leu Thr Cys
370                 375                 380
Leu Val Lys Gly Phe Tyr Pro Ser Asp Ile Ala Val Glu Trp Glu Ser
385                 390                 395                 400
Asn Gly Gly Gly Ser Gly Gly Gly Ser Gly Gly Gly Ser
            405                 410                 415
Gly Gly Gly Gly Ser Gly Gly Gly Ser Glu Ile Val Leu Thr Gln
            420                 425                 430
Ser Pro Ala Thr Leu Ser Leu Ser Pro Gly Glu Arg Ala Thr Leu Ser
            435                 440                 445
Cys Arg Ala Ser Lys Gly Val Ser Thr Ser Gly Tyr Ser Tyr Leu His
            450                 455                 460
Trp Tyr Gln Gln Lys Pro Gly Gln Ala Pro Arg Leu Leu Ile Tyr Leu
465                 470                 475                 480
Ala Ser Tyr Leu Glu Ser Gly Val Pro Ala Arg Phe Ser Gly Ser Gly
            485                 490                 495
Ser Gly Thr Asp Phe Thr Leu Thr Ile Ser Ser Leu Glu Pro Glu Asp
            500                 505                 510
Phe Ala Val Tyr Tyr Cys Gln His Ser Arg Asp Leu Pro Leu Thr Phe
            515                 520                 525
Gly Gly Gly Thr Lys Val Glu Ile Lys Arg Thr Val Ala Ala Pro Ser
            530                 535                 540
Val Phe Ile Phe Pro Pro Ser Asp Glu Gln Leu Lys Ser Gly Thr Ala
545                 550                 555                 560
Ser Val Val Cys Leu Leu Asn Asn Phe Tyr Pro Arg Glu Ala Lys Val
            565                 570                 575
Gln Trp Lys Val Asp Asn Ala Leu Gln Ser Gly Asn Ser Gln Glu Ser
            580                 585                 590
Val Thr Glu Gln Asp Ser Lys Asp Ser Thr Tyr Ser Leu Ser Ser Thr
            595                 600                 605
Leu Thr Leu Ser Lys Ala Asp Tyr Glu Lys His Lys Val Tyr Ala Cys
            610                 615                 620
Glu Val Thr His Gln Gly Leu Ser Ser Pro Val Thr Lys Ser Phe Asn
625                 630                 635                 640
Arg Gly Glu Cys Gly Gly Gly Gly Ser Gly Gly Gly Gly Ser Gly Gly
            645                 650                 655
Gly Gly Ser Gly Gly Gly Gly Ser Gln Pro Glu Asn Asn Tyr Lys Thr
            660                 665                 670
Thr Pro Pro Val Leu Asp Ser Asp Gly Ser Phe Phe Leu Tyr Ser Arg
            675                 680                 685
Leu Thr Val Asp Lys Ser Arg Trp Gln Glu Gly Asn Val Phe Ser Cys
            690                 695                 700
Ser Val Met His Glu Ala Leu His Asn His Tyr Thr Gln Lys Ser Leu
705                 710                 715                 720
Ser Leu Ser Leu Gly Lys
            725
```

BISPECIFIC BINDING MOLECULES THAT TARGET THE TUMOR MICROENVIRONMENT AND AN IMMUNE CHECKPOINT PROTEIN

This application claims priority to U.S. provisional application No. 62/827,381, filed Apr. 1, 2019, the contents of which are hereby incorporated by reference in their entirety.

FIELD OF THE INVENTION

Bispecific binding molecules are provided that are useful for treating cancer and other diseases.

BACKGROUND

Immune checkpoints proteins act as immune system regulators and are a key part of the mechanism of self-tolerance. Inhibitory immune checkpoint proteins include: Programmed cell death protein 1 (PD-1); programmed cell death ligand 1 (PD-L1); Adenosine A2A receptor (A2AR); B7-H3 (CD276); B7-H4 (VTCN1), B and T Lymphocyte Attenuator (BTLA); Cytotoxic T-Lymphocyte-Associated protein 4 (CTLA-4, CD152); Indoleamine 2,3-dioxygenase (IDO); Killer-cell Immunoglobulin-like Receptor (KIR); Lymphocyte Activation Gene-3 (LAG3); Nicotinamide adenine dinucleotide phosphate NADPH oxidase isoform 2 (NOX2); T-cell Immunoglobulin domain and Mucin domain 3 (TIM-3); V-domain Ig suppressor of T cell activation (VISTA); Sialic acid-binding immunoglobulin-type lectin 7 (SIGLEC7, CD328); and Sialic acid-binding immunoglobulin-type lectin 9 (SIGLEC9, CD329).

Programmed cell death protein 1 (PD-1) is a receptor protein expressed on T-cells that acts as an immune checkpoint. PD-1 expression is unregulated on activated T cells as part of the mechanism of immune tolerance. The ligand for PD-1 is programmed cell death ligand 1 (PD-L1), and binding of PD-L1 to PD-1 transmits an inhibitory signal that reduces the activation and proliferation of antigen-specific T-cells in lymph nodes, and reduces apoptosis in regulatory T cells. Tumor cells often overexpress PD-L1 as a mechanism for avoiding immune surveillance. Monoclonal antibodies that inhibit binding between PD-1 and PD-L1—by binding either the ligand or receptor—have been shown to be effective either as monotherapy or in combination with other agents, in subpopulations of patients with a number of cancers, while being ineffective or refractory in many other cancers. Pembrolizumab is a humanized antibody that was first approved by the FDA in 2014 and that is used for treatment of a variety of cancers where the tumor cells express elevated PD-L1. Robert et al., *N Engl. J Med.* 372:2521-2532 (2015) Nivolumab is a fully human antibody that was first approved by the FDA in 2014 and also is used for treating a variety of cancers.

Tumor-associated macrophages (TAMs) are a class of immune cells present in high numbers in the tumor microenvironment (TME), and are associated with cancer-related inflammation. Expression of PD-1 on TAM cells has been shown to decrease macrophage phagocytosis of tumor cells and confers "immunity" on the tumor cells. Gordon et al, *Nature* 545:495 (2017).

Interleukin-1β (IL-1β) is a pro-inflammatory cytokine that is associated with chronic and acute inflammation and plays an important role in multiple inflammation-associated diseases. Elevated levels of IL-1β have also been shown to recruit TAM cells and myeloid-derived suppressor cells (MDSC) to the TME and to promote tumor growth and metastasis in breast cancer. Guo et al., *Sci. Rep.* 6, 36107; doi: 10.1038/srep36107 (2016). In other studies, lung lesions have been shown to be populated with TAM whose pro-tumor activity is up-regulated by activation of the NLRP3 inflammasome and the release of IL-1β. (Terlizzi et al., *Oncotarget* 7:58181 (2016)). Finally, IL-1β has been shown to promote a pro-tumor phenotype of TAM cells and the level of the cytokine has been correlated to tumor size & stage in renal cell carcinoma (Chittezhath et al., *Immunity* 41:815 (2014)).

In mice deficient in IL-1β, fewer animals developed tumors and tumor development was slower. Apte, et al., *European Journal of Cancer*, 42:751 (2006). Additionally, it was shown that the lung cancer risk genotype IL-1β-31TT results in increased expression of IL-1β, providing a microenvironment with elevated inflammatory stimuli and increase lung cancer risk. Bhat et al., *Meta Gene* 2:123 (2014). An IL-1 receptor antagonist was shown to suppress metastasis and tumor proliferation by inhibiting angiogenic factors such as VEGF and IL-8. Konishi et al., *Oncology* 68:138 (2005); Lewis et al, *J. Transl. Med.* 4:48 (2006). Canakinumab, a monoclonal antibody that inhibits IL-1β activity, has been shown to reduce incident lung cancer and lung cancer mortality. Ridker et al., *Lancet*, 390:P1833-1842, (2017).

Engineered bispecific monoclonal antibodies are non-naturally occurring proteins containing immunoglobulin domains that can simultaneously bind to two different types of antigen. Bispecific antibodies can be made in a variety of format and have been used, for example, for cancer immunotherapy and drug delivery. See, for example, Fan et al., *J. Hemat. Oncol.* 8:130 (2015); Brinkmann and Kontermann, *mAbs* 9:182 (2017); and Spiess et al., *Molecular Immunology*, 67: 95-106 (2015).

SUMMARY OF THE INVENTION

What is provided is a binding protein that may contain a first binding domain and a second binding domain, where the first binding domain specifically binds and inhibits activation of an immune checkpoint protein, and where the second binding domain specifically binds and inhibits the activity of IL-β or IL-1R. The immune checkpoint protein may be, for example, PD-1 or PD-L1. The first and second binding domains may contain immunoglobulin binding domains, such as human immunoglobulin binding domains. These binding protein may further contain a third binding domain that specifically binds and inhibits activation of an immune checkpoint protein, such as PD-1 or PD-L1, and a fourth binding domain that specifically binds and inhibits the activity of IL-β or IL-1R. The first and the third binding domains may contain the same CDR regions and the second and the fourth binding domains may contain the same CDR regions.

In one embodiment these protein the first binding domain may contain a) a heavy chain CDR1 of SEQ ID NO.:1; (b) a heavy chain CDR2 of SEQ ID NO.:2; (c) a heavy chain CDR3 of SEQ ID NO.:3; (d) a light chain CDR1 of SEQ ID NO.:4; (e) a light chain CDR2 of SEQ ID NO.:5; and (f) a light chain CDR3 of SEQ ID NO.:6. In this binding protein the first binding domain may contain the heavy chain variable region of SEQ ID NO: 37 and the light chain variable region of SEQ ID NO:38.

In another embodiment the first binding domain may contain a) a heavy chain CDR1 of SEQ ID NO.:7; (b) a heavy chain CDR2 of SEQ ID NO.8; (c) a heavy chain CDR3 of SEQ ID NO.:9; (d) a light chain CDR1 of SEQ ID NO.:10; (e) a light chain CDR2 of SEQ ID NO.:11; and (f) a light chain CDR3 of SEQ ID NO.:12. In this binding protein the first binding domain may contain the heavy chain variable region of SEQ ID NO: 39 and the light chain variable region of SEQ ID NO:40.

In a further embodiment the first binding domain may contain a) a heavy chain CDR1 of SEQ ID NO.:13; (b) a heavy chain CDR2 of SEQ ID NO.15; (c) a heavy chain CDR3 of SEQ ID NO.:15; (d) a light chain CDR1 of SEQ ID NO.:16; (e) a light chain CDR2 of SEQ ID NO.:17; and (f) a light chain CDR3 of SEQ ID NO.:18. In this binding protein the first binding domain may contain the heavy chain variable region of SEQ ID NO: 41 and the light chain variable region of SEQ ID NO:42.

In a still further embodiment the first binding domain may contain (a) a heavy chain CDR1 of SEQ ID NO.:19; (b) a heavy chain CDR2 of SEQ ID NO.:20; (c) a heavy chain CDR3 of SEQ ID NO.:21; (d) a light chain CDR1 of SEQ ID NO.:22; (e) a light chain CDR2 of SEQ ID NO.:23; and (f) a light chain CDR3 of SEQ ID NO.:24. In this binding protein the first binding domain may contain the heavy chain variable region of SEQ ID NO: 43 and the light chain variable region of SEQ ID NO:44.

In yet a further embodiment the first binding domain may contain (a) a heavy chain CDR1 of SEQ ID NO.:25; (b) a heavy chain CDR2 of SEQ ID NO.:26; (c) a heavy chain CDR3 of SEQ ID NO.:27; (d) a light chain CDR1 of SEQ ID NO.:28; (e) a light chain CDR2 of SEQ ID NO.:29; and (f) a light chain CDR3 of SEQ ID NO.:30. In this binding protein the first binding domain may contain the heavy chain variable region of SEQ ID NO: 45 and the light chain variable region of SEQ ID NO:46.

In a further embodiment the first binding domain may contain (a) a heavy chain CDR1 of SEQ ID NO.:31; (b) a heavy chain CDR2 of SEQ ID NO.:32; (c) a heavy chain CDR3 of SEQ ID NO.:33; (d) a light chain CDR1 of SEQ ID NO.:34; (e) a light chain CDR2 of SEQ ID NO.:35; and (f) a light chain CDR3 of SEQ ID NO.:36. In this binding protein the first binding domain may contain the heavy chain variable region of SEQ ID NO: 47 and the light chain variable region of SEQ ID NO:48.

In any of the these binding proteins the second binding domain may contain (a) a heavy chain CDR1 of SEQ ID NO.:49; (b) a heavy chain CDR2 of SEQ ID NO.:50; (c) a heavy chain CDR3 of SEQ ID NO.:51; (d) a light chain CDR1 of SEQ ID NO.:52; (e) a light chain CDR2 of SEQ ID NO.:53; and (f) a light chain CDR3 of SEQ ID NO.:54. In this binding protein the first binding domain may contain the heavy chain variable region of SEQ ID NO: 55 and the light chain variable region of SEQ ID NO:56.

Further provided are binding proteins where the first binding domain is an antibody binding domain that specifically binds and inhibits activation of PD-1 or PD-L1, and where the second binding domain contains an interleukin-1β-binding domain from an interleukin-1 receptor type 1 (IL-1R1) or interleukin-1 receptor type 2 (IL-1R2), optionally coupled to a ligand binding domain from IL-1R accessory protein. For example, such a binding protein may contain a first protein chain containing (a) an interleukin-1β-binding domain of IL-1R1 linked to (b) a VH domain of an immunoglobulin that binds and inhibits PD-1 or PD-L1 linked to (c) an immunoglobulin Fc domain; and a second protein chain containing a VL domain of the immunoglobulin that binds PD-1 or PD-L1. In another example, the binding protein may contain a first protein chain containing (a) a VH domain of an immunoglobulin that binds that binds and inhibits PD-1 or PD-L1 linked to (b) an interleukin-1β-binding domain of IL-1R1 linked to (c) an immunoglobulin Fc domain; and a second protein chain containing a VL domain of the immunoglobulin that binds and inhibits PD-1 or PD-L1. In yet another example, the binding protein may contain two identical protein chains where each protein chain contains (a) an interleukin-1β-binding domain of IL-1R1 linked to (b) an immunoglobulin Fc domain linked to (c) an scFV domain that binds and inhibits activation of PD-1 or PD-L1. In a further example, the binding protein may contain: a first protein chain containing (a) an interleukin-1β-binding domain of IL-1R1 linked to (b) VL and CL domains of an immunoglobulin that binds and inhibits PD-1 or PD-L1 linked to (c) an immunoglobulin Fc domain; and a second protein chain containing VH and CH1 domains of the immunoglobulin that binds and inhibits PD-1 or PD-L1. In still another example, the binding protein may contain: a first protein chain containing (a) VL and CL domains of an immunoglobulin that binds that binds and inhibits PD-1 or PD-L1 linked to (b) an interleukin-1β-binding domain of IL-1R1 linked to (c) an immunoglobulin Fc domain; and a second protein chain containing VH and CH1 domains of the immunoglobulin that binds and inhibits PD-1 or PD-L1.

Nucleic acid molecules that encode the protein chains described above are provided, together with vectors, including expression vectors that contain these nucleic acid molecules.

Methods also are provided for the preparation of a binding protein as described above, where the method includes the steps of a) transforming a host cell with vectors that containing nucleic acid molecules encoding the first binding domains and the second binding domain; b) culturing the host cell under conditions that allow synthesis of the binding protein; and c) recovering the binding protein from the culture. The host cell may contain vectors containing nucleic acid molecules encoding the first binding domain and second binding domain.

Pharmaceutical compositions also are provided that contain a binding protein as described above, together with a pharmaceutically acceptable excipient.

Also provided are bispecific binding proteins ("FAT" binding proteins) that contain a first protein chain, a second protein chain and a third protein chain, where the first protein chain contains a heavy chain having VH, CH1, CH2, and CH3 domains, and a first Fab domain (Fab1) at a solvent exposed loop in the CH2 domain, the CH3 domain, or at the interface of the CH2 and CH3 domains; where the second chain contains a second Fab domain and where the third chain contains a third Fab domain. In these binding proteins the second chain Fab domain associates with the VH and CH1 domains of the first protein chain to form a first binding domain, and the third chain Fab domain associates with the first Fab domain at the solvent exposed loop in the first protein to form a second binding domain. In these binding proteins the solvent exposed loop may contain an amino acid sequence from the CH2 domain, such as ISRTP (SEQ ID NO:57). The solvent exposed loop may contain an amino acid sequence from the CH3 domain, such as SNG. The solvent exposed loop may contain an amino acid sequence from the interface of the CH2 domain and the CH3 domain, such as AKGQP (SEQ ID NO:58). The CH1 domain may be connected to the CH2 domain via an antibody hinge region. The CH2 and CH3 domains may contain an Fc region, such as an Fc region from an IgG1, IgG2, IgG3, IgG4, IgA, IgM, IgE, and IgD. The first protein chain further may contain a first peptide linker between a first terminus of the first Fab domain and the CH2 domain, CH3 domain, or interface of the CH2 and CH3 domains, and/or a second peptide linker between the second terminus of the first Fab domain and the CH2 domain, CH3 domain, or interface of the CH2 and CH3 domains. The first and the second peptide linker may be, for example, (G4S)2 (SEQ ID NO:59), (G4S)3, (SEQ ID NO:60), and (G4S)4 (SEQ ID NO:61). In a first embodiment, the first protein chain may contain the following polypeptide domains, from N-terminus to C-terminus: VH1-CH1-hinge-CH2(N-term)-Fab1-CH2(C-term)-CH3, or in a second embodiment may contain the following polypeptide domains, from N-terminus to C-terminus: VH1-CH1-hinge-CH2-CH3(N-term)-Fab1-CH3(C-term). In a third embodiment the first protein chain may contain the following polypeptide domains, from N-terminus to C-terminus: VH1-CH1-CH2-Fab1-CH3. The first binding domain may bind specifically to PD-1 or PD-L1 and the second binding domain may bind specifically to IL-1β or IL-1R, or the first binding domain may bind specifically to IL-1β or IL-1R and the second binding domain may bind specifically to PD-1 or PD-L1.

In some embodiments of a FAT binding protein the CDR regions of the first binding domain may be selected from the group consisting of the CDR domains of SEQ ID NO:1-6: the CDR domains of SEQ ID NO:7-12; the CDR domains of SEQ ID NO:13-18; the CDR domains of SEQ ID NO:19-24, the CDR domains of SEQ ID NO:25-30; and the CDR domains of SEQ ID NO:31-36 and the CDR regions of the second binding domain may be the CDR domains of SEQ ID NO:49-54.

In further embodiments of the FAT binding proteins the CDR regions of the first binding domain may be the CDR domains of SEQ ID NO:49-54 and the CDR regions of the second binding domain may be selected from the group consisting of: CDR domains of SEQ ID NO:1-6: the CDR domains of SEQ ID NO:7-12; the CDR domains of SEQ ID NO:13-18; the CDR domains of SEQ ID NO:19-24, the CDR domains of SEQ ID NO:25-30; and the CDR domains of SEQ ID NO:31-36.

Nucleic acid molecules that encode the FAT binding protein chains described above are provided, together with vectors, including expression vectors that contain these nucleic acid molecules.

Also provided are pharmaceutical compositions containing one or more FAT binding proteins and a pharmaceutically acceptable carrier.

Methods for the preparation of a FAT binding protein are provided that include the steps of a) transforming a host cell with vectors that may contain nucleic acid molecules encoding the first, second and third protein chains; b) culturing the host cell under conditions that allow synthesis of the binding protein; and c) recovering the FAT binding protein from the culture. The vectors may contain nucleic acid molecules encoding the first, second and protein chains of the FAT protein.

Methods of treating cancer in a subject are provided that include administering a binding protein or pharmaceutical composition as described above to a subject in need thereof. These methods optionally include administering an antitumor agent to the subject in addition to the binding protein.

In these methods of treating cancer, the subject may previously have been treated with cancer immune therapy or have been found to be resistant to the therapy. The subject may have previously been treated with cancer immune therapy or been found to be refractory to cancer immune therapy. The cancer immune therapy may be, for example, treatment with at least one immune checkpoint inhibitor.

The methods of treating cancer may also include administering an additional anti-tumor therapy to the subject, such as chemotherapy, immune therapy, treatment with biologics or small molecules, vaccination, and/or a cell therapy.

Also provided are methods of preventing or reducing the risk of cancer in a subject at risk thereof, that include administering to the subject an effective amount of a binding protein or pharmaceutical composition as described above. The subject may previously have been diagnosed with cancer and be in remission or may previously have been treated for cancer. The subject may be considered to be at risk of cancer due to environmental exposure, tobacco use or exposure, genetic mutation, or a family history of cancer.

In these methods of cancer treatment, the cancer may be lung cancer, such as small cell lung cancer, combined small-cell lung carcinoma, and/or non-small cell lung cancer. The non-small cell lung cancer may be, for example, squamous cell lung carcinoma, large cell lung carcinoma, lung adenocarcinoma, pulmonary pleomorphic carcinoma, lung carcinoid tumor, salivary gland carcinoma, or carcinoma NOS (not otherwise specified). The cancer may be combined small-cell lung carcinoma, extrapulmonary small-cell carcinoma, extrapulmonary small-cell carcinoma localized in the lymph nodes or small-cell carcinoma of the prostate, or may be a cancer with microsatellite instability.

Other objects, features and advantages of the present disclosure will become apparent from the following detailed description. It should be understood, however, that the detailed description and the specific examples are given by way of illustration only, since various changes and modifications within the spirit and scope of the disclosure will become apparent to those skilled in the art from this detailed description.

BRIEF DESCRIPTION OF THE DRAWINGS

FIG. 5 shows the amino acid sequences of bispecific antibodies that bind IL-1β and PD-1. FIG. 5A shows the amino acid sequence of ITA101; FIG. 5B shows the amino acid sequence of ITA102; FIG. 5C shows the amino acid sequence of ITA103 and ITA104; FIG. 5D shows the amino acid sequence of ITA201; FIG. 5E shows the amino acid sequence of ITA202; FIG. 5F shows the amino acid sequence of ITA203; FIG. 5G shows the amino acid sequence of ITA204; FIG. 5H shows the amino acid sequence of ITA301; FIG. 5I shows the amino acid sequence of ITA302; FIG. 5J shows the amino acid sequence of ITA303; FIG. 5K shows the amino acid sequence of ITA304; ITA401 shows the amino acid sequence of ITC401, ITC402, ITC 403, ITC404, and ITC 405; FIG. 5L shows the amino acid sequence of ITA402; FIG. 5M shows the amino acid sequence of ITA403; FIG. 5N shows the amino acid sequence of ITA404; FIG. 5O shows the amino acid sequence of ITB101; FIG. 5P shows the amino acid sequence of ITB102; FIG. 5Q shows the amino acid sequence of ITB103; FIG. 5R shows the amino acid sequence of ITB104; FIG. 5S shows the amino acid sequence of ITB105; FIG. 5T shows the amino acid sequence of ITB106; FIG. 5U shows the amino acid sequence of ITB107; FIG. 5V shows the amino acid sequence of ITB108; FIG. 5W shows the amino acid sequence of ITB109; FIG. 5X shows the amino acid sequence of ITE101; FIG. 5Y shows the amino acid sequence of ITE102; FIG. 5Z shows the amino acid sequence of ITE201; FIG. 5AA shows the amino acid sequence of ITE202; FIG. 5BB shows the amino acid sequence of ITE301; FIG. 5C shows the amino acid sequence of ITE302; FIG. 5DD shows the amino acid sequence of ITF101; FIG. 5EE shows the amino acid sequence of ITF102; FIG. 5FF shows the amino acid sequence of ITF103; FIG. 5GG shows the amino acid sequence of ITF201; FIG. 5HH shows the amino acid sequence of ITF202; FIG. 5II shows the amino acid sequence of ITF301; FIG. 5JJ shows the amino acid sequence of ITF302; FIG. 5KK shows the amino acid sequence of ITF401; FIG. 5LL shows the amino acid sequence of ITF402; FIG. 5MM shows the amino acid sequence of ITF403.

FIGS. 6A-6C show a table of known antibodies and binding molecules that bind IL-1β, IL-1R, PD-1 or PD-L1.

FIGS. 12A and 12B show that bispecific antibodies block IL-1β activity in a IL-1β functional assay. Variable blockade activities are demonstrated of the ITA series of bispecific antibodies. All the blockade activies are substantially higher than control human IgG.

DETAILED DESCRIPTION

Bispecific binding proteins are provided that contain at least one first binding domain that specifically binds an immune checkpoint protein and at least one second binding protein that binds IL-1β. The immune checkpoint protein may be, for example, PD-1, PD-L1, A2AR, B7-H3 (CD276), B7-H4 (VTCN1), BTLA, CTLA-4 (CD152), IDO. KIR, LAG3, NOX2, TIM-3, VISTA, SIGLEC7, (CD328), or SIGLEC9 (CD329). Advantageously, the checkpoint protein is PD-1 or PD-L1.

A binding protein simultaneously binds the checkpoint protein PD-1 or PD-L1 and IL-1β or IL-1R and thereby inhibits binding between PD-1 on CD8 T-cells and PD-L1 on a target cell, such as a tumor cell, and IL-1β activity. Simultaneous inhibition of IL-1β activity and PD-1/PD-L1 binding in this fashion provides for improved methods for cancer treatment. The first and second binding domains advantageously are human antibody variable domains. Novel bispecific binding protein formats also are provided that allow for specific binding of two antigens including, but not limited to, a checkpoint protein and a cytokine such as IL-1β. Methods of using the bispecific binding proteins for treating disease, such as cancer, also are provided.

Binding Domains

The binding domains that may be used in the binding proteins as described herein may be in any format that specifically binds the target protein. For example, for binding IL-1β the ligand binding domain of the interleukin type I or type II receptor may be used, optionally fused to a sequence from the IL-1 receptor accessory protein, as in Rilonacept. Advantageously, however, the binding domains are derived from the variable domains of human immunoglobulin molecules. Specifically, the binding domains may be derived from an antibody that binds a checkpoint protein and an antibody that binds IL-1β or IL-1R. Methods of making fully human antibodies that bind a preselected antigen are well known in the art. For example, human antibodies can be selected from large libraries of antibodies displayed on filamentous phage, and the heavy and light chain variable regions of the selected antibodies identified by methods that are well known. See, for example, Winter et al., *Annual Review of Immunology* 12:433-455 (1994). The nucleic acids encoding these variable regions are then used in constructing the genes encoding the bispecific binding proteins described herein. Alternatively, antibody variable domains from known antibodies may be used. In particular, human antibodies again IL-1β, PD-1 and PD-L1 have been approved for use in treating a variety of disease states in humans, and the variable regions from these antibodies can be used to construct the bispecific binding proteins described herein. Examples of suitable antibodies are shown below in Tables 1 and 6.

Figure 1:
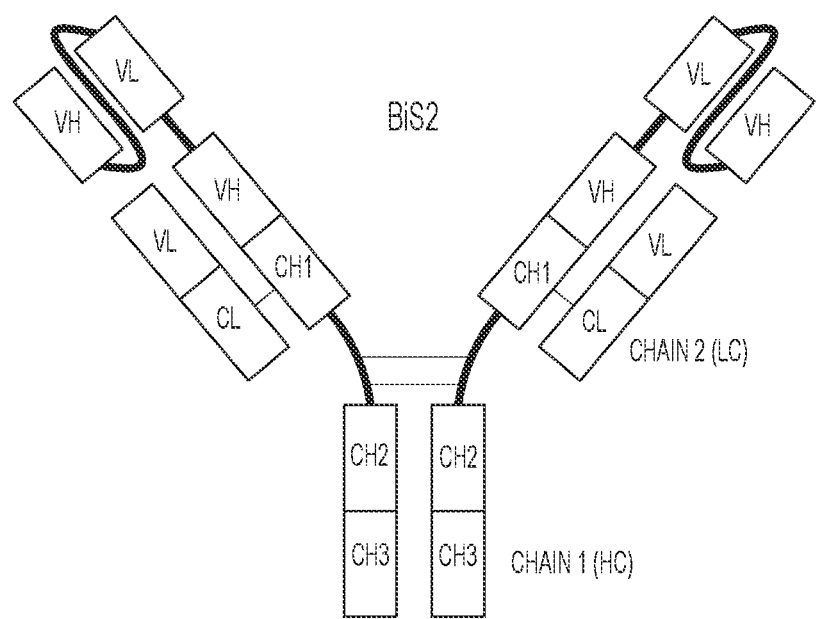
FIG. 1 shows the chain structure of a BiS2 bispecific antibody.

Alternatively, the CDR regions from an antibody with known specificity against IL-1β, IL-1R, PD-1 or PD-L1 can be inserted into known human framework regions using methods of CDR grafting that are well known in the art. See, for example, Williams and Matthews, "Humanising Antibodies by CDR Grafting" in *Antibody Engineering* (Kontermann and Dübel, Eds.) pp 319-339 (Springer, 2010). These CDR regions may be derived from the CDR regions shown or FIG. 1 or from the CDR regions of the antibodies described in Table 6. The skilled artisan will recognize that other antibodies that specifically bind IL-1β, IL-1R, PD-1 or PD-L1 exist in addition to those described herein, and that the CDR regions of those antibodies may be used in constructing the binding proteins as described herein.

With respect to IL-1β, canakinumab is an FDA-approved human antibody that binds IL-1β, and the amino acid sequences of the heavy and light chain variable regions are well known. See Rondeau et al., *MAbs* 7:1151 (2015). The entire heavy and light chain variable regions of canakinumab can be used to construct the bispecific protein proteins as described herein; alternatively, the CDR regions of canakinumab can be inserted into alternative human variable framework sequences using methods of CDR grafting that are well known in the art. See, for example, Winter and Harris, *Trends in Pharmacological Sciences* 14:139-143 (1993). An alternative IL-1β binding antibody is the humanized SK48-E26 antibody described in WO1995/01997.

With respect to IL-1R, anakinra is an FDA-approved, recombinant, nonglycosylated form of human interleukin-1 receptor antagonist (IL-1Ra) Compared to native human IL-1Ra, anakinra contains an extra N-terminal methionine residue. Anakinra competitively inhibits binding of IL-1α and IL-1β to the receptor type 1. This IL-1R1 binding domain can be used in construction of bispecific proteins to block binding of IL-1β to the IL-1 receptor. The sequence of the IL-1R1 binding portion of anakinra, which may be used as a suitable binding domain, is (SEQ ID NO: 72)
MRPSGRKSSKMQAFRIWDVNQKTFYLRNNQLVAGYLQGPNVNLEEKIDVVP

IEPHALFLGIHGGKMCLSCVKSGDETRLQLEAVNITDLSENRKQDKRFAFI

RSDSGPTTSFESAACPGWFLCTAMEADQPVSLTNMPDEGVMVTKFYFQEDE

With respect to PD-1, pembrolizumab is a humanized antibody that was first approved by the FDA in 2014 and that is used for treatment of a variety of cancers where the tumor cells express elevated PD-1. Nivolumab is a fully human antibody that was first approved by the FDA in 2014 and also is used for treating a variety of cancers. Cemiplimab is a human antibody that was first approved in 2018 for treatment of metastatic cutaneous squamous cell carcinoma. The amino acid sequences for the heavy and light chain variable domains of pembrolizumab, nivolumab, and cemiplimab, are known, as are the sequences of the CDR regions.

With respect to PD-L1, durvalumab is a human antibody that was first approved in 2017 for treatment of metastatic urothelial cancer. Atezolizumab was first approved in 2016 and is used for treating lung cancer. The amino acid sequences for the heavy and light chain variable domains of durvalumab and atezolizumab are known, as are the sequences of the CDR regions.

The sequences of the variable domains and CDR regions of pembrolizumab, nivolumab, cemeplimab, atezolizumab, avelumab, durvalumab and canakinumab are shown in Table 1 below. A list of other known antibodies again IL-1β, PD-1 and PD-L1 is shown in FIG. 6.

TABLE 1

| Antibody | Domain | Sequence | SEQ ID NO |
|---|---|---|---|
| Pembrolizumab | VH CDR1 | NYYMY | 1 |
| | VH CDR2 | GINPSNGGTNFNEKFKN | 2 |
| | VH CDR3 | RDYRFDMGFDY | 3 |
| | VL CDR1 | RASKGVSTSGYSYLH | 4 |
| | VL CDR2 | LASYL | 5 |
| | VL CDR3 | QHSRDLPLT | 6 |
| | VH | QVQLVQSGVEVKKPGASVKVSCKASGYTFTNYYM YWVRQAPGQGLEWMGGINPSNGGTNFNEKFKN RVILTTDSSITTAYMELKSLQFDDTAVYYCARRDY RFDMGFDYWGQGTTVTVSS | 37 |
| | VL | EIVLTQSPATLSLSPGERATLSCRASKGVSTSGYSYL HWYQQKPGQAPRLLIYLASYLESGVPARFSGSGSG TDFTLTISSLEPEDFAVYYCQHSRDLPLTFGGGTKVE IK | 38 |
| Nivolumab | VH CDR1 | NSGMH | 7 |
| | VH CDR2 | VIWYDGSKRYYADSVKG | 8 |
| | VH CDR3 | NDDY | 9 |
| | VL CDR1 | RASQSVSSYLA | 10 |
| | VL CDR2 | DASNRAT | 11 |
| | VL CDR3 | QQSSNWPRT | 12 |
| | VH | QVQLVESGGGVVQPGRSLRLDCKASGITFSNSGM HWVRQAPGKGLEWVAVIWYDGSKRYYADSVKGR FTISRDNSKNTLFLQMNSLRAEDTAVYYCATNDDY WGQGTLVTVSS | 39 |
| | VL | s | 40 |
| Cemiplimab | VH CDR1 | GFTFSNFG | 13 |
| | VH CDR2 | ISGGGRDT | 14 |
| | VH CDR3 | VKWGNIYFDY | 15 |
| | VL CDR1 | LSINTF | 16 |
| | VL CDR2 | AAS | 17 |
| | VL CDR3 | QQSSNTPFT | 18 |
| | VH | EVQLLESGGVLVQPGGSLRLSCAASGFTFSNFGMT WVRQAPGKGLEWVSGISGGGRDTYFADSVKGRF TISRDNSKNTLYLQMNSLKGEDTAVYYCVKWGNIY FDYWGQGTLVTVSS | 41 |

TABLE 1-continued

| Antibody | Domain | Sequence | SEQ ID NO |
|---|---|---|---|
| | VL | DIQMTQSPSSLSASVGDSITITCRASLSINTFLNWY QQKPGKAPNLLIYAASSLHGGVPSRFSGSGSGTDF TLTIRTLQPEDFATYYCQQSSNTPFTFGPGTVVDFR | 42 |
| SK48-E26 | VH CDR1 | SYDMS | 62 |
| | VH CDR2 | YISSGGGGTYYPDTVKG | 63 |
| | VH CDR3 | GGVRRGYFDV | 64 |
| | VL CDR1 | RASGNIHNYLT | 65 |
| | VL CDR2 | NAKTLAD | 66 |
| | VL CDR3 | QHFWSIPYT | 67 |
| | VH | EVQLVESGGGVVQPGRSLRLSCSSSGFIFSSYDMS WVRQAPGKGLEWVAYISSGGGGTYYPDTVKGRFT ISRDNSKNTLFLQMDSLRPEDTGVYFCARGGVRRG YFDVWGQGTPVTVSS | 68 |
| | VL | DIQMTQSPSSLSASVGDRVTITCRASGNIHNYLTW YQQTPGKAPKLLIYNAKTLADGVPSRFSGSGSGTD YTFTISSLQPEDIATYYCQHFWSIPYTFGQGTKLQIT | 69 |
| Atezolizumab | VH CDR1 | GFTFSDSWIH | 19 |
| | VH CDR2 | AWISPYGGST | 20 |
| | VH CDR3 | RHWPGGFDY | 21 |
| | VL CDR1 | RASQDVSTAVA | 22 |
| | VL CDR2 | SASFLYS | 23 |
| | VL CDR3 | QQYLYHPAT | 24 |
| | VH | EVQLVESGGGLVQPGGSLRLSCAASGFTFSDSWIH WVRQAPGKGLEWVAWISPYGGSTYYADSVKGRF TISADTSKNTAYLQMNSLRAEDTAVYYCARRHWP GGFDYWGQGTLVTVSS | 43 |
| | VL | DIQMTQSPSSLSASVGDRVTITCRASQDVSTAVA WYQQKPGKAPKLLIYSASFLYSGVPSRFSGSGSGT DFTLTISSLQPEDFATYYCQQYLYHPATFGQGTKVE IK | 44 |
| Avelumab | VH CDR1 | SYIM | 25 |
| | VH CDR2 | SIYPSGGITFYADTVKG | 26 |
| | VH CDR3 | IKLGTVTTVDY | 27 |
| | VL CDR1 | TGTSSDVGGYNYVS | 28 |
| | VL CDR2 | DVSNRPS | 29 |
| | VL CDR3 | SSYTSSSTRV | 30 |
| | VH | EVQLLESGGGLVQPGGSLRLSCAASGFTFSSYIMM WVRQAPGKGLEWVSSIYPSGGITFYADTVKGRFTI SRDNSKNTLYLQMNSLRAEDTAVYYCARIKLGTVT TVDYWGQGTLVTVSS | 45 |
| | VL | QSALTQPASVSGSPGQSITISCTGTSSDVGGYNYVS WYQQHPGKAPKLMIYDVSNRPSGVSNRFSGSKSG NTASLTISGLQAEDEADYYCSSYTSSSTRVFGTGTK VTVL | 46 |
| Durvalumab | VH CDR1 | RYWMS | 31 |
| | VH CDR2 | NIKQDGSEKYYVDSVKG | 32 |
| | VH CDR3 | EGGWFGELAFDY | 33 |
| | VL CDR1 | RASQRVSSSYLA | 34 |
| | VL CDR2 | DASSRAT | 35 |
| | VL CDR3 | QQYGSLPWT | 36 |
| | VH | EVQLVESGGGLVQPGGSLRLSCAASGFTFSRYWM SWVRQAPGKGLEWVANIKQDGSEKYYVDSVKGR FTISRDNAKNSLYLQMNSLRAEDTAVYYCAREGG WFGELAFDYWGQGTLVTVSS | 47 |
| | VL | EIVLTQSPGTLSLSPGERATLSCRASQRVSSSYLAW YQQKPGQAPRLLIYDASSRATGIPDRFSGSGSGTDF TLTISRLEPEDFAVYYCQQYGSLPWTFGQGTKVEIK | 48 |
| Canakinumab | VH CDR1 | VYGMN | 49 |
| | VH CDR2 | IIWYDGDNQYYADSVKG | 50 |
| | VH CDR3 | DLRTGP | 51 |
| | VL CDR1 | RASQSIGSSLH | 52 |
| | VL CDR2 | ASQSFS | 53 |
| | VL CDR3 | HQSSSLP | 54 |
| | VH | QVQLVESGGGVVQPGRSLRLSCAASGFTFSVYGM NWVRQAPGKGLEWVAIIWYDGDNQYYADSVKG RFTISRDNSKNTLYLQMNGLRAEDTAVYYCARDLR TGPFDYWGQGTLVTVSS | 55 |
| | VL | EIVLTQSPDFQSVTPKEKVTITCRASQSIGSSLHWY QQKPDQSPKLLIKYASQSFSGVPSRFSGSGSGTDFT LTINSLEAEDAAAYYCHQSSSLPFTFGPGTKVDIK | 56 |

The 1L-1 Receptor type has a binding domain with the sequence:

```
                                          (SEQ ID NO: 70)
KCKEREEKIILVSSANEIDVRPCPLNPNEHKGTITWYKDDSKTPVSTEQAS

RIHQHKEKLWFVPAKVEDSGHYYCVVRNSSYCLRIKISAKFVENEPNLCYN

AQAIFKQKLPVAGDGGLVCPYMEFFKNENNELPKLQWYKDCKPLLLDNIHF

SGVKDRLIVMNVAEKHRGNYTCHASYTYLGKQYPITRVIEFITLEENKPTR

PVIVSPANETMEVDLGSQIQLICNVTGQLSDIAYWKWNGSVIDEDDPVLGE

DYYSVENPANKRRSTLITVLNISEIESRFYKHPFTCFAKNTHGIDAAYIQL

IYPVTN
```

Rilonacept is an immunoglobulin fusion protein, where the binding domain contains the IL-1 receptor accessory protein (IL-1RAP) fused to the type I IL-1 receptor. The sequence of the IL-1-binding portion of Rilonacept, which may be used as a suitable binding domain, is:

```
                                          (SEQ ID NO: 71)
SERCDDWGLDTMRQIQVFEDEPARIKCPLFEHFLKFNYSTAHSAGLTLIWY
WTRQDRDLEEPINFRLPENRISKEKDVLWFRPTLLNDTGNYTCMLRNTTYC
SKVAFPLEVVQKDSCFNSPMKLPVHKLYIEYGIQRITCPNVDGYFPSSVKP
TITWYMGCYKIQNFNNVIPEGMNLSFLIALISNNGNYTCVVTYPENGRTFH
LTRTLTVKVVGSPKNAVPPVIHSPNDHVVYEKEPGEELLIPCTVYFSFLMD
SRNEVWWTIDGKKPDDITIDVTINESISHSRTEDETRTQILSIKKVTSEDL
KRSYVCHARSAKGEVAKAAKVKQKVPAPRYTVEKCKEREEKIILVSSANEI
DVRPCPLNPNEHKGTITWYKDDSKTPVSTEQASRIHQHKEKLWFVPAKVED
SGHYYCVVRNSSYCLRIKISAKFVENEPNLCYNAQAIFKQKLPVAGDGGLV
CPYMEFFKNENNELPKLQWYKDCKPLLLDNIHFSGVKDRLIVMNVAEKHRG
NYTCHASYTYLGKQYPITRVIEFITLEENKPTRPVIVSPANETMEVDLGSQ
IQLICNVTGQLSDIAYWKWNGSVIDEDDPVLGEDYYSVENPANKRRSTLIT
VLNISEIESRFYKHPFTCFAKNTHGIDAAYIQLIYPVTN
```

Bispecific Binding Protein Structure

Once the appropriate binding domains are selected, they are incorporated into a format that contains at least one binding domain that specifically binds IL-1β or IL-1R and at least one domain that specifically binds a checkpoint protein. Advantageously, the format of the binding protein is that of a bivalent or multivalent bispecific antibody, containing immunoglobulin variable and constant chain domains arranged to contain two different binding domains, as opposed to the naturally occurring homodimeric structure of a bivalent but monospecific human antibody.

Methods of making bispecific antibodies are well known in the art and are described in, for example, Brinkmann and Kontermann, *mAbs* 9:182 (2017) and Spiess et al., *Molecular Immunology,* 67: 95-106 (2015). The bispecific binding proteins described herein can be in any format known in the art that is stable, suitable for administering to a subject, and contains at least one binding domain the binds IL-1β or IL-1R and at least one binding domain that binds a checkpoint protein.

Examples of suitable bispecific binding protein formats known in the art include: Fc-less bispecific antibody formats, including: two scFv molecules joined by a linker (Kontermann, *Acta Pharmacol Sin* 26:1-9 (2005)); bispecific single-domain antibody fusion proteins (Weidle et al., *Cancer Genomics Proteomics* 10:155-68 (2013;)) and diabodies (Atwell et al., *Mol Immunol* 33:1301-12 (1996)); Fab fusion proteins (Schoonjans et al., *J Immunol;* 165:7050-7 (2000); and miniantibodies (Pluckthun and Pack, *Immunotechnology* 3:83-105 (1997) and Muller et al., *FEBS Lett* 432:45 49(1998));

Asymmetric IgGs with heavy and light chains from two different antibodies (Suresh et al, *Methods Enzymol;* 121: 210-28 (1986)); and Bispecific IgGs with an asymmetric Fc region, e.g. asymmetric Fc regions using the "knobs into holes" method (Ridgway et al., *Protein Eng;* 9:617-21 (1996); Shatz et al., *MAbs;* 5:872-81 (2013)); Sampei et al., *PLoS One;* 8:e57479 (2013); Spiess et al., *Biotechnol;* 31:753-8 (20130; Juntilla et al., *Cancer Res.* 74:5561-71 (2014); and Sun et al., *J Clin Invest.* 125):4077-4090 (2015)).

The skilled artisan will recognize that a large number of bispecific antibody formats in addition to the specific formats described above can be used to construct a bispecific antibody that binds IL-1β or IL-1R and a checkpoint protein. Advantageously, the bispecific antibody is either a 2+2 scFv-based structure or a 2+2 Fab-based structure as described in more detail below.

2+2 scFv-Based Structures

A first 2+2 scFv-based structure is the structure shown in FIG. 1, referred to herein as BiS2. As shown in FIG. 1, the BiS2 format contains two protein chains:

(1) a heavy chain that contains (from N- to C-terminus): a single chain Fv containing a first VH domain and a first VL domain (arranged VH-VL or VL-VH, i.e. the domains can be in either order), where the scFv binds the first target (IL-1β, IL-1R or the checkpoint protein, respectively); a second VH domain; and CH1, CH2, and CH3 domains, and (2) a light chain that contains (from N- to C-terminus): a second VL domain and a CL domain.

The BiS2 protein assembles via non-covalent homodimeric binding of the CH3 and CH2 domains and heterodimeric binding between the CH1 and CL domains on the heavy chain and the second VH and VL domains on the light chain. The binding between the CH1 and CL domains and the VH and VL domains forms a Fab domain that binds the second target (the checkpoint protein or IL-1β/IL-1R, respectively). Advantageously, disulfide bonds also form between the hinge regions, and between the CH1 and CL domains in the same manner as are found in naturally-occurring IgG molecules.

A second 2+2 sc Fv-based structure is the structure shown in FIG. 2A, referred to herein as BiS3. As shown in FIG. 2A, the BiS3 format also contains two protein chains:

(1) a heavy chain that contains (from N- to C-terminus): a first VH domain; CH1, CH2, and CH3 domains; and a single chain Fv containing a second VH domain and a second VL domain (where the VH and VL domains can be in either order), where the scFv binds the first target (IL-1β or the checkpoint protein, respectively);

(2) a light chain that contains (from N- to C-terminus): a second VL domain and a CL domain.

The BiS3 protein also assembles via homodimeric binding of the CH3 and CH2 domains and heterodimeric binding between the CH1 and CL domains on the heavy chain and the second VH and VL domains on the light chain. The binding between the CH1 and CL domains and the VH and VL domains forms a Fab domain that binds the second target (the checkpoint protein or IL-1β/IL-1R, respectively). Advantageously, disulfide bonds also form between the CH2 domains, and between the CH1 and CL domains in the same manner as are found in naturally-occurring IgG molecules.

Figure 2A:
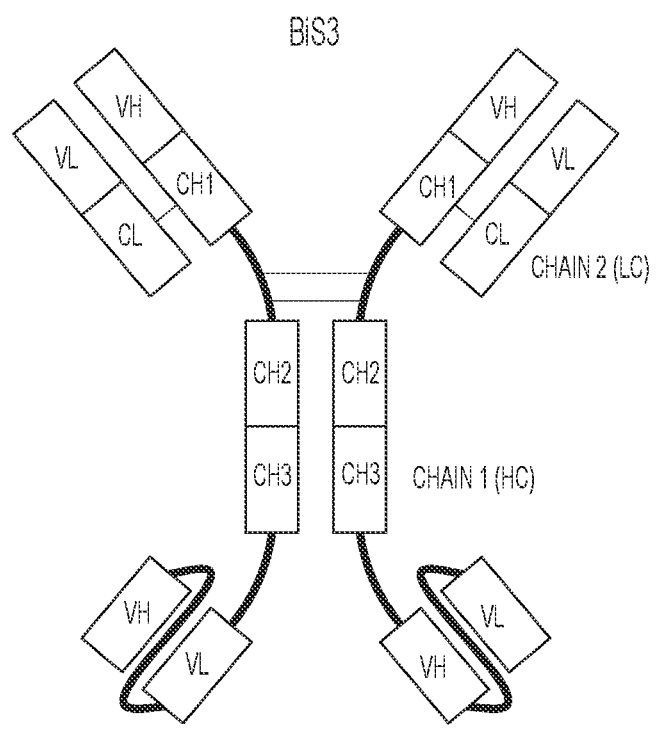
FIG. 2A shows the chain structure of a BiS3 bispecific antibody.
Figure 2B:
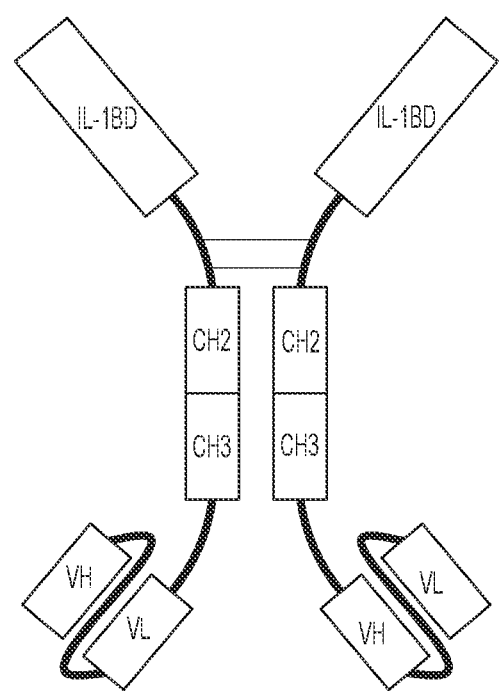
FIG. 2B shows the chain structure of a binding molecule containing (a) an IL-β binding domain derived from IL-1R1 and IL-1R accessory protein and (b) an antibody binding domain.

An alternative binding protein structure is the homodimeric structure shown in FIG. 2B, in which the heavy chain VH and CH1 domains are replaced by a binding domain derived from the extracellular ligand binding domain of an interleukin-1 receptor. This binding domain contains all or part of the extracellular binding domain from type 1 or type 2 IL-1R, optionally conjugated to the extracellular protein binding domain from interleukin-1 accessory protein (IL-1RAcP). IL-1RAcP is a receptor subunit of the functional IL-1 receptor and forms a receptor heterodimer with IL-1RI. In the structure shown in FIG. 2B the binding protein assembles via non-covalent homodimeric binding of the CH3 and CH2 domains. Advantageously, disulfide bonds also form between the CH2 domains, and between the hinge domains in the same manner as are found in naturally-occurring IgG molecules.

2+2 Fab-Based Structures

Figure 3A:
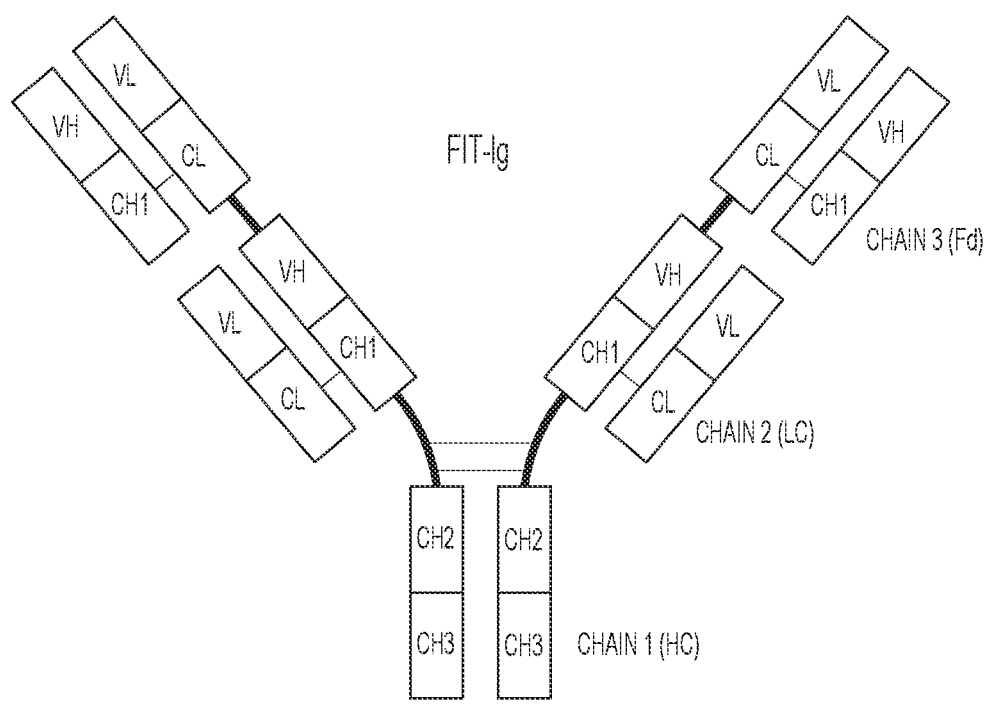
FIG. 3A shows the chain structure of a FIT-Ig bispecific antibody.
Figure 3B:
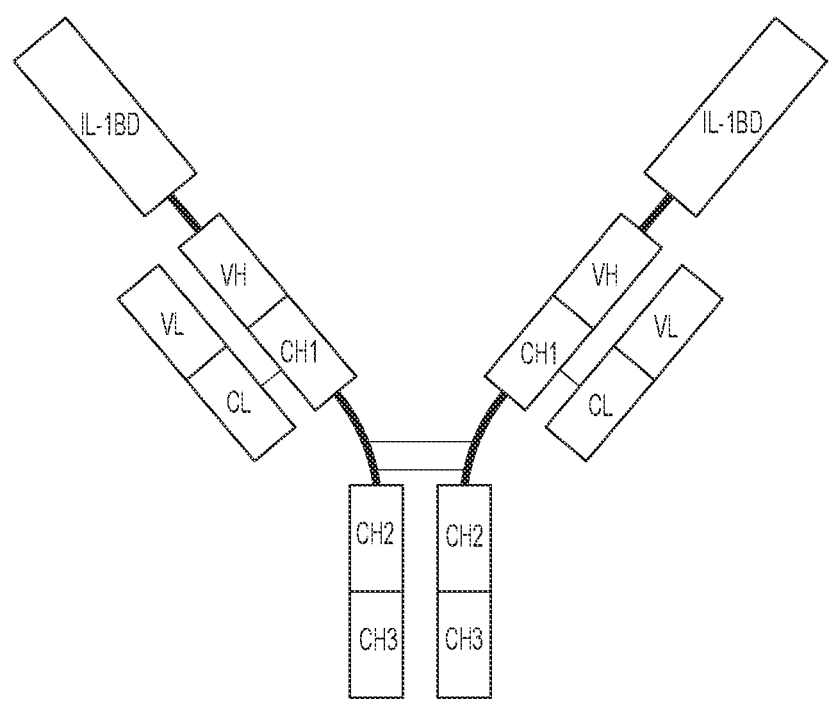
FIG. 3B-3E show the chain structures of four binding molecule containing (a) an IL-1β binding domain derived from IL-1R1 and IL-1R accessory protein and (b) an antibody binding domain
Figure 3C:
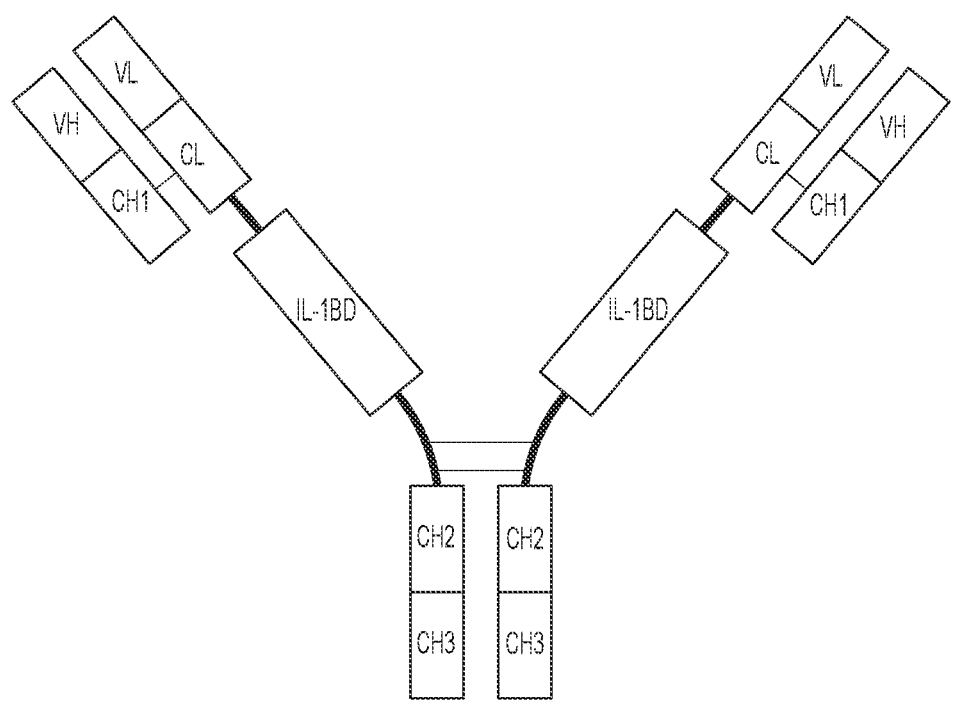
Figure 3D:
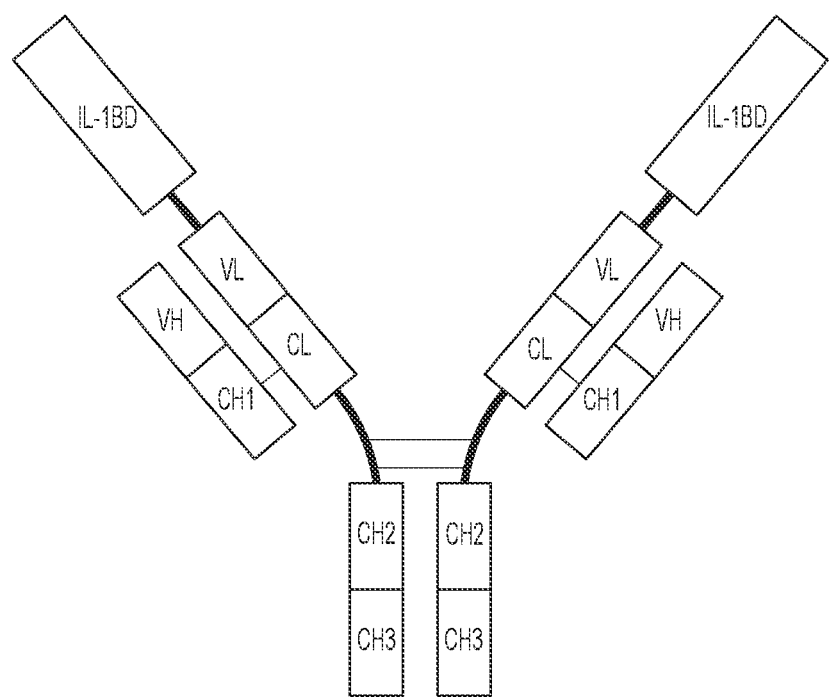
Figure 3E:
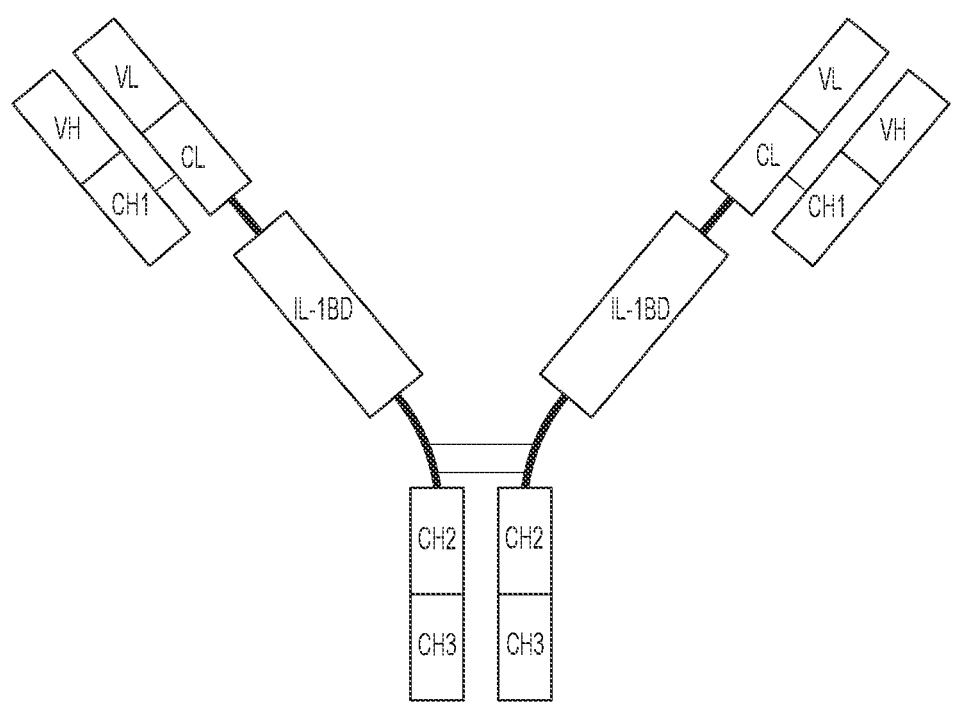

A first 2+2 Fab-based structure is the structure shown in FIG. 3A, referred to herein as FIT-Ig (see Gong et al., *MABS*, 2017, 9:1118-1128 (2017)). As shown in FIG. 3A, the FIT-Ig format contains three protein chains:

(1) a heavy chain that contains (from N- to C-terminus): a first VL domain; a first CL domain, a first VH domain, a first CH1 domain, and CH2 and CH3 domains;

(2) a light chain that contains (from N- to C-terminus): a second VL domain and a second CL domain; and (3) an Fd chain that contains (from N- to C-terminus): a second VH domain and second CH1 domain.

In the heavy chain the first CL domain may be linked to the first VH domain via a peptide linker such as, for example, a flexible hydrophilic linker having the sequence (GGGGS)$_x$, where x is 1-5 (SEQ ID NO:123). Advantageously, however, the linker is absent.

The FIT-Ig protein assembles via: non-covalent homodimeric binding of the CH3 and CH2 domains; heterodimeric binding between the first VH and CH1 domains on the heavy chain and the second VL and CL domains on the light chain; and heterodimeric binding between the first VL and CL domains and the second VH and CH1 domains on the Fd chain Two identical Fab binding domains are formed by binding of the heavy chain to the light chain, and two distinct but identical Fab domains are formed by binding of the heavy chain to the Fd chain as shown in FIG. 3. Advantageously, disulfide bonds also form between the CH2 domains, and between the hinge domains in the same manner as are found in naturally-occurring IgG molecules.

An alternative 2+2 binding protein is shown in FIGS. 3B-3E, in which one of the antibody Fab binding domains is replaced by a binding domain derived from the extracellular ligand binding domain of an interleukin-1 receptor. This binding domain contains all or part of the extracellular binding domain from type 1 or type 2 IL-1R, optionally conjugated to the extracellular protein binding domain from interleukin-1 accessory protein (IL-1RAcP). IL-1RAcP is a receptor subunit of the functional IL-1 receptor and forms a receptor heterodimer with IL-1RI. In the structures shown in FIGS. 3B-E the binding proteins assemble via non-covalent homodimeric binding of the CH3 and CH2 domains; heterodimeric binding between the VH and CH1 domains on one chain and the VL and CL domains on the second protein chain. Advantageously, disulfide bonds also form between: the CH1 and CL domains, between the CH2 domains, and between the hinge domains in the same manner as are found in naturally-occurring IgG molecules.

Figure 4:
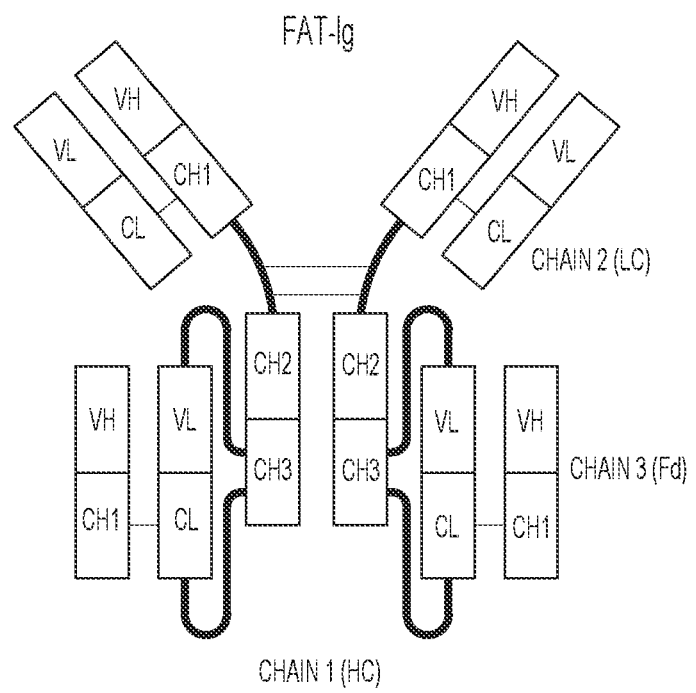
FIG. 4 shows the chain structure of a FAT-Ig bispecific antibody.

A second 2+2 Fab-based structure is the novel structure shown in FIG. 4, referred to herein as FAT-Ig. As shown in FIG. 4, the FAT-Ig format contains three protein chains:

(1) a heavy chain that contains (from N- to C-terminus): a first VH domain; a first CH1 domain, and CH2 and CH3 domains; plus first VL and a first CL domain, where the first VL and first CL domains are disposed at a solvent exposed loop in the CH2 domain, the CH3 domain, or at the interface of the CH2 and CH3 domains. Advantageously, the first CL and first CL domains are disposed at a solvent-exposed loop in the CH3 domain.

(2) a light chain that contains (from N- to C-terminus): a second VL domain and a second CL domain; and (3) an Fd chain that contains (from N- to C-terminus): a second VH domain and second CH1 domain.

In the heavy chain, the first VL and CL disposed at the solvent-exposed loop are connected to the CH2 domain, CH3 domain, or interface of the CH2 and CH3 domains via flexible peptide linkers. The linkers can have 4-25 amino acids and advantageously comprise (GGGGS)$_x$ units, where x=1-5 (SEQ ID NO:123). Other linkers may also be used, as described in more detail below.

The FAT-Ig protein assembles as shown in FIG. 4 via: non-covalent homodimeric binding of the CH3 and CH2 domains; heterodimeric binding of the heavy chain CH1 and VH domains with the light chain CL and VL domains; and heterodimeric binding of the heavy chain CL and VL domains with the Fd chain CH1 and VH domains. Two identical Fab binding domains are formed by binding of the heavy chain to the light chain, and two distinct but identical Fab domains are formed by binding of the heavy chain to the Fd chain as shown in FIG. 4. Advantageously, disulfide bonds also form between the hinge domains, and between the CH1 and CL domains in the same manner as are found in naturally-occurring IgG molecules. One of ordinary skill in the art will recognize that the novel FAT-Ig antibody format can be used to bind any two desired antigens, and is not limited to IL-1β/IL-1R and a checkpoint protein.

In each of the four specific binding proteins described above the binding domains that specifically bind IL-1β/IL-1R and the checkpoint protein are disposed asymmetrically within the binding protein i.e. the structure of the binding protein is different when the first binding domain binds IL-1β/IL-1R and the second binding domain binds the checkpoint protein compared to when the first binding domain binds the checkpoint protein and the second binding domain binds IL-1β/IL-1R. Accordingly, each of the four specific binding proteins can exist in two alternative forms for any given pair of binding domains.

Polypeptide Linkers

The domains of the bispecific binding proteins described herein may be joined into contiguous protein chains using linkers. The linkers may be used, for example, to connect the variable heavy and light chains of an scFv, or to connect the CL/VL domains into the heavy chain constant domains in the FAT-Ig format.

Suitable linkers are well known in the art and, when present, advantageously contain at least four amino acids, although longer or shorter linkers may also be used. The linkers advantageously are flexible, hydrophilic and have little or no secondary structure of their own. Linkers may be approximately 1, 2, 3, 4, 5, 6, 7, 8, 9, 10, 11, 12, 13, 14, 15, 16, 17, 18, 19, 20, 25, 30, 35, 40, 45, or approximately 50 residues in length. When multiple linkers are used to interconnect portions of a bispecific protein as described herein, the linkers may be the same, or have different lengths and/or amino acid sequences.

The linker(s) facilitate formation of the desired bispecific binding protein structure. Linkers may contain (Gly-Ser)$_x$ units, where x=1-5. Glutamic acid or lysine residues may also be placed in the linker sequences to increase solubility if necessary. The length of the linker may be varied to facilitate protein folding, target binding, and/or expression. For example, different multiples of (Gly-Ser)$_x$ units may be used to improve or optimize protein folding, target binding, and/or expression using methods that are well-known in the art.

Preparation of Bispecific Binding Proteins

Methods of making bispecific binding proteins such as Fc-less bispecific antibodies, asymmetric IgGs with heavy and light chains from two different antibodies and bispecific IgGs with an asymmetric Fc region, are well known in the art and are described in the references provided above.

The particular 2+2 bispecific antibodies described above may each be produced using suitable expression constructs in recombinant host cells. Nucleic acids encoding the heavy, light and Fd chains can be prepared synthetically using, for example, a commercial gene synthesis vendor such as Thermo Fisher (Carlsbad, Calif.). Advantageously the host cells are eukaryotic cells and the gene for each chain advantageously is synthesized with a sequence that encodes an N-terminal signal sequence that causes secretion of the translated protein from the host cell. The gene for each chain is inserted into a suitable expression vector, for example, pTT5 vector (Durocher et al., *Nucleic Acids Res.* 30:E9 (2002)), and the resulting expression constructs are then transfected into a culture of suitable host cells for transient expression. Methods of efficiently transfecting expression vectors into host cells are well known in the art using, for example, cationic lipids. See Felgner et al., *Proc. Nat'l Acad. Sci USA* 84:7413 (1987). Other methods of delivering expression vectors into cells also are well known in the art. Methods of making host cells that provide stable expression of a desired protein by integrating expression constructs into the genome of suitable host cells also are well known, as are methods of stable expression using episomal vectors containing a mammalian origin of replication that act as extra-chromosomal elements in the nucleus of the host cell.

The host cells advantageously are eukaryotic cells, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Advantageously, the host cell is a CHO cell, such as CHO-3E7.

Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. The term "host cell" as used herein refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein. Suitable cell culture media for growing eukaryotic host cells are well known in the art and are commercially available from, for example, Thermo Fisher (Grand Island, NY).

The host cells are cultured under suitable conditions to allow assembly of the protein chains in the endoplasmic reticulum of the host cell, followed by secretion of the bispecific binding proteins into the cell culture supernatant. The assembly of the correct structure of the binding protein (as opposed to, for example, non-specific pairing of the chains leading to formation of inactive proteins) can be improved by altering the relative ratios of the expression vectors used to transfect the host cells. This variation in the vector ratio also can be used to counteract, say, less efficient production of one of the chains compared to a different chain. One skilled in the art will recognize that methods of optimizing the vector ratio(s) are well known in the art.

After the host cells are cultured in an appropriate expression medium for a suitable length of time, the conditioned medium containing the bispecific binding protein is collected, and the bispecific binding protein is purified using methods that are well known in the art. For example, the binding protein can be purified using methods that may include ion-exchange chromatography, size-exclusion chromatography, and affinity chromatography, such as protein A affinity chromatography. Methods of protein purification are described in, for example, Burgess and Deutscher (Eds) "Guide to Protein Purification, Volume 436 (Methods in Enzymology) 2nd Edition (2009). Purity of the protein can be confirmed using methods well-known in the art, such as RT-HPLC, SDS-PAGE and the like.

The correct assembly of the multichain binding protein can be shown by, for example, non-denaturing gel electrophoresis, to show that the binding protein has the expected molecular weight. SDS-PAGE can be used to show that each of the expected protein chains is present and has the expected molecular weight. Western blotting using a suitable anti-Human IgG antibody can further show that the measured proteins are immunoglobulin chains.

Pharmaceutical Compositions and Methods of Administration

Methods of preparing and administering the bispecific binding molecules to a subject in need thereof are well known to or are readily determined by those skilled in the art. The route of administration of the binding molecule can be, for example, oral, parenteral, by inhalation or topical. The term parenteral as used herein includes, for example, intravenous, intraarterial, intraperitoneal, intramuscular, subcutaneous, rectal, or vaginal administration. However, in other methods compatible with the teachings herein, the binding molecules may be delivered directly to the site of the adverse cellular population thereby increasing the exposure of the diseased tissue to the therapeutic agent.

The binding molecules may be administered in a pharmaceutically effective amount for the treatment of diseases such as certain types of cancers. The pharmaceutical compositions can comprise pharmaceutically acceptable carriers, including, for example, water, ion exchangers, proteins, buffer substances, and salts. Preservatives and other additives can also be present. The carrier can be a solvent or dispersion medium. Suitable formulations for use in the therapeutic methods disclosed herein are described in Remington's Pharmaceutical Sciences (Mack Publishing Co.) 16th ed. (1980).

In any case, sterile injectable solutions can be prepared by incorporating the binding molecule(s) by itself or in combination with other active agents in an effective amount in an appropriate solvent followed by filtered sterilization. The preparations may also be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, for example, once a week or monthly, or on an "as needed" basis.

The composition can be administered as a single dose, multiple doses or over an established period of time in an infusion. Dosage regimens also can be adjusted to provide the optimum desired response (for example, a therapeutic or prophylactic response).

The composition may be used for treatment of cell-mediated diseases such as certain types of cancers including for example, bone cancer, pancreatic cancer, cancer of the head and neck, cutaneous or intraocular melanoma, uterine cancer, cancer of the central nervous system (CNS), ovarian cancer, rectal cancer, cancer of the anal region, stomach cancer, colon cancer, breast cancer, melanoma, colorectal cancer, testicular cancer, Hodgkin's disease, cancer of the esophagus, cancer of the small intestine, cancer of the endocrine system, sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter, adrenocortical carcinoma, AIDS-related cancers, Childhood Cerebellar Astrocytoma, Childhood Cerebral Astrocytoma, Basal Cell Carcinoma, extrahepatic bile duct cancer, osteosarcoma/malignant fibrous histiocytoma bone cancer, brain tumors, bronchial adenomas/carcinoids, carcinoid tumor, gastrointestinal carcinoid tumor, cerebellar astrocytoma, cerebral astrocytoma/malignant glioma, cervical cancer, childhood cancers, CMML, Chronic Lymphocytic Leukemia, Chronic Myelogenous Leukemia, Chronic Myeloproliferative Disorders, ependymoma, Ewing's Family of Tumors, extracranial germ cell tumor, extragonadal germ cell tumor, extrahepatic bile duct cancer, gallbladder cancer, gastrointestinal carcinoid tumor, germ cell tumors, gestational trophoblastic tumor, glioma, hairy cell leukemia, hepatocellular cancer, hypopharyngeal cancer, hypothalamic and visual pathway glioma, islet cell carcinoma, Kaposi's Sarcoma, laryngeal cancer, leukemia, lip and oral cavity cancer, non-small cell lung cancer (including squamous cell lung carcinoma, large cell lung carcinoma, lung adenocarcinoma, pulmonary pleomorphic carcinoma, lung carcinoid tumor, salivary gland carcinoma), small cell lung cancer (including combined small-cell carcinoma), "not otherwise specified" (NOS) lung cancer, extrapulmonary small-cell carcinoma (including extrapulmonary small-cell carcinoma localized in the lymph nodes and small-cell carcinoma of the prostate), lymphoma, Waldenstrom's Macroglobulinemia, medulloblastoma, mesothelioma, metastatic squamous neck cancer with occult primary, multiple endocrine neoplasia syndrome, multiple myeloma/plasma cell neoplasm, mycosis fungoides, myelodysplastic syndromes, myelodysplastic/myeloproliferative diseases, nasal cavity and paranasal sinus cancer, nasopharyngeal cancer, neuroblastoma, oral cancer, oropharyngeal cancer, ovarian epithelial cancer, ovarian germ cell tumor, ovarian low malignant potential tumor, islet cell pancreatic cancer, parathyroid cancer, pheochromocytoma, pineoblastoma, pituitary tumor, pleuropulmonary blastoma, ureter transitional cell cancer, retinoblastoma, rhabdomyosarcoma, salivary gland cancer, Sezary Syndrome, skin cancer, non-melanoma skin cancer, Merkel Cell Skin Carcinoma, squamous cell carcinoma, testicular cancer, thymoma, gestational trophoblastic tumor, Wilms' Tumor, and cancers with microsatellite instability.

With respect to esophageal cancer, the cancer may be, for example, esophageal squamous-cell carcinomas (ESCC) or esophageal adenocarcinomas (EAC). With respect to pancreatic cancer, the cancer may be, for example, exocrine cancer, pancreatic adenocarcinoma, pancreatic ductal carcinoma, acinar cell carcinoma of the pancreas, cystadenocarcinoma, pancreatoblastoma, adenosquamous carcinomas, undifferentiated carcinomas, pancreatic mucinous cystic neoplasms, neuroendocrine, or pancreatic neuroendocrine tumors (PanNETs). With respect to hepatic cancer, the cancer may be, for example, hepatocellular carcinoma (HCC), hepatoblastoma, cholangiocarcinoma, cholangiocellular cystadenocarcinoma, angiosarcoma, or leiomyosarcoma. With respect to colorectal cancer the cancer may be adenocarcinoma, carcinoid tumors, gastrointestinal stromal tumors (GIST), lymphoma, sarcomas, adenosquamous carcinoma (Ad-SCC) or squamous carcinoma (SCC). With respect to breast cancer, the cancer may be In situ, ductal carcinoma in situ (DCIS), invasive, invasive ductal carcinoma (IDC), invasive lobular carcinoma (ILC), triple-negative breast cancer, inflammatory breast cancer, angiosarcoma, or Paget disease of the breast. With respect to ovarian cancer, the cancer may be epithelial tumors, benign epithelial ovarian tumors, borderline epithelial ovarian tumors, malignant epithelial ovarian tumors, germ cell tumors, teratoma, dysgerminoma, endodermal sinus tumor and choriocarcinoma, primary peritoneal carcinoma, fallopian tube cancer or ovarian stromal tumors. With respect to multiple myeloma & precancerous conditions, the cancer may be light chain myeloma, non-secretory myeloma, solitary plasmacytoma, extramedullary plasmacytoma, monoclonal gammopathy of undetermined significance (MGUS), smoldering multiple myeloma (SMM), Immunoglobulin D (IgD) myeloma or Immunoglobulin E (IgE) myeloma.

Therapeutically effective doses of the compositions for treating these diseases vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The amount of at least one binding molecule to be administered can be readily determined by one of ordinary skill in the art without undue experimentation. Factors influencing the mode of administration and the respective amount of at least one binding molecule include, but are not limited to, the severity of the disease, the history of the disease, and the age, height, weight, health, and physical condition of the individual undergoing therapy. Similarly, the amount of binding molecule, to be administered will depend upon the mode of administration and whether the subject will undergo a single dose or multiple doses of this agent.

The binding molecule, may also be used in the manufacture of a medicament for treating a type of cancer, including, for example, the cancers listed above.

The subject treated with the compositions described herein may be treatment naïve or may be pretreated with one or more other therapies (for example, at least one other anti-cancer therapy) prior to receiving the medicament comprising the binding molecule. It is not necessary that the subject was a responder to pretreatment with the prior therapy or therapies. Thus, the subject that receives the medicament comprising the binding molecule, could have responded, responded poorly, responded initially but subsequently failed to respond, or could have failed to respond to pretreatment with the prior therapy, or to one or more of the prior therapies where pretreatment comprised multiple therapies. Accordingly, the present disclosure provides methods to treat patients that are poor responders or non-responders to other therapies comprising administering a binding molecule as described herein. Also provided are methods to overcome or prevent resistance to cancer therapies or to prevent or delay relapse, comprising administering a binding molecule as disclosed herein, or a composition as described herein.

Even if a patient has been previously treated with an anti-cancer medicament, a person skilled in the art can determine whether a person showed no response or was refractory to that medicament. For example, a non-response to an anti-cancer medicament may be reflected in an increased suffering from cancer, such as an increased growth of a cancer/tumor and/or increase in the size of a tumor, in the formation of (or increase in) metastases or an increase in the number or size of metastases. A non-response may also be the development of a tumor or metastases, for example after resection of a tumor, in the shortening of time to disease progression, or in the increase in the size of (a) tumor(s) and/or (a) metastases, for example in neoadjuvant therapy. Based on these parameters or other parameters known in the art, a patient group can be identified that does not respond to treatment with anti-cancer medicaments and this group of patients may then be treated with the binding molecules described herein.

The binding molecules and compositions containing the binding molecules may also be used to treat patients that are, for example, poor-responders or non-responders to another therapy. The term "non-responder" as used herein can refer to an individual/patient/subject that is less likely to respond to a treatment using an anti-cancer medicament. "Less likely to respond" as used herein refers to a decreased likeliness that a pathological complete response will occur in a patient treated with an anti-cancer medicament. In some aspects, a patient can be initially a good responder, and resistance to treatment can develop during treatment with such an anti-cancer medicament, leading to poor or no-response to the treatment.

The term "good responder" as used herein refers to an individual whose tumor does not demonstrate growth, metastases, increase in number or size of metastases, etc. during or after treatment using an anti-cancer medicament, for example based on serial imaging studies, an individual that does not experience tumor growth, metastases, increase in number or size of metastases, etc. over a period of time (for example, about 1 year following initial diagnosis), and/or an individual that experiences a certain life span (for example, about 2 years or more following initial diagnosis).

The term "poor responder" as used herein refers to an individual whose tumor grows or metastasizes during or shortly thereafter standard therapy, for example using an anti-cancer medicament, or who experiences adverse clinical effects attributable to the tumor.

The term "poor responder" also includes indivduals who transitioned from "good responder" to 'poor responder" during treatment with an anti-cancer medicament.

In cases where it is assessed that the subject is a "non-responder," a "poor-responder" or is "less likely to respond" (based, for example, on the presence of certain biomarkers in the cancer cells), the subject could be treated with the binding molecules disclosed herein.

Methods also are provided for the co-administration of a binding molecule as described herein and at least one other therapy. The binding molecule and the at least one other therapy can be co-administered together in a single composition or can be co-administered together at the same time or overlapping times in separate compositions. In some aspects, a binding molecule can be used as an adjuvant therapy.

The binding molecule may also be used in the manufacture of a medicament for treating a subject suffering from a cancer, where the binding molecule is administered before a subject has been treated with at least one other therapy.

The binding molecules can also be used in methods of preventing or reducing the risk of cancer in a subject by administering to the subject an effective amount of a binding protein or composition containing the binding protein. The cancer may be lung cancer and the patient may be in remission from a previously diagnosed and/or previously treated cancer. The patient may be considered to be at risk of cancer due to environmental exposure, tobacco use or exposure, genetic mutation, or a family history of cancer.

EXAMPLES

In the examples below the binding domains are based on heavy and light chain variable regions from human antibodies that have received regulatory approval for use in humans. "O," "E" and "K" indicate domains that bind IL-1β, while "M" and "B" indicate binding domains that bind PD-1. The amino acid sequences of the chains of the binding proteins are shown in FIG. 5

Example 1

Expression of Bispecific Antibodies

1. Plasmid Preparation

Target DNA sequences encoding the binding proteins were synthesized and subcloned into the pTT5 vector (Durocher et al., *Nucleic Acids Res.* 30:E9 (2002) for expression in CHO-3E7 cells. The amino acid sequences of the coding sequences are shown in FIG. 5.

2. Cell Culture and Transient Transfection

CHO-3E7 cells were grown in serum-free FreeStyle™ CHO Expression Medium (Life Technologies, Carlsbad, Calif., USA). The cells were maintained in Erlenmeyer Flasks (Corning Inc., Acton, Mass.) at 37° C. with 5% $CO_2$ on an orbital shaker (VWR Scientific, Chester, Pa.). One day before transfection, the cells were seeded in Corning Erlenmeyer Flasks. On the day of transfection, DNA and transfection reagent were mixed and then added into the cells culture, during which the recombinant plasmids encoding target antibody were transiently transfected into CHO-3E7 cells. The cell culture supernatant collected on day 6 was used for purification. Table 2 lists the heavy chain, light chain and Fd chain combination of each antibody and each of the plasmid ratios that were screened.

7.2. The antibodies were further purified by standard techniques. For example, some samples were further purified by size exclusion chromatography (SEC) using a Superdex 200 Increase 10/300 GL column or by ceramic hydroxyapatite chromatography using a CHT™ ceramic hydroxyapatite column (Bio-Rad). For other proteins, Protein A affinity chromatography was used for initial purification, followed by SEC if necessary.

TABLE 2

Summary of heavy chain (HC), light chain (LC) and Fd chain (Fd) combinations and plasmid ratios for each antibody.

| Antibody name | Antibody format | HC name | LC name | Fd | Ratio 1 HC:LC:Fd | Ratio 2 HC:LC:Fd | Ratio 3 HC:LC:Fd | Ratio 4 HC:LC:Fd |
|---|---|---|---|---|---|---|---|---|
| ITA101 | BiS2-OB | BscFv-OHC | OLC | / | 1:1:0 | 3:1:0 | 1:3:0 | / |
| ITA102 | BiS2-OM | MscFv-OHC | OLC | / | 1:1:0 | 3:1:0 | 1:3:0 | / |
| ITA103 | BiS2-PC | OscFv-BHC | BLC | / | 1:1:0 | 3:1:0 | 1:3:0 | / |
| ITA104 | BiS2-MO | OscFv-MHC | MLC | / | 1:1:0 | 3:1:0 | 1:3:0 | / |
| ITA201 | BiS3-OB | OHC-BscFv | OLC | / | 1:1:0 | 3:1:0 | 1:3:0 | / |
| ITA202 | BiS3-OM | OHC-MscFv | OLC | / | 1:1:0 | 3:1:0 | 1:3:0 | / |
| ITA203 | BiS3-BO | BHC-OscFv | BLC | / | 1:1:0 | 3:1:0 | 1:3:0 | / |
| ITA204 | BiS3-MO | MHC-OscFv | MLC | / | 1:1:0 | 3:1:0 | 1:3:0 | / |
| ITA301 | FiT-OB | BLC-OHC | OLC | BFd | 1:1:1 | 1:3:3 | 1:1:3 | 1:3:1 |
| ITA302 | FiT-OM | MLC-OHC | OLC | MFd | 1:1:1 | 1:3:3 | 1:1:3 | 1:3:1 |
| ITA303 | FiT-BO | OLC-BHC | BLC | OFd | 1:1:1 | 1:3:3 | 1:1:3 | 1:3:1 |
| ITA304 | FiT-MO | OLC-MHC | MLC | OFd | 1:1:1 | 1:3:3 | 1:1:3 | 1:3:1 |
| ITA401 | FAT-OB | OHC-BLC | OLC | BFd | 1:1:1 | 1:3:3 | 1:1:3 | 1:3:1 |
| ITA402 | FAT-OM | OHC-MLC | OLC | MFd | 1:1:1 | 1:3:3 | 1:1:3 | 1:3:1 |
| ITA403 | FAT-BO | BHC-OLC | BLC | OFd | 1:1:1 | 1:3:3 | 1:1:3 | 1:3:1 |
| ITA404 | FAT-MO | MHC-OLC | MLC | OFd | 1:1:1 | 1:3:3 | 1:1:3 | 1:3:1 |
| ITB101 | FP2-BK | K BHC | B LC | / | 1:1 | | | |
| ITB102 | FP2-MK | K MHC | M LC | / | 1:1 | | | |
| ITB103 | FFP1(FIT)- KM | MFd-K-G4P | M LC | / | 1:1 | | | |
| ITB104 | FFP1(FIT)-KB | BFd-K-G4P | B LC | / | 1:1 | | | |
| ITB105 | FFP3-KM | K-G4P-MscFv | / | / | N/A | | | |
| ITB106 | FP1-(crossmab)BK | K-BLC-Fc | / | B Fd | 1:1 | | | |
| ITB107 | FP1-(crossmab) MK | K-MLC-Fc | / | M Fd | 1:1 | | | |
| ITB108 | FFP2-KM | MLC-KG4P | / | M Fd | 1:1 | | | |
| ITB109 | FFP2-KB | BLC-K-G4P | / | B Fd | 1:1 | | | |
| ITC401 | FAT-O/B 1 + 5 | O HC-B LC 1 + 5 | O LC | B Fd | 1:1:1 | 1:3:3 | 1:1:3 | 1:3:1 |
| ITC402 | FAT-O/B 3 + 3 | O HC-B LC 3 + 3 | O LC | B Fd | 1:1:1 | 1:3:3 | 1:1:3 | 1:3:1 |
| ITC403 | FAT-O/B 4 + 2 | O HC-B LC 4 + 2 | O LC | B Fd | 1:1:1 | 1:3:3 | 1:1:3 | 1:3:1 |
| ITC404 | FAT-O/B 5 + 1 | O HC-B LC 5 + 1 | O LC | B Fd | 1:1:1 | 1:3:3 | 1:1:3 | 1:3:1 |
| ITC405 | FAT-O/B 4 + 4 | O HC-B LC 4 + 4 | O LC | B Fd | 1:1:1 | 1:3:3 | 1:1:3 | 1:3:1 |
| ITC406 | FAT-O/B 2 + 2 | O HC-B LC 2 + 2 | O LC | B Fd | 1:1:1 | 1:3:3 | 1:1:3 | 1:3:1 |
| ITD401 | FAT-O/B 5 + 5 | FAT-O/B 5 + 5 | O LC | B Fd | 1:1:1 | 1:3:3 | 1:1:3 | 1:3:1 |
| ITD402 | FAT-O/B 4 + 5 | FAT-O/B 4 + 5 | O LC | B Fd | 1:1:1 | 1:3:3 | 1:1:3 | 1:3:1 |
| ITD403 | FAT-O/B 5 + 4 | FAT-O/B 5 + 4 | O LC | B Fd | 1:1:1 | 1:3:3 | 1:1:3 | 1:3:1 |
| ITE101 | BiS2-O/M VH/VL DSB | M scFv-O HC VH/VL DSB | O LC | / | 1:1:0 | 3:1:0 | 1:3:0 | / |
| ITE102 | BiS2-O/M VL/VH DSB | M scFv-O HC VL/VH DSB | O LC | / | 1:1:0 | 3:1:0 | 1:3:0 | / |
| ITE201 | BiS3-M/O VH/VL DSB | M HC-O scFv_VH/VL DSB | M LC | / | 1:1:0 | 3:1:0 | 1:3:0 | |
| ITE202 | BiS3-M/O VL/VH DSB | M HC-O scFv_VL/VH DSB | M LC | / | 1:1:0 | 3:1:0 | 1:3:0 | |
| ITE301 | FIT-B/O-L3 | O LC-B HC-L3 | B LC | O Fd | 1:1:1 | 1:3:3 | 1:1:3 | 1:3:1 |
| ITE302 | FIT-B/O-L7 | O LC-B HC-L7 | B LC | O Fd | 1:1:1 | 1:3:3 | 1:1:3 | 1:3:1 |
| ITF101 | BiS2-E/M VL/VH DSB | BiS2-M/E VL/VH DSB | E13 LC | / | 1:1:0, | 1:3:0 | 3:1:0 | |
| ITF102 | BiS2-M/E VL/VH DSB | BiS2-M/E VL/VH DSB | M LC | / | 1:1:0, | 1:3:0 | 3:1:0 | |
| ITF103 | BiS2-M/E VH/VL DSB | BiS2-M/E VH/VL DSB | M LC | / | 1:1:0, | 1:3:0 | 3:1:0 | |
| ITF201 | BiS3-M/E VL/VH DSB | BiS3-M/E VL/VH DSB | M LC | / | 1:1:0, | 1:3:0 | 3:1:0 | |
| ITF202 | BiS3-M/E VH/VL DSB | BiS3-M/E VH/VL DSB | M LC | / | 1:1:0, | 1:3:0 | 3:1:0 | |
| ITF301 | FIT-B/E L3 | FIT-B/E-L3 | B LC | E Fd | 1:1:1 | 1:1:1, | 1:1:1, | 1:1:1, |
| ITF302 | FIT-B/E L7 | FIT-B/E-L7 | B LC | E Fd | 1:1:1 | 1:1:1, | 1:1:1, | 1:1:1, |
| ITF401 | FAT-E/B | FAT-E/B | E13LC | B Fd | 1:1:1 | 1:1:1, | 1:1:1, | 1:1:1, |
| ITF402 | FAT-B/E | FAT-B/E | B LC | E Fd | 1:1:1 | 1:1:1, | 1:1:1, | 1:1:1, |
| ITF403 | FAT-M/E | FAT-M/E | M LC | E Fd | 1:1:1 | 1:1:1, | 1:1:1, | 1:1:1, |

3. Purification and Results

Cell culture supernatant was centrifuged followed by filtration. The filtered supernatant was loaded onto Monofinity A Resin Prepacked Column 1 ml (GenScript, Cat. No. L00433-11) at 1.0 ml/min. After a washing step, the antibodies were eluted and then buffer exchanged to PBS, pH Each of the expressed proteins was analyzed by SDS-PAGE under reducing and non-reducing conditions and Western blot analysis (using Goat Anti-Human IgG-HRP (GenScript, Cat. No. A00166), which showed that proteins and constituent chains had the desired molecular weights. Purity of the proteins was assessed using size-exclusion HPLC

Example 2

Figure 7:
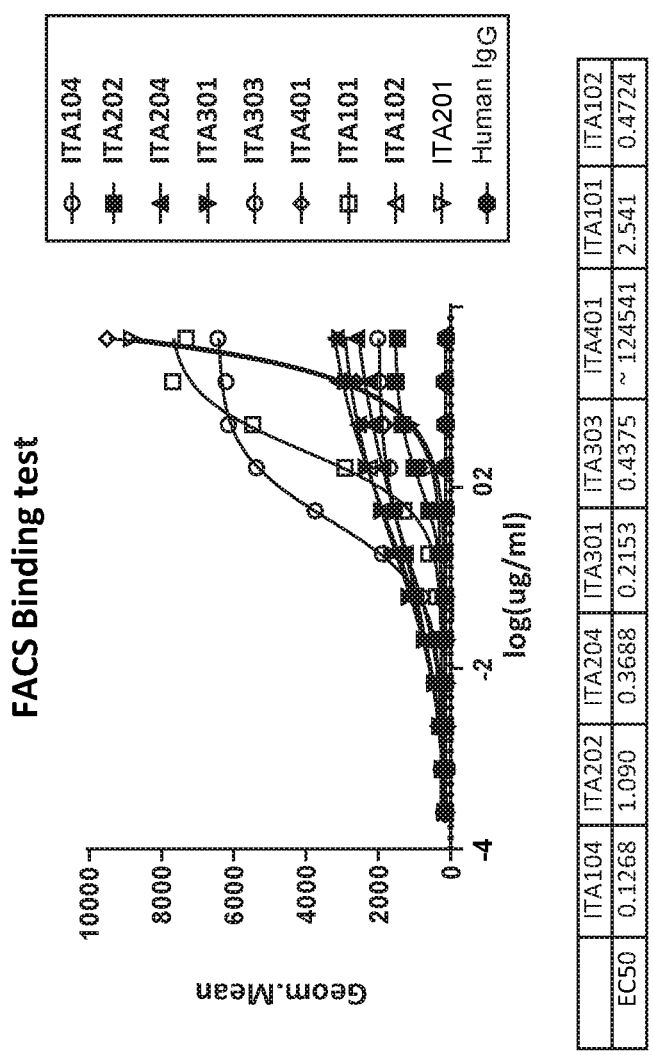
FIG. 7 shows binding of bispecific antibodies to cell membrane-bound PD-1 and soluble IL-1β simultaneously in a multiple-dose sandwich assay, as detected by flow cytometry. Variable binding affinities of ITA series of bispecific antibodies are demonstrated, and all the binding affinities are substantially higher than control human IgG.

Nine of the sixteen different bispecific antibodies described in Example 1 were analyzed for binding to PD-1 on the surface of cells using flow cytometry. Cell lines used were CHO-K1 cells (negative control) and a CHO-K1/PD-1 expressing. Antibodies used were an irrelevant human IgG (negative control), and commercially available anti-PD-1 (positive controls). The secondary antibody used was a goat anti Human IgG(H+L) iFluor 647 (1 μg/ml) (data not shown). In order to demonstrate concurrent binding of the bispecific molecules to PD1 and IL-1β, a sandwich FACS assay was performed. The binding curves are shown in FIG. 7. CHO cells expressing PD1 were bound by bispecific antibodies at the indicated concentrations. Unbound antibody was washed away and detection was performed using biotinylated IL-1β (2 μg/ml) followed by SA-iFluor 647 (1 μg/ml). Fluorescence intensity is indicative of both BiSAb immobilization on PD1+ cells and ability to concurrently bind IL-1β. Various combinations of anti-IL-1β VH/VL binding domains with two different pairs of anti-PD-1 VH/VL binding domains were formatted as BiS2, BiS3, FIT-IG or FAT-IG molecules. Of the constructs tested, the four binding molecules having anti-PD-1 VH/VL binding regions containing the CDR regions defined by the sequences of SEQ ID Nos: 1-6 all achieved a higher mean fluorescence intensity compared to the five binding molecules having anti-PD-1 VH/VL binding regions containing the CDR regions defined by the sequences of SEQ ID Nos: 6-12.

Figure 8:
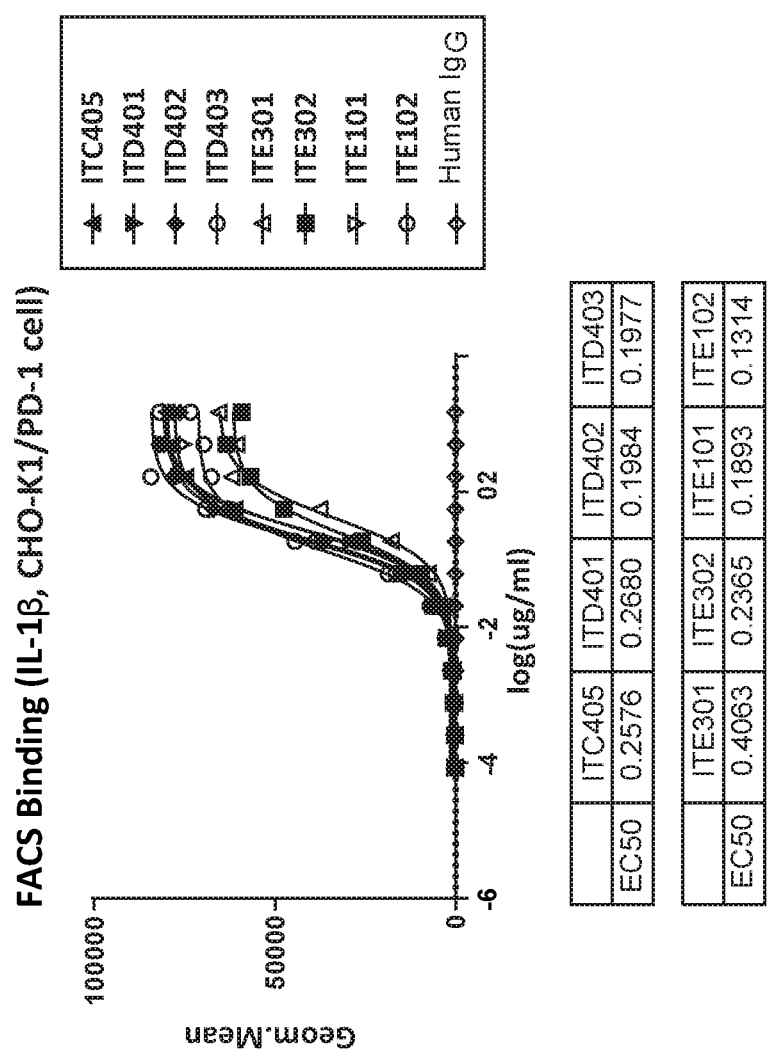
FIG. 8 shows binding of bispecific antibodies to cell membrane-bound PD-1 and soluble IL-1β simultaneously in a multiple-dose sandwich assay, as detected by flow cytometry. Variable binding affinities of ITC, ITD and ITE series of bispecific antibodies are demonstrated, and all the binding affinities are substantially higher than control human IgG.

FIGS. 8-12 show additional binding data for additional binding proteins. FIG. 8 shows binding curves for binding of bispecific antibodies to cell membrane-bound PD-1 and soluble IL-1β simultaneously in a multiple-dose sandwich assay, as detected by flow cytometry. Variable binding affinities of the ITC, ITD and ITE series of bispecific antibodies are shown. All the binding affinities are substantially higher than control human IgG.

Figure 9A:
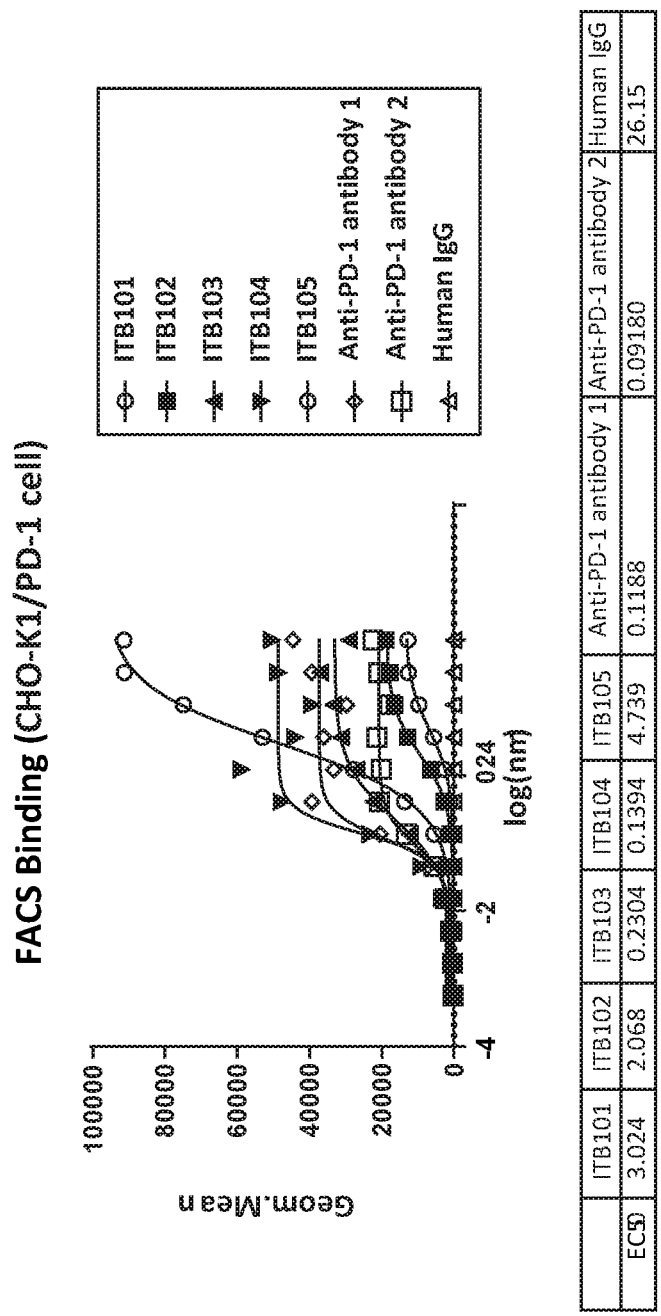
FIGS. 9A-C show binding of bispecific antibodies to cell membrane-bound PD-1 in a multiple-dose sandwich assay, as detected by flow cytometry. Variable binding affinities of ITB and ITF series of bispecific antibodies are demonstrated, and all the binding affinities are substantially higher than control human IgG.
Figure 9B:
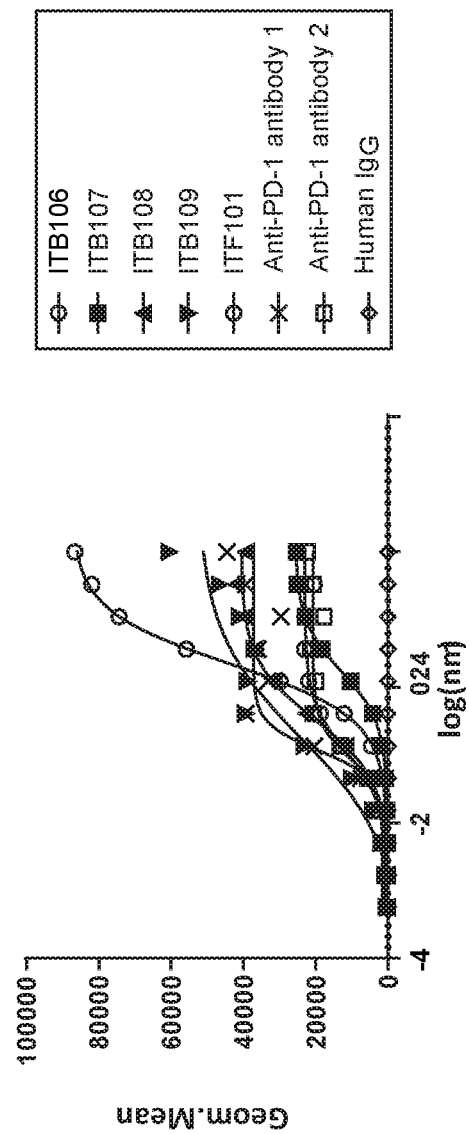
Figure 9C:
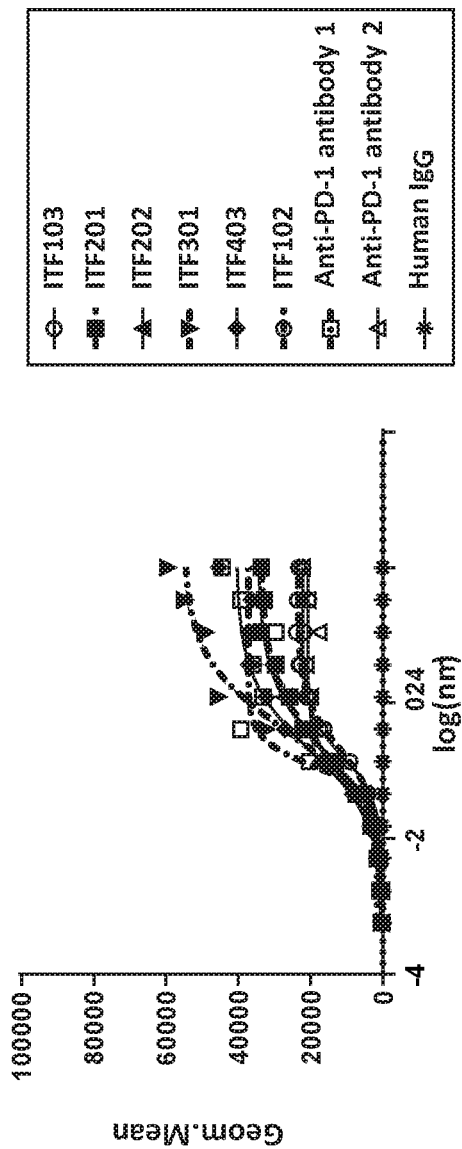

FIG. 9 shows binding curves for binding to cell membrane-bound PD-1 in a multiple-dose sandwich assay, as detected by flow cytometry. Variable binding affinities of the ITB and ITF series of bispecific antibodies are shown. All the binding affinities are substantially higher than control human IgG.

Figure 10A:
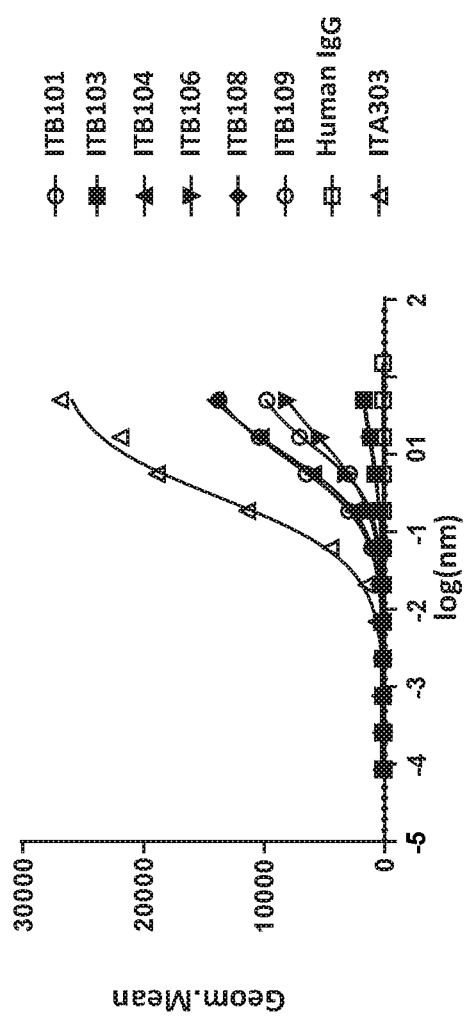
FIGS. 10A and 10B show binding of bispecific antibodies to cell membrane-bound PD-1 and soluble IL-1β simultaneously in a multiple-dose sandwich assay, as detected by flow cytometry. Variable binding affinities of ITB and ITF series of bispecific antibodies are demonstrated. All the binding affinities are substantially higher than control human IgG.
Figure 10B:
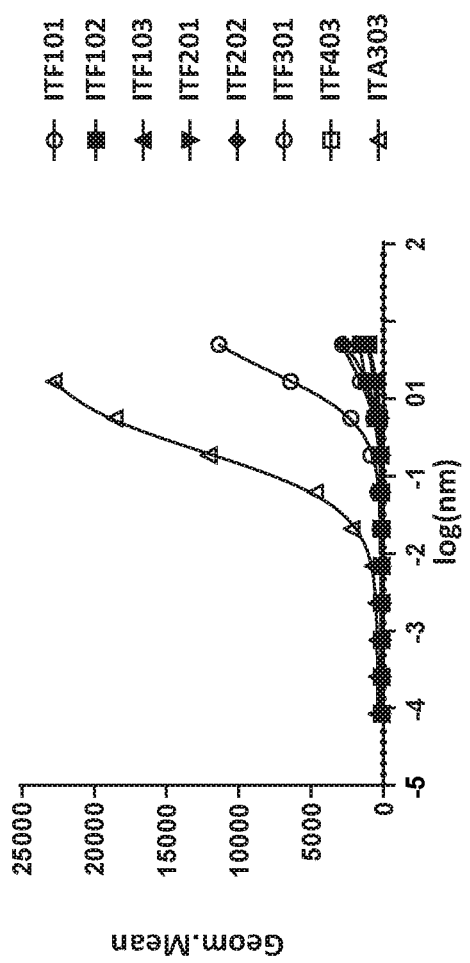

FIG. 10 shows binding curves for binding to cell membrane-bound PD-1 and soluble IL-1β simultaneously in a multiple-dose sandwich assay, as detected by flow cytometry. Variable binding affinities of ITB and ITF series of bispecific antibodies are shown. All the binding affinities are substantially higher than control human IgG.

Figure 11:
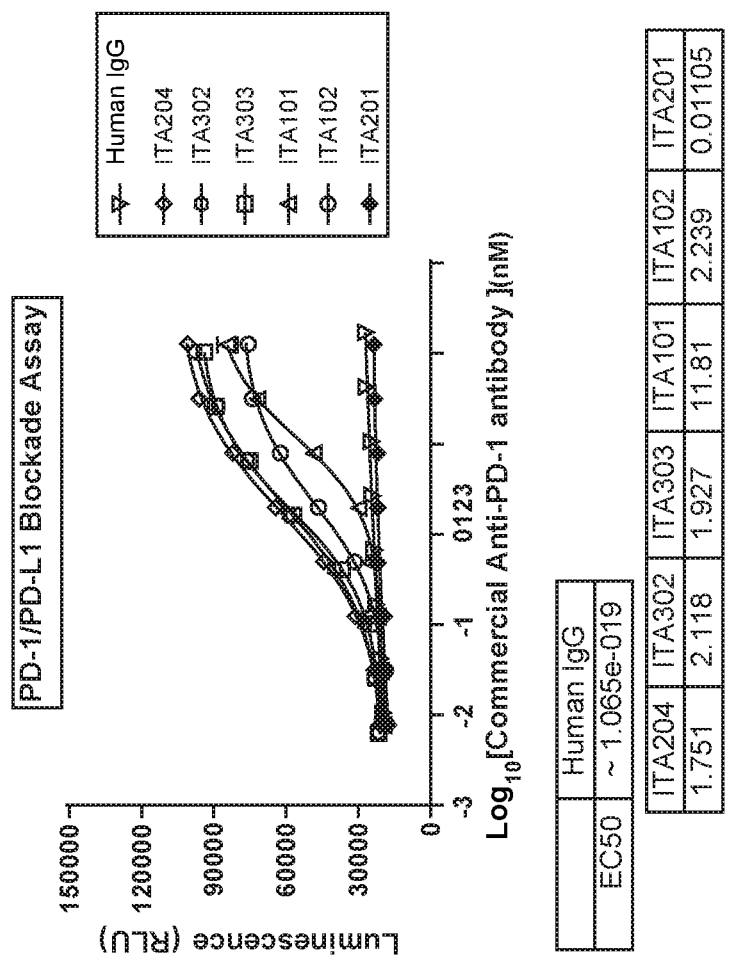
FIG. 11 shows that bispecific antibodies block PD-1 activity in a PD-1/PD-L1 reporter assay. Variable blockade activities are demonstrated for the ITA series of bispecific antibodies. All the blockade activies are substantially higher than control human IgG.

FIG. 11 shows that bispecific antibodies block PD-1 activity in a PD-1/PD-L1 reporter assay. Variable blockade activities are shown for the ITA series of bispecific antibodies. All the blockade activies are substantially higher than control human IgG.

Figure 12A:
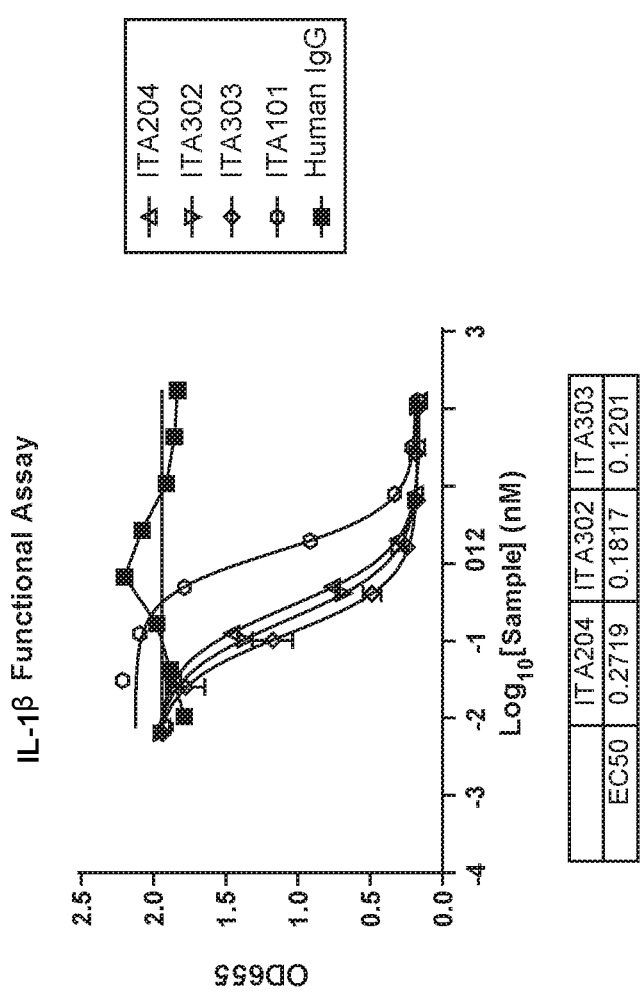

FIG. 12 shows that bispecific antibodies block IL-1β activity in a IL-1β functional assay. Variable blockade activities are demonstrated of the ITA series of bispecific antibodies. All the blockade activies are substantially higher than control human IgG.

What is claimed is:

1. A binding protein comprising a first binding domain and a second binding domain, wherein said first binding domain specifically binds and inhibits activation of PD-1, and wherein said second binding domain specifically binds and inhibits the activity of IL-1β, wherein said binding protein comprises:
   (a) a heavy chain comprising, from N- to C-terminus, a single chain Fv comprising a first VH domain and a first VL domain, linked to a second VH domain,
   wherein said scFv form said first binding domain, and
   wherein said first VH domain comprises a CDR1 of SEQ ID NO.:7, a CDR2 of SEQ ID NO.8, and a CDR3 of SEQ ID NO.:9,
   wherein said first VL domain comprises a CDR1 of SEQ ID NO.:10, a CDR2 of SEQ ID NO.:11; and CDR3 of SEQ ID NO.:12,
   and
   wherein said second VH domain comprises a CDR1 of SEQ ID NO:49, a CDR2 of SEQ ID NO.:50 and a CDR3 of SEQ ID NO.:51, wherein said heavy chain further comprises CH1, CH2, and CH3 domains;
   and
   (b) a light chain comprising a second VL domain comprising a CDR1 of SEQ ID NO.:52, a CDR2 of SEQ ID NO.:53, and a CDR3 of SEQ ID NO.:54, wherein said light chain further comprises a CL domain;
   wherein said second VH domain and said second VL domain form said second binding domain.

2. The binding protein according to claim 1 wherein said binding domains are human immunoglobulin binding domains.

3. A pharmaceutical composition comprising a binding protein according to claim 1 and a pharmaceutically acceptable excipient.

4. A method of treating cancer in a subject comprising administering a binding protein according to claim 1 to a subject in need thereof.

5. A binding protein according to claim 1, wherein the CH1 domain is connected to the CH2 domain via an antibody hinge region and further comprising at least one disulfide bond between the hinge regions, and at least one disulfide bond between the CH1 and CL domains.

6. A binding protein according to claim 1, wherein said heavy chain comprises the amino acid sequence of SEQ ID NO: 106.

7. A binding protein according to claim 1, wherein said light chain comprises the amino acid sequence of SEQ ID NO:74.

8. A binding protein according to claim 5, wherein said heavy chain comprises the amino acid sequence of SEQ ID NO: 106 and said light chain comprises the amino acid sequence of SEQ ID NO:74.

* * * * *